US008299296B2

(12) United States Patent
Shimada et al.

(10) Patent No.: US 8,299,296 B2
(45) Date of Patent: Oct. 30, 2012

(54) SPIRO COMPOUNDS AND PHARMACEUTICAL USE THEREOF

(75) Inventors: Takashi Shimada, Takatsuki (JP); Hiroshi Ueno, Takatsuki (JP); Kazuhiro Tsutsumi, Takatsuki (JP); Kouichi Aoyagi, Takatsuki (JP); Tomoyuki Manabe, Takatsuki (JP); Shin-Ya Sasaki, Takatsuki (JP); Susumu Katoh, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 841 days.

(21) Appl. No.: 12/258,033

(22) Filed: Oct. 24, 2008

(65) Prior Publication Data
US 2009/0170908 A1    Jul. 2, 2009

Related U.S. Application Data

(60) Provisional application No. 61/001,823, filed on Nov. 5, 2007.

(30) Foreign Application Priority Data

Oct. 26, 2007   (JP) ................................. 2007-279697

(51) Int. Cl.
C07C 62/00 (2006.01)
C07C 65/00 (2006.01)
A01N 43/40 (2006.01)

(52) U.S. Cl. ........................................ 562/466; 514/345

(58) Field of Classification Search .................. None
See application file for complete search history.

(56) References Cited

U.S. PATENT DOCUMENTS

| | | | |
|---|---|---|---|
| 7,005,538 B1 | 2/2006 | Malm et al. | |
| 7,319,163 B2 | 1/2008 | Malm et al. | |
| 7,456,218 B2 | 11/2008 | Yasuma et al. | |
| 7,465,804 B2 | 12/2008 | Houze et al. | |
| 7,517,910 B2 | 4/2009 | Yasuma et al. | |
| 7,582,803 B2 | 9/2009 | Akerman et al. | |
| 7,649,110 B2 | 1/2010 | Akerman et al. | |
| 7,820,837 B2 | 10/2010 | Yasuma et al. | |
| 7,932,289 B2 | 4/2011 | Suzuki et al. | |
| 2006/0004012 A1 | 1/2006 | Akerman et al. | |
| 2006/0258722 A1 | 11/2006 | Yasuma et al. | |
| 2006/0270724 A1 | 11/2006 | Houze et al. | |
| 2007/0066647 A1 | 3/2007 | Akerman et al. | |
| 2007/0142384 A1 | 6/2007 | Akerman et al. | |
| 2007/0149608 A1 | 6/2007 | Yasuma et al. | |
| 2008/0090840 A1 | 4/2008 | Beck et al. | |
| 2008/0119511 A1 | 5/2008 | Brown et al. | |
| 2008/0167378 A1 | 7/2008 | Fukatsu et al. | |
| 2008/0319077 A1 | 12/2008 | Suzuki et al. | |
| 2009/0012093 A1 | 1/2009 | Fukatsu et al. | |

FOREIGN PATENT DOCUMENTS

| | | |
|---|---|---|
| EP | 1559422 | 8/2005 |
| EP | 1731505 | 12/2006 |
| JP | 2005-15461 | 1/2005 |
| JP | 2006-83154 | 3/2006 |
| JP | 2007-525516 | 9/2007 |
| WO | WO 01/036365 | 5/2001 |
| WO | WO 2005/051373 | 6/2005 |
| WO | WO 2005/086661 | 9/2005 |
| WO | WO 2005/095338 | 10/2005 |
| WO | WO 2006/011615 | 2/2006 |
| WO | WO 2006/127503 | 11/2006 |
| WO | WO 2007/033002 | 3/2007 |
| WO | WO 2008/030520 | 3/2008 |
| WO | WO 2008/030618 | 3/2008 |
| WO | WO 2009/157418 | 12/2009 |

OTHER PUBLICATIONS

Stoddart et al., Mol.Pharm., 2007, 71, 994-1005.*
Telvekar et al. Current Drug Targets, 2008, 9, 899-910.*
Salsali et al., American Journal of Therapeutics, 2006, 13, 349.*
Briscoe, C.P. et al. "Pharmacological regulation of insulin secretion in MIN6 cells through the fatty acid receptor GPR40: identification of agonist and antagonist small molecules" British Journal of Pharmacology, vol. 148:619-628 (2006).
Briscoe, C.P. et al., "The orphan G protein-coupled receptor GPR40 is activated by medium and long chain fatty acids", J. Biol. Chem. 278(13):11303-11311 (2003).
Garrido, D.M., et al., "Synthesis and activity of small molecule GPR40 agonists", Bioorganic & Medicinal Chemistry Letters vol. 16:1840-1845 (2006).
Itoh, Y. et al. "Free fatty acids regulate insulin secretion from pancreatic β cells through GPR40" Nature, vol. 422:173-176 (2003).
Itoh, Y. et al. "GPR40, a free fatty acid receptor on pancreatic β cells, regulates insulin secretion" Hepatology Research, vol. 33:171-173 (2005).
Rayasam, G. V. et al. "Fatty acid receptors as new therapeutic targets for diabetes" Expert Opin. Ther. Targets, vol. 11(5):661-671 (2007).

(Continued)

Primary Examiner — Susanna Moore
Assistant Examiner — Jennifer C Sawyer
(74) Attorney, Agent, or Firm — Fish & Richardson P.C.

(57) ABSTRACT

The spiro compound represented by the following general formula [Ia], its pharmaceutically acceptable salt or a solvate thereof

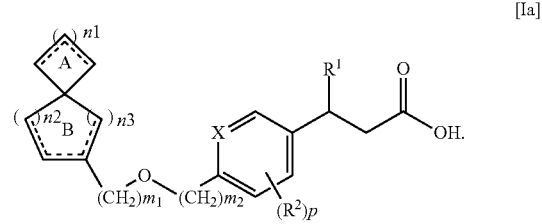

44 Claims, No Drawings

OTHER PUBLICATIONS

Song, F. et al., "Synthesis and biological evaluation of 3-aryl-3-(4-phenoxy)-propionic acid as a novel series of G protein-coupled receptor 40 agonists", J. Med. Chem. vol. 50:2807-2817 (2007).

Steneberg, P. et al. "The FFA receptor GPR40 links hyperinsulinemia, hepatic steatosis, and impaired glucose homeostatsis in mouse" Cell Metabolism, vol. 1:245-258 (2005).

Press Release, "TAK-875 enters into phase III clinical trials for the treatment of type 2 diabetes in Japan", Takeda Pharmaceutical Company Limited, Sep. 12, 2011, www.takeda.com/press/article_42854.html.

Press Release, "Late breaking data presented at the American Diabetes Associates 71$^{st}$ Annual Scientific Sessions evaluate the safety and tolerability of TAK-875, Takeda's investigational compound for the treatment of type 2 diabetes TAK-875 is the first GPR40 agonist to reach clinical development", Takeda Pharmaceutical Company Limited, Jun. 29, 2011, www.takeda.com/press/article_42237.html.

* cited by examiner

SPIRO COMPOUNDS AND PHARMACEUTICAL USE THEREOF

TECHNICAL FIELD

The present invention relates to spiro compounds having GPR40 agonist activity, a pharmaceutically acceptable salt thereof or a solvate thereof, a pharmaceutical composition containing the same and a pharmaceutical use thereof.

BACKGROUND ART

Diabetes mellitus (DM) is a disease characterized by sugar and lipid metabolic disorder, and there is a risk that it may lead to various pathognomonic complexities resulting from an abnormally high blood sugar level (blood glucose level). The number of patients with diabetes mellitus in the world is estimated to exceed 180 million as of 2006.

The onset of diabetes mellitus has been reported to relate to environmental factors such as overeating, obesity, lack of exercise in addition to genetic factors. Diabetes mellitus is mainly classified into type 1 diabetes mellitus (insulin-dependent diabetes mellitus (IDDM)) and type 2 diabetes mellitus (non-insulin-dependent diabetes mellitus (NIDDM)). Most of the patients (about 90%) suffer from type 2 diabetes mellitus.

Type 1 diabetes mellitus is characterized by loss of insulin-secreting β cells of the islets of Langerhans in the pancreas and type 2 diabetes mellitus is caused by two factors which are deficient insulin secretion due to reduced glucose sensitivity of pancreatic β cells and reduced insulin sensitivity of peripheral tissues such as muscle, adipose and liver.

Currently, exercise therapy and diet therapy are used in the treatment and prevention of diabetes mellitus, and medication therapy is used as well.

A typical medication therapy in current use includes insulin therapy and oral hypoglycemic agents. The oral hypoglycemic agents (OHAs) include sulfonylureas (SUs), biguanides, α-glucosidase inhibitors (α GIs) and thiazolidine derivatives (TZDs).

However, these medicines have side effects such as hypoglycemia, liver damage and gastrointestinal disease, and therefore an effective method for using these medicines has been studied and developed. In addition, the research on a novel mechanism-based treatment and prevention method has been underway actively.

Recent studies of G protein-coupled receptors (GPCRs) have led to the discovery of GPR40 (G protein-coupled receptor 40), also known as free fatty acid receptor 1 (FFR1), which is a protein having seven transmembrane domains and whose ligand is a free fatty acid, in particular a mid- and long-chain fatty acid. GPR40 is known to highly express in the pancreas of rodents, in particular in pancreatic β cells. Meanwhile, GPR40 is shown to express in the brain as well as pancreatic β cells of human.

With regard to the function of GPR40, it is known that a free fatty acid, a ligand for GPR40, acts on GPR40 in pancreatic βcells, and thereby β cells secrete insulin depending on glucose level. In addition, analysis of GPR40 knockout mice reveals that GPR40 may be involved in pathology of obesity and diabetes mellitus.

As a GPR40-related disease, diabetes mellitus, hyperglycemia, impaired glucose tolerance, insulin resistance, impaired fasting glucose, diabetic neuropathy, diabetic nephropathy, diabetic retinopathy, ketoacidosis, hyperlipidemia, hypercholesterolemia, hypertriglyceridemia, dyslipemia, hyperlipoproteinemia, metabolic syndrome, obesity, atherosclerosis, etc. are known. For these reasons, attention has been drawn to GPR40 as a novel target of diabetes mellitus.

DISCLOSURE OF THE INVENTION

Problem to be Solved by the Invention

The object of the present invention is to provide a medicament for modulating the function of GPR40, in particular, a medicament as GPR40 agonist for treating or preventing diabetes mellitus, hyperglycemia, impaired glucose tolerance, impaired fasting glucose and the like.

Means for Solving the Problem

The present inventors have intensively carried out investigations to develop a medicament as GPR40 agonist for treating or preventing diabetes mellitus, hyperglycemia, impaired glucose tolerance, impaired fasting glucose and the like, and found a spiro compound having GPR40 agonist activity. Based on the findings, the present inventors have carried out further investigations and completed the present invention.

Namely, the present invention relates to the followings.

1) A spiro compound of the following general formula [Ia]:

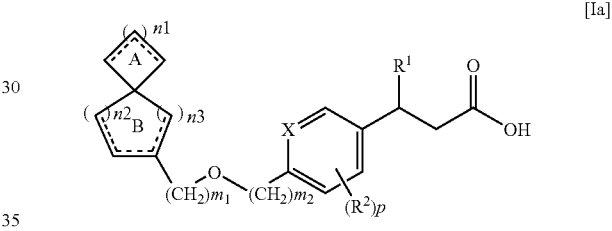

[Ia]

(wherein $R^1$ is
(1) a hydrogen atom,
(2) a $C_1$-$C_6$ alkyl group,
(3) a $C_2$-$C_6$ alkenyl group,
(4) a $C_2$-$C_6$ alkynyl group,
(5) a $C_1$-$C_6$ alkoxy group,
(6) a hydroxy $C_1$-$C_6$ alkyl group,
(7) a $C_1$-$C_6$ alkoxy($C_1$-$C_6$)alkyl group,
(8) —$CONR^{11}R^{12}$ in which $R^{11}$ and $R^{12}$ are the same or different and each represents a hydrogen atom or a $C_1$-$C_6$ alkyl group,
(9) a phenyl group or
(10) a five-membered heteroaryl group which has at least one heteroatom selected from the group consisting of a nitrogen atom, an oxygen atom and a sulfur atom, and which may be substituted by a $C_1$-$C_6$ alkyl group;
$R^2$ is
(1) a halogen atom,
(2) a $C_1$-$C_6$ alkyl group,
(3) a hydroxy group or
(4) a $C_1$-$C_6$ alkoxy group;
p is 0, 1, 2 or 3;
X is a carbon atom or a nitrogen atom;
m1 is 0, 1 or 2;
m2 is 0 or 1;
a spiro-ring AB may be substituted by 1 to 5 same or different substituent(s) selected from the group consisting of
(1) a hydroxy group,
(2) a $C_1$-$C_6$ alkyl group,
(3) a $C_1$-$C_6$ alkoxy group and
(4) an oxo group;

n1 is 0, 1, 2, 3 or 4;
n2 is 1, 2, 3 or 4;
n3 is 0, 1 or 2 with the proviso that n2+n3 is 2, 3 or 4; and a bond represented by the symbol: 
means a single bond or a double bond with proviso that three contiguous carbon atoms do not constitute an allene bond represented by the formula:

$$C=C=C),$$

a pharmaceutically acceptable salt thereof or a solvate thereof.

2) The spiro compound, the pharmaceutically acceptable salt thereof or the solvate thereof according to the above 1), wherein the spiro-ring AB is represented by the formula:

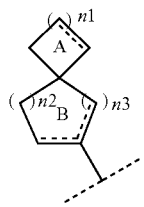

(wherein each symbol is as defined above).

3) The spiro compound, the pharmaceutically acceptable salt thereof or the solvate thereof according to the above 1) or 2, wherein the number of the double bond in ring A of the spiro-ring AB is 0 or 1.

4) The spiro compound, the pharmaceutically acceptable salt thereof or the solvate thereof according to any one of the above 1) to 3), wherein the number of the double bond in ring B of the spiro-ring AB is 0 or 1.

5) The spiro compound, the pharmaceutically acceptable salt thereof or the solvate thereof according to any one of the above 1) to 4), wherein n3 is 1 or 2.

6) The spiro compound, the pharmaceutically acceptable salt thereof or the solvate thereof according to any one of the above 1) to 5), wherein the spiro-ring AB may be substituted by 1 to 3 same or different substituent(s).

7) The spiro compound, the pharmaceutically acceptable salt thereof or the solvate thereof according to any one of the above 1) to 6),
wherein $R^1$ is
(1) a hydrogen atom,
(2) a $C_1$-$C_6$ alkyl group,
(3) a $C_2$-$C_6$ alkenyl group,
(4) a $C_2$-$C_6$ alkynyl group,
(5) a $C_1$-$C_6$ alkoxy group,
(6) a $C_1$-$C_6$ alkoxy($C_1$-$C_6$)alkyl group,
(7) —$CONR^{11}R^{12}$ in which $R^{11}$ and $R^{12}$ are the same or different and each represents a hydrogen atom or a $C_1$-$C_6$ alkyl group, or
(8) a five-membered heteroaryl group which has at least one heteroatom selected from the group consisting of a nitrogen atom, an oxygen atom and a sulfur atom, and which may be substituted by a $C_1$-$C_6$ alkyl group.

8) The spiro compound, the pharmaceutically acceptable salt thereof or the solvate thereof according to any one of the above 1) to 7),
wherein $R^1$ is
(1) a hydrogen atom,
(2) a $C_2$-$C_6$ alkenyl group,
(3) a $C_2$-$C_6$ alkynyl group,
(4) a $C_1$-$C_6$ alkoxy group or
(5) a five-membered heteroaryl group which has at least one heteroatom selected from the group consisting of a nitrogen atom, an oxygen atom and a sulfur atom, and which may be substituted by a $C_1$-$C_6$ alkyl group.

9) The spiro compound, the pharmaceutically acceptable salt thereof or the solvate thereof according to any one of the above 1) to 8), wherein p is 0 or 1.

10) The spiro compound, the pharmaceutically acceptable salt thereof or the solvate thereof according to any one of the above 1) to 9),
wherein $R^2$ is
(1) a $C_1$-$C_6$ alkyl group,
(2) a hydroxy group or
(3) a $C_1$-$C_6$ alkoxy group.

11) The spiro compound, the pharmaceutically acceptable salt thereof or the solvate thereof according to any one of the above 1) to 10), wherein m1 is 0 or 1.

12) A pharmaceutical composition, which comprises the spiro compound, the pharmaceutically acceptable salt thereof or the solvate thereof according to any one of the above 1) to 11), and a pharmaceutically acceptable carrier.

13) A GPR40 agonist medicament, which comprises the spiro compound, the pharmaceutically acceptable salt thereof or the solvate thereof according to any one of the above 1) to 11), as an effective ingredient.

14) An insulin secretion-promoting agent or a hypoglycemic agent, which comprises the spiro compound, the pharmaceutically acceptable salt thereof or the solvate thereof according to any one of the above 1) to 11), as an effective ingredient.

15) A pharmaceutical composition for treating or preventing a disease selected from the group-consisting of diabetes mellitus, hyperglycemia, impaired glucose tolerance and impaired fasting glucose, which comprises the spiro compound, the pharmaceutically acceptable salt thereof or the solvate thereof according to any one of the above 1) to 11), as an effective ingredient.

16) A use of the spiro compound, the pharmaceutically acceptable salt thereof or the solvate thereof according to any one of the above 1) to 11), for the production of a GPR40 agonist medicament.

17) A use of the spiro compound, the pharmaceutically acceptable salt thereof or the solvate thereof according to any one of the above 1) to 11), for the production of an insulin secretion-promoting agent or a hypoglycemic agent.

18) A use of the spiro compound, the pharmaceutically acceptable salt thereof or the solvate thereof according to any one of the above 1) to 11), for the production of a pharmaceutical composition for treating or preventing a disease selected from the group consisting of diabetes mellitus, hyperglycemia, impaired glucose tolerance and impaired fasting glucose.

19) A method for activating GPR40, which comprises administration of the spiro compound, the pharmaceutically acceptable salt thereof or the solvate thereof according to any one of the above 1) to 11) to a mammal in a pharmaceutically effective amount.

20) A method for promoting insulin secretion or lowering blood glucose level, which comprises administration of the spiro compound, the pharmaceutically acceptable salt thereof or the solvate thereof according to any one of the above 1) to 11) to a mammal in a pharmaceutically effective amount.

21) A method for treating or preventing a disease selected from the group consisting of diabetes mellitus, hyperglycemia, impaired glucose tolerance and impaired fasting glucose, which comprises administration of the spiro compound, the pharmaceutically acceptable salt thereof or the solvate thereof according to any one of the above 1) to 11) to a mammal in a pharmaceutically effective amount.

22) A spiro compound of the following general formula [I]:

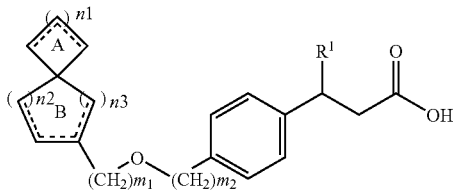

[I]

(wherein $R^1$ is
(1) a hydrogen atom,
(2) a $C_1$-$C_4$ alkyl group,
(3) a $C_2$-$C_4$ alkenyl group,
(4) a $C_2$-$C_4$ alkynyl group,
(5) a $C_1$-$C_4$ alkoxy group,
(6) a hydroxy $C_1$-$C_4$ alkyl group,
(7) a $C_1$-$C_4$ alkoxy($C_1$-$C_4$)alkyl group,
(8) —$CONR^{11}R^{12}$ in which $R^{11}$ and $R^{12}$ are the same or different and each represents a hydrogen atom or a $C_1$-$C_4$ alkyl group,
(9) a phenyl group or
(10) a five-membered heteroaryl group which has at least one heteroatom selected from a nitrogen atom, an oxygen atom and a sulfur atom, and which may be substituted by a $C_1$-$C_4$ alkyl group;
m1 is 0, 1 or 2;
m2 is 0 or 1;
a spiro-ring AB may be substituted by 1 to 5 same or different substituent(s) selected from
(1) a hydroxy group and
(2) a $C_1$-$C_4$ alkyl group;
n1 is 2, 3 or 4;
n2 is 1, 2 or 3;
n3 is 0, 1 or 2 with the proviso that n2+n3 is 2 or 3; and a bond represented by the symbol: 
means a single bond or a double bond with proviso that three contiguous carbon atoms do not constitute an allene bond represented by the formula:

C═C═C), a pharmaceutically acceptable salt thereof or a solvate thereof.

23) The spiro compound, the pharmaceutically acceptable salt thereof or the solvate thereof according to the above 22), wherein the spiro-ring AB is represented by the formula:

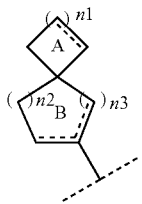

(wherein each symbol is as defined above).

24) The spiro compound, the pharmaceutically acceptable salt thereof or the solvate thereof according to the above 22), wherein the number of the same or different substituent(s) of the spiro-ring AB is 1, 2 or 3.

25) The spiro compound, the pharmaceutically acceptable salt thereof or the solvate thereof according to the above 22), wherein $R^1$ is
(1) a hydrogen atom,
(2) a $C_1$-$C_4$ alkyl group,
(3) a $C_2$-$C_4$ alkenyl group,
(4) a $C_2$-$C_4$ alkynyl group,
(5) a $C_1$-$C_4$ alkoxy group,
(6) a $C_1$-$C_4$ alkoxy($C_1$-$C_4$)alkyl group,
(7) —$CONR^{11}R^{12}$ in which $R^{11}$ and $R^{12}$ are the same or different and each represents a hydrogen atom or a $C_1$-$C_4$ alkyl group, or
(8) a five-membered heteroaryl group which has at least one heteroatom selected from a nitrogen atom, an oxygen atom and a sulfur atom, and which may be substituted by a $C_1$-$C_4$ alkyl group.

26) The spiro compound, the pharmaceutically acceptable salt thereof or the solvate thereof according to the above 23), wherein $R^1$ is
(1) a hydrogen atom,
(2) a $C_2$-$C_4$ alkenyl group,
(3) a $C_2$-$C_4$ alkynyl group,
(4) a $C_1$-$C_4$ alkoxy group or
(5) a five-membered heteroaryl group which has at least one heteroatom selected from a nitrogen atom, an oxygen atom and a sulfur atom, and which may be substituted by a $C_1$-$C_4$ alkyl group.

27) The spiro compound, the pharmaceutically acceptable salt thereof or the solvate thereof according to the above 22), wherein m1 is 0 or 1.

28) The spiro compound, the pharmaceutically acceptable salt thereof or the solvate thereof according to the above 22), wherein m2 is 0.

29) The spiro compound, the pharmaceutically acceptable salt thereof or the solvate thereof according to the above 22), wherein n1 is 2 or 3.

30) The spiro compound, the pharmaceutically acceptable salt thereof or the solvate thereof according to the above 22), wherein n2 is 1 or 2.

31) The spiro compound, the pharmaceutically acceptable salt thereof or the solvate thereof according to the above 22), wherein n3 is 1 or 2.

32) A pharmaceutical composition, which comprises the spiro compound, the pharmaceutically acceptable salt thereof or the solvate thereof according to any one of the above 22) to 31), and a pharmaceutically acceptable carrier.

33) A GPR40 agonist medicament, which comprises the spiro compound, the pharmaceutically acceptable salt thereof or the solvate thereof according to any one of the above 22) to 31), as an effective ingredient.

34) An insulin secretion-promoting agent or a hypoglycemic agent, which comprises the spiro compound, the pharmaceutically acceptable salt thereof or the solvate thereof according to any one of the above 22) to 31), as an effective ingredient.

35) A pharmaceutical composition for treating or preventing a disease selected from the group consisting of diabetes mellitus, hyperglycemia, impaired glucose tolerance and impaired fasting glucose, which comprises the spiro compound, the pharmaceutically acceptable salt thereof or the solvate thereof according to any one of the above 22) to 31), as an effective ingredient.

36) A use of the spiro compound, the pharmaceutically acceptable salt thereof or the solvate thereof according to any one of the above 22) to 31), for the production of a GPR40 agonist medicament.

37) A use of the spiro compound, the pharmaceutically acceptable salt thereof or the solvate thereof according to any one of the above 22) to 31), for the production of an insulin secretion-promoting agent or a hypoglycemic agent.

38) A use of the spiro compound, the pharmaceutically acceptable salt thereof or the solvate thereof according to any one of the above 22) to 31), for the production of a pharmaceutical composition for treating or preventing a disease selected from the group consisting of diabetes mellitus, hyperglycemia, impaired glucose tolerance and impaired fasting glucose.

Effect of the Invention

The spiro compound, the pharmaceutically acceptable salt thereof and the solvate thereof according to the present invention are useful as a medicament for modulating the function of GPR40, in particular, an insulin secretion-promoting agent or a hypoglycemic agent to serve as GPR40 agonist. The spiro compound, the pharmaceutically acceptable salt thereof and the solvate thereof are also useful as a medicament for treating or preventing diabetes mellitus, hyperglycemia, impaired glucose tolerance, impaired fasting glucose and the like.

BEST MODE FOR CARRYING OUT THE INVENTION

The substituents as used herein are defined as follows.

"$C_1$-$C_6$ alkyl" refers to a linear or branched alkyl group having 1 to 6 carbon atoms and includes, for example, methyl, ethyl, n-propyl, isopropyl, n-butyl, isobutyl, sec-butyl, tert-butyl, n-pentyl, isopentyl, neopentyl, tert-pentyl and hexyl. Preferred is a linear or branched alkyl group having 1 to 4 carbon atoms. More preferred is ethyl, n-propyl, isopropyl, n-butyl, isobutyl or sec-butyl.

"$C_2$-$C_6$ alkenyl" refers to a linear or branched alkenyl group having 2 to 6 carbon atoms, and includes, for example, vinyl, 1-propenyl, 2-propenyl, isopropenyl, 1-butenyl, 2-butenyl, 3-butenyl, 2-methyl-2-propenyl, n-pentenyl, isopentenyl, neopentenyl, 1-methylpropenyl, n-hexenyl, isohexenyl, 1,1-dimethylbutenyl, 2,2-dimethylbutenyl, 3,3-dimethylbutenyl, 3,3-dimethylpropenyl and 2-ethylbutenyl. Preferred is a linear or branched alkenyl group having 2 to 4 carbon atoms. More preferred is vinyl, 1-propenyl, 2-propenyl or isopropenyl.

"$C_2$-$C_6$ alkynyl" refers to a linear or branched alkynyl group having 2 to 6 carbon atoms, and includes, for example, ethynyl, prop-2-yn-1-yl(propargyl), prop-1-yn-1-yl, 1-butyn-1-yl, 1-butyn-3-yl, 1-butyn-4-yl, 2-butyn-1-yl, pentynyl and hexynyl. Preferred is a linear or branched alkynyl group having 2 to 4 carbon atoms. More preferred is ethynyl, prop-2-yn-1-yl (propargyl) or prop-1-yn-1-yl.

"$C_1$-$C_6$ alkoxy" is a substituent represented by the formula: —O—($C_1$-$C_6$ alkyl), and includes, for example, methoxy, ethoxy, n-propoxy, isopropyloxy, n-butoxy, isobutyloxy, sec-butyloxy, tert-butyloxy(tert-butoxy), pentyloxy, tert-pentyloxy and hexyloxy. Preferred is a $C_1$-$C_4$ alkoxy group, an alkoxy group represented by the formula: —O—($C_1$-$C_4$ alkyl). More preferred is methoxy, ethoxy, n-propoxy or isopropyloxy.

"$C_2$-$C_6$ alkylene" refers to a linear alkylene group having 2 to 6 carbon atoms and it may be substituted by a $C_1$-$C_6$ alkyl, $C_1$-$C_6$ alkoxy, hydroxy or oxo group. Its examples include —(CH$_2$)$_2$—, —(CH$_2$)$_3$—, —(CH$_2$)$_4$—, —(CH$_2$)$_5$— and —(CH$_2$)$_6$—.

"Hydroxy $C_1$-$C_6$ alkyl" refers to the above-defined "$C_1$-$C_6$ alkyl" group mono- or di-substituted by a hydroxy group, preferably mono-substituted by a hydroxy group, and includes, for example, hydroxymethyl, 2-hydroxyethyl, 1-hydroxy-1-methylethyl, 1,2-dihydroxyethyl, 3-hydroxypropyl, 4-hydroxybutyl, 5-hydroxypentyl and 6-hydroxyhexyl. Preferred is hydroxy $C_1$-$C_4$ alkyl. More preferred is hydroxylmethyl.

"$C_1$-$C_6$ alkoxy($C_1$-$C_6$)alkyl" refers to the above-defined "$C_1$-$C_6$ alkyl" group mono- or di-substituted by the above-defined "$C_1$-$C_6$ alkoxy" group, and includes, for example, methoxymethyl, ethoxymethyl, n-propoxymethyl, t-butoxymethyl, 2-methoxyethyl, 1-methoxy-1-methylethyl, 1,2-dimethoxyethyl, 3-methoxypropyl, 3-ethoxypropyl, 2,3-diethoxypropyl, 4-methoxybutyl, 5-methoxypentyl, 5-ethoxypentyl, 6-methoxyhexyl, 6-ethoxyhexyl, pentyloxymethyl and hexyloxymethyl. Preferred is $C_1$-$C_4$ alkoxy ($C_1$-$C_4$)alkyl. More preferred is mono-($C_1$-$C_4$ alkoxy)-substituted ($C_1$-$C_4$)alkyl such as methoxymethyl, ethoxymethyl, n-propoxymethyl, t-butoxymethyl, 2-methoxyethyl, 1-methoxy-1-methylethyl, 3-methoxypropyl, 3-ethoxypropyl and 4-methoxybutyl. Even more preferred is methoxymethyl.

The group represented by the formula: —CONR$^{11}$R$^{12}$ includes, for example, carbamoyl, methylaminocarbonyl, dimethylaminocarbonyl, ethylaminocarbonyl, diethylaminocarbonyl, methyl(ethyl)aminocarbonyl, n-propylaminocarbonyl, methyl(n-propyl)aminocarbonyl, n-butylaminocarbonyl, di-n-butylaminocarbonyl, n-pentylaminocarbonyl, di-n-pentylaminocarbonyl, methyl(n-pentyl)aminocarbonyl, hexylaminocarbonyl, di-hexylaminocarbonyl and methyl(hexyl)aminocarbonyl. Preferred is methylaminocarbonyl or dimethylaminocarbonyl.

"A five-membered heteroaryl group having at least one heteroatom selected from a nitrogen atom, an oxygen atom and a sulfur atom", which is also called a five-membered heteroaryl group having at least one heteroatom selected from the group consisting of a nitrogen atom, an oxygen atom and a sulfur atom, is preferably a five-membered heteroaryl group having at least one nitrogen atom. More preferred is a five-membered heteroaryl group having 1 to 4 nitrogen atoms and, one oxygen atom or/and one sulfur atom. Examples of the five-membered heteroaryl group include pyrolyl, imidazolyl, triazolyl, tetrazolyl, furyl, thienyl, thiazolyl, isothiazolyl, oxazolyl, oxadiazolyl, isoxazolyl, 1,2,4-thiadiazolyl, 1,2,5-thiadiazolyl and 1,3,4-thiadiazolyl. Preferred is tetrazolyl, oxazolyl or thiazolyl and more preferred is tetrazolyl or oxazolyl. Especially preferred is tetrazolyl.

A substituent for the five-membered heteroaryl group is preferably a $C_1$-$C_6$ alkyl group, more preferably a $C_1$-$C_4$ alkyl group. Even more preferred is methyl, ethyl, n-propyl or isopropyl. Especially preferred is methyl.

"A halogen atom" refers to a fluorine atom, a chlorine atom, a bromine atom or an iodine atom, and is preferably a fluorine atom or a chlorine atom.

"A leaving group" refers to a chlorine atom, a bromine atom, an iodine atom, a methanesulfonyloxy group, a para-toluenesulfonyloxy group, a benzenesulfonyloxy group, an acetyl group or a trifluoromethanesulfonyloxy group, and is preferably a bromine atom or an iodine atom.

In the following explanation of the preparation method, a leaving group of Lv$_1$ is preferably a chlorine atom, a bromine atom, a methanesulfonyloxy group, a para-toluenesulfonyloxy group, a benzenesulfonyloxy group or a trifluoromethanesulfonyloxy group, more preferably a chlorine atom, a bromine atom or a methanesulfonyloxy group.

A leaving group of Lv$_2$ is preferably a chlorine atom, a bromine atom, a methanesulfonyloxy group, a para-toluenesulfonyloxy group, a benzenesulfonyloxy group, an acetyl group or a trifluoromethanesulfonyloxy group, more preferably a methanesulfonyloxy group, a trifluoromethanesulfonyloxy group or an acetyl group.

Preferably, $L_1$ and $L_2$ are each independently a chlorine atom, a bromine atom, a methanesulfonyloxy group, a para-toluenesulfonyloxy group, a benzenesulfonyloxy group, a dimethylsulfonium group or a trifluoromethanesulfonyloxy group. More preferably, $L_1$ and $L_2$ are each independently a bromine atom or a methanesulfonyloxy group.

"A hydroxy protecting group" as used herein refers to an ether-based or acetyl-based hydroxy protecting group. The ether-based hydroxy protecting group refers to, for example, a tetrahydropyranyl group, a benzyl group, a paramethoxy benzyl group, a tert-butyldiphenylsilyl group, a tert-butyldimethylsilyl group or a trimethylsilyl group, and is preferably a tetrahydropyranyl group, a paramethoxy benzyl group, a tert-butyldiphenylsilyl group or a tert-butyldimethylsilyl group. The acetyl-based hydroxy protecting group is an acetyl group, a benzoyl group or a para-nitrobenzoyl group, preferably an acetyl group.

"Spiro-ring AB" represented by the following partial structural formula:

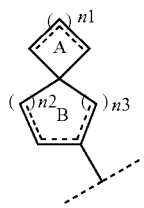

(wherein each symbol is as defined above)
refers to a monospiro hydrocarbon with two monocyclic rings, in which a carbon atom a of ring A represented by the following partial structural formula:

is a spiro carbon atom identical with a carbon atom β of ring B represented by the following partial structural formula:

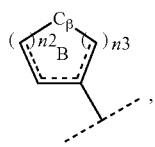

and both rings are spiro-condensed (spiro-bonded) at the spiro carbon atom. The following symbol bound to the ring B

refers to the following partial structural formula:

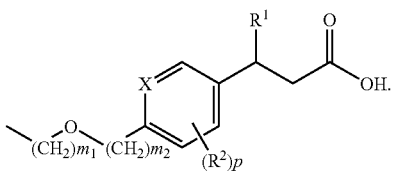

"Ring A of the spiro-ring AB" refers to a ring A part of the above-mentioned spiro-ring AB, which is a 3- to 7-membered saturated or unsaturated hydrocarbon ring optionally having 1 to 3 double bonds, preferably one double bond in the ring.
n1 is 0, 1, 2, 3 or 4, preferably 2 or 3.
Examples of "the ring A of the spiro-ring AB" are as follows:

ringA3a

ringA3b

ringA4a

ringA4b

ringA5a

ringA5b

ringA5c

ringA5d

ringA6a

ringA6b

-continued ringA6c 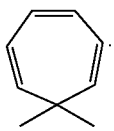

ringA6d 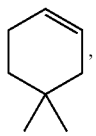

ringA6e 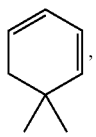

ringA7a 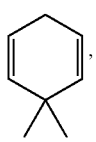

ringA7b 

ringA7c 

ringA7d 

ringA7e 

ringA7f 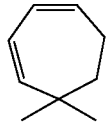

ringA7g 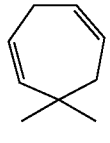

ringA7h 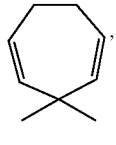, or ringA7i 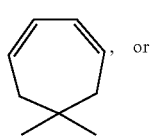

Preferred is ring A3a, ring A4a, ring A5a, ring A5b, ring A5c, ring A5d, ring A6a, ring A6b, ring A6c, ring A6d, ring A6e, ring A7a, ring A7b, ring A7c, ring A7d, ring A7e, ring A7f, ring A7g, ring A7h or ring A7I. More preferred is ring A3a, ring A4a, ring A5a, ring A5b, ring A5c, ring A5d, ring A6a, ring A6b, ring A6c, ring A6d, ring A6e, ring A7a, ring A7b, ring A7c or ring A7d. Even more preferred is ring A3a, ring A4a, ring A5a, ring A6a, ring A6b or ring A7a.

In another embodiment of the present invention, preferred is ring A5a, ring A5b, ring A5c, ring A5d, ring A6a, ring A6b, ring A6c, ring A6d, ring A6e, ring A7a, ring A7b, ring A7c, ring A7d, ring A7e, ring A7f, ring A7g, ring A7h or ring A7I. More preferred is ring A5a, ring A5b, ring A5c, ring A6a, ring A6b, ring A6c, ring A7a, ring A7b, ring A7c or ring A7d. Even more preferred is ring A5a, ring A6a, ring A6b or ring A7a.

"Ring B of the spiro-ring AB" refers to a ring B part of the above-mentioned spiro-ring AB, which is a 5-, 6- or 7-membered saturated or unsaturated hydrocarbon ring optionally having 1 or 2 double bonds, preferably one double bond in the ring.

n2 is 1, 2, 3 or 4; n3 is 0, 1 or 2; and n2+n3 is 2, 3 or 4. Preferably, n2 is 1, 2 or 3; n3 is 0, 1, or 2; and n2+n3 is 2 or 3. More preferably, n2 is 1 or 2; n3 is 1 or 2; and n2+n3 is 3.

Examples of "the ring B of the spiro-ring AB" are as follows:

ringB5a 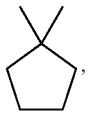

ringB5b 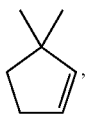

ringB5c 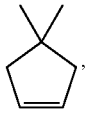

ringB5d 

ringB6a 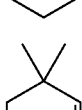

ringB6b 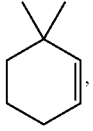

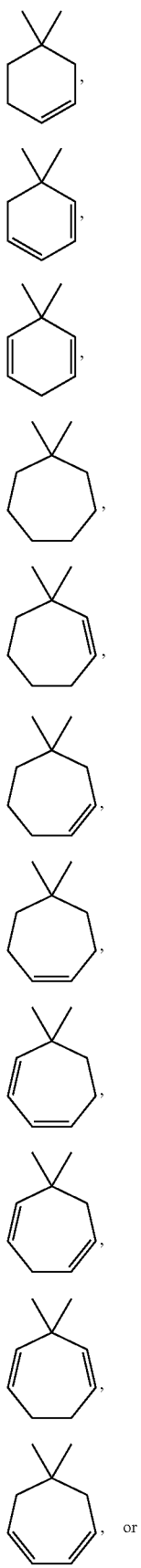

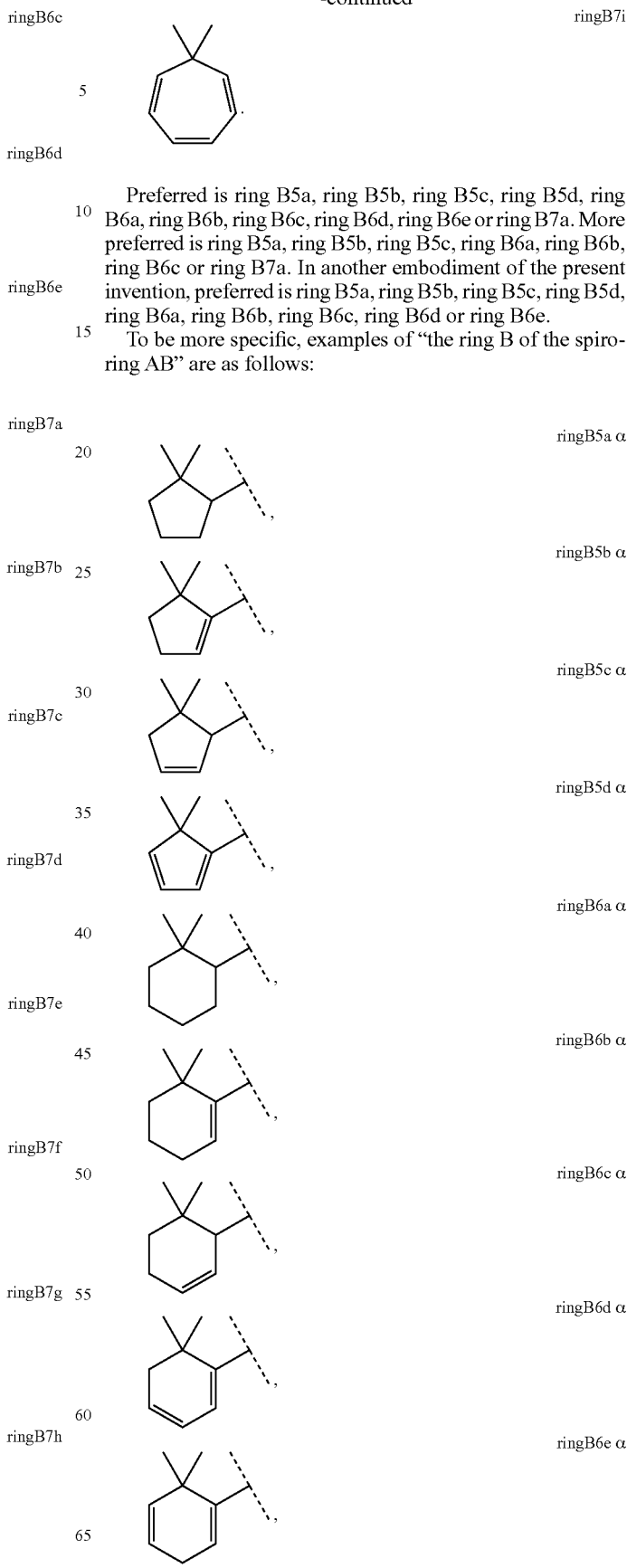

Preferred is ring B5a, ring B5b, ring B5c, ring B5d, ring B6a, ring B6b, ring B6c, ring B6d, ring B6e or ring B7a. More preferred is ring B5a, ring B5b, ring B5c, ring B6a, ring B6b, ring B6c or ring B7a. In another embodiment of the present invention, preferred is ring B5a, ring B5b, ring B5c, ring B5d, ring B6a, ring B6b, ring B6c, ring B6d or ring B6e.

To be more specific, examples of "the ring B of the spiro-ring AB" are as follows:

-continued
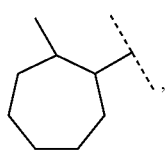
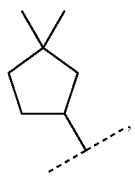
ringB5a β
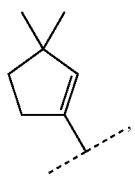
ringB5b β
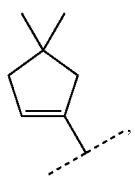
ringB5c β
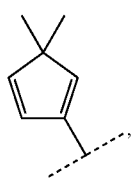
ringB5d β
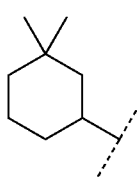
ringB6a β
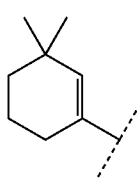
ringB6b β
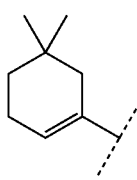
ringB6c β
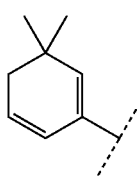
ringB6d β
-continued
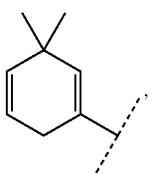
ringB7a α
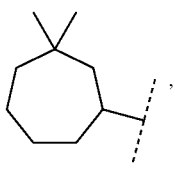
ringB7a β
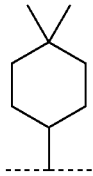
ringB6a γ
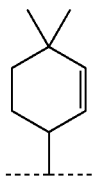
ringB6b γ
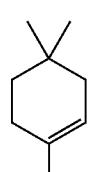
ringB6c γ
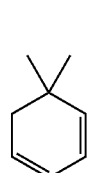
ringB6d γ
ringB6e γ
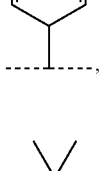
, or
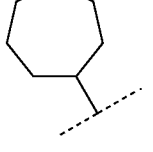
ringB7a γ
ringB6e β
ringB7a β
ringB6a γ
ringB6b γ
ringB6c γ
ringB6d γ
ringB6e γ
ringB7a γ

Preferred is as follows:
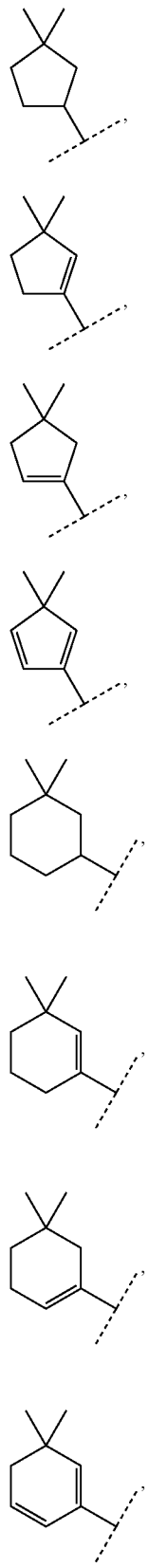
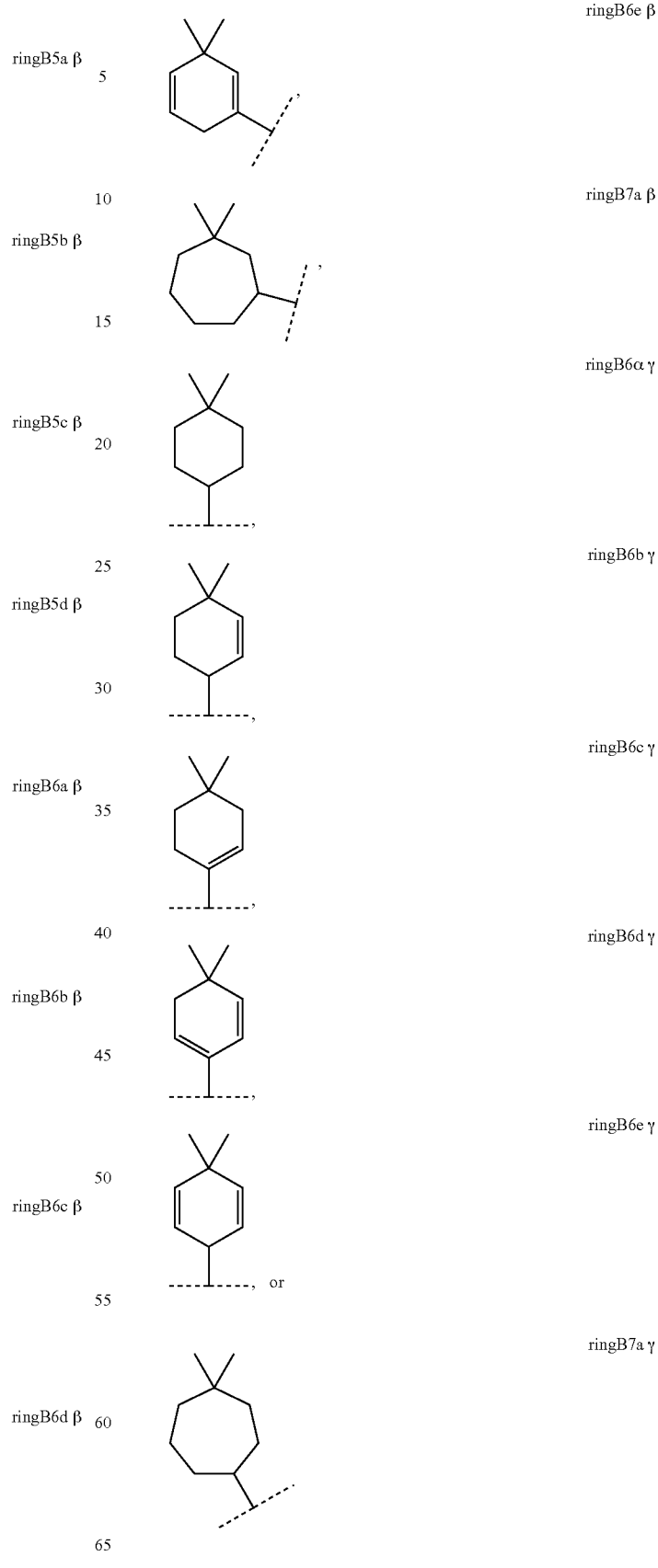

The spiro-ring AB is preferably as follows:
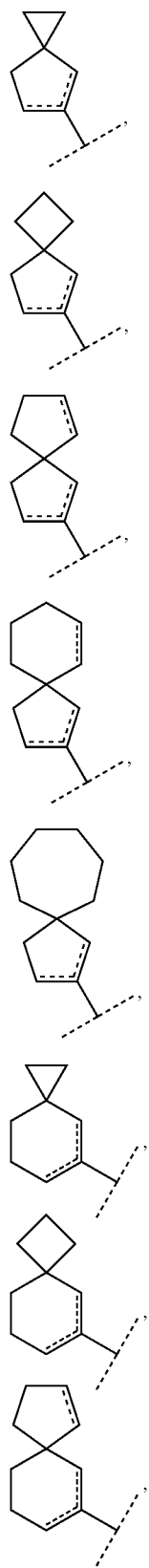
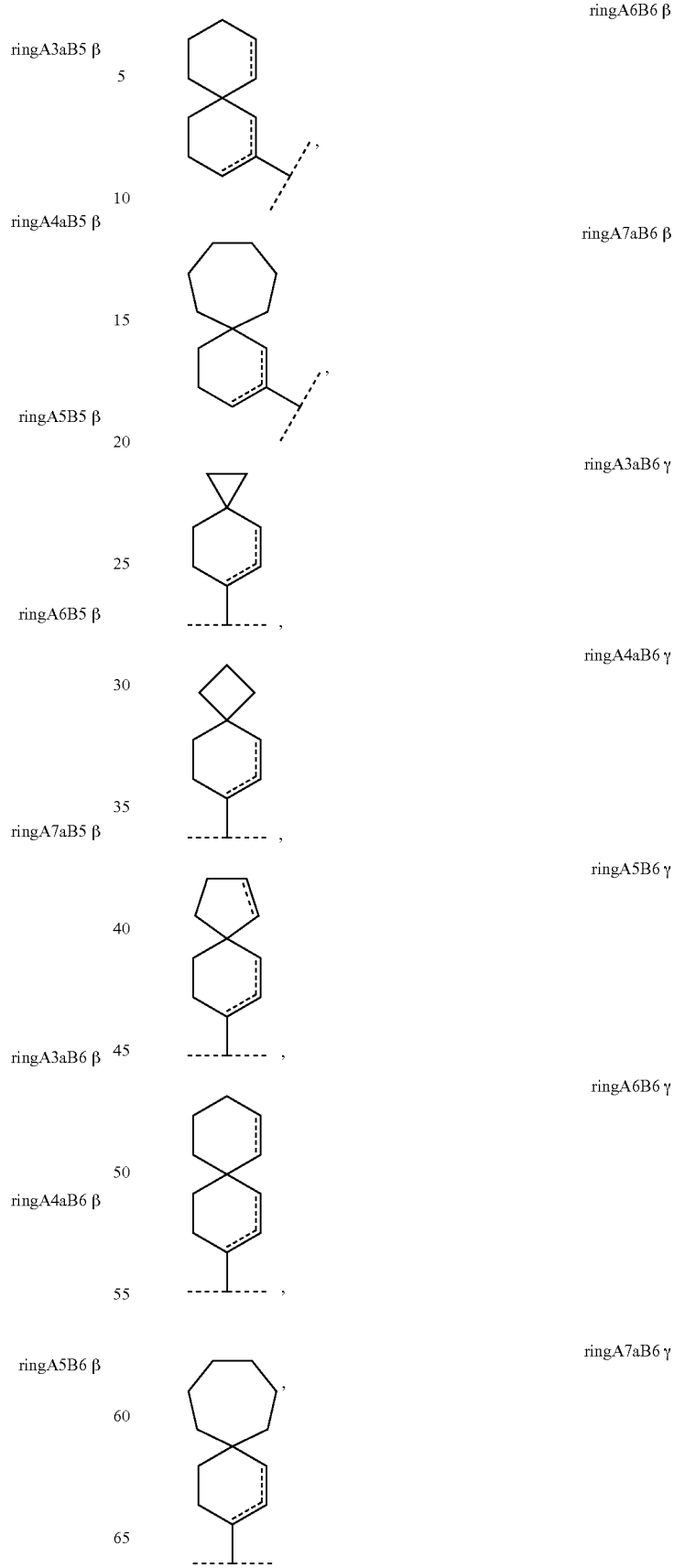

ringA3aB7 β

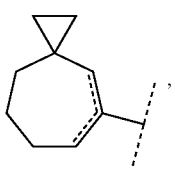

ringA4aB7 β

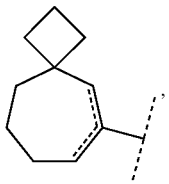

ringA5B7 β

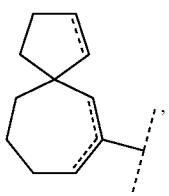

ringA6B7 β

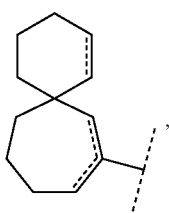

ringA7aB7 β

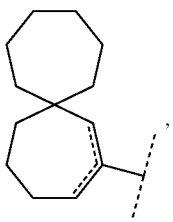

ringA3aB7 γ

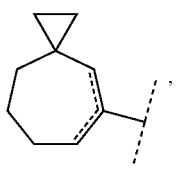

ringA4aB7 γ

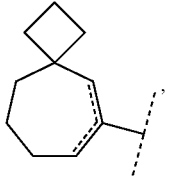

ringA5B7 γ

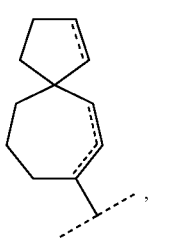

ringA6B7 γ

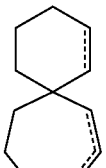, or ringA7aB7 γ

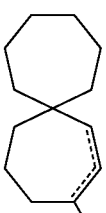

(wherein the symbol represented by the following: -----
means a single bond or a double bond with the proviso that three contiguous carbon atoms do not constitute an allene bond represented by the formula:

C=C=C.)

More preferably, the spiro-ring AB is represented by the following:

ringA4aB5a β

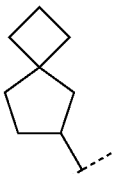

ringA4aB5b β

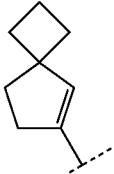

ringA5aB5a β

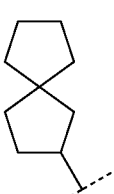

ringA5aB5b β

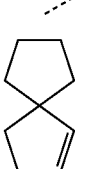

ringA5aB5c β
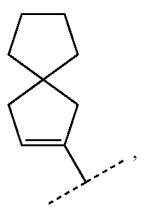
ringA6aB5a β
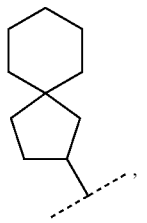
ringA6aB5b β
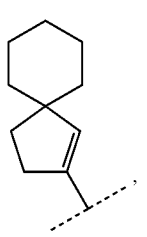
ringA6aB5c β
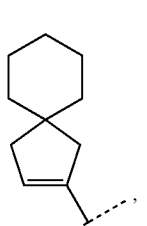
ringA7aB5a β
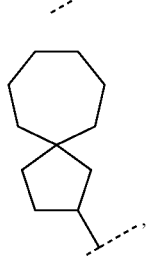
ringA5aB6a β
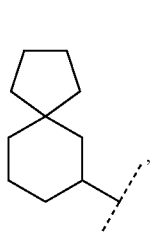
ringA5aB6b β
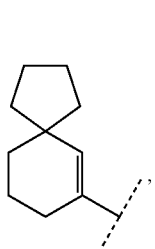
ringA5aB6c β
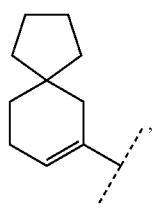
ringA6aB6a β
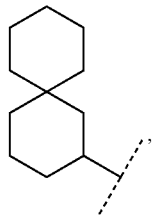
ringA6aB6b β
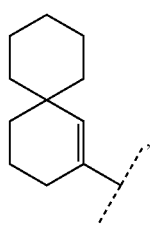
ringA6aB6c β
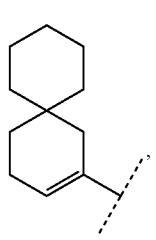
ringA6bB6a β
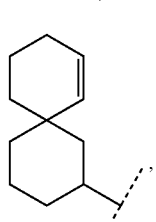
ringA7aB6a β
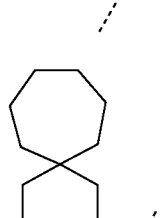
ringA7aB6c β
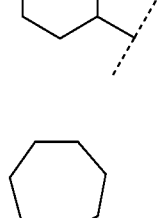

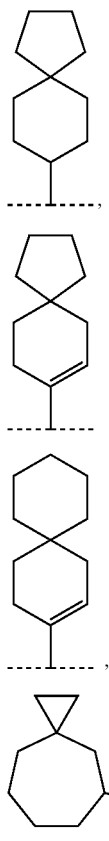

and namely, it is a spiro-ring having no double bonds such as ring A4aB5aβ, ring A5aB5aβ, ring A6aB5aβ, ring A7aB5aβ, ring A5aB6aβ, ring A6aB6aβ, ring A7aB6aβ, ring A5aB6aγ or A3aB7aβ; or a spiro-ring having one double bond such as ring A4aB5bβ, ring A5aB5bβ, ring A5aB5cβ, ring A5aB6bβ, ring A5aB6cβ, ring A6aB6bβ, ring A6aB6cβ, ring A6bB6aβ, ring A7aB6cβ, ring A5aB6cγ or ring A6aB6cγ.

Even more preferred is ring A5aB6aβ, ring A5aB6bβ, ring A5aB6cβ, ring A6aB6aβ, ring A6aB6bβ or ring A6aB6cβ.

As a spiro-ring having no double bonds, ring A5aB6aβ or ring A6aB6aβ is especially preferable.

As a spiro-ring having one double bond, ring A5aB6bβ, ring A5aB6cβ, ring A6aB6bβ or ring A6aB6cβ is especially preferable.

Similarly, in another embodiment, the spiro-ring AB is preferably a combination of ring A5a, ring A5b, ring A5c, ring A6a, ring A6b, ring A6c, ring A7a, ring A7b, ring A7c or ring A7d with ring B5a, ring B5b, ring B5c, ring B6a, ring B6b or ring B6c. The spiro-ring AB is more preferably a combination of ring A5a, ring A6a, ring A6b, ring A7a or ring A7d with ring B5a, ring B5b, ring B5c, ring B6a, ring B6b or ring B6c.

Even more preferably, the spiro-ring AB is a combination of ring A5a with ring B5a, ring B5b, ring B5c, ring B6a, ring B6b or ring B6c; a combination of ring A6a with ring B5a, ring B5b, ring B5c, ring B6a, ring B6b or ring B6c; a combination of ring A6b with ring B6a; a combination of ring A7a with ring B5a, ring B6a or ring B6c; or a combination of ring A7d with ring B5a, ring B6a or ring B6c.

Similarly, in another embodiment, the spiro-ring AB is more preferably a combination of ring B5a with ring A5a, ring A6a, ring A7a or ring A7d; a combination of ring B5b with ring A5a or ring A6a; a combination of ring B5c with ring A5a or ring A6a; a combination of ring B6a with ring A5a, ring A6a, ring A6b, ring A7a or ring A7d; a combination of ring B6b with ring A5a or ring A6a; or a combination of ring B6c with ring A5a, ring A6a, ring A7a or ring A7d.

Further, in another embodiment of the present invention, the spiro-ring AB is preferably a combination of ring A3a, ring A4a, ring A5a, ring A6a, ring A6b, ring A7a or ring A7d with ring B5a, ring B5b, ring B5c, ring B6a, ring B6b, ring B6c, ring B7a or ring B7b. More preferably, the spiro-ring AB is a combination of ring A3a with ring B7a or ring B7b; a combination of ring A4a with ring B5a or ring B5c; a combination of ring A5a with ring B5a, ring B5b, ring B5c, ring B6a, ring B6b or ring B6c; a combination of ring A6a with ring B5a, ring B5b, ring B5c, ring B6a, ring B6b or ring B6c; a combination of ring A6b with ring B6a; a combination of ring A7a with ring B5a, ring B6a or ring B6c; or a combination of ring A7d with ring B5a, ring B6a or ring B6c.

Similarly, in another embodiment, the spiro-ring AB is preferably a combination of ring B5a with ring A5a, ring A6a, ring A7a or ring A7d; a combination of ring B5b with ring A5a or ring A6a; a combination of ring B5c with ring A5a or ring A6a; a combination of ring B6a with ring A5a, ring A6a, ring A6b, ring A7a or ring A7d; a combination of ring B6b with ring A5a or ring A6a; a combination of ring B6c with ring A5a, ring A6a, ring A7a, or ring A7d; a combination of ring B7a with ring A3a; or a combination of ring B7b with ring A3a.

"May be substituted by the same or different substituent (s)" means that a spiro-ring AB is non-substituted or substituted by one or more same or different substituents.

The substituent(s) of "the spiro-ring AB" is/are 1 to 5, preferably 1 to 3, same or different $C_1$-$C_6$ alkyl, hydroxy, oxo or $C_1$-$C_6$ alkoxy groups, more preferably to 3 same or different $C_1$-$C_6$ alkyl or hydroxy groups. The $C_1$-$C_6$ alkyl group is preferably a $C_1$-$C_4$ alkyl group. Further, the substituent (s) of the spiro-ring AB is/are even more preferably 1 to 5 same or different methyl, ethyl, n-propyl, isopropyl or hydroxy groups. Especially preferred are 1 to 3 same or different methyl, ethyl, n-propyl, isopropyl or hydroxy groups.

Furthermore, a non-substituted spiro-ring AB is preferable.

The substituent(s) of "the ring A of the spiro-ring AB" is/are 1 to 5, preferably 1 to 3, same or different $C_1$-$C_6$ alkyl, hydroxy, oxo or $C_1$-$C_6$ alkoxy groups, more preferably 1 to 3 same or different $C_1$-$C_6$ alkyl, hydroxy or oxo groups. The $C_1$-$C_6$ alkyl group is preferably a $C_1$-$C_4$ alkyl group. Further, the substituent(s) of the ring A is/are even more preferably 1 to 5 same or different methyl, ethyl, n-propyl or isopropyl groups. Especially more preferred are 1 to 3 same or different methyl, ethyl, n-propyl or isopropyl groups.

Furthermore, "the ring A of the spiro-ring AB" is preferably non-substituted.

The substituent(s) of "the ring B of the spiro-ring AB" is/are 1 to 5, preferably 1 to 3, same or different $C_1$-$C_6$ alkyl, hydroxy, oxo or $C_1$-$C_6$ alkoxy groups. Preferred are 1 to 5 (preferably 1 to 3) same or different $C_1$-$C_6$ alkyl, hydroxy or oxo groups. More preferred are 1 to 5 same or different $C_1$-$C_4$ alkyl or hydroxy groups. Even more preferred are 1 to 3 same or different $C_1$-$C_4$ alkyl or hydroxy groups.

Furthermore, "the ring B of the spiro-ring AB" is preferably non-substituted.

$R^1$ is preferably a $C_2$-$C_6$ alkynyl group or a $C_1$-$C_6$ alkoxy group.

The configuration of the carbon atom bound to $R^1$ is racemate (RS or (+−)), R, S, (−) or (+), and preferably S or (−). $R^2$ is preferably a $C_1$-$C_6$ alkyl group, a hydroxy group or a $C_1$-$C_6$ alkoxy group.

p is 0, 1, 2 or 3, preferably 0 or 1, more preferably 0.
X is preferably a carbon atom.
m1 is preferably 0 or 1, more preferably 1.
m2 is preferably 0.

The general formula [Ia] is preferably the following:

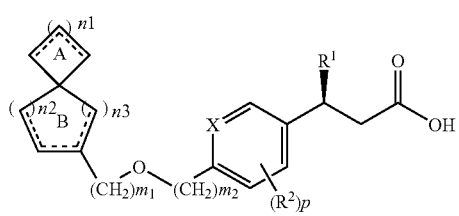

[Ia-2]

(wherein each symbol is as defined above).

Similarly, preferred is

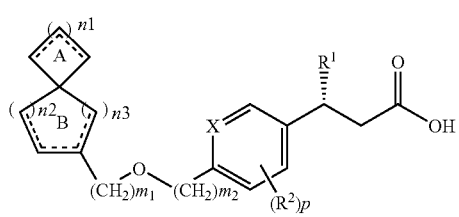

[Ia-3]

(wherein each symbol is as defined above).

More preferred is the general formula [Ia-2] or [Ia-3] in which "the spiro-ring AB" is as follows:

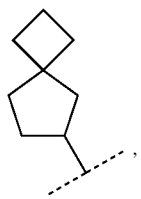

ringA4aB5a β

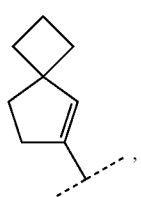

ringA4aB5b β

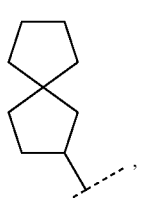

ringA5aB5a β

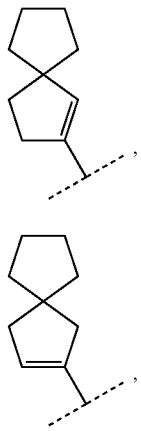

ringA5aB5b β ringA5aB5c β

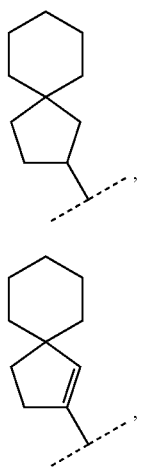

ringA6aB5a β ringA6aB5b β

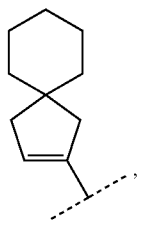

ringA6aB5c β

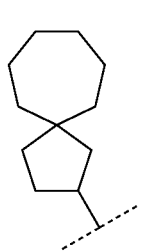

ringA7aB5a β

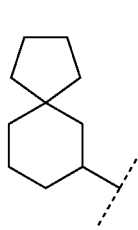

ringA5aB6a β ringA5aB6b β
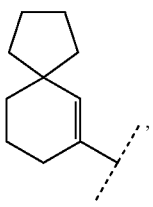

ringA5aB6c β
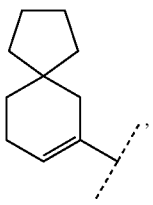

ringA6aB6a β
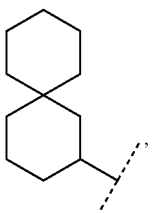

ringA6aB6b β
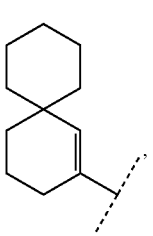

ringA6aB6c β
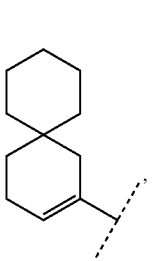

ringA6bB6a β
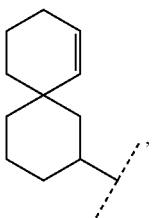

ringA7aB6a β
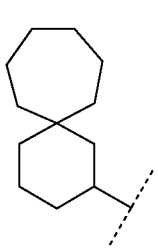

ringA7aB6c β
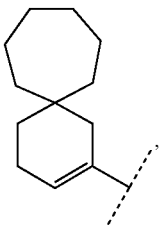

ringA5aB6a γ
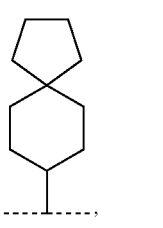

ringA5aB6c γ
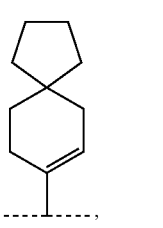

ringA6aB6c γ
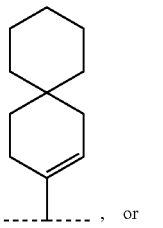
, or ringA3aB7a β
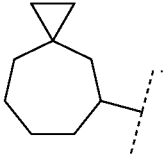

"The benzylic carbon atom" refers to the carbon atom which is represented by "$C_A$" as below and substituted by $R^1$ in the general formula [Ia] or [I] (i.e., the carbon atom in a methine group):

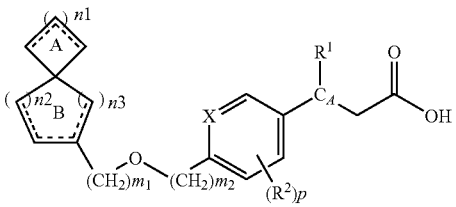
[Ia]

(wherein each symbol is as defined above).

If the carbon atom is a chiral carbon atom, "the chirality at the benzylic carbon" refers to the chirality of the above-mentioned "benzylic carbon atom". The chirality is expressed as, for example, racemate, R-isomer, S-isomer, (−)-isomer or (+)-isomer. The same will apply to such a carbon atom in the general formulae [I], [Ia] and intermediates thereof as used in the present description.

"The carbon atom at the spiro junction" refers to the carbon atom represented by C* as below among the carbon atoms of the ring B of the spiro-ring AB in the general formula [Ia] or [I]:

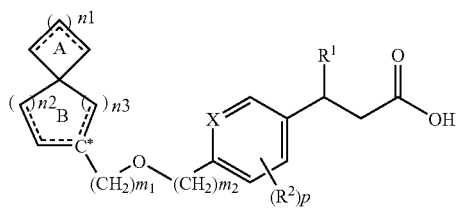

[Ia]

(wherein each symbol is as defined above).

If the carbon atom is a chiral carbon atom, "the chirality of the carbon at the spiro junction" refers to the chirality of the above-mentioned "carbon atom at the spiro junction". The chirality is expressed as, for example, racemate, R-isomer, S-isomer, (−)-isomer, (+)-isomer, chiral: A or chiral: B. The same will apply to such a carbon atom in the general formulae [I], [Ia] and intermediates thereof as used in the present description.

"A pharmaceutically acceptable salt of the compound represented by the general formula [I] (hereinafter referred to as the compound of the present invention or Compound [I])" or "a pharmaceutically acceptable salt of the compound represented by the general formula [Ia] (hereinafter referred to as the compound of the present invention or Compound [Ia])" may be any salt with the proviso that it is a non-toxic salt formed with the compound of the present invention. For example, in the case of the compound having a basic group such as an amino group in the molecule, a salt with an inorganic acid, a salt with an organic acid and a salt with an acidic amino acid can be used. In the case of the compound having an acidic group such as a carboxyl group and a sulfonic group in the molecule, a salt with an inorganic base, a salt with an organic base and a salt with a basic amino acid, etc. can be used.

Examples of the salt with an inorganic acid include a salt with hydrochloric acid, nitric acid, sulfuric acid, phosphoric acid, hydrobromic acid or the like.

Examples of the salt with an organic acid include a salt with oxalic acid, maleic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid or the like. Examples of the salt with an acidic amino acid include a salt with aspartic acid, glutamic acid or the like.

Examples of the salt with an inorganic base include a sodium salt, a potassium salt, a calcium salt, a magnesium salt or an ammonium salt. Preferred is a sodium salt, a potassium salt or a calcium salt, and more preferred is a sodium salt or a calcium salt.

Examples of the salt with an organic base include a salt with methylamine, diethylamine, trimethylamine, triethylamine, ethanolamine, diethanolamine, triethanolamine, ethylenediamine, tris(hydroxymethyl)methylamine, dicyclohexylamine, N,N-dibenzylethylenediamine, guanidine, pyridine, picoline, choline, cinchonine, meglumine or the like. Preferred is a salt with ethanolamine, diethanolamine, triethanolamine, dicyclohexylamine or N,N-dibenzylethylenediamine.

Examples of the salt with a basic amino acid include a salt with lysine, arginine or the like. Preferred is a salt with lysine.

Each salt can be obtained by reacting the compound represented by the general formula [I] or [Ia] with an inorganic base, an organic base, an inorganic acid, an organic acid or a basic or acidic amino acid in accordance with a method known per se.

"The solvate" refers to the compound represented by the general formula [I] or [Ia], or a pharmaceutical acceptable salt thereof to which a solvent molecule coordinates, including a hydrate. The solvate is preferably a pharmaceutically acceptable solvate, and includes, for example, a monohydrate, a ½-hydrate, a dihydrate, a sodium salt monohydrate, a monomethanolate, a monoethanolate, a 1-propanolate, a 2-propanolate, a monoacetonitrilate and a dihydrochloride ⅔ ethanolate of the compound represented by the general formula [I] or [Ia].

The solvate can be obtained by a method known per se.

In addition, there exist various isomers of the compound represented by the formula [I] or [Ia]. For example, E- and Z-geometric isomers can exist. Also, in the case where a chiral carbon atom is present in the molecule, enantiomers and diastereomers can exist as a stereoisomer based on the chiral carbon atom. In the case where an axial chirality is present in the molecule, there can exist stereoisomers based on the axial chirality. In some cases, tautomeric isomers also can exist. Accordingly, all these isomers and a mixture thereof are included in the scope of the present invention.

The compound represented by the general formula [I] or [Ia] may be labeled with an isotope such as $^3$H, $^{14}$C and $^{35}$S.

It is preferable that the compound represented by the general formula [I] or [Ia], a pharmaceutically acceptable salt thereof or a solvate thereof is substantially purified. More preferably, the compound represented by the general formula [I] or [Ia], a pharmaceutically acceptable salt thereof or a solvate thereof is purified so that it has a purity of 80% or more.

According to the present invention, a pro-drug of the compound represented by the general formula [I] or [Ia] can be useful as a medicament. "The pro-drug" refers to a derivative of the compound of the present invention which has a chemically or metabolically degradable group and reveals an original pharmaceutical effect after regaining its original compound form by, for example, hydrolysis, solvolysis or degradation under a physiological condition once administered to a living body. A non-covalently bonded complex and a salt may be also included. The pro-drug is, for example, used for improving the absorption rate in oral administration or delivering a drug to the target site. A modification site of the compound of the present invention may be a highly reactive functional group such as a hydroxy group, a carboxyl group, an amino group and a mercapto group.

Specifically, a modifying group for a hydroxy group includes an acetyl group, a propionyl group, an isobutyryl group, a pivaloyl group, a palmitoyl group, a benzoyl group, 4-methylbenzoyl, a dimethylcarbamoyl group, a dimethylaminomethylcarbonyl group, a sulfo group, an alanyl group or a fumaryl group. A sodium salt of a 3-carboxybenzoyl or 2-carboxyethylcarbonyl group, etc. is also included.

Specifically, a modifying group for a carboxyl group includes a methyl group, an ethyl group, a propyl group, an isopropyl group, a butyl group, an isobutyl group, a tert-butyl group, a pivaloyloxymethyl group, a carboxymethyl group, a dimethylaminomethyl group, a 1-(acetyloxy)ethyl group, a 1-(ethoxycarbonyloxy)ethyl group, a 1-(isopropyloxycarbonyloxy)ethyl group, a 1-(cyclohexyloxycarbonyloxy)ethyl group, a (5-methyl-2-oxo-1,3-dioxol-4-yl)methyl group, a benzyl group, a phenyl group, an o-tolyl group, a morpholino ethyl group, an N,N-diethylcarbamoylmethyl group or a phthalidyl group.

Specifically, a modifying group for an amino group include a tert-butyl group, a docosanoyl group, a pivaloylmethyloxy group, an alanyl group, a hexylcarbamoyl group, a pentylcarbamoyl group, a 3-methylthio-1-(acetylamino)propylcarbonyl group, a 1-sulfo-1-(3-ethoxy-4-hydroxyphenyl)methyl group, a (5-methyl-2-oxo-1,3-dioxol-4-yl)methyl group, a (5-methyl-2-oxo-1,3-dioxol-4-yl)methoxycarbonyl group, a tetrahydrofuranyl group or a pyrolidyl methyl group.

In the present invention, the spiro compound represented by the following general formula [IIa] or [II], a pharmaceutically acceptable salt thereof or a solvate thereof exhibits the same effect as the compound represented by the general formula [I] or [Ia], a pharmaceutically acceptable salt thereof or a solvate thereof, and can be used like the compound represented by the general formula [I] or [Ia], a pharmaceutically acceptable salt thereof or a solvate thereof.

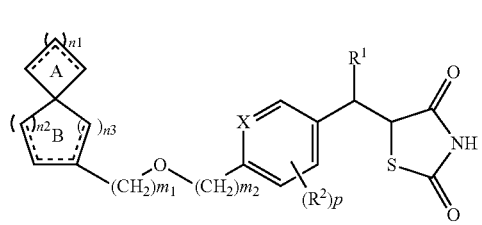

[IIa]

(wherein each symbol is as defined above.)

A preferable example of the compound represented by the general formula [IIa] is the compound represented by the following formula:

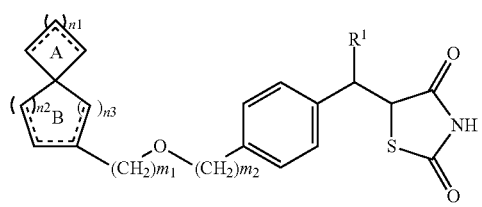

[II]

(wherein each symbol is as defined above).
Also, each substituent in the general formulae [IIa] and [II] is as defined in the general formula [I] or [Ia].

The pharmaceutical composition of the present invention can be prepared by appropriately mixing the spiro compound represented by the general formula [I] or [Ia], a pharmaceutically acceptable salt thereof or a solvate thereof with at least one kind of a pharmaceutically acceptable carrier and the like in appropriate amounts according to known methods per se in the art of pharmaceutical preparations. The amount of the compound represented by the general formula [I] or [Ia], a pharmaceutically acceptable salt thereof or a solvate thereof in the pharmaceutical composition is about 0.1 to 100% by weight of the total weight of the composition, but it varies depending on a dosage form, a dose and the like.

Examples of the pharmaceutical composition of the present invention include oral preparations such as tablets, capsules, granules, powders, troches, syrups, emulsions, suspensions, etc. or parenteral preparations such as external preparations, suppositories, injections, eye drops, transnasal agents, transpulmonary agents, etc.

"The pharmaceutically acceptable carrier" includes various organic or inorganic carrier substances used commonly as a material for pharmaceutical preparations, and the examples are fillers, disintegrants, binders, fluidizers, lubricants, etc. in the form of a solid preparation, or solvents, solubilizing agents, suspending agents, tonicity agents, buffering agents, soothing agents, etc. in the form of a liquid preparation. Furthermore, other excipients such as preservatives, antioxidants, colorants and sweeteners may be used if needed.

Examples of the filler include lactose, saccharose, D-mannitol, D-sorbitol, cornstarch, dextrin, microcrystalline cellulose, crystalline cellulose, carmellose, carmellose calcium, sodium carboxymethyl starch, low substituted hydroxypropyl cellulose, gum arabic and light anhydrous silicic acid.

Examples of the disintegrant include carmellose, carmellose calcium, carmellose sodium, sodium carboxymethyl starch, croscarmellose sodium, crospovidone, low substituted hydroxypropyl cellulose, hydroxypropyl methyl cellulose and crystalline cellulose.

Examples of the binder include hydroxypropyl cellulose, hydroxypropyl methylcellulose, povidone, crystalline cellulose, saccharose, dextrin, starch, gelatin, carmellose sodium, gum arabic and polyvinyl pyrrolidone.

Examples of the fluidizer include light anhydrous silicic acid and magnesium stearate.

Examples of the lubricant include magnesium stearate, calcium stearate, talc and colloidal silica.

Examples of the solvent include purified water, ethanol, propylene glycol, macrogol, sesame oil, corn oil and olive oil.

Examples of the solubilizing agent include propylene glycol, D-mannitol, benzyl benzoate, ethanol, triethanolamine, sodium carbonate and sodium citrate.

Examples of the suspending agent include benzalkonium chloride, carmellose, hydroxypropyl cellulose, propylene glycol, povidone, methylcellulose and glycerol monostearate.

Examples of the tonicity agent include glucose, D-sorbitol, sodium chloride and D-mannitol.

Examples of the buffering agent include sodium hydrogen phosphate, sodium acetate, sodium carbonate and sodium citrate.

Examples of the soothing agent include benzyl alcohol.

Examples of the preservative include ethyl parahydroxybenzoate, chlorobutanol, benzyl alcohol, sodium dehydroacetate and sorbic acid.

Examples of the antioxidant include sodium sulfite and ascorbic acid.

Examples of the colorant include a food coloring (e.g. food red No. 2 or 3, or food yellow No. 4 or 5, etc.) and β-carotene.

Examples of the sweetener include sodium saccharin, dipotassium glycyrrhizate and aspartame.

The pharmaceutical composition of the present invention can be administered orally or parenterally (e.g. topically, rectally, intravenously, etc.) into, not only human, but also the other mammals (e.g. mouse, rat, hamster, guinea pig, rabbit, cat, dog, pig, bovine, horse, sheep, monkey, etc.). A dose differs according to the subject, disease, symptom, dosage form, dosing route, etc. For example, when the composition is orally administered to an adult patient weighing about 60 kg, the dose of the compound represented by the general formula [I] or [Ia] of the present invention, a pharmaceutically acceptable salt thereof or a solvate thereof, which is an effective ingredient, usually ranges from about 1 mg to 2 g daily. The above-mentioned dose can be administered at one time or in several divided portions.

The compound represented by the general formula [I] or [Ia], a pharmaceutically acceptable salt thereof or a solvate thereof is suitable for treating or preventing a GPR40-related disease.

"The GPR40-related disease" includes diabetes mellitus, hyperglycemia, impaired glucose tolerance, insulin resistance, impaired fasting glucose, diabetic neuropathy, diabetic nephropathy, diabetic retinopathy, ketoacidosis, hyperlipidemia, hypercholesterolemia, hypertriglyceridemia, dyslipemia, hyperlipoproteinemia, metabolic syndrome, obesity and atherosclerosis. Especially, it is exemplified by diabetes mellitus, hyperglycemia, impaired glucose tolerance and impaired fasting glucose.

Diabetes mellitus refers to type 1 and 2 diabetes mellitus, and preferably type 2 diabetes mellitus.

A suitable subject administered with the compound represented by the general formula [I] or [Ia], a pharmaceutically acceptable salt thereof, a solvate thereof or a pharmaceutical composition containing any of them is preferably a patient with such a GPR40-related disease, most preferably a patient with a disease selected from the group consisting of diabetes mellitus, hyperglycemia, impaired glucose tolerance and impaired fasting glucose.

"Treating", "being treated" and "treatment" refer to ameliorating or curing a symptom or a disease and/or a sign associated therewith, and ameliorating the same.

"Preventing", "being prevented" and "prevention" refer to a method for delaying or preventing the onset of a symptom or a disease and a sign associated therewith, a method for preventing the subject from acquiring a symptom or a disease, or a method for reducing the subject's risk of acquiring a symptom or a disease.

The compound represented by the general formula [I] or [Ia], a pharmaceutically acceptable salt thereof or a solvate thereof is useful as a medicament for modulating the function of GPR40 (GPR40 agonist medicament), and particularly as an insulin secretion-promoting agent and a hypoglycemic agent due to its GPR40 agonist activity.

For example, the diagnostic criteria for diabetes mellitus recommended in Japan, United States and World Health Organization (WHO) are as follows.

According to the diagnostic criterion for diabetes mellitus issued by Japan Diabetes Society (JDS) in 1999, diabetes mellitus refers to any of the following conditions: fasting plasma glucose level (FPG) of 126 mg/dl or higher, 2-hour post-load plasma glucose level (2hPG) in 75 g oral glucose tolerance test (OGTT) of 200 mg/dl or higher and basal plasma glucose level of 200 mg/dl or higher.

Also, the case which belongs neither to the above diabetes mellitus and nor to the normal type having a condition of fasting plasma glucose level of lower than 110 mg/dl or 2-hour post-load plasma glucose level in 75 g oral glucose tolerance test (OGTT) of lower than 140 mg/dl is defined as the borderline type (impaired glucose regulation: IGR).

According to the diagnostic criteria for diabetes mellitus issued by WHO in 1998 and by American Diabetes Association (ADA) in 1997, diabetes mellitus refers to a condition of fasting plasma glucose level of 126 mg/dl or higher and 2-hour post-load plasma glucose level in 75 g oral glucose tolerance test of 200 mg/dl or higher.

These criteria also heavily focus on detecting a high-risk diabetic population (prediabetes). The symptoms during transition from prediabetes to diabetes mellitus include impaired glucose tolerance (IGT), impaired fasting glucose (IFG) and a combination thereof. Impaired glucose tolerance refers to a condition which meets fasting plasma glucose level <126 mg/dl and 2-hour post-load plasma glucose level in 75 g oral glucose tolerance test ≧140 mg/dl but <200 mg/dl. Impaired fasting glucose refers to a condition which meets fasting plasma glucose level ≧110 mg/dl but <126 mg/dl and 2-hour post-load plasma glucose level in 75 g oral glucose tolerance test <140 mg/dl (ADA defines impaired fasting glucose as a condition which meets fasting plasma glucose level ≧100 mg/dl but <126 mg/dl).

The compound of the present invention, a pharmaceutically acceptable salt thereof or a solvate thereof can be also used as a medicament for preventing or treating the diabetes mellitus, borderline diabetes mellitus, impaired glucose tolerance and impaired fasting glucose determined by the above-mentioned new criteria. Further, the compound of the present invention, a pharmaceutically acceptable salt thereof or a solvate thereof can prevent diabetes mellitus and the progression of borderline diabetes mellitus, impaired glucose tolerance and impaired fasting glucose into diabetes mellitus.

The compound of the present invention, a pharmaceutically acceptable salt thereof or a solvate thereof is useful as a medicament for treating diabetes mellitus with secondary failure of sulfonylurea therapy. In the treatment of diabetes mellitus with secondary failure of sulfonylurea therapy, a sulfonylurea compound or a fast-acting insulin secretion-promoting agent cannot exert insulin secretion-promoting effect, and therefore its hypoglycemic effect is unsatisfactory. Even for the patients with such diabetes mellitus, the compound of the present invention, a pharmaceutically acceptable salt thereof or a solvate thereof can be used.

The sulfonylurea compound refers to a compound having a sulfonylurea backbone or a derivative thereof, and includes tolbutamide, glibenclamide, gliclazide, chlorpropamide, tolazamide, acetohexamide, glyclopyramide, glimepiride, glipizide and glybuzole.

The fast-acting insulin secretion-promoting agent refers to a compound having no sulfonylurea backbones and promoting the insulin secretion from pancreatic β cells like a sulfonylurea compound, and includes a glinide compound such as repaglinide, senaglinide, nateglinide, mitiglinide or a calcium salt hydrate thereof.

The spiro compound represented by the general formula [I] or [Ia], a pharmaceutically acceptable salt thereof or a solvate thereof can be used in combination (sometimes hereinafter referred to combined use) with one or more drugs (sometimes hereinafter referred to drugs in combined use) in a conventional manner in the pharmaceutical field.

The spiro compound represented by the general formula [I] or [Ia], a pharmaceutically acceptable salt thereof or a solvate thereof and the drug in combined use can be administered without limitation as to the timing. These may be administered to the subject in the form of a combination preparation, or administered simultaneously or separately at a certain interval. They may be used as a medicament in the form of a kit comprising the pharmaceutical composition of the present invention and the drug in combined use. A dose of the drug in combined use may be employed in compliance with the dose used in the clinical field and can be appropriately selected according to the subject, disease, symptom, dosage form, dosing route, dosing duration, combination, etc. The dosing method of the drug in combined use is not particularly limited and any method may be employed as long as the compound of the present invention, a salt thereof or a solvate thereof, and the drug in combined use are combined.

The drug in combined use includes
(1) a drug for treating or preventing hyperlipidemia;
(2) a drug for treating or preventing obesity;
(3) a drug for treating or preventing diabetes mellitus;
(4) a drug for treating or preventing diabetes complication; and
(5) a drug for treating or preventing hypertension. One to three of the above-combined drugs can be used in combination with the spiro compound represented by the general formula [I] or [Ia], a pharmaceutically acceptable salt thereof or a solvate thereof.

"The drug for treating and/or preventing hyperlipidemia" includes, for example, apolipoprotein-A1 (Apo-A1) inducer, cholesteryl ester transfer protein (CETP) inhibitor, endothelial lipase inhibitor, HMG-CoA reductase inhibitor, lipoprotein lipase (LPL) activator, microsomal triglyceride transfer protein (MTP) inhibitor, PPARα receptor agonist and PPARδ receptor agonist.

"The drug for treating and/or preventing obesity" includes, for example, acetyl-CoA carboxylase 1 (ACC1) inhibitor, acetyl-CoA carboxylase 2 (ACC2) inhibitor, bombesin receptor subtype 3 (BRS-3) agonist, diacylglycerol acyltransferase (DGAT) inhibitor, glucose-dependent insulinotropic polypeptide (GIP) receptor antagonist, leptin receptor agonist, melanocortin (MC) receptor agonist, neuropeptide Y5 (NPY5) receptor antagonist, perilipin inhibitor, uncoupling protein (UCP) inducer/activator, 11β-HSD-1 inhibitor, adiponectin receptor agonist, AMP-activated protein kinase (AMPK) activator, PPARγ receptor agonist/antagonist and β3 adrenergic receptor agonist.

"The drug for treating and/or preventing diabetes mellitus" includes, for example, insulin preparation (injection), fructose-1,6-bisphosphatase (FBPase) inhibitor, glucagon receptor antagonist, glucocorticoid receptor antagonist, glucokinase activator, glutamine:fructose-6-phosphate aminotransferase (GFAT) inhibitor, glycogen phosphorylase (GP) inhibitor, glycogen synthase kinase 3 (GSK-3) inhibitor, GPR40 agonist, phosphoenolpyruvate carboxykinase (PEPCK) inhibitor, protein tyrosine phosphatase 1B (PTPase 1B) inhibitor, pyruvate dehydrogenase kinase (PDHK) inhibitor, SGLUT inhibitor, SH2 domain-containing inositol phosphatase (SHIP2) inhibitor, dipeptidyl peptidase IV (DPP-IV) inhibitor, tGLP-1 peptide analog, α-glucosidase inhibitor, insulin sensitivity enhancer, sulfonylurea receptor agonist (SU agent), fast-acting insulin secretion-promoting drug (nateglinide), low-molecular weight agonist of tGLP-1 receptor, oral low-molecular weight insulin preparation, biguanides, 11β-HSD-1 inhibitor, adiponectin receptor agonist, AMP-activated protein kinase (AMPK) activator, PPARγ receptor agonist/antagonist and β3 adrenergic receptor agonist.

"The drug for treating or preventing diabetes complication" includes, for example, advanced glycation end products (AGE) production inhibitor, aldose reductase inhibitor, angiotensin II receptor antagonist, angiotensin-converting enzyme (ACE) inhibitor and protein kinase Cβ (PKC β) inhibitor.

"The drug for treating or preventing hypertension" includes, for example, α blocker, β blocker, angiotensin-converting enzyme inhibitor (ACE inhibitor), calcium channel blocker and renin inhibitor.

An exemplary method for preparing the compound of the present invention will be hereinafter explained, but the present invention is not limited thereto. It will be understood that the compound of the present invention can be prepared in accordance with a method known per se. Upon the preparation of the compound of the present invention, the order of reactions can be changed appropriately. Namely, any step may be performed first or any substituent may be subjected to the first reaction as long as it is considered to be reasonable.

Any step to convert a substituent (i.e., conversion or additional modification of a substituent, including, for example oxidation or reduction of a substituent) may be optionally inserted between each step. A reactive functional group, if any, may be appropriately protected or deprotected. Further, any other reagent than the exemplified reagents can be used appropriately to promote the reaction forward. Also, a reaction can be performed under anhydrous condition (for example, under nitrogen atmosphere).

A compound obtained at each step may be isolated and purified by a conventional method appropriately selected from crystallization, recrystallization, distillation, liquid-liquid separation, column chromatography and preparative HPLC, etc. or a combination thereof. In some cases, the next step can be started without isolating or purifying a compound obtained at each step.

In the preparation methods hereinafter, "room temperature" refers to a temperature of 1 to 40° C. Also in the following formulae, a bond represented by the symbol: -----
means a single bond or a double bond with the proviso that three contiguous carbon atoms do not constitute an allene bond represented by the formula:

Also, for example, "a compound represented by (General) Formula (1)" can also be represented as "Compound (1)".
Preparation Method A

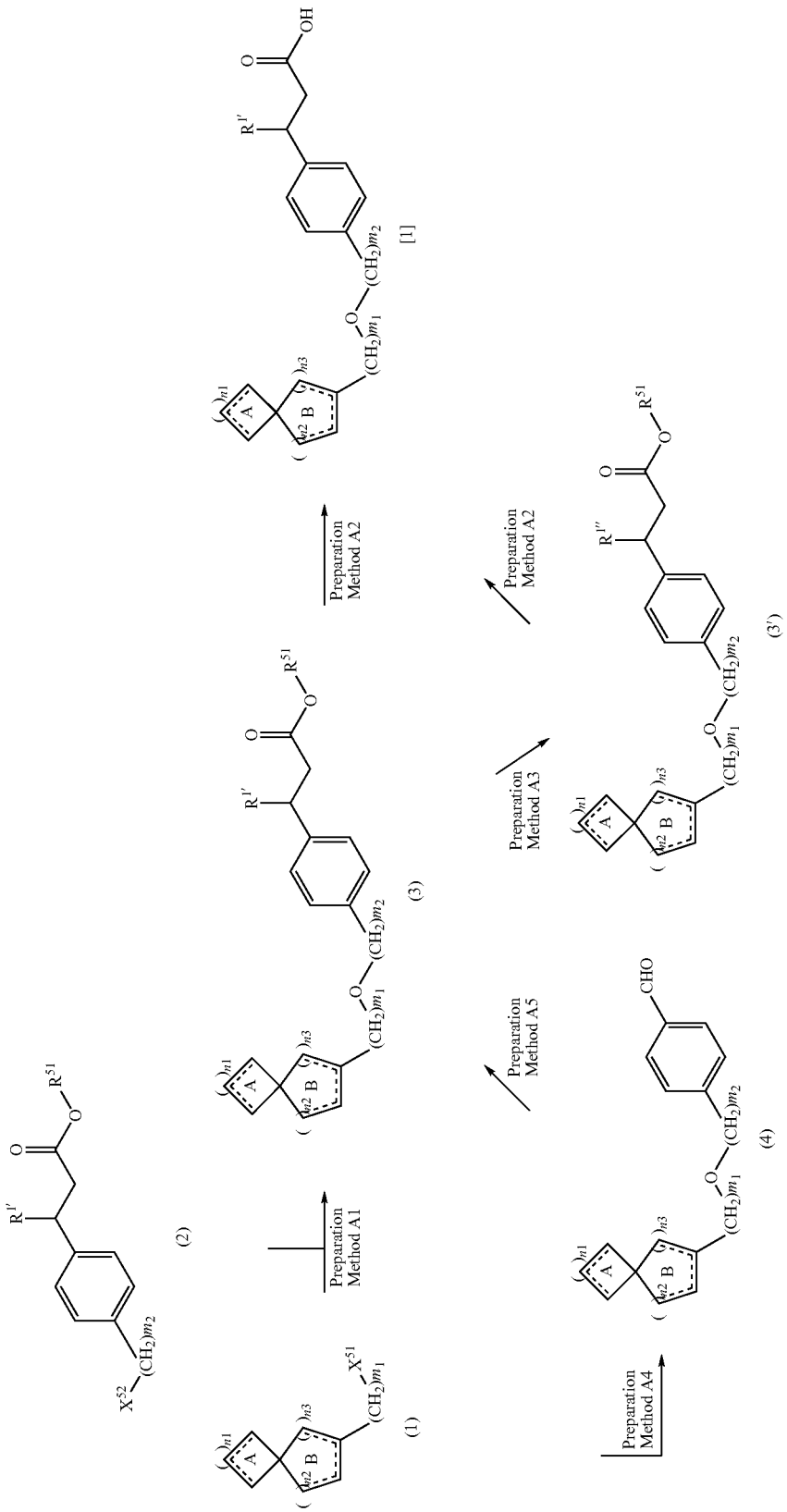

(wherein $R^{1'}$ is a $C_1$-$C_6$alkyl group, a $C_2$-$C_6$alkenyl group, a $C_2$-$C_6$alkynyl group, a phenyl group, a hydroxy group, a five-membered heteroaryl group which has at least one heteroatom selected from a nitrogen atom, an oxygen atom and a sulfur atom, and which may be substituted by a $C_1$-$C_6$alkyl group, or a di($C_1$-$C_6$alkoxy)methyl group);
$R^{1'}$ is a $C_1$-$C_6$alkoxy group, a hydroxy $C_1$-$C_6$alkyl group, a $C_1$-$C_6$alkoxy($C_1$-$C_6$)alkyl group, —$CONR^{11}R^{12}$ ($R^{11}$ and $R^{12}$ are the same or different and each represents a hydrogen atom or a $C_1$-$C_6$ alkyl group), or a five-membered heteroaryl group which has at least one heteroatom selected from a nitrogen atom, an oxygen atom and a sulfur atom, and which may be substituted by a $C_1$-$C_6$alkyl group;
$X^{51}$ and $X^{52}$ are the same or different and each represents a hydroxy group or a leaving group;
$R^{51}$ is a $C_1$-$C_6$alkyl group; and other symbols are as defined above.)

Examples of the Preparation Method A are shown in Preparation Methods A1 to A5 below.

Preparation Method A1

Compound (3) can be obtained from Compound (1) and Compound (2) according to the following Step 1 or Step 1'.

Step 1

Compound (3) can be obtained by condensation of Compound (1) in which $X^{51}$ is a hydroxy group and Compound (2) in which $X^{52}$ is a hydroxy group in a solvent at room temperature or with heat. The reagent is preferably 1,1'-(azodicarbonyl)dipiperidine, triphenylphosphine, or the like. The solvent is preferably, for example, an ether solvent such as tetrahydrofuran.

Step 1'

Compound (3) can be obtained by reaction of Compound (1) in which $X^{51}$ is a hydroxy group and Compound (2) in which $X^{52}$ is a leaving group, or Compound (1) in which $X^{51}$ is a leaving group and Compound (2) in which $X^{52}$ is a hydroxy group, in a solvent in the presence of a base at room temperature or with heat. The leaving group is preferably a chlorine atom, a bromine atom, an iodine atom or a methanesulfonyloxy group, and more preferably a chlorine atom, a bromine atom or an iodine atom. The base is preferably an alkali metal carbonate such as potassium carbonate or cesium carbonate. The solvent is preferably a polar solvent such as N,N-dimethylformamide.

Preparation Method A2

A compound represented by the general formula [I] can be obtained by hydrolysis of Compound (3) or Compound (3'), in a solvent in the presence of a base at room temperature or with heat. The base is preferably an aqueous solution of sodium hydroxide, potassium hydroxide, or the like. The solvent is preferably, for example, an ether solvent such as tetrahydrofuran, an alcoholic solvent such as methanol, or a mixture thereof.

Preparation Method A3

Compound (3') can be obtained from Compound (3) according to the following method.

Examples of the Preparation Method A3 are shown in Preparation Methods A3-1 to A3-5 below.

Preparation Method A3-1

Compound (3') in which $R^{1'''}$ is a hydroxy $C_1$-$C_6$alkyl group can be obtained from Compound (3) in which $R^{1'}$ is a di($C_1$-$C_6$alkoxy)methyl group according to the following steps.

Step 1

An aldehyde intermediate can be obtained by deprotection of Compound (3) in which $R^{1'}$ is a di($C_1$-$C_6$alkoxy)methyl group in a solvent under acidic condition at room temperature or with heat. The acid is preferably camphorsulfonic acid, trifluoroacetic acid, or the like. The solvent is preferably a ketone solvent such as acetone.

Step 2

Compound (3') in which $R^{1'''}$ is a hydroxy $C_1$-$C_6$alkyl group can be obtained by reduction of the aldehyde intermediate obtained in the above Step 1 in a solvent at room temperature or with heat. The reducing agent is preferably sodium borohydride. The solvent is preferably an alcoholic solvent such as methanol.

Preparation Method A3-2

Compound (3') in which $R^{1'''}$ is a $C_1$-$C_6$ alkoxy($C_1$-$C_6$)alkyl group can be obtained by alkylation of Compound (3') in which $R^{1'''}$ is a hydroxy $C_1$-$C_6$ alkyl group obtained in the above Preparation Method A3-1 Step 2 in a solvent in the presence of a base, and in the presence of an additive as needed, with cooling or heating. The base is preferably an organic amine such as N,N-diisopropylethylamine or 2,6-di-tert-butyl-4-methylpyridine. The alkylating agent is preferably tri($C_1$-$C_6$alkyl)oxonium tetrafluoroborate or $C_1$-$C_6$alkyl bromide or iodide. The tri($C_1$-$C_6$alkyl)oxonium tetrafluoroborate is preferably trimethyloxonium tetrafluoroborate or triethyloxonium tetrafluoroborate. The $C_1$-$C_6$alkyl iodide is preferably methyl iodide, ethyl iodide, n-propyl iodide or isopropyl iodide. When the alkylating agent is $C_1$-$C_6$alkyl bromide or iodide, the additive is preferably silver(I)oxide or silver(I)trifluoromethanesulfonate. The solvent is preferably a halogenated hydrocarbon solvent such as chloroform or dichloromethane.

Preparation Method A3-3

Compound (3') in which $R^{1'''}$ is —$CONR^{11}R^{12}$ ($R^{11}$ and $R^{12}$ are the same or different and each represents a hydrogen atom or a $C_1$-$C_6$alkyl group) can be obtained from the aldehyde intermediate obtained in the above Preparation Method A3-1 Step 1 according to the following steps.

Step 1

A carboxylic acid intermediate can be obtained by oxidation of the aldehyde intermediate obtained in the above Preparation Method A3-1 Step 1 in a solvent in the presence of an additive at room temperature or with heat. The oxidant is preferably sodium chlorite, and the additive is preferably sodium dihydrogen phosphate and 2-methyl-2-butene. The solvent is preferably an alcoholic solvent such as tert-butanol, a polar solvent such as water, or a mixture thereof.

Step 2

Compound (3') in which $R^{1'''}$ is —$CONR^{11}R^{12}$ ($R^{11}$ and $R^{12}$ are the same or different and each represents a hydrogen atom or a $C_1$-$C_6$ alkyl group) can be obtained by condensation of the carboxylic acid intermediate obtained in the above Step 1 and $HNR^{11}R^{12}$ ($R^{11}$ and $R^{12}$ are as defined above) in the usual manner.

Preparation Method A3-4

Compound (3') in which $R^{1'''}$ is an N—($C_1$-$C_6$alkyl)tetrazole group can be obtained by reaction of Compound (3') in which $R^{1'''}$ is —$CONR^{11}R^{12}$ ($R^{11}$ is a hydrogen atom here, and other symbols are as defined above), obtained in the above Preparation Method A3-3 Step 2 in a solvent in the presence of an azidation agent and a dehydrating agent at room temperature or with heat. The dehydrating agent is preferably trifluoromethanesulfonic anhydride. The azidation agent is preferably sodium azide. The solvent is preferably a polar solvent such as acetonitrile.

Preparation Method A3-5

Compound (3') in which $R^{1'''}$ is a $C_1$-$C_6$alkoxy group can be obtained from Compound (3) in which $R^{1'}$ is a hydroxy group in the same manner as in the above Preparation Method A3-2.

Preparation Method A4

Compound (4) can be obtained from Compound (1) and the following Compound (20):

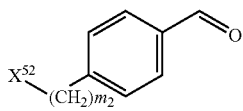
(20)

(wherein symbols are as defined above,)
in the same manner as in the above Preparation Method A1 Step 1 or Step 1'. The Compound (20) is preferably 4-hydroxybenzaldehyde.

Preparation Method A5

Compound (3) can be obtained from Compound (4) according to the following method.

Examples of the Preparation Method A5 are shown in Preparation Methods A5-1 to A5-2 below.

Preparation Method A5-1

Compound (3) in which $R^{1'}$ is a hydroxy group can be obtained by aldol reaction of Compound (4) with an acetate represented by the formula: $CH_3CO_2R^{51}$ (the symbol is as defined above) in a solvent in the presence of a base with cooling or at room temperature. The base is preferably lithium diisopropylamide. The solvent is preferably an ether solvent such as tetrahydrofuran.

Preparation Method A5-2

Compound (3) in which $R^{1'}$ is a hydrogen atom, can be obtained from Compound (4) according to the following steps.

Step 1

An α,β-unsaturated ester intermediate can be obtained by reaction of Compound (4) with di($C_1$-$C_6$)alkyl phosphonoacetic acid reagent in a solvent in the presence of a base at room temperature or with heat. The base is preferably sodium hydride or the like. The di($C_1$-$C_6$)alkyl phosphonoacetic acid reagent is preferably triethyl phosphonoacetate. The solvent is preferably an ether solvent such as tetrahydrofuran.

Step 2

Compound (3) in which $R^{1'}$ is a hydrogen atom, can be obtained by reduction of the α,β-unsaturated ester intermediate obtained in the above Step 1 in a solvent at room temperature or with heat. The reduction method is preferably catalytic hydrogenation in the presence of a catalyst. The catalyst is preferably palladium-carbon. The solvent is preferably a polar solvent such as ethyl acetate. Optionally, diphenylsulfide or the like can be added as an additive.

Preparation Method B

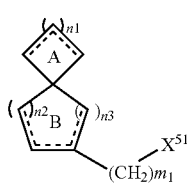
(1)

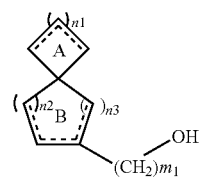
(1a)

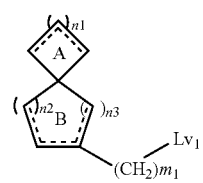
(1b)

(wherein $Lv_1$ is a leaving group, and other symbols are as defined above.)

Compound (1) means Compound (1a) or Compound (1b), and Compound (1b) can be produced by converting Compound (1a) into a compound having a leaving group by a general method. For example, Compound (1b) can be obtained by reacting Compound (1a) and a halogenating agent in a solvent in the presence of an additive at room temperature or with heat. The halogenating agent is preferably N-bromosuccinimide. The additive is preferably triphenylphosphine. The solvent is preferably a halogenated hydrocarbon solvent such as chloroform.

Preparation Method C

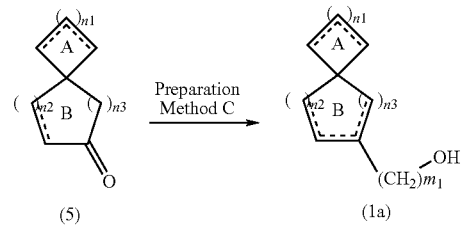

(wherein symbols are as defined above.)

Compound (1a) can be obtained from Compound (5) according to the following Preparation Method C1 for preparing Compound (1a-1), Compound (1a-2) or Compound (1a-5) in which the carbon atom at the spiro junction of the ring B of the spiro-ring AB to which a side chain $(CH_2)_{m1}OH$ binds is an $sp^2$ carbon atom; or the following Preparation Method C2 for preparing Compound (1a-6), Compound (1a-7), Compound (1a-8) or Compound (1a-9) in which the same carbon atom at the spiro junction is an $sp^3$ carbon atom. Examples are shown in Preparation Methods C1 to C2 below.

Preparation Method C1

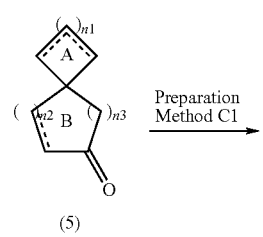
(5)

-continued

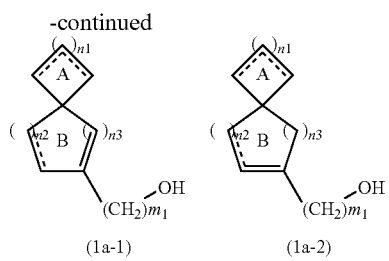

(wherein symbols are as defined above.)

Examples of the Preparation Method C1 are shown in Preparation Methods C1-1 to C1-3 below.

Preparation Method C1-1

When n3 is 1 in Compound (1a-1) (in the case of Compound (1a-1a)):

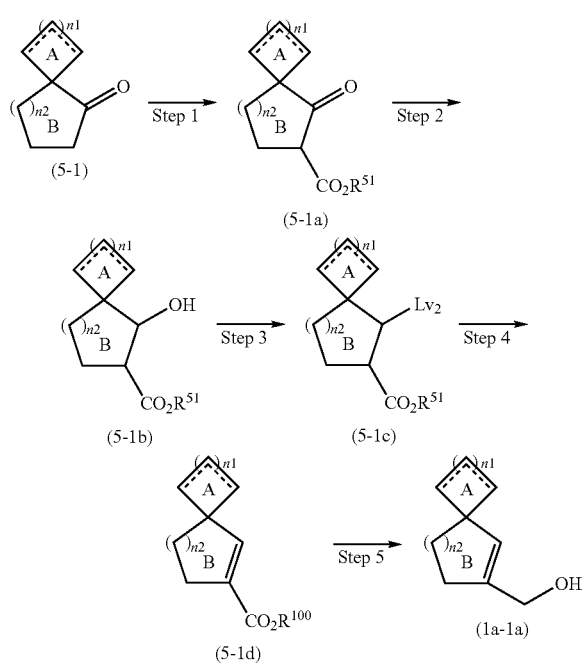

(wherein $R^{100}$ is a $C_1$-$C_6$alkyl group, $Lv_2$ is a leaving group, and other symbols are as defined above.)

Step 1

Compound (5-1a) can be obtained by reaction of Compound (5-1) with di($C_1$-$C_6$alkyl) carbonate in a solvent in the presence of a base at room temperature or with heat. The di($C_1$-$C_6$alkyl) carbonate is preferably dimethyl carbonate. The base is preferably Sodium hydride, potassium tert-butoxide, or the like. The solvent is preferably an ether solvent such as tetrahydrofuran.

Step 2

Compound (5-1b) can be obtained by reaction of Compound (5-1a) with a reducing agent such as sodium borohydride in a solvent at room temperature or with heat, or by catalytic reduction of Compound (5-1a) with a catalyst such as platinum oxide in an atmosphere of hydrogen. The solvent is preferably an ether solvent such as tetrahydrofuran, an alcoholic solvent such as methanol, or a mixture thereof.

Step 3

Compound (5-1c) can be obtained by reaction of Compound (5-1b) with methanesulfonyl chloride or the like in a solvent under basic condition at room temperature or with heat. The base is preferably an organic base such as triethylamine or pyridine. The solvent is preferably a halogenated hydrocarbon solvent such as chloroform. Optionally, 4-dimethylaminopyridine or the like can be added as an additive.

Step 4

Compound (5-1d) can be obtained by reaction of Compound (5-1c) in a solvent under basic condition at room temperature or with heat. The base is preferably an organic base such as 1,8-diazabicyclo[5.4.0]undec-7-ene. The solvent is preferably an ether solvent such as tetrahydrofuran.

Step 5

Compound (1a-1a) can be obtained by reduction of Compound (5-1d) in a solvent with cooling or at room temperature. The reducing agent is preferably diisobutylaluminum hydride. The solvent is preferably an ether solvent such as tetrahydrofuran.

Preparation Method C1-2

When n2 is 2 and n3 is 1 in Compound (1a-2) (in the case of Compound (1a-2a)):

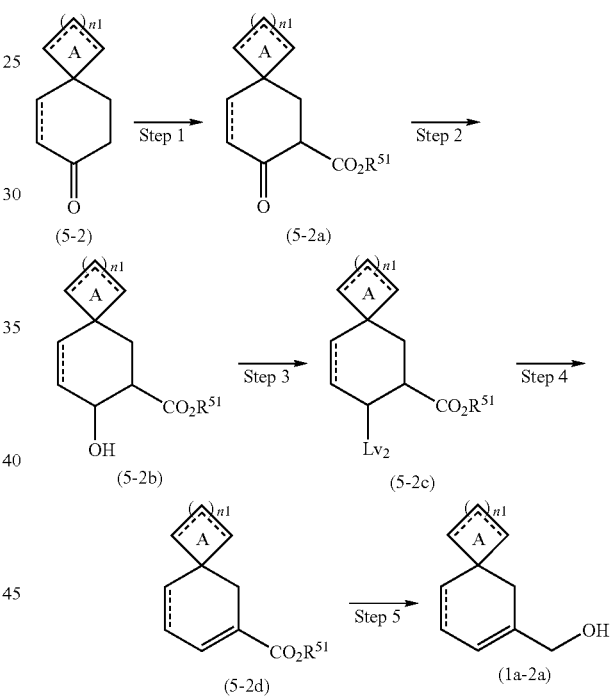

(wherein symbols are as defined above.)

Step 1

Compound (5-2a) can be obtained by reaction of Compound (5-2) with di($C_1$-$C_6$alkyl) carbonate in a solvent in the presence of a base at room temperature or with heat. The di($C_1$-$C_6$alkyl) carbonate is preferably dimethyl carbonate. The base is preferably Sodium hydride, or the like. The solvent is preferably an ether solvent such as tetrahydrofuran.

Step 2

Compound (5-2b) can be obtained by reaction of Compound (5-2a) with a reducing agent such as sodium borohydride in a solvent at room temperature or with heat. The solvent is preferably an ether solvent such as tetrahydrofuran, an alcoholic solvent such as methanol, or a mixture thereof.

Step 3

Compound (5-2c) can be obtained by reaction of Compound (5-2b) with methanesulfonyl chloride or the like in a solvent under basic condition at room temperature. The base is preferably an organic base such as triethylamine or pyridine.

The solvent is preferably a halogenated hydrocarbon solvent such as chloroform. Optionally, 4-dimethylaminopyridine or the like can be added as an additive.

Step 4

Compound (5-2d) can be obtained by reaction of Compound (5-2c) in a solvent under basic condition at room temperature or with heat. The base is preferably an organic base such as 1,8-diazabicyclo[5.4.0]undec-7-ene. The solvent is preferably an ether solvent such as tetrahydrofuran.

Step 5

Compound (1a-2a) can be obtained by reduction of Compound (5-2d) in a solvent with cooling or at room temperature. The reducing agent is preferably diisobutylaluminum hydride. The solvent is preferably an ether solvent such as tetrahydrofuran.

Preparation Method C1-3

When n2 is 1 and n3 is 2 in Compound (1a-2) (in the case of Compound (1a-5)):

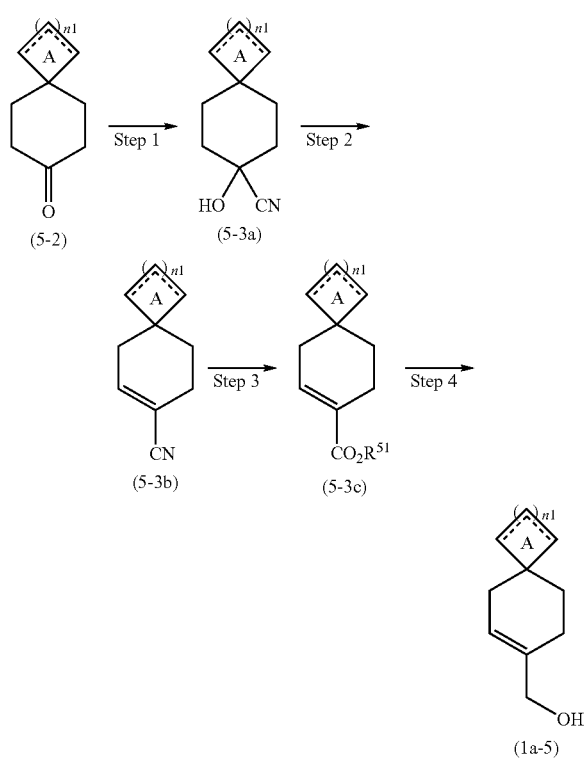

(wherein symbols are as defined above.)

Step 1

Compound (5-3a) can be obtained by reaction of Compound (5-2) with a cyanating agent in the presence of an additive in a solvent at room temperature or with heat. The cyanating agent is preferably trimethylsilylcyanide. The additive is preferably tetra-n-butylammonium fluoride. The solvent is preferably an ether solvent such as tetrahydrofuran.

Step 2

Compound (5-3b) can be obtained by reaction of Compound (5-3a) with a chlorinating agent in a solvent in the presence of a base at room temperature or with heat. The base is preferably pyridine. The chlorinating agent is preferably thionyl chloride. The solvent is preferably an ether solvent such as tetrahydrofuran.

Step 3

Compound (5-3c) can be obtained by reaction of Compound (5-3b) in a solvent under acidic condition at room temperature or with heat. The acid is preferably concentrated sulfuric acid. The solvent is preferably an alcoholic solvent such as ethanol.

Step 4

Compound (1a-5) can be obtained by reaction of Compound (5-3c) in the same manner as in the Preparation Method C1-1 Step 5.

Preparation Method C2

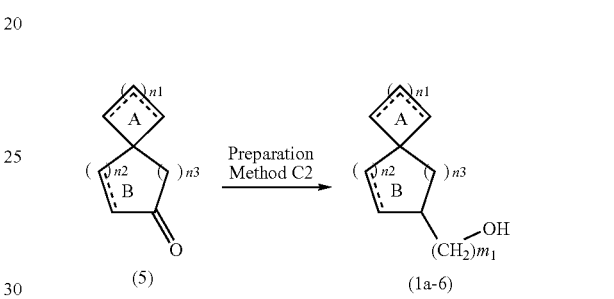

(wherein symbols are as defined above.)

Examples of the Preparation Method C2 are shown in Preparation Methods C2-1 to C2-3 below.

Compound (1a-6) in which the carbon atom at the spiro junction of the ring B of the spiro-ring AB to which a side chain $(CH_2)_{m_1}OH$ binds is an $sp^3$ carbon atom, can be obtained by the following preparation methods as well as by reducing the compound obtained in the above Preparation Method C1, namely C1-1, C1-2 or C1-3 (i.e., Compound (1a-1a), Compound (1a-2a) or Compound (1a-5)) by catalytic hydrogenation reaction.

Preparation Method C2-1

When $m_1$ is 0 in Compound (1a-6) (in the case of Compound (1a-7)):

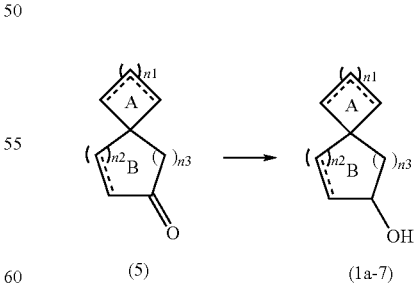

(wherein symbols are as defined above.)

Compound (1a-7) can be obtained by reaction of Compound (5) with a reducing agent such as sodium borohydride in a solvent at room temperature or with heat. The solvent is preferably an alcoholic solvent such as methanol.

Preparation Method C2-2
When $m_1$ is 1 in Compound (1a-6) (in the case of Compound (1a-8)):

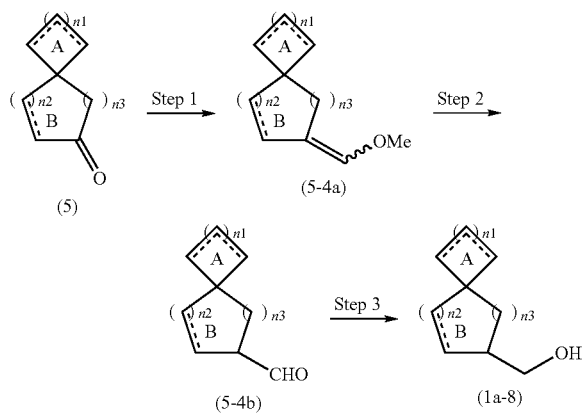

(wherein symbols are as defined above.)

Compound (1a-8) can be obtained through the following steps.

Step 1

Compound (5-4a) can be obtained by reaction of Compound (5) with a diazophosphonate compound in a solvent in the presence of a base at room temperature or with heat. The diazophosphonate compound is preferably dimethyl(1-diazo-2-oxo-propyl)phosphonate. The base is preferably an alkali metal carbonate such as potassium carbonate. The solvent is preferably an alcoholic solvent such as methanol.

Step 2

Compound (5-4b) can be obtained by reaction of the above Compound (5-4a) in a solvent under acidic condition at room temperature. The acid is preferably dilute aqueous hydrochloric acid solution. The solvent is preferably a polar solvent such as acetonitrile.

Step 3

Compound (1a-8) can be obtained by reaction of the above Compound (5-4b) with a reducing agent such as sodium borohydride in a solvent at room temperature or with heat. The solvent is preferably an alcoholic solvent such as methanol.

Preparation Method C2-3
When mL is 2 in Compound (1a-6) (in the case of Compound (1a-9)):

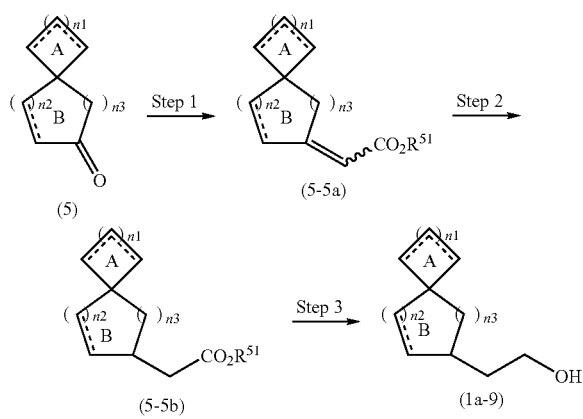

(wherein symbols are as defined above.)

Compound (1a-9) can be obtained through the following steps.

Step 1

Compound (5-5a) can be obtained by Horner-Emmons reaction of Compound (5) in a solvent in the presence of a base at room temperature or with heat. The base is preferably Sodium tert-butoxide. The solvent is preferably an aromatic hydrocarbon solvent such as toluene.

Step 2

Compound (5-5b) can be obtained by reduction of the above Compound (5-5a) in a solvent at room temperature. The reduction method is preferably catalytic hydrogenation in the presence of a catalyst. The catalyst is preferably palladium-carbon. The solvent is preferably an alcoholic solvent such as ethanol.

Step 3

Compound (1a-9) can be obtained by reduction of the above Compound (5-5b) in a solvent with cooling or at room temperature. The reducing agent is preferably lithium aluminum hydride, or the like. The solvent is preferably an ether solvent such as tetrahydrofuran.

Preparation Method D

(wherein symbols are as defined above.)

Compound (5) can be obtained according to the following Preparation Method D1 for Forming a Ring a in a Compound Having the ring B of a spiro-ring AB, or the following Preparation Method D2 for forming a ring B in a compound having the ring A of a spiro-ring AB. Examples are shown in Preparation Methods D1 to D2 below.

Preparation Method D1

Examples of the Preparation Method D1 are shown in Preparation Methods D1-1 to D1-2 below.

Preparation Method D1-1

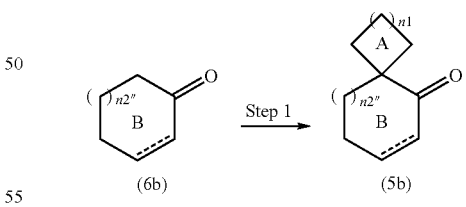

(wherein n2" is 0, 1 or 2, and other symbols are as defined above.)

Step 1

Compound (5b) can be obtained by reaction of Compound (6b) with $L_1$-$C_2$-$C_6$alkylene-$L_2$ ($L_1$ and $L_2$ are the same or different and each represents a leaving group) in a solvent in the presence of a base at room temperature or with heat. The base is preferably potassium tert-butoxide. The $L_1$-$C_2$-$C_6$alkylene-$L_2$ is preferably L-$C_2$-$C_6$alkylene-L (L is preferably a halogen atom such as a chlorine atom or a bromine atom). The solvent is preferably an aromatic hydrocarbon solvent such as toluene. Optionally, ultrasound can be used for reaction.

Preparation Method D1-2

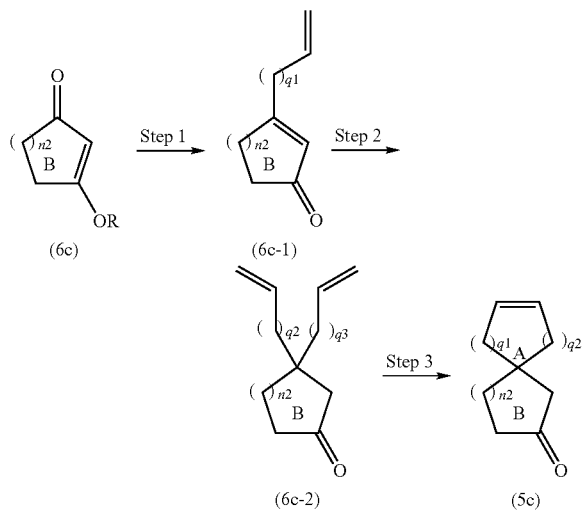

(wherein R is a $C_1$-$C_6$alkyl group, q1 is 1 or 2, q2 is 1 or 2, and other symbols are as defined above.)

Step 1

Compound (6c-1) can be obtained by Grignard reaction of Compound (6c) in a solvent with cooling or at room temperature. The solvent is preferably an ether solvent such as tetrahydrofuran.

Step 2

Compound (6c-2) can be obtained by Grignard reaction of Compound (6c-1) in a solvent in the presence of an additive at room temperature or with heat. The additive is preferably a copper halide such as copper(I) iodide or an alkali metal halide such as lithium bromide. The solvent is preferably an ether solvent such as tetrahydrofuran.

Step 3

Compound (5c) can be obtained by reaction of Compound (6c-2) in a solvent in the presence of a catalyst at room temperature or with heat. The catalyst is preferably a Grubbs catalyst such as benzylidene[1,3-bis(2,4,6-trimethylphenyl)-2-imidazolidinylidene]dichloro(tricyclohexylphosphine)ruthenium. The solvent is preferably an aromatic hydrocarbon solvent such as toluene.

Preparation Method D2

Examples of the Preparation Method D2 are shown in Preparation Methods D2-1 to D2-3 below.

Preparation Method D2-1

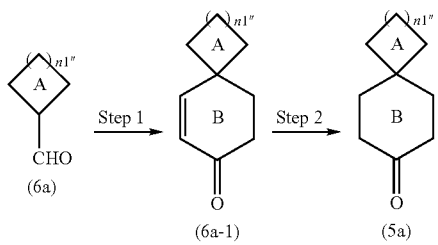

(wherein n1″ is 2, 3, 4 or 5, and other symbols are as defined above.)

Step 1

Compound (6a-1) can be obtained by reaction of Compound (6a) with methyl vinyl ketone in a solvent in the presence of an acid catalyst at room temperature or with heat. The acid catalyst is preferably concentrated sulfuric acid. The solvent is preferably an aromatic hydrocarbon solvent such as toluene.

Step 2

Compound (5a) can be obtained by reduction of Compound (6a-1) in a solvent at room temperature. The reduction method is preferably catalytic hydrogenation in the presence of a catalyst. The catalyst is preferably palladium-carbon. The solvent is preferably an ether solvent such as tetrahydrofuran.

Preparation Method D2-2

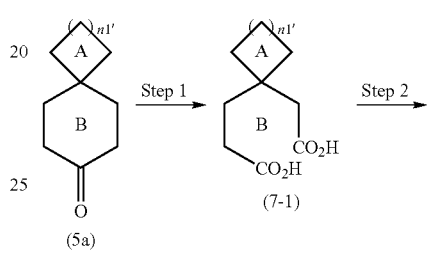

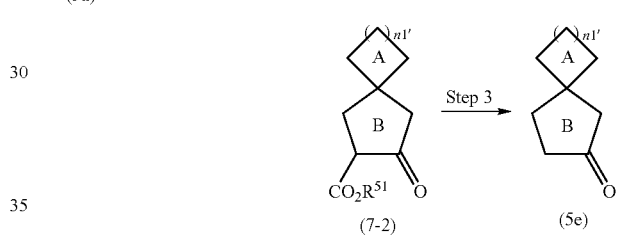

(wherein n1′ is 2, 3 or 4, and other symbols are as defined above.)

Step 1

Compound (7-1) can be obtained by oxidation of Compound (5a) obtained in the Preparation Method D2-1 in a solvent under basic condition at room temperature or with heat. The base is preferably sodium hydroxide, and the oxidant is preferably potassium permanganate. The solvent is preferably a polar solvent such as water.

Step 2

Compound (7-2) can be obtained by reaction of Compound (7-1) in a solvent in the presence of an alkylating agent under basic condition at room temperature or with heat. The base is preferably an alkali metal carbonate such as potassium carbonate or cesium carbonate. The alkylating agent is preferably benzyl bromide. The solvent is preferably a polar solvent such as acetonitrile or N,N-dimethylformamide.

Step 3

Compound (5e) can be obtained by decarboxylation of Compound (7-2) in a solvent by a general method. For example, Compound (5e) can be obtained by hydrolyzing Compound (7-2) and subsequent heating.

Meanwhile, Compound (1a-3) in which n1 is 2, 3 or 4, can be obtained by reaction of Compound (7-2) obtained above in the same manner as in the Preparation Method C1-1 Steps 2 to 5.

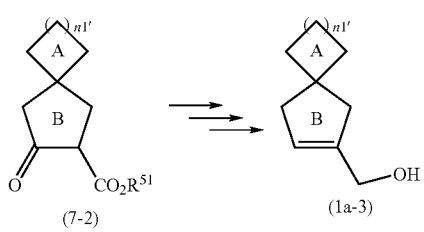

(wherein symbols are as defined above.)
Preparation Method D2-3

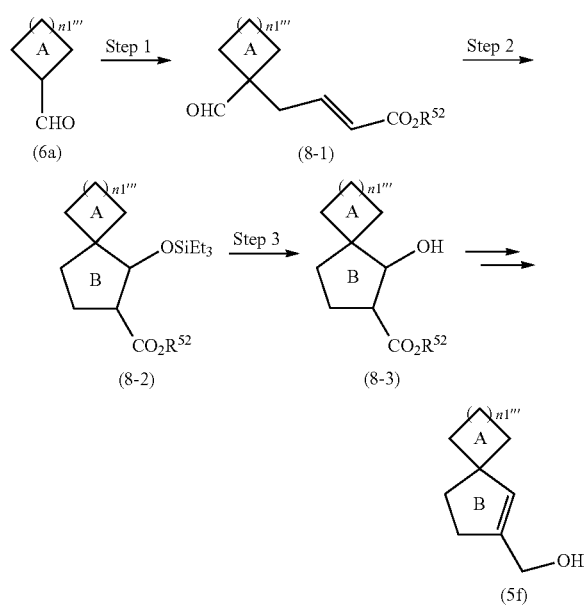

(wherein $n1'''$ is 2 or 3, $R^{52}$ is a $C_1$-$C_6$alkyl group, and other symbols are as defined above.)

Step 1

Compound (8-1) can be obtained by reaction of Compound (6a) with 2-hydroxy-3-butenoic acid methyl ester in a solvent in the presence of an acid catalyst at room temperature or with heat. The acid catalyst is preferably p-toluenesulfonic acid or the like. The solvent is preferably an aromatic hydrocarbon solvent such as toluene.

Step 2

Compound (8-2) can be obtained by reaction of Compound (8-1) with triethylsilane in a solvent in the presence of a catalyst at room temperature or with heat. The catalyst is preferably tris(triphenylphosphine)rhodium(I) chloride. The solvent is preferably an aromatic hydrocarbon solvent such as toluene.

Step 3

Compound (8-3) can be obtained by deprotection of Compound (8-2) in the usual manner.

Compound (5f) can be obtained by reaction of Compound (8-3) obtained above in the same manner as in the Preparation Method C1-1 Step 3 to Step 5.

Preparation Method E

Compound (2) in the Preparation Method A can be obtained as the following Compound (2a), (2b), (2c) or (2d).

Examples of the Preparation Method E are shown in Preparation Methods E1 to E3 below.

Preparation Method E1

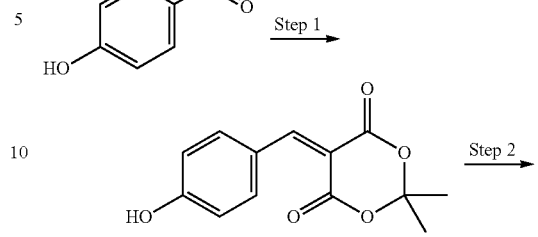

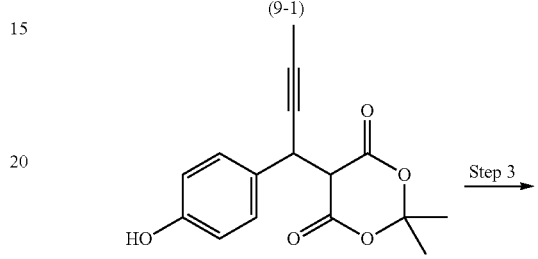

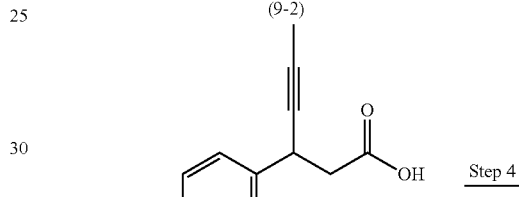

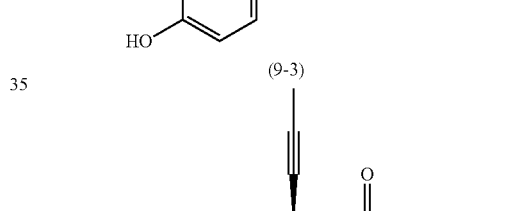

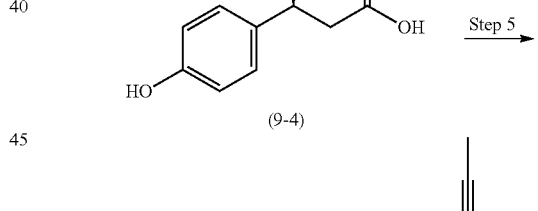

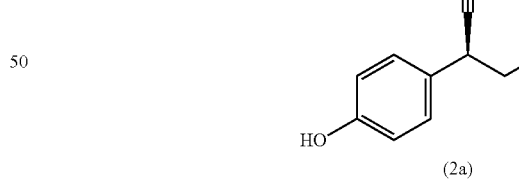

Step 1

Compound (9-1) can be obtained by reaction of 4-hydroxybenzaldehyde with Meldrum's acid in a solvent at room temperature or with heat. The solvent is preferably a polar solvent such as water.

Step 2

Compound (9-2) can be obtained by reaction of Compound (9-1) with 1-propynylmagnesium bromide in a solvent with cooling or at room temperature. The solvent is preferably an ether solvent such as tetrahydrofuran.

Step 3

Compound (9-3) can be obtained by heating Compound (9-2) in a solvent. The solvent is preferably a ketone solvent such as 3-pentanone, a polar solvent such as water, or a mixture thereof.

Step 4

Optically active Compound (9-4) can be obtained by reaction of Compound (9-3) with an optically active basic compound in a solvent followed by recrystallization and desalination in the usual manner. The solvent is preferably an alcoholic solvent such as 2-propanol. The optically active basic compound is preferably (1S,2R)-1-amino-2-indanol or (S)-α-methylbenzylamine.

Step 5

Compound (2a) can be obtained by reaction of Compound (9-4) with an alkylating agent in a solvent with cooling or at room temperature. The alkylating agent is preferably trimethylsilyldiazomethane, or the like. The solvent is preferably an aromatic hydrocarbon solvent such as toluene, an alcoholic solvent such as methanol, or a mixture thereof.

Compound (2a), which is racemate, can be obtained from Compound (9-3) by performing this Step.

Preparation Method E2

Compound (2b) or (2c) can be obtained according to the following methods as well as the Preparation Method E1.

An example of the Preparation Method E2 is shown in Preparation Method E2-1 below.

Preparation Method E2-1 atom, an oxygen atom and a sulfur atom, and which may be substituted by a $C_1$-$C_6$alkyl group (for example, a 2-oxazolyl group) or a di($C_1$-$C_6$alkoxy)methyl group; and other symbols are as defined above.)

Step 1

Compound (10-2) can be obtained by reaction of Compound (10-1) with Meldrum's acid in a solvent in the presence of an acid catalyst and an additive at room temperature or with heat. The acid is preferably acetic acid. The additive is preferably pyrrolidine. The solvent is preferably an aromatic hydrocarbon solvent such as toluene.

Step 2

Compound (10-3) can be obtained by reaction of Compound (10-2) with a nucleophilic agent in a solvent with cooling or at room temperature. The nucleophilic agent is preferably $C_2$-$C_6$alkynylmagnesium bromide, phenylmagnesium bromide, or the like. The solvent is preferably an ether solvent such as tetrahydrofuran.

Step 3

Compound (10-4) can be obtained by heating Compound (10-3) in a solvent. The solvent is preferably an alcoholic solvent such as ethanol, a polar solvent such as pyridine, or a mixture thereof.

Step 5

Compound (2b) can be obtained by deprotection of $X^{53}$, which is a hydroxy protecting group in Compound (10-4) or Compound (10-5), in the usual manner. For example, when the protecting group is a tetrahydropyranyl group, the com-

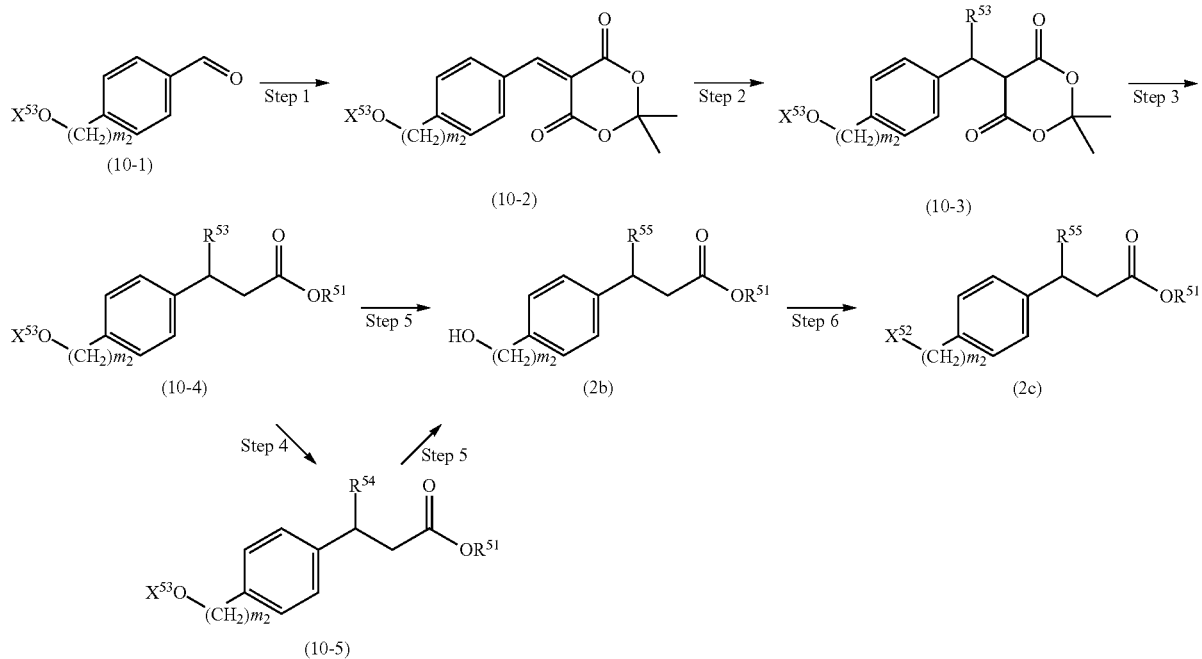

(wherein $X^{53}$ is a hydroxy protecting group, $R^{53}$ is a $C_2$-$C_6$alkynyl group, a phenyl group, or a five-membered heteroaryl group which has at least one heteroatom selected from a nitrogen atom, an oxygen atom and a sulfur atom, and which may be substituted by a $C_1$-$C_6$alkyl group (for example, a 2-oxazolyl group); $R^{54}$ is a $C_1$-$C_6$alkyl group, a $C_2$-$C_6$alkenyl group, or a di($C_1$-$C_6$alkoxy)methyl group; $R^{55}$ is a $C_1$-$C_6$alkyl group, a $C_2$-$C_6$alkenyl group, a $C_2$-$C_6$alkynyl group, a phenyl group, a five-membered heteroaryl group which has at least one heteroatom selected from a nitrogen pound can be obtained by reaction of Compound (10-4) or Compound (10-5) in a solvent in the presence of an acid catalyst at room temperature or with heat. The acid is preferably camphorsulfonic acid. The solvent is preferably an alcoholic solvent such as ethanol.

Step 6

Compound (2c) can be obtained by reaction of Compound (2b) with a halogenating agent in a solvent in the presence of an additive at room temperature or with heat. The halogenating agent is preferably N-bromo-succinimide. The additive is preferably triphenylphosphine. The solvent is preferably a halogenated hydrocarbon solvent such as chloroform.

Step 4

Compound (10-5) can be obtained from Compound (10-4) according to the following methods.

Step 4-1

Compound (10-5) in which $R^{54}$ is a $C_1$-$C_6$alkyl group can be obtained by reduction of Compound (10-4) in which $R^{53}$ is a $C_2$-$C_6$alkynyl group in a solvent at room temperature. The reduction method is preferably catalytic hydrogenation, and the catalyst is preferably palladium-carbon. The solvent is preferably an ether solvent such as tetrahydrofuran, an alcoholic solvent such as methanol, or a mixture thereof.

Step 4-2

Compound (10-5) in which $R^{54}$ is a $C_2$-$C_6$alkenyl group can be obtained by reduction of Compound (10-4) in which $R^{53}$ is a $C_2$-$C_6$alkynyl group in a solvent at room temperature. The reduction method is preferably catalytic hydrogenation, and the catalyst is preferably palladium-barium sulfate. The solvent is preferably an ether solvent such as tetrahydrofuran, an alcoholic solvent such as methanol, or a mixture thereof.

Step 4-3

Compound (10-5) in which $R^{54}$ is a di($C_1$-$C_6$alkoxy)methyl group, can be obtained from Compound (10-5) in which $R^{54}$ is a $C_2$-$C_6$alkenyl group, through the following steps.

Step 4-3-1

Compound (10-5) in which $R^{54}$ is an aldehyde group can be obtained by two-step oxidation of Compound (10-5) in which $R^{54}$ is a $C_2$-$C_6$alkenyl group in a solvent in the presence of a base at room temperature. The base is preferably 2,6-lutidine. The oxidant for the first step is preferably osmium tetroxide, and the oxidant for the second step is preferably sodium periodate. The solvent is preferably an ether solvent such as 1,4-dioxane, a polar solvent such as water, or a mixture thereof.

Step 4-3-2

Compound (10-5) in which $R^{54}$ is a di($C_1$-$C_6$alkoxy)methyl group can be obtained by reaction of Compound (10-5) in which $R^{54}$ is an aldehyde group, obtained in the above Step 4-3-1, in a solvent in the presence of an acid catalyst at room temperature or with heat. The acid is preferably camphorsulfonic acid. The solvent is preferably an alcoholic solvent such as methanol.

Preparation Method E3

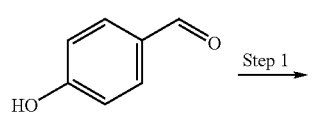

Step 1

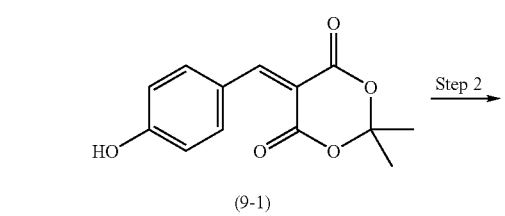

(9-1)

Step 2

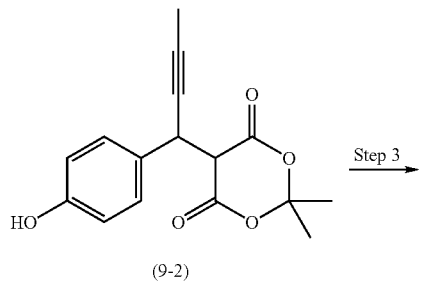

(9-2)

Step 3

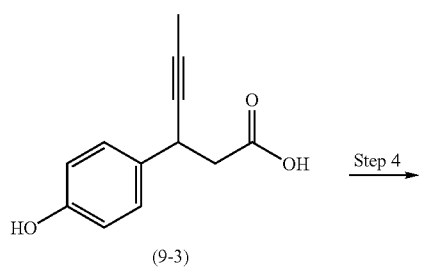

(9-3)

Step 4

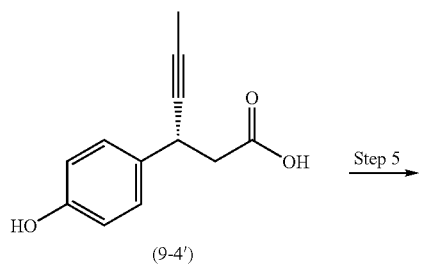

(9-4')

Step 5

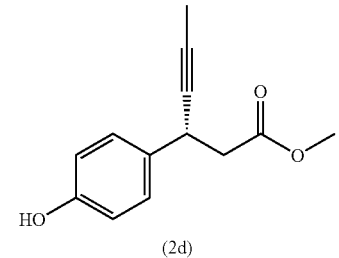

(2d)

Compound (9-4') or Compound (2d) can be obtained by the same reaction as in the Preparation Method E1-1 using (1R, 2S)-1-amino-2-indanol or (R)-α-methylbenzylamine as an optically active basic compound in Step 4.

Preparation Method as of a Compound Represented by the general formula [Ia] (Preparation Method A1s, A2s, A3s, A4s and A5s) can be performed in the same manner as in Preparation Method A of a compound represented by the above general formula [I] (Preparation Method A1, A2, A3, A4 and A5), respectively.

Preparation Method As

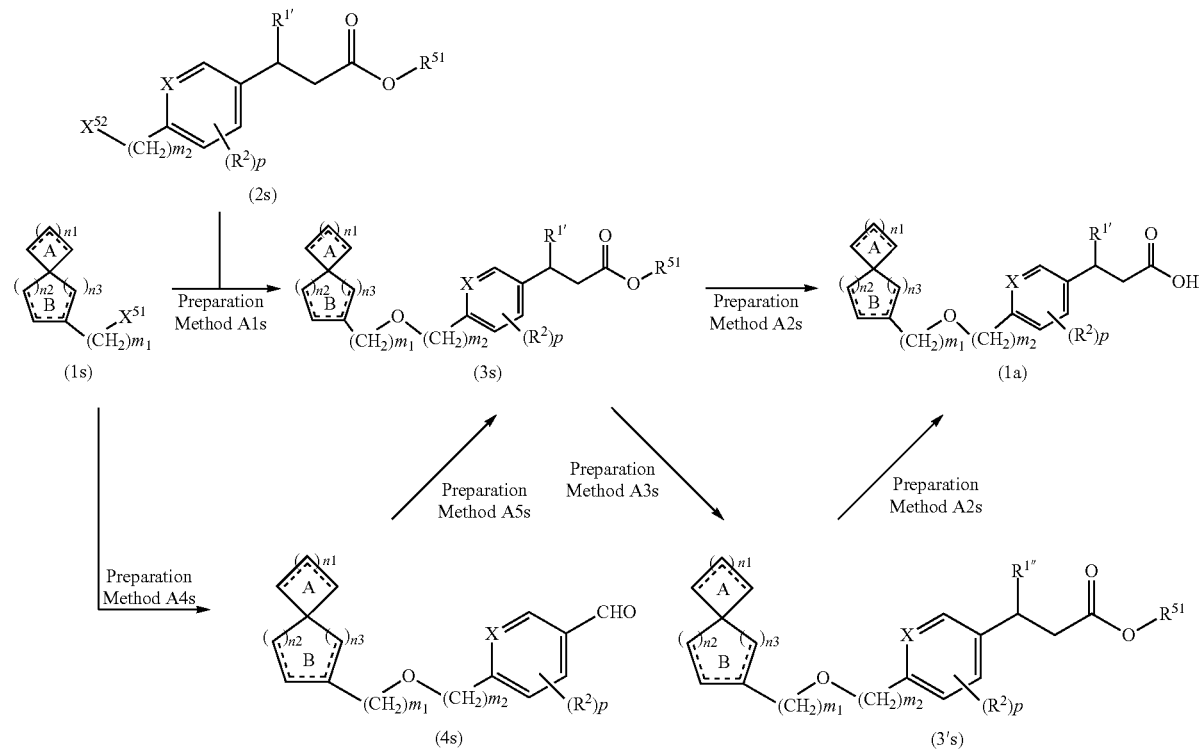

(wherein symbols are as defined above, and in Preparation Method A4s, the following Compound (20s):

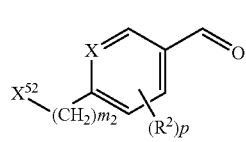

(wherein symbols are as defined above) can be used.)

When X is a nitrogen atom and $m_2$ is 0 in the general formula [Ia], the Preparation Method A1s below is preferable to the above Preparation Method A1.

Preparation Method A1s

Step 1

Compound (3s) in which X in the general formula [Ia] is a nitrogen atom, can be obtained by reaction of Compound (1s) in which $X^{51}$ is a hydroxy group and Compound (2s) in which $m_2$ is 0 and $X^{52}$ is a bromine atom or an iodine atom, in a solvent in the presence of a base and an additive at room temperature or with heat. The base is preferably cesium carbonate. The additive is preferably palladium(II) acetate, 2-(di-tert-butylphosphino)-1,1'-binaphthyl or the like. The solvent is, for example, preferably an aromatic hydrocarbon solvent such as toluene.

Preparation Method Es

Compound (2s) in the Preparation Method As can be obtained as the following Compound (2s-a), Compound (2s-b), Compound (2s-c) or Compound (2s-d). These compounds can be obtained in the same manner as in the above Preparation Method E (Preparation Method E1, E2 or E3).

Examples of the Preparation Method Es are shown in Preparation Methods Es1 to Es3 below.

Preparation Method Es1

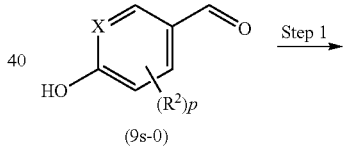

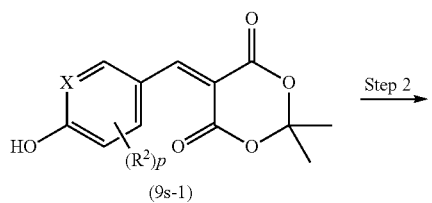

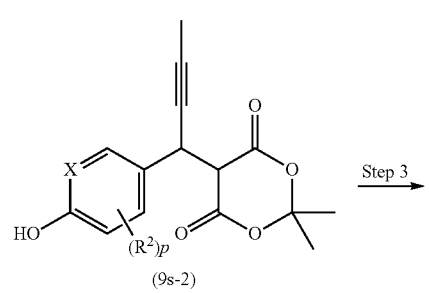

Preparation Method Es3
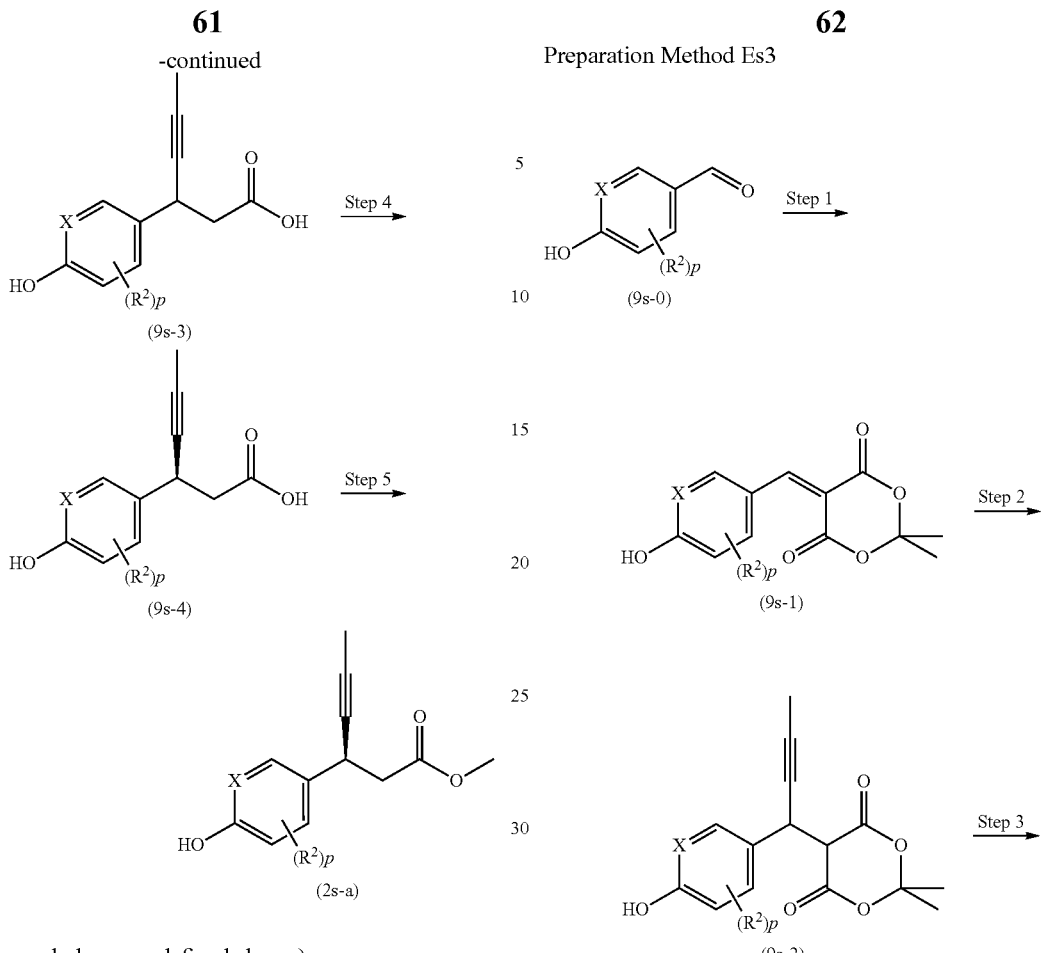
(wherein symbols are as defined above.)
Preparation Method Es2
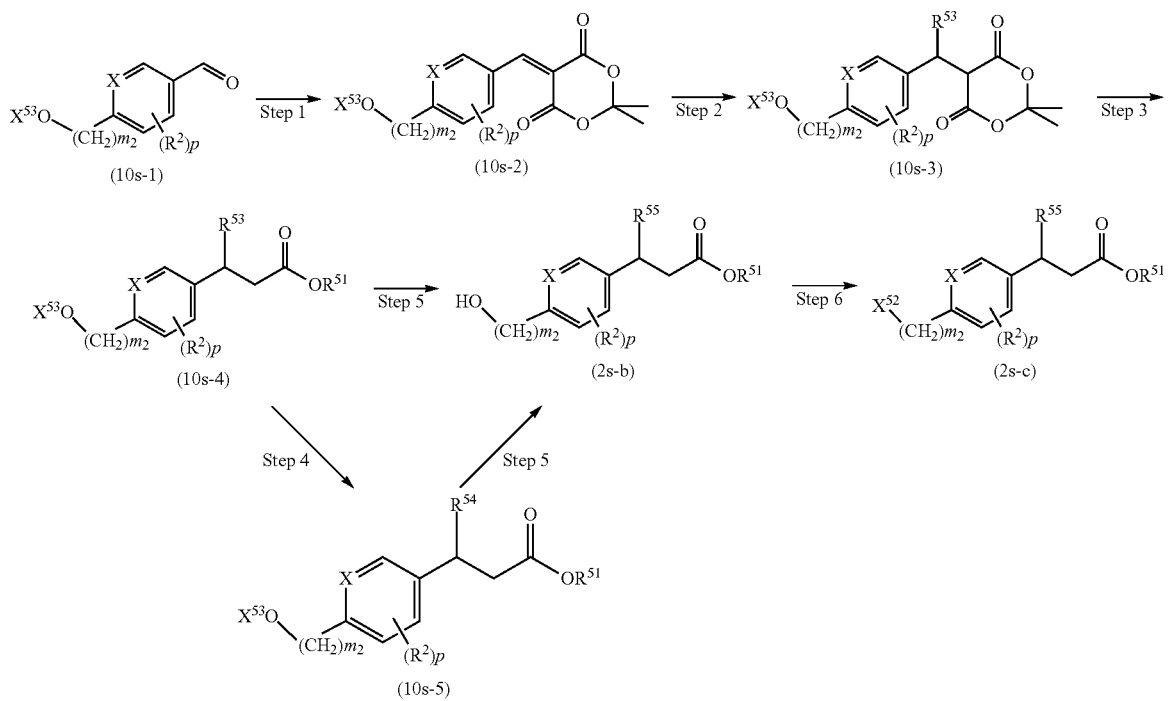
(wherein symbols are as defined above.)

63
-continued

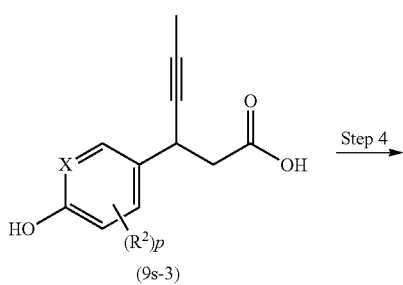

(9s-3)

Step 4 →

64
-continued

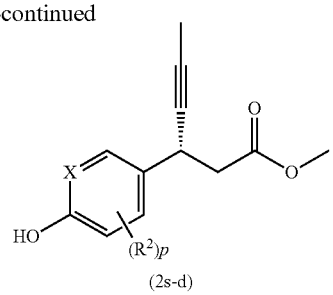

(2s-d)

(wherein symbols are as defined above.)

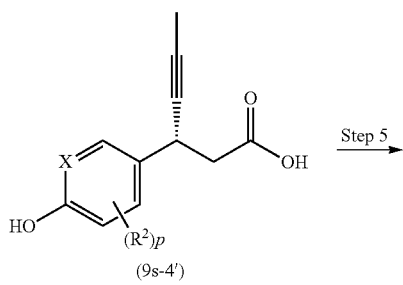

(9s-4')

Step 5 →

EXAMPLE

The preparation method for the compound of the present invention will be hereinafter explained in detail with examples provided, but the present invention is not limited thereto.

In the following examples, "room temperature" refers to a temperature of 1 to 40° C. In the examples, "%" refers to % by weight unless otherwise specified.

Example 1

Preparation of (S)-3-[4-(spiro[5.5]undec-2-en-2-ylmethoxy)-phenyl]-hex-4-ynoic acid

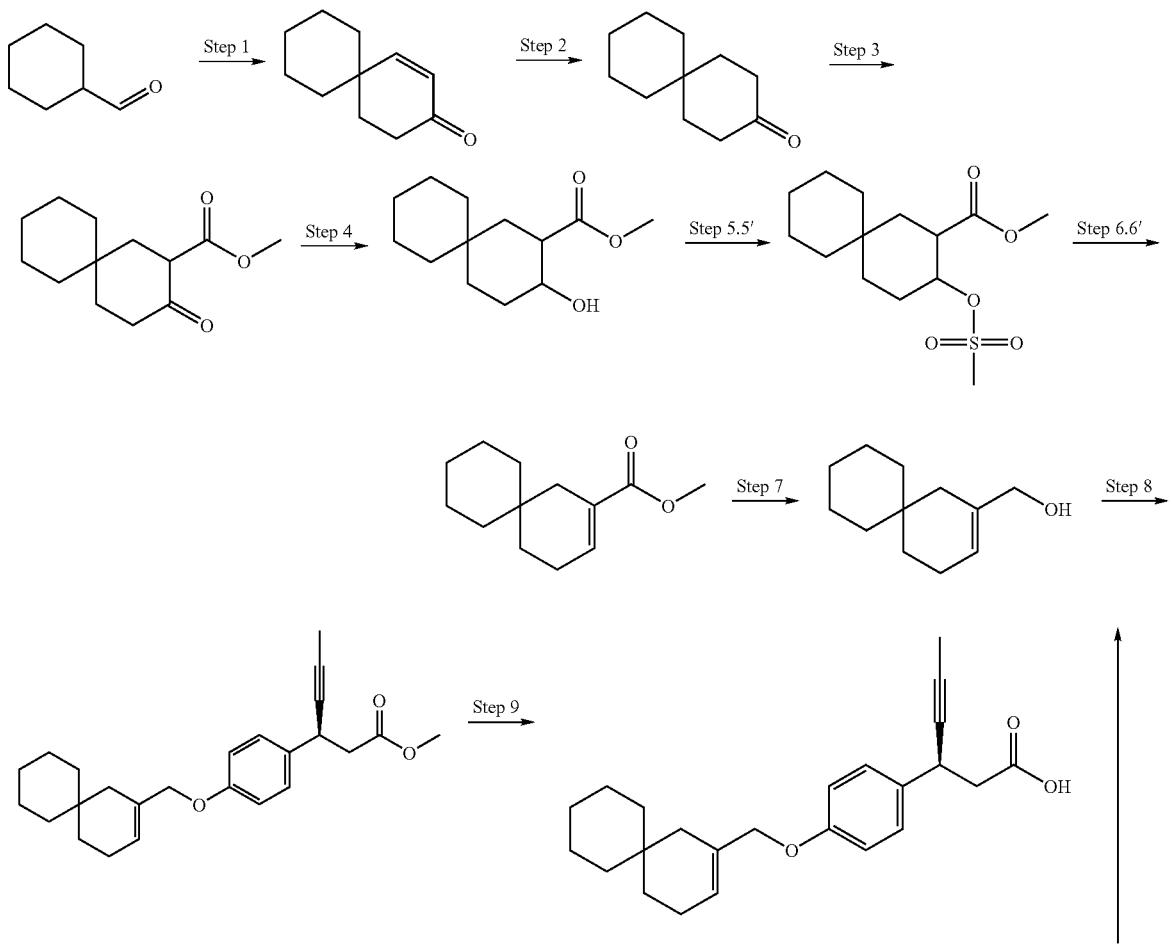

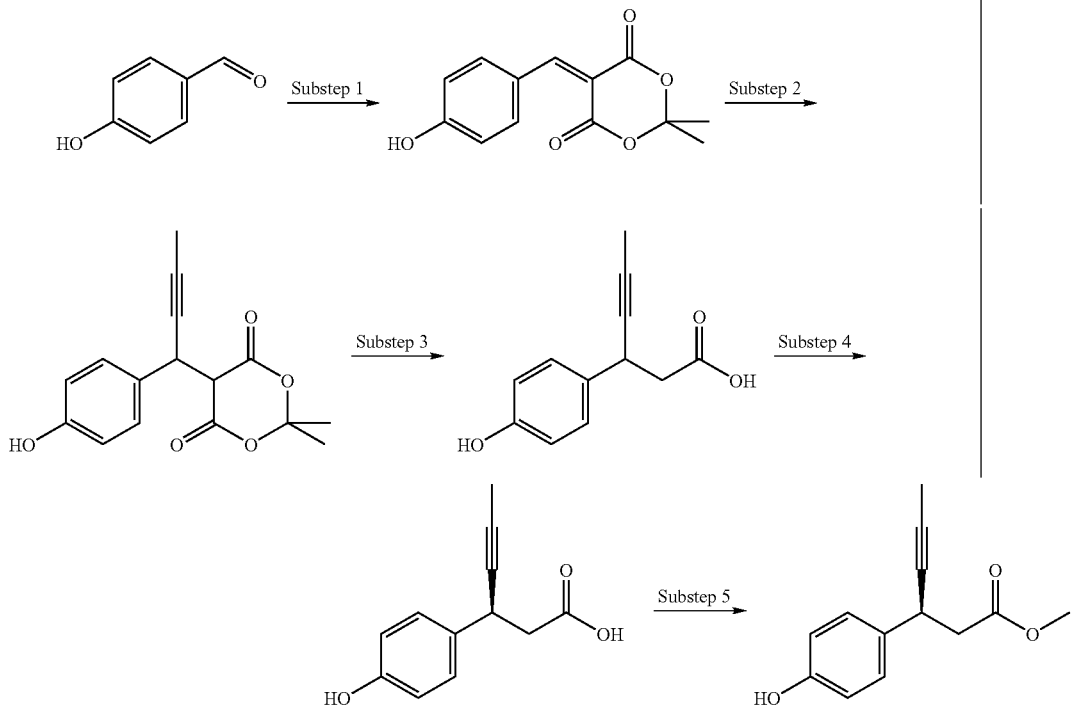

Step 1

To a solution of cyclohexanecarbaldehyde (10.7 mL) in toluene (100 mL) were added successively methyl vinyl ketone (15 mL) and concentrated sulfuric acid (0.1 mL). The reaction mixture was stirred at room temperature for 1 hour and then heated under reflux while stirring for 4 hours. After cooling down to room temperature, saturated aqueous sodium bicarbonate solution was added to the reaction mixture, followed by separation of the organic layer. Then, after the aqueous layer was extracted with toluene, the organic layers were combined, washed with saturated brine, dried and concentrated. The residue was purified by column chromatography on silica gel (ethyl acetate:hexane (volume ratio)=1:20 to 1:12) to give spiro[5.5]undec-1-en-3-one (8.9 g).

$^1$H-NMR (CDCl$_3$) δ: 1.63-1.45 (10H, m), 92 (2H, t, J=6.5 Hz), 2.44 (2H, t, J=6.5 Hz), 5.89 (1H, d, J=10.2 Hz), 6.85 (1H, d, J=10.2 Hz).

Step 2

To a solution of spiro[5.5]undec-1-en-3-one (8.9 g) obtained in Step 1 in tetrahydrofuran (360 mL) was added 5% palladium carbon (0.89 g), followed by stirring the reaction mixture at room temperature in an atmosphere of hydrogen under normal pressure for 2 hours. Then, the reaction mixture was filtered through Celite and the filtrate was concentrated to obtain spiro[5.5]undecan-3-one (9.3 g).

$^1$H-NMR (CDCl$_3$) δ: 1.54-1.43 (10H, m), 1.71 (4H, t, J=7.2 Hz), 2.33 (4H, t, J=7.2 Hz).

Step 3

To a solution of dimethyl carbonate (17.9 g) in tetrahydrofuran (130 mL) were added 60% sodium hydride (9.9 g) and potassium tert-butoxide (0.14 g). To the mixture was added a solution of spiro[5.5]undecan-3-one (20.6 g) obtained in the same manner as in Step 2 in tetrahydrofuran (120 mL) at 85° C. over 2 hours, followed by stirring the reaction mixture at 85° C. for 1.5 hours. After cooling down to room temperature and adding 15% aqueous acetic acid solution (94.2 mL), the reaction mixture was extracted with ethyl acetate. The organic layer was washed with saturated brine, dried and concentrated to give 3-oxo-spiro[5.5]undecane-2-carboxylic acid methyl ester (29.6 g).

$^1$H-NMR (CDCl$_3$) δ: 1.26-1.53 (14H, brm), 2.07 (2H, s), 2.26 (2H, t, J=6.7 Hz), 3.76 (3H, s), 12.13 (1H, s).

Step 4

To a solution of 3-oxo-spiro[5.5]undecane-2-carboxylic acid methyl ester (29.6 g) obtained in Step 3 in a mixed solvent of methanol (200 mL)-tetrahydrofuran (50 mL), sodium borohydride (4.67 g) was added in three portions under ice-cooling, followed by stirring the reaction mixture under ice-cooling for 1 hour. Then, after addition of 1N aqueous hydrochloric acid solution to the reaction mixture, the resulting insolubles were filtered off. Methanol in the filtrate was evaporated off in vacuo, followed by extraction with ethyl acetate. The organic layer was washed with saturated brine, dried and concentrated. The residue was purified by column chromatography on silica gel (ethyl acetate:hexane (volume ratio)=1:10 to 1:3) to give trans-3-hydroxy-spiro[5.5]undecane-2-carboxylic acid methyl ester (4.15 g) and cis-3-hydroxy-spiro[5.5]undecane-2-carboxylic acid methyl ester (4.9 g).

$^1$H-NMR (trans-isomer, CDCl$_3$) δ: 1.05-1.25 (3H, m), 1.37-1.52 (10H, m), 1.68-1.76 (1H, m), 1.77-1.85 (1H, m), 1.90-1.97 (1H, m), 2.44-2.51 (1H, m), 2.74 (1H, brs), 3.72 (3H, s), 3.74-3.80 (1H, m).

$^1$H-NMR (cis-isomer, CDCl$_3$) δ: 1.23-1.31 (3H, m), 1.67-1.36 (11H, m), 1.69-1.77 (2H, m), 2.58 (1H, td, J=8.6, 2.3 Hz), 3.08 (1H, brs), 3.71 (3 H, s), 4.16-4.20 (1H, m).

Step 5

To a solution of trans-3-hydroxy-spiro[5.5]undecane-2-carboxylic acid methyl ester (2.0 g) obtained in the same manner as in Step 4 in chloroform (40 mL) were added successively triethylamine (1.7 mL) and methanesulfonyl chloride (0.75 mL) under ice-cooling, followed by stirring the reaction mixture at room temperature for 1.5 hours. Then, to the reaction mixture was added saturated aqueous sodium bicarbonate solution, followed by extraction with chloroform. The organic layer was dried and concentrated to give trans-3-methanesulfonyloxy-spiro[5.5]undecane-2-carboxylic acid methyl ester (3.0 g).

$^1$H-NMR (CDCl$_3$) δ: 1.14-1.31 (5H, m), 1.40-1.46 (8H, brm), 1.72-1.81 (2H, m), 1.95 (1H, d, J=13.2 Hz), 2.17-2.23 (1H, m), 2.77 (1H, ddd, J=5.0, 13.2, 11.4 Hz), 3.00 (3H, s), 3.72 (3H, s).

Step 5'

To a solution of cis-3-hydroxy-spiro[5.5]undecane-2-carboxylic acid methyl ester (1.2 g) obtained in the same manner as in Step 4 in chloroform (25 mL) were added successively pyridine (0.6 mL), 4-dimethylaminopyridine (32 mg) and methanesulfonyl chloride (1.85 mL) under ice-cooling, followed by stirring the reaction mixture at room temperature for 1.5 hours. Then, to the reaction mixture was added saturated aqueous sodium bicarbonate solution, followed by extraction with chloroform twice. The organic layer was dried and concentrated to give cis-3-methanesulfonyloxy-spiro[5.5]undecane-2-carboxylic acid methyl ester (1.7 g).

$^1$H-NMR (CDCl$_3$) δ: 1.27-1.60 (10H, brm), 1.65 (2H, d, J=8.5 Hz), 1.70-1.76 (1H, m), 1.84 (1H, dt, J=15.1, 2.2 Hz), 2.13 (1H, dd, J=15.1, 3.2 Hz), 2.58 (1H, td, J=8.5, 2.2 Hz), 2.69 (1H, dt, J=13.1, 3.2 Hz), 3.00 (3H, s), 3.07-3.09 (1H, m), 3.72 (3H, s).

Step 6

To a solution of trans-3-methanesulfonyloxy-spiro[5.5]undecane-2-carboxylic acid methyl ester (3.0 g) obtained in Step 5 in tetrahydrofuran (20 mL) was added 1,8-diazabicyclo[5.4.0]undec-7-ene (2.65 mL), followed by stirring the reaction mixture at 70° C. for 6 hours. After cooling down to room temperature and adding 2N aqueous hydrochloric acid solution, the reaction mixture was extracted with ethyl acetate. The organic layer was washed with saturated brine, dried and concentrated to give spiro[5.5]undec-2-ene-2-carboxylic acid methyl ester (1.9 g).

$^1$H-NMR (CDCl$_3$) δ: 1.23-1.37 (4H, m), 1.41-1.50 (8H, m), 2.10-2.13 (2H, m), 2.16-2.22 (2H, m), 3.74 (3H, s), 6.94-6.96 (1H, m).

Step 6'

Cis-3-methanesulfonyloxy-spiro[5.5]undecane-2-carboxylic acid methyl ester (1.7 g) obtained in Step 5' was subjected to the reaction in the same condition as in Step 6, to give spiro[5.5]undec-2-ene-2-carboxylic acid methyl ester (0.42 g).

Step 7

To a solution of spiro[5.5]undec-2-ene-2-carboxylic acid methyl ester (1.9 g) obtained in the same manner as in Step 6 or 6' in tetrahydrofuran (40 mL) was added dropwise a 1M toluene solution of diisobutylaluminum hydride (21 mL) under argon atmosphere at −70° C., followed by stirring the reaction mixture at −70° C. for 1 hour. Then, after addition of 2N aqueous hydrochloric acid solution, the reaction mixture was heated up to room temperature and extracted with ethyl acetate. The organic layer was washed with saturated brine, dried and concentrated. The residue was purified by column chromatography on silica gel (ethyl acetate:hexane (volume ratio)=1:4) to give spiro[5.5]undec-2-en-2-yl-methanol (1.59 g).

$^1$H-NMR (CDCl$_3$) δ: 1.22-1.35 (4H, m), 1.40-1.49 (8H, m), 1.85-1.88 (2H, m), 2.01-2.07 (2H, m), 3.98 (2H, d, J=4.9 Hz), 5.61-5.65 (1H, m).

Step 8

To a solution of spiro[5.5]undec-2-en-2-yl-methanol (0.45 g) obtained in the same manner as in Step 7 in tetrahydrofuran (7 mL) were added successively (S)-3-(4-hydroxyphenyl)-hex-4-ynoic acid methyl ester (0.73 g) obtained in Substep 5 described below, triphenylphosphine (0.92 g) and 1,1'-azobis (N,N-dimethylformamide) (0.6 g), followed by stirring the reaction mixture at room temperature for 4 hours. Then, the reaction mixture was concentrated and the residue was purified by column chromatography on silica gel (ethyl acetate: hexane (volume ratio)=1:4) to give (S)-3-[4-(spiro[5.5]undec-2-en-2-ylmethoxy)-phenyl]-hex-4-ynoic acid methyl ester (0.82 g).

$^1$H-NMR (CDCl$_3$) δ: 1.24-1.34 (5H, m), 1.40-1.46 (7H, m), 1.83 (3H, d, J=2.3 Hz), 1.90 (2H, s), 2.04 (2H, s), 2.64 (1H, dd, J=15.1, 7.1 Hz), 2.75 (1H, dd, J=15.1, 8.3 Hz), 3.66 (3H, s), 4.02-4.09 (1H, m), 4.34 (2H, s), 5.73 (1H, s), 6.85 (2H, d, J=8.7 Hz), 7.26 (2H, d, J=8.7 Hz).

Step 9

To a solution of (S)-3-[4-(spiro[5.5]undec-2-en-2-yl-methoxy)-phenyl]-hex-4-ynoic acid methyl ester (0.82 g) obtained in Step 8 in a mixed solvent of tetrahydrofuran (4 mL)-methanol (4 mL) was added 2N aqueous sodium hydroxide solution (2 mL), followed by stirring the reaction mixture at room temperature for 14 hours. Then, after addition of 1N aqueous hydrochloric acid solution, the reaction mixture was extracted with ethyl acetate. The organic layer was washed with saturated brine, dried and concentrated. The residue was purified by column chromatography on silica gel (ethyl acetate:hexane (volume ratio)=1:1) to give (S)-3-[4-(spiro[5.5]undec-2-en-2-ylmethoxy)-phenyl]-hex-4-ynoic acid (0.77 g) as the desired compound.

Substep 1

To a suspension of 4-hydroxybenzaldehyde (35 g) in water (300 mL) heated up to 75° C. was added a suspension of Meldrum's acid (43.4 g) in water (300 mL), followed by stirring the reaction mixture successively at 75° C. for 8.5 hours, at room temperature for 14 hours and under ice-cooling for 2 hours. The resulting crystal was filtered, washed with ice-cold water and dried in vacuo to give 5-(4-hydroxybenzylidene)-2,2-dimethyl-[1,3]dioxane-4,6-dione (47.3 g).

$^1$H-NMR (DMSO-d$_6$) δ: 1.71 (6H, s), 6.89 (2H, d, J=8.8 Hz), 8.17 (2H, d, J=8.8 Hz), 8.25 (1H, s), 10.93 (1H, s).

Substep 2

To a 0.5M tetrahydrofuran solution of 1-propynylmagnesium bromide (800 mL) was added dropwise a solution of 5-(4-hydroxybenzylidene)-2,2-dimethyl-[1,3]dioxane-4,6-dione (47.3 g) obtained in Substep 1 in tetrahydrofuran (650 mL) under argon atmosphere at 11° C. over 40 minutes, followed by stirring the reaction mixture at room temperature for 1 hour. Then, to the reaction mixture were added successively aqueous ammonium chloride solution (34 g/1 L) and hexane (1 L), followed by removing the organic layer. After adding saturated aqueous potassium hydrogen sulfate solution to the aqueous layer and adjusting a pH to 1, the aqueous layer was extracted with ethyl acetate twice. The organic layer was dried and concentrated to give 5-[1-(4-hydroxyphenyl)-but-2-ynyl]-2,2-dimethyl-[1,3]dioxan e-4,6-dione (54.8 g).

$^1$H-NMR (DMSO-d$_6$) δ: 1.60 (3H, s), 1.77 (3H, s), 1.81 (3H, d, J=2.6 Hz), 4.60 (1H, t, J=2.4 Hz), 4.83 (1H, d, J=2.8 Hz), 6.67 (2H, d, J=8.6 Hz), 7.30 (2H, d, J=8.6 Hz), 9.30 (1H, s).

Substep 3

To a suspension of 5-[1-(4-hydroxyphenyl)-but-2-ynyl]-2, 2-dimethyl-[1,3]dioxan e-4,6-dione (54.8 g) obtained in Substep 2 in 3-pentanone (200 mL) was added water (100 mL), followed by stirring the reaction mixture at 100° C. for 2 days. After cooling down to room temperature, the aqueous layer of the reaction mixture was saturated with sodium chloride, followed by extraction with 3-pentanone. The organic layer was dried and concentrated, followed by recrystallizing the residue from an ethyl acetate-hexane mixed solvent to give 3-(4-hydroxyphenyl)-hex-4-ynoic acid (34.2 g).

$^1$H-NMR (DMSO-d$_6$) δ: 1.76 (3H, brs), 2.55 (2H, d, J=7.7 Hz), 3.87 (1H, t, J=7.7 Hz), 6.68 (2H, dd, J=8.6, 1.4 Hz), 7.13 (2H, dd, J=8.6, 1.2 Hz), 9.28 (1H, s), 12.20 (1H, s).

Substep 4

To a solution of 3-(4-hydroxyphenyl)-hex-4-ynoic acid (34.2 g) obtained in the same manner as in Substep 3 in 2-propanol (560 mL) was added a solution of (1S,2R)-1-amino-2-indanol (26.1 g) in 2-propanol (560 mL) at 70° C. After this mixture was stirred at room temperature for 20 hours, the resulting crystal was filtered and heat-dissolved in 2-propanol (1.1 L). After this mixture was further stirred at room temperature for 15 hours, the resulting crystal was filtered and heat-dissolved in 2-propanol (800 mL). After this mixture was stirred at room temperature for 18 hours, the resulting crystal was filtered and suspended in ethyl acetate (150 mL)-water (60 mL). To the suspension was added aqueous potassium hydrogen sulfate solution with vigorous stirring until the suspension became a solution. The reaction mixture was extracted with ethyl acetate twice. The organic layer was washed with saturated brine, dried and concentrated to give (S)-3-(4-hydroxyphenyl)-hex-4-ynoic acid (10.9 g, 99.4% ee). The optical purity was determined by chiral HPLC analysis (column: DaicelChiralpakAD-RH, mobile phase: 15 v/v % aqueous acetonitrile solution containing 0.1% trifluoroacetic acid).

Substep 5

To a solution of (S)-3-(4-hydroxyphenyl)-hex-4-ynoic acid (10.9 g) obtained in Substep 4 in a mixed solvent of toluene (100 mL)-methanol (33 mL) was added dropwise a hexane solution of trimethylsilyldiazomethane (2M, 32 mL) under ice-cooling for 10 minutes, followed by stirring at room temperature for 1 hour. Then, to the reaction mixture was added acetic acid (0.93 mL), followed by concentration. The residue was purified by column chromatography on silica gel (ethyl acetate:hexane (volume ratio)=1:3 to 1:2) to give (S)-3-(4-hydroxyphenyl)-hex-4-ynoic acid methyl ester (10.6 g).

$^1$H-NMR (CDCl$_3$) δ: 1.84 (3H, d, J=2.6 Hz), 2.66 (1H, dd, J=15.2, 7.1 Hz), 2.77 (1H, dd, J=15.3, 8.3 Hz), 3.67 (3H, s), 4.03-4.09 (1H, m), 4.80 (1H, s), 6.78 (2H, d, J=8.6 Hz), 7.25 (2H, d, J=8.6 Hz).

Example 2

Preparation of (S)-3-[4-(spiro[5.5]undec-2-en-2-ylmethoxy)-phenyl]-hex-4-ynoic acid sodium salt

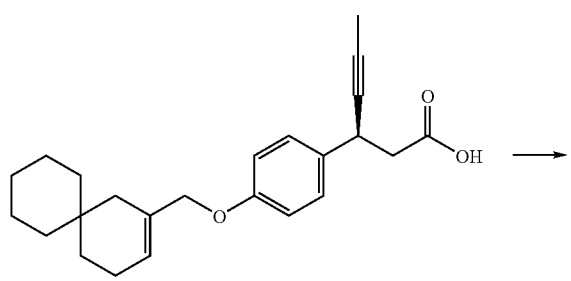

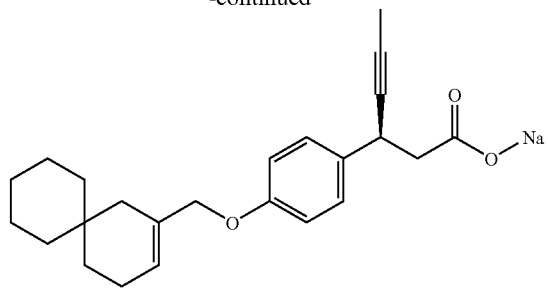

To a solution of the compound (0.77 g) obtained in Example 1 in ethanol (7 mL) was added 4N aqueous sodium hydroxide solution (0.5 mL), followed by stirring at room temperature for 30 minutes. The reaction mixture was concentrated, and after addition of ethanol to the residue, the reaction mixture was further concentrated by azeotropic distillation twice (hereinafter abbreviated as "distilled azeotropically with ethanol"). The residue was dried in vacuo to give (S)-3-[4-(spiro[5.5]undec-2-en-2-ylmethoxy)-phenyl]-hex-4-ynoic acid sodium salt (0.73 g) as the desired compound.

Example 3

Preparation of (S)-3-[4-(spiro[5.6]dodec-2-en-2-ylmethoxy)-phenyl]-hex-4-ynoic acid Step 1

In the same manner as in Steps 1 to 7 of Example 1, spiro[5.6]dodec-2-en-2-yl-methanol was obtained from cycloheptanecarbaldehyde.

$^1$H-NMR (CDCl$_3$) δ: 1.65-1.20 (14H, m), 1.78-1.80 (2H, m), 2.00-2.06 (2H, m), 3.98 (2H, s), 5.65-5.68 (1H, m).

Step 2

In the same manner as in Steps 8 to 9 of Example 1, the desired (S)-3-[4-(spiro[5.6]dodec-2-en-2-ylmethoxy)-phenyl]-hex-4-ynoic acid was obtained from the compound obtained in the above Step 1.

Example 4

Preparation of (S)-3-[4-(spiro[5.6]dodec-2-en-2-ylmethoxy)-phenyl]-hex-4-ynoic acid sodium salt In the same manner as in Example 2, the desired compound was obtained from the compound obtained in Example 3.

Example 5

Preparation of (S)-3-[4-(spiro[4.5]dec-7-en-7-ylmethoxy)-phenyl]-hex-4-ynoic acid Step 1

In the same manner as in Steps 1 to 7 of Example 1, spiro[4.5]dec-7-en-7-yl-methanol was obtained from cyclopentanecarbaldehyde.

$^1$H-NMR (CDCl$_3$) δ: 1.22 (1H, brs), 1.37-1.42 (4H, m), 1.46 (2H, t, J=6.4 Hz), 1.61-1.68 (4H, m), 1.89-1.92 (2H, m), 2.06-2.12 (2H, m), 3.98 (2H, s), 5.64-5.68 (1H, m).

Step 2

In the same manner as in Steps 8 to 9 of Example 1, the desired compound was obtained from the compound obtained in the above Step 1.

Example 6

Preparation of (S)-3-[4-(spiro[4.5]dec-7-en-7-yl-methoxy)-phenyl]-hex-4-ynoic acid sodium salt In the same manner as in Example 2, the desired compound was obtained from the compound obtained in the same manner as in Example 5.

Example 7

Preparation of (S)-3-[4-(spiro[4.5]dec-6-en-7-yl-methoxy)-phenyl]-hex-4-ynoic acid

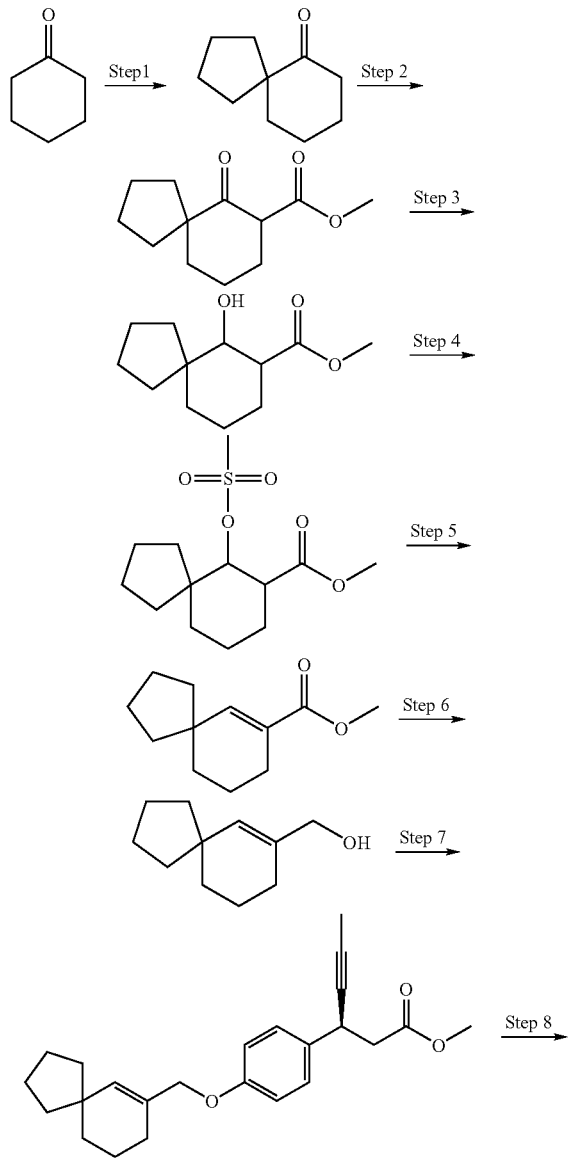

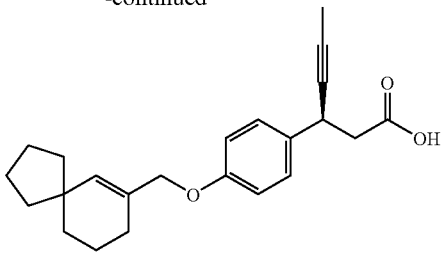

Step 1

To a suspension of potassium tert-butoxide (22.4 g) in toluene (120 mL) was added a solution of cyclohexanone (9.82 g) and 1,4-dibromobutane (21.6 g) in toluene (30 mL) while stirring, followed by stirring the reaction mixture at 95° C. for 3.5 hours. After cooling down to room temperature and adding ice-cold water (100 mL) and 2N aqueous hydrochloric acid solution (50 mL) to the reaction mixture, the organic layer was separated. Then, after the aqueous layer was extracted with ethyl acetate, the organic layers were combined, washed with saturated brine, dried and concentrated. The residue was distilled in vacuo (90 to 100° C./3 to 4 mmHg) to give spiro[4.5]decan-6-one (7.85 g).

$^1$H-NMR (CDCl$_3$) δ: 1.36-1.43 (2H, m), 1.54-1.63 (4H, m), 1.69-1.74 (4H, m), 1.79-1.86 (2H, m), 2.01-2.09 (2H, m), 2.38-2.42 (2H, m).

Step 2

To a suspension of 60% sodium hydride (4.59 g) and potassium tert-butoxide (1.52 g) in tetrahydrofuran (100 mL) was added dimethyl carbonate (7.89 mL) under argon atmosphere at 85° C. To this mixture was added dropwise a solution of spiro[4.5]decan-6-one (8.74 g) obtained in the same manner as in Step 1 in tetrahydrofuran (70 mL) over 1.5 hours. The reaction mixture was heated under reflux for 3 hours. After ice-cooling, to the reaction mixture were added successively acetic acid (7.3 mL), water (85 mL) and ethyl acetate (175 mL), followed by separation of the organic layer. The organic layer was washed with saturated brine, dried and concentrated. The residue was purified by column chromatography on silica gel (ethyl acetate:hexane (volume ratio)=1:100 to 1:90) to give 6-oxo-spiro[4.5]decane-7-carboxylic acid methyl ester (9.99 g).

$^1$H-NMR (CDCl$_3$) δ: 1.07-1.18 (0.5H, m), 1.39-1.50 (1.5H, m), 1.53-1.87 (8.5H, m), 1.98-2.29 (3H, m), 2.37-2.44 (0.5H, m), 3.57 (0.5H, dd, J=12.2, 6.2 Hz), 3.74 (1.5H, s), 3.74 (1.5H, s), 12.41 (0.5H, s).

Step 3

To a solution of 6-oxo-spiro[4.5]decane-7-carboxylic acid methyl ester (9.99 g) obtained in Step 2 in methanol (200 mL) was added platinum oxide (0.2 g) in an atmosphere of hydrogen (<0.3 Mpa) at room temperature overnight. Then, the reaction mixture was filtered through Celite and the filtrate was concentrated. After adding ethyl acetate (30 mL) and n-hexane (30 mL) to the residue, the resulting insolubles were filtered off. The filtrate was concentrated and then dried in vacuo to give 6-hydroxy-spiro[4.5]decane-7-carboxylic acid methyl ester (10.11 g).

$^1$H-NMR (CDCl$_3$) δ: 1.18-2.12 (13H, m), 2.31-2.56 (2H, m), 2.86 (1H, d, J=2.3 Hz), 3.64-3.75 (4H, m).

Step 4

To a solution of 6-hydroxy-spiro[4.5]decane-7-carboxylic acid methyl ester (10.1 g) obtained in Step 3 and triethylamine (19.9 mL) in chloroform (100 mL) was added dropwise methanesulfonyl chloride (5.2 mL) under ice-cooling, followed by stirring the reaction mixture at room temperature for 2 hours. Then, after addition of triethylamine (10 mL), the reaction mixture was stirred at room temperature for 30 minutes. After ice-cooling, ice-cold water (30 mL) and saturated aqueous sodium bicarbonate solution (50 mL) were added to the reaction mixture, followed by separation of the organic layer. The organic layer was washed with saturated brine, dried and concentrated to give a crude 6-methanesulfonyloxy-spiro[4.5]decane-7-carboxylic acid methyl ester (22 g).
Step 5

To a solution of the crude 6-methanesulfonyloxy-spiro [4.5]decane-7-carboxylic acid methyl ester (22 g) obtained in Step 4 in tetrahydrofuran (135 mL) was added 1,8-diazabicyclo[5.4.0]undec-7-ene (13.8 mL), followed by stirring the reaction mixture at 60° C. for 1.5 hours. After ice-cooling and adding 1N aqueous hydrochloric acid solution (102 mL), the reaction mixture was extracted with ethyl acetate. The organic layer was washed with saturated brine, dried and concentrated. The residue was purified by column chromatography on silica gel (ethyl acetate:hexane (volume ratio)=3:97 to 25:75) to give spiro[4.5]dec-6-ene-7-carboxylic acid methyl ester (5.485 g).

$^1$H-NMR (CDCl$_3$) δ: 1.44-1.75 (12H, m), 2.22 (2H, ddd, J=6.3, 6.3, 1.9 Hz), 3.72 (3H, s), 6.76 (1H, brs).
Step 6

To a solution of spiro[4.5]dec-6-ene-7-carboxylic acid methyl ester (3.50 g) obtained in Step 5 in tetrahydrofuran (70 mL) was added dropwise a 1M toluene solution of diisobutylaluminum hydride (54.6 mL) under argon atmosphere at −70° C. over 15 minutes, followed by stirring the reaction mixture at −70° C. for 2 hours. After raising the temperature up to −15° C., to the reaction mixture were added successively 2N aqueous hydrochloric acid solution (60 mL) and ethyl acetate (100 mL), followed by separation of the organic layer. The organic layer was washed with saturated brine, dried and concentrated. The residue was purified by column chromatography on silica gel (ethyl acetate:hexane (volume ratio)=3:97 to 15:85) to give spiro[4.5]dec-6-ene-7-methanol (2.375 g).

$^1$H-NMR (CDCl$_3$) δ: 1.25-1.30 (1H, m), 1.42-1.47 (6H, m), 1.60-1.69 (6H, m), 1.97 (2H, brdd, J=6.3, 6.3 Hz), 3.98 (2H, s), 5.46 (1H, s).
Step 7

To a solution of spiro[4.5]dec-6-ene-7-methanol (1.0 g) obtained in Step 6, (S)-3-(4-hydroxyphenyl)-hex-4-ynoic acid methyl ester (1.77 g) obtained in the same manner as in Substep 5 of Example 1 and triphenylphosphine (2.64 g) in tetrahydrofuran (14 mL) was added 1,1′-(azodicarbonyl)dipiperidine (2.26 g) under ice-cooling, followed by stirring at room temperature for 1.5 hours. After the reaction mixture was concentrated, toluene (15 mL) and hexane (45 mL) were added to the residue, followed by stirring at room temperature for 10 minutes. The resulting insolubles were filtered off and the filtrate was concentrated. The residue was purified by column chromatography on silica gel (ethyl acetate:hexane (volume ratio))=4:96 to 8:92) to give (S)-3-[4-(spiro[4.5]dec-6-en-7-ylmethoxy)-phenyl]-hex-4-ynoic acid methyl ester (2.085 g).

$^1$H-NMR (CDCl$_3$) δ: 1.45-1.48 (6H, m), 1.62-1.69 (6H, m), 1.82 (3H, d, J=2.4 Hz), 2.03 (2H, brdd, J=6.3, 6.3 Hz), 2.65 (1H, dd, J=15.2, 7.0 Hz), 2.75 (1H, dd, J=15.2, 8.2 Hz), 3.66 (3H, s), 4.02-4.08 (1H, m), 4.33 (2H, s), 5.58 (1H, s), 6.84-6.88 (2H, m), 7.24-7.27 (2H, m).
Step 8

To a solution of (S)-3-[4-(spiro[4.5]dec-6-en-7-ylmethoxy)-phenyl]-hex-4-ynoic acid methyl ester (1.33 g) obtained in Step 7 in a mixed solvent of tetrahydrofuran (13 mL)-methanol (13 mL) was added 2N aqueous sodium hydroxide solution (4.6 mL), followed by stirring the reaction mixture at room temperature overnight. Then, to the reaction mixture were added successively 2N aqueous hydrochloric acid solution (5.1 mL), ethyl acetate (100 mL) and sodium sulfate (50 g), followed by stirring for 30 minutes. The reaction mixture was filtered and the filtrate was concentrated. The residue was purified by column chromatography on silica gel (ethyl acetate:hexane (volume ratio)=20:80) to give (S)-3-[4-(spiro[4.5]dec-6-en-7-ylmethoxy)-phenyl]-hex-4-ynoic acid (895 mg) as the desired compound.

Example 8

Preparation of (S)-3-[4-(spiro[4.5]dec-6-en-7-ylmethoxy)-phenyl]-hex-4-ynoic acid sodium salt

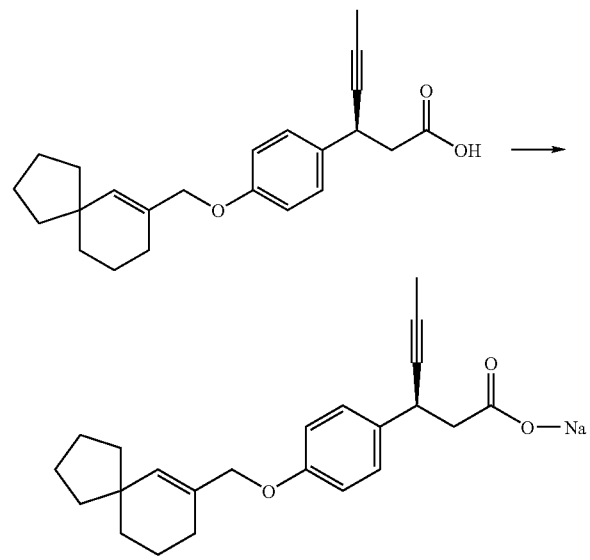

To a solution of (S)-3-[4-(spiro[4.5]dec-6-en-7-ylmethoxy)-phenyl]-hex-4-ynoic acid (1.12 g) obtained in the same manner as in Example 7 in ethanol (30 mL) was added 1N aqueous sodium hydroxide solution (2.97 mL), followed by stirring the reaction mixture at room temperature for 1.5 hours. The reaction mixture was concentrated and the residue was distilled azeotropically with ethanol twice. The residue was dried in vacuo at 60° C. for one day to give (S)-3-[4-(spiro[4.5]dec-6-en-7-ylmethoxy)-phenyl]-hex-4-ynoic acid sodium salt (1.15 g) as the desired compound.

Example 9

Preparation of (S)-3-[4-(spiro[5.5]undec-1-en-2-ylmethoxy)-phenyl]-hex-4-ynoic acid Step 1

In the same manner as in Steps 1 to 6 of Example 7, spiro[5.5]undec-1-en-2-yl-methanol was obtained from cyclohexanone and 1,5-dibromopentane.

$^1$H-NMR (CDCl$_3$) δ: 1.24-1.53 (12H, m), 1.55-1.57 (1H, m), 1.62 (2H, tt, J=9.2, 3.1 Hz), 1.97 (2H, t, J=6.2 Hz), 3.99 (2H, d, J=6.0 Hz), 5.55 (1H, s).

Step 2

In the same manner as in Steps 7 to 8 of Example 7, the desired compound was obtained from the compound obtained in the above Step 1.

Example 10

Preparation of (S)-3-[4-(spiro[5.5]undec-1-en-2-ylmethoxy)-phenyl]-hex-4-ynoic acid sodium salt In the same manner as in Example 8, the desired compound was obtained from the compound obtained in the same manner as in Example 9.

Example 11

Preparation of (S)-3-[4-(spiro[4.4]non-2-en-2-yl-methoxy)-phenyl]-hex-4-ynoic acid

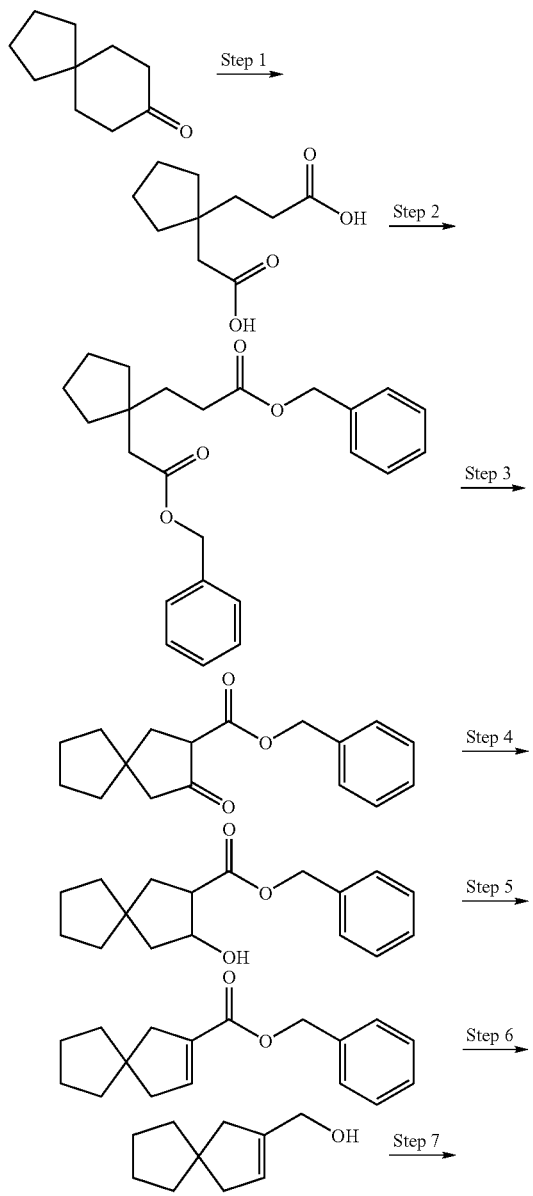

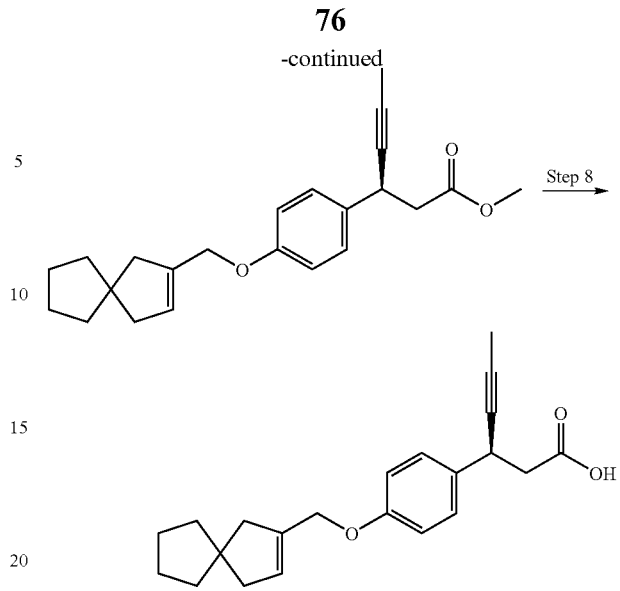

Step 1

To a solution of potassium permanganate (55.3 g) in 1N aqueous sodium hydroxide solution (300 mL) was added spiro[4.5]decan-8-one (10.6 g) obtained from cyclopentanecarbaldehyde in the same manner as in Steps 1 and 2 of Example 1, followed by stirring the reaction mixture at room temperature for 3 hours. Then, to the reaction mixture was added aqueous sodium sulfite solution, followed by stirring the reaction mixture at room temperature for 15 minutes. The insolubles in the reaction mixture were filtered off and the filtrate was washed with diethyl ether. The resulting aqueous solution was acidified by addition of concentrated hydrochloric acid thereto and extracted with ethyl acetate. The organic layer was washed with water, dried and concentrated to give a crude product (12.75 g) containing 3-(1-carboxymethyl-cyclopentyl)-propionic acid.

Step 2

To a solution of the crude product (12.75 g) containing 3-(1-carboxymethyl-cyclopentyl)-propionic acid obtained in Step 1 in a mixed solvent of acetonitrile (150 mL)-N,N-dimethylformamide (50 mL) were added successively benzyl bromide (18.3 mL) and cesium carbonate (0.57 g) at 0.50° C., followed by stirring at 50° C. for 2 hours. Then, after addition of benzyl bromide (9 mL) and cesium carbonate (30 g), the reaction mixture was heated at 60° C. for 45 minutes. After cooling down to room temperature and adding ice-cold water to the reaction mixture, the reaction mixture was extracted with diethyl ether. The organic layer was washed with water, dried and concentrated. The residue was purified by column chromatography on silica gel (hexane:ethyl acetate (volume ratio)=10:1) to give a crude product (14.9 g) containing 3-(1-benzyloxycarbonylmethyl-cyclopentyl)-propionic acid benzyl ester.

Step 3

To a solution of the crude product (14.9 g) containing 3-(1-benzyloxycarbonylmethyl-cyclopentyl)-propionic acid benzyl ester obtained in Step 2 in tetrahydrofuran (150 mL) was added potassium tert-butoxide (6.6 g), followed by stirring at room temperature for 2 hours. Then, to the reaction mixture was added dropwise a solution of acetic acid (5 mL) in water (100 mL) under ice-cooling, followed by extraction with ethyl acetate. The organic layer was washed with water, dried and concentrated. The residue was purified by column chromatography on silica gel (hexane:ethyl acetate (volume ratio)=20:1 to 10:1) to give a crude product (5.23 g) containing 3-oxo-spiro[4.4]nonane-2-carboxylic acid benzyl ester.

Step 4

To a solution of the crude product (5.23 g) containing 3-oxo-spiro[4.4]nonane-2-carboxylic acid benzyl ester obtained in Step 3 in methanol (100 mL) was added sodium borohydride (254 mg) under ice-cooling, followed by stirring under ice-cooling for 30 minutes. Then, after addition of 10% aqueous potassium hydrogen sulfate solution (10 mL) to the reaction mixture, methanol was evaporated off in vacuo, followed by extraction with ethyl acetate. The organic layer was dried and concentrated. The residue was purified by column chromatography on silica gel (hexane:ethyl acetate (volume ratio)=10:1 to 3:1) to give 3-hydroxy-spiro[4.4]nonane-2-carboxylic acid benzyl ester (less-polar isomer; 1.29 g, more-polar isomer; 2.23 g).

Less-Polar Isomer $^1$H-NMR (CDCl$_3$) δ: 1.45-1.66 (9H, m), 1.78 (1H, dd, J=13.1, 10.1 Hz), 1.93-2.02 (2H, m), 2.13 (1H, d, J=3.8 Hz), 2.80-2.88 (1H, m), 4.46 (1H, dd d, J=15.1, 7.4, 3.8 Hz), 5.17 (2H, s), 7.30-7.42 (5H, m).

More-Polar Isomer $^1$H-NMR (CDCl$_3$) δ: 1.37-1.51 (2H, m), 1.68-1.52 (7H, m), 1.74 (1H, dd, J=14.1, 3.2 Hz), 1.82-1.91 (2H, m), 2.88-2.94 (2H, m), 4.45-4.51 (1H, m), 5.17 (2H, d, J=1.9 Hz), 7.29-7.42 (5H, m).

Step 5

3-Hydroxy-spiro[4.4]nonane-2-carboxylic acid benzyl ester (less-polar isomer; 1.29 g, more-polar isomer; 2.23 g) obtained in Step 4 was subjected to the reaction in the same condition as in Steps 5, 5' and 6 of Example 1 to give spiro[4.4]non-2-ene-2-carboxylic acid benzyl ester (3.2 g).

$^1$H-NMR (CDCl$_3$) δ: 1.71-1.44 (8H, m), 2.42 (2H, q, J=2.5 Hz), 2.52 (2H, q, J=2.2 Hz), 5.18 (2H, s), 6.75-6.78 (1H, m), 7.29-7.39 (5H, m).

Step 6

Spiro[4.4]non-2-ene-2-carboxylic acid benzyl ester (3.2 g) obtained in Step 5 was subjected to the reaction in the same condition as in Step 7 of Example 1 to give spiro[4.4]non-2-en-2-yl-methanol (1.8 g).

$^1$H-NMR (CDCl$_3$) δ: 1.58-1.54 (4H, m), 1.62-1.68 (4H, m), 2.25-2.30 (4H, m), 4.16 (2H, s), 5.53-5.57 (1H, m).

Step 7

Spiro[4.4]non-2-en-2-yl-methanol (0.8 g) obtained in Step 6 and (S)-3-(4-hydroxy-phenyl)-hex-4-ynoic acid methyl ester (1.6 g) obtained in the same manner as in Substep 5 of Example 1 were subjected to the reaction in the same condition as in Step 8 of Example 1 to give (S)-3-[4-(spiro[4.4]non-2-en-2-ylmethoxy)-phenyl]-hex-4-ynoic acid methyl ester (1.55 g).

$^1$H-NMR (CDCl$_3$) δ: 1.59-1.56 (4H, m), 1.62-1.67 (4H, m), 1.84 (3H, d, J=2.5 Hz), 2.29-2.33 (4H, m), 2.66 (1H, dd, J=15.3, 6.8 Hz), 2.76 (1H, dd, J=15.3, 8.3 Hz), 3.67 (3H, s), 4.03-4.09 (1H, m), 4.52 (2H, s), 5.64-5.68 (1H, m), 6.87 (2H, d, J=8.3 Hz), 7.27 (3H, d, J=8.3 Hz).

Step 8

(S)-3-[4-(spiro[4.4]non-2-en-2-ylmethoxy)-phenyl]-hex-4-ynoic acid methyl ester (1.55 g) obtained in step 7 was subjected to the reaction in the same condition as in Step 9 of Example 1 to give (S)-3-(spiro[4.4]non-2-en-2-yl-methoxy)-phenyl]-hex-4-ynoic acid (1.37 g) as the desired compound.

Example 12

Preparation of (S)-3-[4-(spiro[4.4]non-2-en-2-yl-methoxy)-phenyl]-hex-4-ynoic acid sodium salt In the same manner as in Example 2 or 4, the desired compound was obtained from the compound obtained in Example 11.

Example 13

Preparation of (S)-3-[4-(spiro[4.5]dec-2-en-2-yl-methoxy)-phenyl]-hex-4-ynoic acid Step 1

In the same manner as in Steps 1 to 6 of Example 11, spiro[4.5]dec-2-en-2-yl-methanol was obtained from cyclohexanecarbaldehyde.

$^1$H-NMR (CDCl$_3$) δ: 1.49-1.36 (10H, m), 2.14-2.19 (4H, m), 4.12-4.16 (2H, m), 5.47-5.50 (1H, m).

Step 2

In the same manner as in Steps 7 to 8 of Example 11, the desired compound was obtained from the compound obtained in the above Step 1.

Example 14

Preparation of (S)-3-[4-(spiro[4.5]dec-2-en-2-yl-methoxy)-phenyl]-hex-4-ynoic acid sodium salt In the same manner as in Example 12, the desired compound was obtained from the compound obtained in the same manner as in Example 13.

Example 15

Preparation of (S)-3-[4-(spiro[4.5]dec-1-en-2-yl-methoxy)-phenyl]-hex-4-ynoic acid

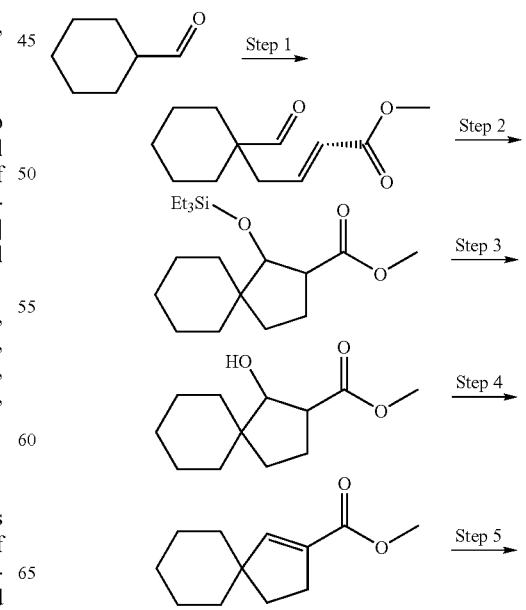

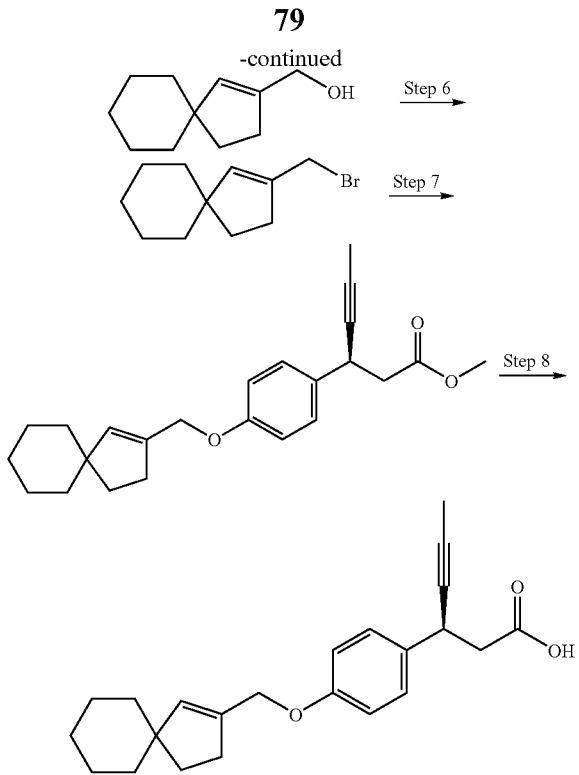

Step 1

To a solution of cyclohexanecarbaldehyde (6.3 mL) and 2-hydroxy-3-butenoic acid methyl ester (5 mL) in toluene (40 mL) was added para-toluenesulfonic acid monohydrate (20 mg), and the reaction mixture was heated under reflux by using a Dean-Stark apparatus for 16.5 hours. After cooling down to room temperature, the reaction mixture was concentrated in vacuo. The residue was purified by column chromatography on silica gel (hexane:ethyl acetate (volume ratio)=50:1 to 10:1) to give 4-(1-formyl-cyclohexyl)-but-2-enoic acid methyl ester (3.7 g).

$^1$H-NMR (CDCl$_3$) δ: 1.30-1.42 (4H, m), 1.53-1.58 (4H, m), 1.85-1.91 (2H, m), 2.33 (2H, dd, J=7.7, 1.3 Hz), 3.72 (3H, s), 5.84 (1H, dt, J=15.7, 1.3 Hz), 6.81 (1H, ddd, J=7.7, 15.7, 7.8 Hz), 9.48 (1H, s).

Step 2

To a solution of 4-(1-formyl-cyclohexyl)-but-2-enoic acid methyl ester (3.7 g) obtained in Step 1 and tris(triphenylphosphine) rhodium(I) chloride (163 mg) in toluene (80 mL) was added dropwise triethylsilane (5.9 mL) under argon atmosphere over 10 minutes, followed by stirring the reaction mixture at 55° C. for 27 hours. After cooling down to room temperature and adding aqueous sodium bicarbonate solution, the reaction mixture was extracted with ethyl acetate. The organic layer was washed with water, dried and concentrated. The residue was purified by column chromatography on silica gel (hexane:ethyl acetate (volume ratio)=20:1) to give 1-triethylsiloxy-spiro[4.5]decane-2-carboxylic acid methyl ester (5.0 g).

Step 3

To a solution of 1-triethylsiloxy-spiro[4.5]decane-2-carboxylic acid methyl ester (5.0 g) obtained in Step 2 in tetrahydrofuran (30 mL) was added a 1M tetrahydrofuran solution of tetra-n-butylammonium fluoride (18.4 mL), followed by stirring the reaction mixture at room temperature for 30 minutes. Then, after addition of aqueous ammonium chloride solution, the reaction mixture was extracted with ethyl acetate. The organic layer was washed with water, dried and concentrated. The residue was purified by column chromatography on silica gel (hexane:ethyl acetate (volume ratio)=5:1) to give 1-hydroxy-spiro[4.5]decane-2-carboxylic acid methyl ester (less-polar isomer; 1.6 g, more-polar isomer; 0.95 g).

More-Polar Isomer $^1$H-NMR (CDCl$_3$) δ: 1.17-1.53 (6H, m), 1.58-1.61 (4H, m), 1.76-1.85 (2H, m), 1.89-1.98 (1H, m), 2.02 (1H, d, J=4.5 Hz), 2.71-2.79 (1H, m), 3.72 (3H, s), 3.77 (1H, dd, J=9.0, 4.2 Hz).

Step 4

1-Hydroxy-spiro[4.5]decane-2-carboxylic acid methyl ester obtained in Step 3 (more-polar isomer; 0.95 g) was subjected to the reaction in the same condition as in Steps 5 and 6 of Example 1 to give spiro[4.5]dec-1-ene-2-carboxylic acid methyl ester (800 mg).

$^1$H-NMR (CDCl$_3$) δ: 1.39-1.52 (10H, brm), 1.77 (2H, t, J=7.4 Hz), 2.56 (2H, td, J=7.4, 1.8 Hz), 3.73 (3H, s), 6.69 (1H, s).

Step 5

Spiro[4.5]dec-1-ene-2-carboxylic acid methyl ester (800 mg) obtained in Step 4 was subjected to the reaction in the same condition as in Step 7 of Example 1 to give spiro[4.5]dec-1-en-2-yl-methanol (675 mg).

$^1$H-NMR (CDCl$_3$) δ: 1.33-1.50 (14H, brm), 1.73 (2H, t, J=7.0 Hz), 2.31 (2H, t, J=7.0 Hz), 4.16 (2H, d, J=6.5 Hz), 5.56 (1H, s).

Step 6

To a solution of spiro[4.5]dec-1-en-2-yl-methanol (50 mg) obtained in Step 5 in chloroform (1 mL) were added triphenylphosphine (87 mg) and N-bromo-succinimide (87 mg) under ice-cooling, followed by stirring the reaction mixture at room temperature for 1 hour. Then, the reaction mixture was concentrated in vacuo and the residue was purified by column chromatography on silica gel (hexane) to give 2-bromomethyl-spiro[4.5]dec-1-ene (55 mg).

$^1$H-NMR (CDCl$_3$) δ: 1.36-1.51 (10H, brm), 1.75 (2H, t, J=7.4 Hz), 2.42 (2H, t, J=7.4 Hz), 4.04 (2H, s), 5.71 (1H, s).

Step 7

To a solution of 2-bromomethyl-spiro[4.5]dec-1-ene (55 mg) obtained in Step 6 in N,N-dimethylformamide (1 mL) were added (S)-3-(4-hydroxyphenyl)-hex-4-ynoic acid methyl ester (60 mg) obtained in the same manner as in Substep 5 of Example 1 and potassium carbonate (93 mg), followed by stirring the reaction mixture at room temperature for 15 hours. Then, after addition of 1N aqueous hydrochloric acid solution, the reaction mixture was extracted with diethyl ether. The organic layer was washed with water, dried and concentrated. The residue was purified by column chromatography on silica gel (hexane:ethyl acetate (volume ratio)=50:1 to 20:1) to give (S)-3-[4-(spiro[4.5]dec-1-en-2-ylmethoxy)-phenyl]-hex-4-ynoic acid methyl ester (71 mg).

$^1$H-NMR (CDCl$_3$) δ: 1.40-1.59 (10H, brm), 1.76 (2H, t, J=8.0 Hz), 1.84 (3H, d, J=2.3 Hz), 2.39 (2H, t, J=8.0 Hz), 2.66 (1H, dd, J=15.3, 7.0 Hz), 2.76 (1H, dd, J=15.3, 7.8 Hz), 3.67 (3H, s), 4.04-4.08 (1H, m), 4.52 (2H, s), 5.68 (1H, s), 6.87 (2H, d, J=8.7 Hz), 7.27 (2H, d, J=8.7 Hz).

Step 8

(S)-3-[4-(spiro[4.5]dec-1-en-2-ylmethoxy)-phenyl]-hex-4-ynoic acid methyl ester (71 mg) obtained in Step 7 was subjected to the reaction in the same condition as in Step 9 of Example 1 to give (S)-3-[4-(spiro[4.5]dec-1-en-2-ylmethoxy)-phenyl]-hex-4-ynoic acid (57 mg) as the desired compound.

Example 16

Preparation of (S)-3-[4-(spiro[4.5]dec-1-en-2-yl-methoxy)-phenyl]-hex-4-ynoic acid sodium salt In the same manner as in Example 2 or 4, the desired compound was obtained from the compound obtained in Example 15.

Example 17

Preparation of (S)-3-[4-(spiro[4.4]non-1-en-2-yl-methoxy)-phenyl]-hex-4-ynoic acid Step 1

In the same manner as in Steps 1 to 5 of Example 15, spiro[4.4]non-1-en-2-yl-methanol was obtained from cyclopentanecarbaldehyde.

$^1$H-NMR (CDCl$_3$) δ: 1.56-1.47 (4H, m), 1.69-1.63 (4H, m), 1.80 (3H, t, J=7.2 Hz), 2.33 (2H, t, J=7.2 Hz), 4.18 (2H, d, J=4.6 Hz), 5.48 (1H, s).

Step 2

In the same manner as in Steps 6 to 8 of Example 15, the desired compound was obtained from the compound obtained in the above Step 1.

Example 18

Preparation of (S)-3-[4-(spiro[4.4]non-1-en-2-yl-methoxy)-phenyl]-hex-4-ynoic acid sodium salt In the same manner as in Example 16, the desired compound was obtained from the compound obtained in Example 17.

Example 19

Preparation of (3S)-3-[4-(11,11-dimethyl-spiro[5.5]undec-7-en-2-ylmethoxy)-phenyl]-hex-4-ynoic acid

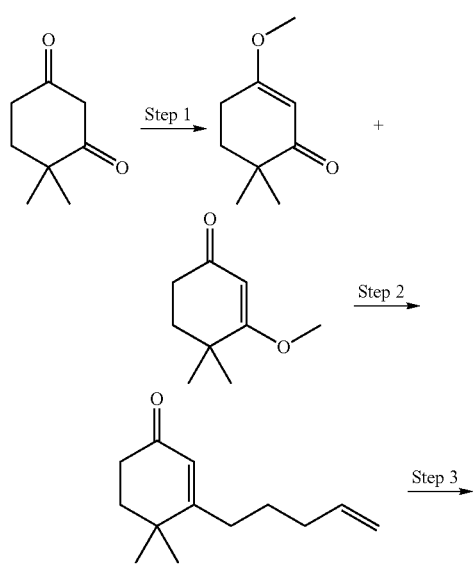

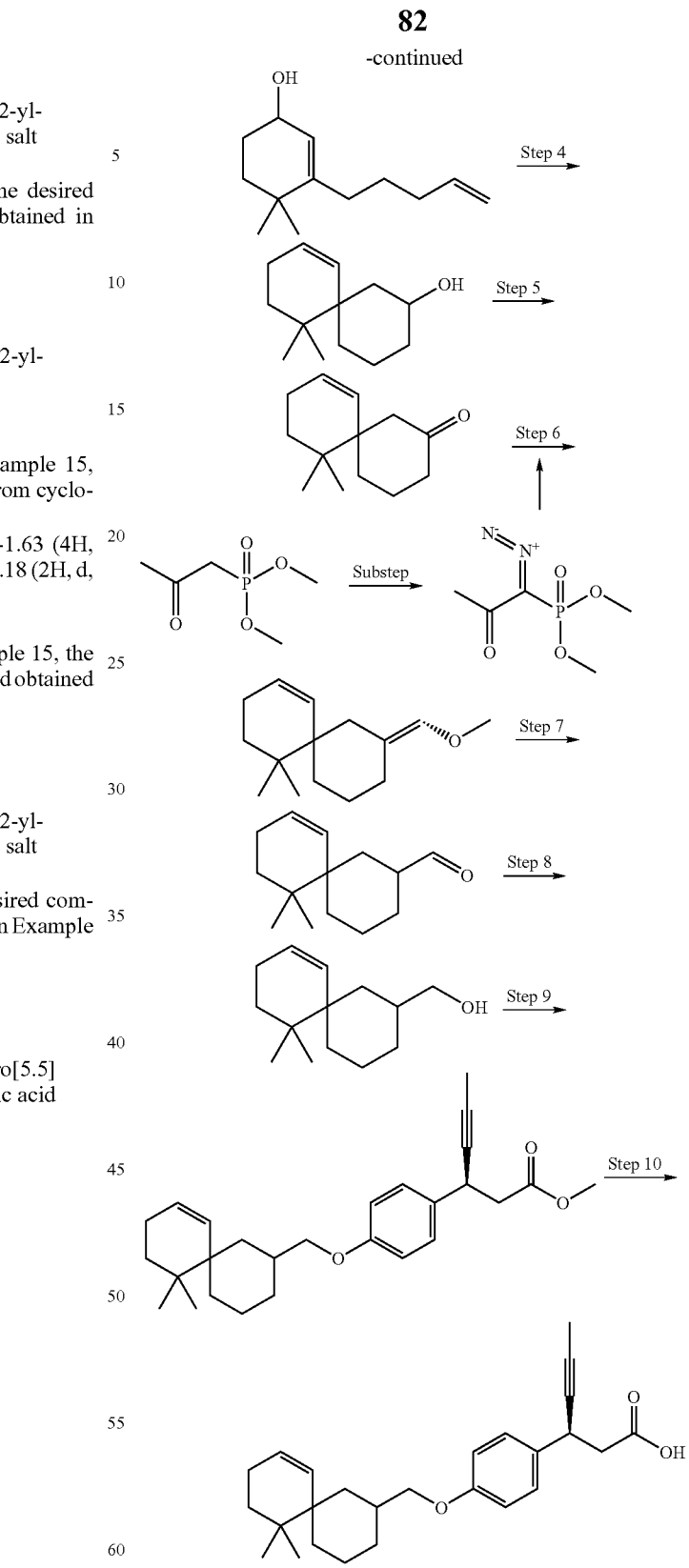

Step 1

To a solution of 4,4-dimethyl-cyclohexane-1,3-dione (6.0 g) in methanol (80 mL) was added para-toluenesulfonic acid monohydrate (813 mg), followed by heating the reaction mixture under reflux for 2 hours. After cooling down to room temperature, the reaction mixture was concentrated. The residue was purified by column chromatography on silica gel (hexane:ethyl acetate (volume ratio)=3:1) to give a less-polar isomer (3.7 g) and a more-polar isomer (1.1 g).

Less-Polar Isomer $^1$H-NMR (CDCl$_3$) δ: 1.12 (6H, s), 1.81 (2H, t, J=6.3 Hz), 2.44 (2H, t, J=6.3 Hz), 3.69 (3H, s), 5.27 (1H, s).

More-Polar Isomer $^1$H-NMR (CDCl$_3$) δ: 1.20 (6H, s), 1.83 (2H, t, J=6.7 Hz), 2.41 (2H, t, J=6.7 Hz), 3.68 (3H, s), 5.26 (1H, s).

Step 2

To magnesium (237 mg) was added dropwise a solution of 5-bromo-1-pentene (1.15 mL) in tetrahydrofuran (15 mL) under argon atmosphere over 20 minutes, followed by stirring the reaction mixture at room temperature for 30 minutes. To the reaction mixture was added dropwise a solution of the less-polar isomer (1.0 g) obtained in Step 1 in tetrahydrofuran (10 mL) under ice-cooling, followed by stirring the reaction mixture at room temperature overnight. Then, after addition of 12% aqueous hydrochloric acid solution (10 mL) under ice-cooling, the reaction mixture was extracted with diethyl ether. The organic layer was washed with water, dried and concentrated. The residue was purified by column chromatography on silica gel (hexane:ethyl acetate (volume ratio)=10:1) to give 4,4-dimethyl-3-pent-4-enyl-cyclohex-2-enone (1.07 g).

$^1$H-NMR (CDCl$_3$) δ: 1.17 (6H, s), 1.61 (2H, tt, J=7.5, 7.5 Hz), 1.86 (2H, t, J=6.8 Hz), 2.12 (2H, q, J=7.5 Hz), 2.22 (2H, t, J=7.5 Hz), 2.45 (2H, t, J=6.8 Hz), 4.95-5.08 (2H, m), 5.75-5.87 (2H, m).

Step 3

To a suspension of lithium aluminum hydride (250 mg) in diethyl ether (20 mL) was added dropwise a solution of 4,4-dimethyl-3-pent-4-enyl-cyclohex-2-enone (1.05 g) obtained in Step 2 in diethyl ether (5 mL) under ice-cooling and nitrogen atmosphere, followed by stirring the reaction mixture under ice-cooling for 30 minutes. Then, after successive dropwise addition of water (0.25 mL), 4N aqueous sodium hydroxide solution (0.25 mL) and water (0.75 mL), the reaction mixture was stirred at room temperature for 30 minutes. After the resulting insolubles were filtered off, the filtrate was concentrated. The residue was purified by column chromatography on silica gel (hexane:ethyl acetate (volume ratio)=15:1 to 10:1) to give 4,4-dimethyl-3-pent-4-enyl-cyclohex-2-enol (830 mg).

$^1$H-NMR (CDCl$_3$) δ: 0.98 (3H, s), 1.04 (3H, s), 1.32-1.65 (5H, m), 1.83-1.92 (1H, m), 1.92-2.02 (2H, m), 2.08 (2H, q, J=7.3 Hz), 4.12-4.21 (1H, m), 4.93-5.06 (2H, m), 5.37-5.41 (1H, m), 5.75-5.90 (1H, m).

Step 4

To 4,4-dimethyl-3-pent-4-enyl-cyclohex-2-enol (810 mg) obtained in Step 3 was added formic acid (60 mL), followed by stirring the reaction mixture at room temperature for 2 hours and then at 50° C. for 3 hours. After cooling down to room temperature and adding water, the reaction mixture was extracted with chloroform. The organic layer was washed with water, dried and concentrated. The residue was reduced in the same condition as in Step 3 to give 11,11-dimethyl-spiro[5.5]undec-7-en-2-ol (340 mg).

$^1$H-NMR (CDCl$_3$) δ: 0.86 (3H, s), 0.89 (3H, s), 1.11 (1H, dq, J=4.6, 11.6H z), 1.21-1.44 (4H, m), 1.49-1.71 (3H, m), 1.79 (1H, dq, J=11.6, 2.1 Hz), 1.98-2.03 (3H, m), 3.82-3.89 (1H, m), 5.57-5.63 (1H, m), 5.71 (1H, dd, J=10.3, 2.0 Hz).

Step 5

To a solution of 11,11-dimethyl-spiro[5.5]undec-7-en-2-ol (320 mg) obtained in Step 4 in chloroform (10 mL) was added 1,1,1-tris(acetyloxy)-1,1-dihydro-1,2-benziodoxol-3-(1H)-on e (Dess-Martin periodinane; 735 mg) under ice-cooling, followed by stirring the reaction mixture under ice-cooling for 3 hours. Then, after addition of aqueous sodium sulfite solution to the reaction mixture, chloroform was evaporated off in vacuo. To the residue was added aqueous sodium bicarbonate solution, followed by extraction with ethyl acetate. The organic layer was washed with water, dried and concentrated. The residue was purified by column chromatography on silica gel (hexane:ethyl acetate (volume ratio)=20:1) to give 11,11-dimethyl-spiro[5.5]undec-7-en-2-one (290 mg).

Step 6

To a solution of 11,11-dimethyl-spiro[5.5]undec-7-en-2-one (290 mg) obtained in Step 5 and dimethyl (1-diazo-2-oxopropyl)-phosphonate (435 mg) obtained in the following Substep in methanol (6 mL) was added potassium carbonate (420 mg) under ice-cooling, followed by stirring the reaction mixture at room temperature overnight. Then, after addition of aqueous ammonium chloride solution, the reaction mixture was extracted with diethyl ether. The organic layer was washed with water, dried and concentrated. The residue was purified by column chromatography on silica gel (hexane:ethyl acetate (volume ratio)=15:1) to give 8-(1-methoxymethylidene)-5,5-dimethyl-spiro[5.5]undec-1-ene (240 mg).

Step 7

To a solution of 8-(1-methoxymethylidene)-5,5-dimethyl-spiro[5.5]undec-1-ene (240 mg) obtained in Step 6 in acetonitrile (6 mL) was added 1N aqueous hydrochloric acid solution (1.1 mL), followed by stirring the reaction mixture at room temperature for 3 hours. Then, after addition of saturated brine, the reaction mixture was extracted with diethyl ether. The organic layer was washed with water, dried and concentrated. The resulting residue was dissolved in a mixed solution of methanol (5.4 mL)-water (0.6 mL). To the solution was added potassium carbonate (150 mg), followed by stirring the reaction mixture at room temperature for 2 hours. Then, after addition of water, the reaction mixture was extracted with diethyl ether. The organic layer was washed with water, dried and concentrated. The residue was purified by column chromatography on silica gel (hexane:ethyl acetate (volume ratio)=40:1) to give 11,11-dimethyl-spiro[5.5]undec-7-ene-2-carbaldehyde (195 mg).

$^1$H-NMR (CDCl$_3$) δ: 0.91-0.86 (6H, m), 1.08-1.79 (9H, m), 1.94-2.06 (3H, m), 2.45-2.56 (1H, m), 5.62-5.70 (1H, m), 5.76-5.83 (1H, m), 9.59-9.63 (1H, m).

Step 8

To a solution of 11,11-dimethyl-spiro[5.5]undec-7-ene-2-carbaldehyde (195 mg) obtained in Step 7 in methanol (5 mL) was added sodium borohydride (55 mg) under ice-cooling, followed by stirring the reaction mixture under ice-cooling for 15 minutes. Then, after addition of 0.5N aqueous sodium hydroxide solution (10 mL), the reaction mixture was extracted with diethyl ether. The organic layer was washed with water, dried and concentrated. The residue was purified by column chromatography on silica gel (hexane:ethyl acetate (volume ratio)=10:1 to 5:1) to give (11,11-dimethyl-spiro[5.5]undec-7-en-2-yl)-methanol (190 mg).

$^1$H-NMR (CDCl$_3$) δ: 0.85 (6H, d, J=2.3 Hz), 1.04 (1H, t, J=12.2 Hz), 1.17-1.85 (10H, m), 1.95-2.02 (2H, m), 3.40-3.47 (2H, m), 5.59 (1H, dt, J=10.2, 3.0 Hz), 5.85 (1H, dt, J=10.2, 2.3 Hz).

Step 9

(11,11-Dimethyl-spiro[5.5]undec-7-en-2-yl)-methanol (67 mg) obtained in Step 8 and (S)-3-(4-hydroxyphenyl)-hex-4-ynoic acid methyl ester (77 mg) obtained in the same manner as in Substep 5 of Example 1 were subjected to the reaction in the same condition as in Step 8 of Example 1 to give (3S)-3-[4-(11,11-dimethyl-spiro[5.5]undec-7-en-2-yl-methoxy)-phenyl]-hex-4-ynoic acid methyl ester (119 mg).

$^1$H-NMR (CDCl$_3$) δ: 0.87 (6H, s), 0.90-0.96 (1H, m), 1.15 (1H, t, J=12.4Hz), 1.68-1.33 (7H, m), 1.83 (3H, d, J=2.3 Hz), 1.93 (1H, d, J=12.5 Hz), 1.98-2.12 (3H, m), 2.66 (1H, dd, J=15.3, 7.0 Hz), 2.76 (1H, dd, J=15.3, 8.3 Hz), 3.67 (3H, s), 3.69-3.76 (2H, m), 4.03-4.09 (1H, m), 5.62 (1H, td, J=3.0, 10.2 Hz), 5.89 (1H, dt, J=10.2, 2.0 Hz), 6.84 (2H, d, J=9.4 Hz), 7.27 (2H, d, J=9.4 Hz).

Step 10

(3S)-3-[4-(11,11-dimethyl-spiro[5.5]undec-7-en-2-ylmethoxy)-phenyl]-hex-4-ynoic acid methyl ester (119 mg) obtained in Step 9 was subjected to the reaction in the same condition as in Step 9 of Example 1 to give (3S)-3-[4-(11,11-dimethyl-spiro[5.5]undec-7-en-2-ylmethoxy)-phenyl]-hex-4-ynoic acid (104 mg) as the desired compound.

Substep

To a suspension of 60% sodium hydride (2.5 g) in toluene (100 mL)-tetrahydrofuran (40 mL) was added dropwise a solution of dimethyl 2-oxopropyl phosphonate (10 g) in tetrahydrofuran (40 mL) under ice-cooling and nitrogen atmosphere over 10 minutes, followed by stirring the reaction mixture under ice-cooling for 1 hour. Then, to the reaction mixture was added dropwise a solution of para-dodecylbenzenesulfonyl azide (22 g) in tetrahydrofuran (40 mL) over 10 minutes, followed by stirring in the range of ice-cooling to room temperature for 3 hours. Then, the reaction mixture was concentrated in vacuo and the resulting residue was purified by column chromatography on silica gel (hexane:ethyl acetate (volume ratio)=1:1) to give dimethyl(1-diazo-2-oxopropyl)-phosphonate (4.2 g).

Example 20

Preparation of (3S)-3-[4-(11,11-dimethyl-spiro[5.5] undec-7-en-2-ylmethoxy)-phenyl]-hex-4-ynoic acid sodium salt In the same manner as in Example 2 or 4, the desired compound was obtained from the compound obtained in Example 19.

Example 21

Preparation of 3-[4-(spiro[4.6]undec-2-ylmethoxy) phenyl]-propionic acid

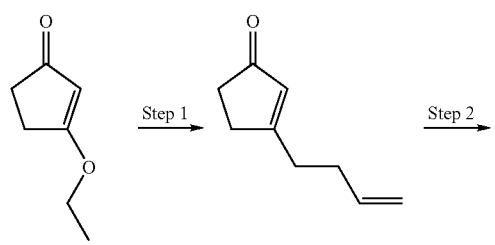

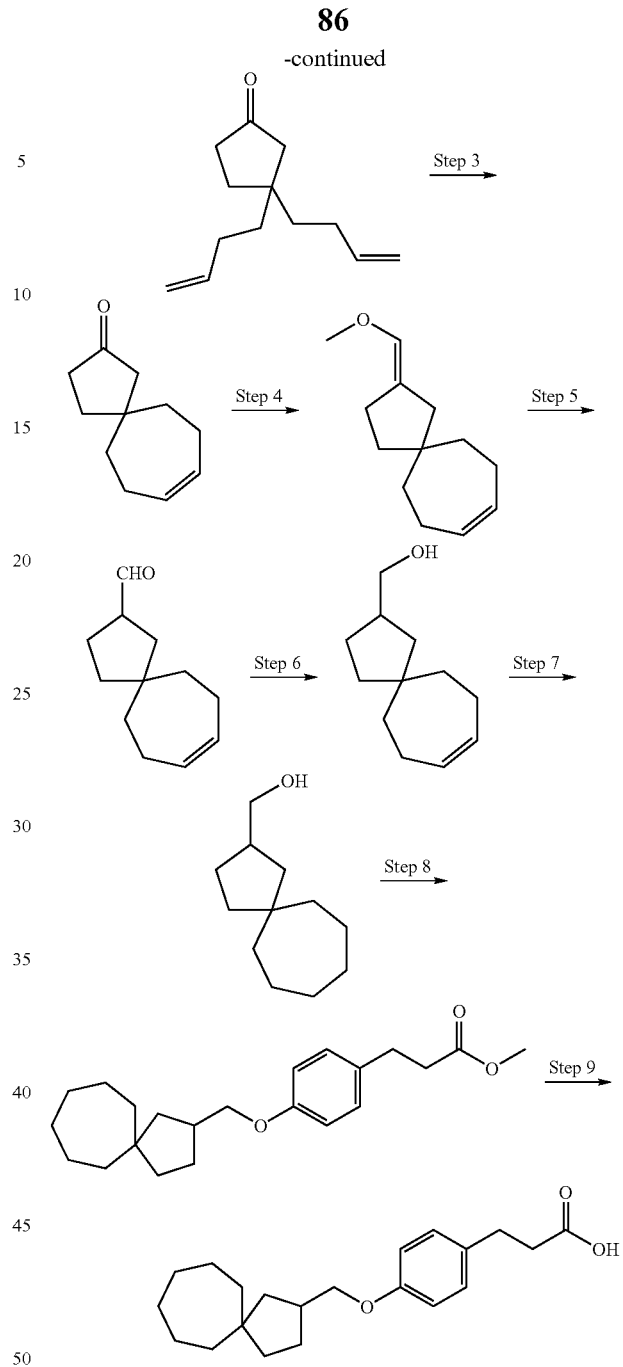

Step 1

To a solution of 3-ethoxycyclopent-2-enone (2.37 g) in tetrahydrofuran (30 mL) was added dropwise a 0.5M tetrahydrofuran solution of 3-butenylmagnesium bromide (38.4 mL) under nitrogen atmosphere at −78° C. over 10 minutes, followed by stirring at −78° C. for 3 hours and then at room temperature overnight. Then, after addition of 2N aqueous hydrochloric acid solution, the reaction mixture was stirred for 30 minutes and then extracted with ethyl acetate twice. The organic layer was washed with saturated brine, dried and concentrated. The residue was purified by column chromatography on silica gel to give 3-(3-butenyl)cyclopent-2-enone (1.1 g).

$^1$H-NMR (CDCl$_3$) δ: 2.37 (4H, dtd, J=17.90, 5.65, 2.95 Hz), 2.50-2.61 (4H, m), 5.04-5.09 (2H, m), 5.75-5.89 (1H, m), 5.98 (1H, s).

Step 2

To a suspension of copper(I) iodide (2.6 g) and lithium bromide (1.2 g) in tetrahydrofuran (25 mL) was added dropwise a 0.5M tetrahydrofuran solution of 3-butenylmagnesium bromide (26.5 mL) under nitrogen atmosphere at −78° C. over 6 minutes, followed by stirring the reaction mixture at −78° C. for 40 minutes. Then, 5 minutes after addition of boron trifluoride diethyl ether complex (0.554 mL), to the reaction mixture was added 3-(3-butenyl)cyclopent-2-enone (0.6 g) obtained in Step 1. Half an hour later, after addition of boron trifluoride diethyl ether complex (0.250 mL), the reaction mixture was stirred at −78° C. for 2 hours, and further stirred at room temperature overnight after removing a dry-ice/ethanol bath. Then, after addition of saturated aqueous ammonium chloride solution and 28% aqueous ammonia solution, the reaction mixture was extracted with ethyl acetate. The organic layer was washed successively with aqueous ammonia solution and saturated brine, dried and concentrated. The residue was purified by column chromatography on silica gel to give 3,3-dibut-3-enylcyclopentanone (380 mg).

$^1$H-NMR (CDCl$_3$) δ: 1.48-1.57 (4H, m), 1.84 (2H, t, J=8.0 Hz), 1.95-2.09 (4H, m), 2.11 (2H, s), 2.28 (2H, t, J=8.0 Hz), 4.95-5.08 (4H, m), 5.79-5.85 (2H, m).

Step 3

A solution of 3,3-dibut-3-enylcyclopentanone (380 mg) obtained in Step 2 in toluene (80 mL) was degassed with argon. After addition of benzylidene[1,3-bis(2,4,6-trimethylphenyl)-2-imidazolidinylidene]dichloro(tricyclohexylphosphine) ruthenium (84 mg), the reaction mixture was heated under reflux for 6 hours. After cooling down to room temperature, the reaction mixture was concentrated. The residue was purified by column chromatography on silica gel to give spiro[4.6]undec-8-en-2-one (350 mg).

Step 4

To a solution of spiro[4.6]undec-8-en-2-one (350 mg) obtained in Step 3 and dimethyl(1-diazo-2-oxo-propyl)-phosphonate (768 mg) obtained in the same manner as in Substep of Example 19 in methanol (10 mL) was added potassium carbonate (830 mg) under ice-cooling, followed by stirring the reaction mixture under ice-cooling for 2.5 hours. Then, the reaction mixture was poured into water, followed by extraction with ethyl acetate. The organic layer was washed successively with water and saturated brine, dried and concentrated to give 2-(1-methoxymethylidene)spiro[4.6]undec-8-ene (900 mg) as a crude product.

Step 5

To a solution of the crude 2-(1-methoxymethylidene)spiro[4.6]undec-8-ene (900 mg) obtained in Step 4 in acetonitrile (10 mL) was added 1N aqueous hydrochloric acid solution (2 mL), followed by stirring at room temperature for 4 hours. Then, the reaction mixture was poured into water, followed by extraction with ethyl acetate. The organic layer was washed with saturated brine, dried and concentrated. The residue was purified by column chromatography on silica gel to give spiro[4.6]undec-8-ene-2-carbaldehyde (44 mg).

Step 6

To a solution of spiro[4.6]undec-8-ene-2-carbaldehyde (44 mg) obtained in Step 5 in methanol (1 mL) was added sodium borohydride (9 mg), followed by stirring at room temperature overnight. Then, after addition of aqueous hydrochloric acid solution, the reaction mixture was extracted with ethyl acetate twice. The organic layer was washed with saturated brine, dried and concentrated to give spiro[4.6]undec-8-ene-2-methanol (44 mg).

Step 7

A suspension of spiro[4.6]undec-8-ene-2-methanol (44 mg) obtained in Step 6 and 5% palladium carbon (4 mg) in tetrahydrofuran (1 mL)-ethanol (1 mL) was stirred in an atmosphere of hydrogen for 3 hours. Then, the reaction mixture was filtered through Celite and the filtrate was concentrated. The residue was purified by column chromatography on silica gel to give spiro[4.6]undecane-2-methanol (43 mg).

$^1$H-NMR (CDCl$_3$) δ: 0.98 (1H, dd, J=12.43, 9.42 Hz), 1.24-1.36 (3H, m), 1.44-1.53 (12H, m), 1.69 (1H, dd, J=12.40, 7.72 Hz), 1.74-1.83 (1H, m), 2.12-2.22 (1H, m), 3.53 (2H, d, J=5.27 Hz).

Step 8

To a solution of spiro[4.6]undecane-2-methanol (43 mg) obtained in Step 7,3-(4-hydroxyphenyl) propionic acid methyl ester (51 mg) and triphenylphosphine (74 mg) in tetrahydrofuran (1 mL) was added 1,1'-azobis(N,N-dimethylformamide) (49 mg) under ice-cooling, followed by stirring the reaction mixture at room temperature overnight. The reaction mixture was concentrated and the residue was purified by column chromatography on silica gel to give 3-[4-(spiro[4.6]undec-2-ylmethoxy)-phenyl]-propionic acid methyl ester (75 mg).

$^1$H-NMR (CDCl$_3$) δ: 1.08 (1H, dd, J=12.6, 9.3 Hz), 1.41-1.49 (15H, m), 1.77-1.85 (2H, m), 2.40-2.43 (1H, m), 2.59 (2H, t, J=7.7 Hz), 2.88 (2H, t, J=7.7 Hz), 3.66 (3H, s), 3.80 (2H, d, J=6.8 Hz), 6.81 (2H, d, J=8.7 Hz), 7.09 (2H, d, J=8.7 Hz).

Step 9

To a solution of 3-[4-(spiro[4.6]undec-2-ylmethoxy)-phenyl]-propionic acid methyl ester (75 mg) obtained in Step 8 in a mixed solvent of ethanol (1 mL)-tetrahydrofuran (1 mL) was added 1N aqueous sodium hydroxide solution (0.22 mL), followed by stirring the reaction mixture at room temperature for 5 hours. Then, after concentrating the reaction mixture, to the residue was added dropwise 2N aqueous hydrochloric acid solution. The precipitate was filtered, washed with water and dried in vacuo to give 3-[4-(spiro[4.6]undec-2-ylmethoxy)-phenyl]-propionic acid (70.6 mg) as the desired compound.

Example 22

Preparation of (S)-3-[4-(spiro[4.5]dec-8-ylmethoxy)-phenyl]-hex-4-ynoic acid

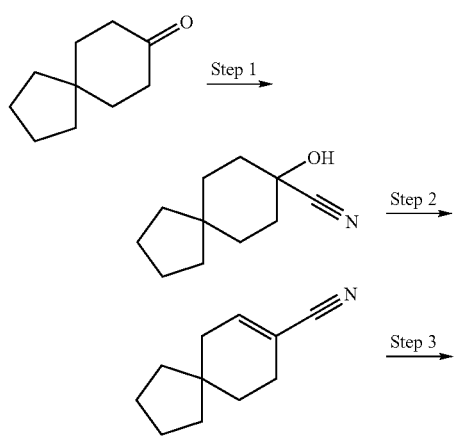

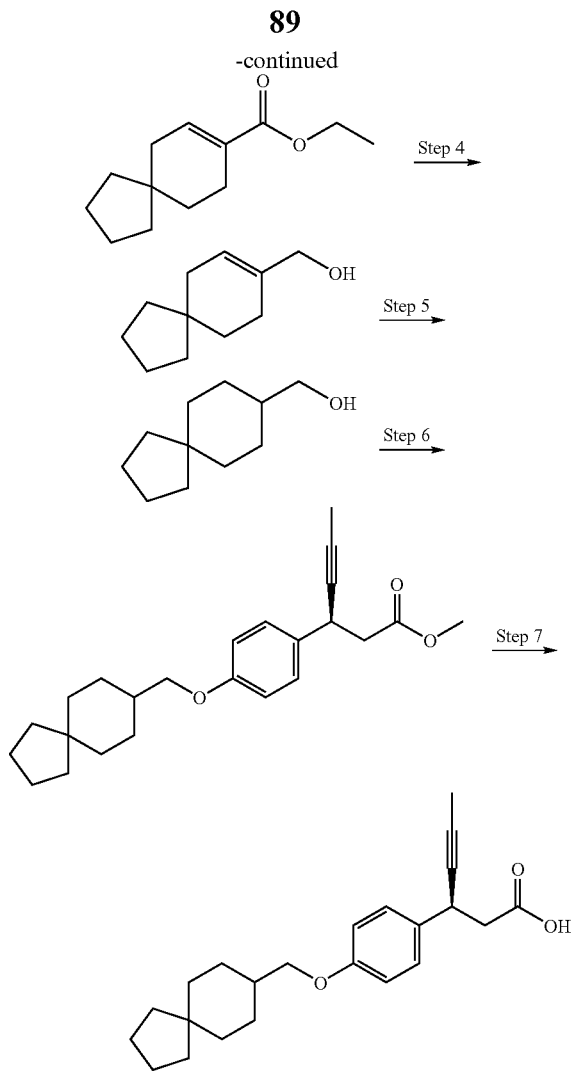

Step 1

To a solution of spiro[4.5]decan-8-one (4.2 g) produced from cyclopentanecarbaldehyde in the same manner as in Steps 1 and 2 of Example 1 in tetrahydrofuran (30 mL) were added successively trimethylsilyl cyanide (2.9 mL) and a tetrahydrofuran solution of tetra-n-butylammonium fluoride (1M, 22 mL), followed by stirring the reaction mixture at room temperature for 4 hours. Then, after addition of saturated aqueous sodium bicarbonate solution, the reaction mixture was extracted with ethyl acetate twice. The organic layer was washed with saturated brine, dried and concentrated to give 8-hydroxy-spiro[4.5]decane-8-carbonitrile (3.9 g).

$^1$H-NMR (CDCl$_3$) δ: 1.41-1.47 (4H, m), 1.54-1.65 (8H, m), 1.76-1.80 (4H, m).

Step 2

To a solution of 8-hydroxy-spiro[4.5]decane-8-carbonitrile (3.9 g) obtained in Step 1 in tetrahydrofuran (30 mL) were added successively pyridine (4.4 mL) and thionyl chloride (1.8 mL), followed by stirring the reaction mixture at room temperature for 15 hours. Then, after addition of 1N aqueous hydrochloric acid solution, the reaction mixture was extracted with diethyl ether. The organic layer was washed successively with 1N aqueous hydrochloric acid solution and saturated brine, dried and concentrated to give spiro[4.5]dec-7-ene-8-carbonitrile (2.8 g).

$^1$H-NMR (CDCl$_3$) δ: 1.35-1.44 (4H, m), 1.54 (2H, t, J=6.4 Hz), 1.62-1.67 (4H, m), 2.06 (2H, dd, J=6.4, 2.4 Hz), 2.24-2.30 (2H, m), 6.55-6.59 (1H, m).

Step 3

To a solution of spiro[4.5]dec-7-ene-8-carbonitrile (2.8 g) obtained in Step 2 in ethanol (30 mL) was added concentrated sulfuric acid (3 mL), followed by heating the reaction mixture under reflux while stirring for 5 days. After cooling down to room temperature and adding water, the reaction mixture was extracted with ethyl acetate twice. The organic layer was washed successively with saturated aqueous sodium bicarbonate solution and saturated brine, dried and concentrated. The residue was purified by column chromatography on silica gel (ethyl acetate:hexane (volume ratio)=1:4) to give spiro[4.5]dec-7-ene-8-carboxylic acid ethyl ester (2.8 g).

$^1$H-NMR (CDCl$_3$) δ: 1.29 (3H, t, J=7.0 Hz), 1.36-1.42 (4H, m), 1.52 (2H, t, J=6.4 Hz), 1.61-1.66 (4H, m), 2.07 (2H, dd, J=6.4, 2.6 Hz), 2.29-2.31 (2H, m), 4.18 (2H, q, J=7.0 Hz), 6.90-6.94 (1H, m).

Step 4

To a solution of spiro[4.5]dec-7-ene-8-carboxylic acid ethyl ester (2.8 g) obtained in Step 3 in tetrahydrofuran (40 mL) was added dropwise a toluene solution of diisobutylaluminum hydride (0.99 M, 41 mL) under argon atmosphere at −78° C., followed by stirring the reaction mixture at −78° C. for 1 hour. Then, after adding 2N aqueous hydrochloric acid solution and raising the temperature to room temperature, the reaction mixture was extracted with ethyl acetate twice. The organic layer was washed with saturated brine, dried and concentrated. The residue was purified by column chromatography on silica gel (ethyl acetate:hexane (volume ratio)=1:4) to give spiro[4.5]dec-7-en-8-yl-methanol (1.95 g).

$^1$H-NMR (CDCl$_3$) δ: 1.37-1.41 (4H, m), 1.51 (2H, t, J=6.5 Hz), 1.59-1.65 (4H, m), 1.90-1.93 (2H, m), 2.04-2.06 (2H, m), 4.00 (2H, s), 5.62 (1H, s

Step 5

To a solution of spiro[4.5]dec-7-en-8-yl-methanol (0.7 g) obtained in Step 4 in a mixed solvent of tetrahydrofuran (7 mL)-methanol (7 mL) was added 5% palladium carbon (70 mg), followed by stirring the reaction mixture at room temperature under normal pressure in an atmosphere of hydrogen for 1.5 hours and then under increased pressure of 0.3 MPa in an atmosphere of hydrogen for 3 hours. Then, the reaction mixture was filtered through Celite and the filtrate was concentrated. The residue was dissolved in methanol (5 mL). To the solution was added sodium borohydride (0.14 g), followed by stirring the reaction mixture at room temperature for 30 minutes. After addition of 1N aqueous hydrochloric acid solution, the reaction mixture was extracted with ethyl acetate twice. The organic layer was washed with saturated brine, dried and concentrated. The residue was purified by column chromatography on silica gel (ethyl acetate:hexane (volume ratio)=1:4) to give spiro[4.5]dec-8-yl-methanol (0.528 g).

$^1$H-NMR (CDCl$_3$) δ: 1.00-1.12 (2H, m), 1.23-1.64 (15H, brm), 3.46 (2H, d, J=6.4 Hz).

Step 6

Spiro[4.5]dec-8-yl-methanol (0.528 g) obtained in Step 5 was subjected to the reaction in the same condition as in Step 8 of Example 1 to give (S)-3-[4-(spiro[4.5]dec-8-yl-methoxy)-phenyl]-hex-4-ynoic acid methyl ester (1.1 g).

$^1$H-NMR (CDCl$_3$) δ: 1.13-1.21 (2H, m), 1.27-1.29 (3H, m), 1.33-1.43 (3H, m), 1.48-1.60 (6H, m), 1.71-1.76 (3H, m), 1.82 (3H, d, J=2.3 Hz), 2.65 (1H, dd, J=15.3, 7.0 Hz), 2.75 (1H, dd, J=15.3, 8.5 Hz), 3.66 (3H, s), 3.74 (2H, d, J=6.0 Hz), 4.02-4.07 (1H, m), 6.83 (2H, d, J=8.6 Hz), 7.26 (2H, d, J=8.6 Hz).

Step 7

(S)-3-[4-(spiro[4.5]dec-8-ylmethoxy)-phenyl]-hex-4-ynoic acid methyl ester (1.3 g) obtained in the same manner as in Step 6 was subjected to the reaction in the same condition as in Step 9 of Example 1 to give (S)-3-[4-(spiro[4.5]dec-8-ylmethoxy)-phenyl]-hex-4-ynoic acid (1.09 g) as the desired compound.

Example 23

Preparation of (S)-3-[4-(spiro[4.5]dec-8-ylmethoxy)-phenyl]-hex-4-ynoic acid sodium salt In the same manner as in Example 2 or 4, the desired compound was obtained from the compound obtained in Example 22.

Example 24

Preparation of (S)-3-[4-(spiro[5.5]undec-3-yl-methoxy)-phenyl]-hex-4-ynoic acid

Step 1

In the same manner as in Steps 1 to 5 of Example 22, spiro[5.5]undec-3-yl-methanol was obtained from spiro[5.5]undecan-3-one obtained in Step 2 of Example 1.

$^1$H-NMR (CDCl$_3$) δ: 1.12-1.02 (4H, m), 1.26-1.21 (4H, m), 1.42-1.39 (7H, m), 1.57-1.51 (2H, m), 1.68-1.65 (2H, m), 3.47 (2H, brs).

Step 2

In the same manner as in Steps 6 to 7 of Example 22, the desired compound was obtained from the compound obtained in the above Step 1.

Example 25

Preparation of (S)-3-[4-(spiro[4.5]dec-7-en-8-yl-methoxy)-phenyl]-hex-4-ynoic acid

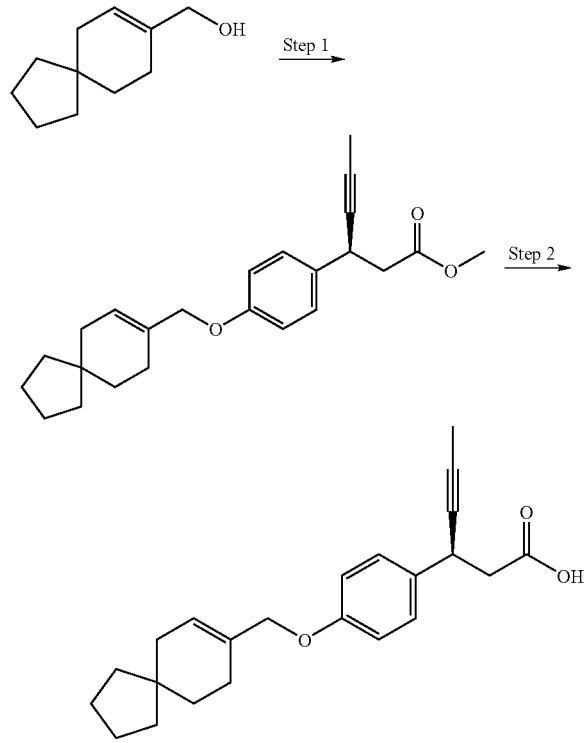

Step 1

Spiro[4.5]dec-7-en-8-yl-methanol (0.5 g) obtained in Step 4 of Example 22 and (S)-3-(4-hydroxy-phenyl)-hex-4-ynoic acid methyl ester (0.803 g) obtained in the same manner as in Substep 5 of Example 1 were subjected to the reaction in the same condition as in Step 8 of Example 1 to give (S)-3-[4-(spiro[4.5]dec-7-en-8-ylmethoxy)-phenyl]-hex-4-ynoic acid methyl ester (1.05 g).

$^1$H-NMR (CDCl$_3$) δ: 1.37-1.40 (4H, m), 1.52-1.56 (2H, m), 1.60-1.65 (4H, m), 1.82 (3H, d, J=2.3 Hz), 1.93-1.96 (2H, m), 2.08-2.13 (2H, m), 2.64 (1H, dd, J=15.1, 7.0 Hz), 2.75 (1H, dd, J=15.1, 8.3 Hz), 3.66 (3H, s), 4.03-4.08 (1H, m), 4.36 (2H, s), 5.73 (1H, s), 6.85 (2H, d, J=8.6 Hz), 7.26 (2H, d, J=8.6 Hz).

Step 2

(S)-3-[4-(spiro[4.5]dec-7-en-8-ylmethoxy)-phenyl]-hex-4-ynoic acid methyl ester (1.0 g) obtained in Step 1 was subjected to the reaction in the same condition as in Step 9 of Example 1 to give (S)-3-[4-(spiro[4.5]dec-7-en-8-ylmethoxy)-phenyl]-hex-4-ynoic acid (0.924 g) as the desired compound.

Example 26

Preparation of (3S)-3-[4-(spiro[4.5]dec-2-yl-methoxy)-phenyl]-hex-4-ynoic acid

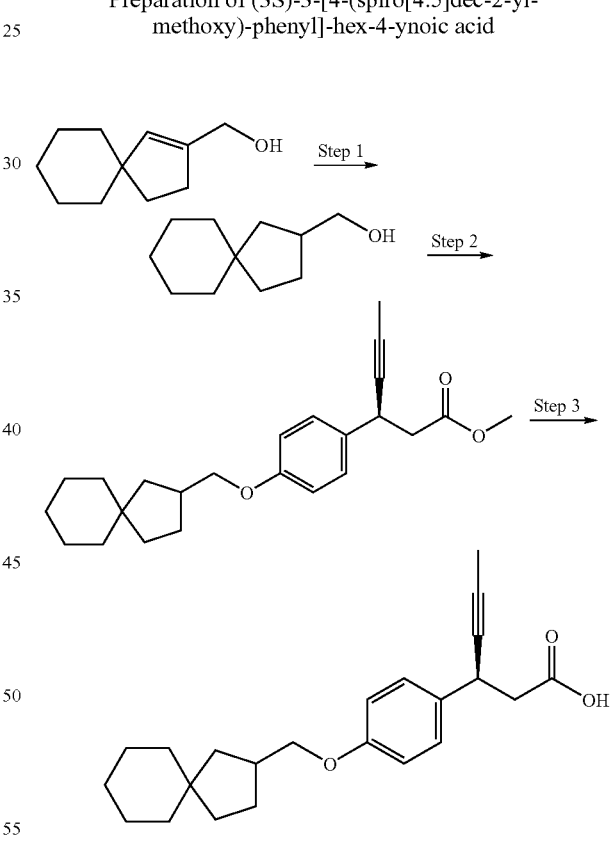

Step 1

To a solution of spiro[4.5]dec-1-en-2-yl-methanol (50 mg) obtained in Step 5 of Example 15 in tetrahydrofuran (1 mL) was added 5% palladium carbon (5 mg), followed by stirring the reaction mixture under normal pressure in an atmosphere of hydrogen at room temperature for 20 hours. Then, the reaction mixture was filtered through Celite and the filtrate was concentrated. The residue was dissolved in methanol (1 mL). To the solution was added sodium borohydride (10 mg), followed by stirring the reaction mixture at room temperature for 1 hour. Then, after addition of 1N aqueous hydrochloric acid solution, the reaction mixture was extracted with ethyl acetate. The organic layer was washed with water, dried and concentrated to give spiro[4.5]dec-2-yl-methanol (30 mg).

$^1$H-NMR (CDCl$_3$) δ: 0.95-1.03 (1H, m), 1.31-1.47 (12H, brm), 1.66-1.81 (3H, m), 2.13-2.23 (1H, m), 3.53 (2H, d, J=6.8 Hz).

Step 2

Spiro[4.5]dec-2-yl-methanol (30 mg) obtained in Step 1 and (S)-3-(4-hydroxyphenyl)-hex-4-ynoic acid methyl ester (52 mg) obtained in the same manner as in Substep 5 of Example 1 were subjected the reaction in the same condition as in Step 8 of Example 1 to give (3S)-3-[4-(spiro[4.5]dec-2-ylmethoxy)-phenyl]-hex-4-ynoic acid methyl ester (49 mg).

$^1$H-NMR (CDCl$_3$) δ: 1.10 (1H, dd, J=13.0, 9.2 Hz), 1.36-1.49 (10H, m), 1.78-1.83 (5H, m), 2.38-2.46 (1H, m), 2.65 (1H, dd, J=15.3, 7.0 Hz), 2.75 (1H, dd, J=15.3, 8.5 Hz), 3.66 (3H, s), 3.81 (2H, d, J=6.7 Hz), 4.02-4.07 (1H, m), 6.83 (2H, d, J=8.7 Hz), 7.26 (2H, d, J=8.7 Hz).

Step 3

(3S)-3-[4-(spiro[4.5]dec-2-ylmethoxy)-phenyl]-hex-4-ynoic acid methyl ester (49 mg) obtained in Step 2 was subjected to the reaction in the same condition as in Step 9 of Example 1 to give (3S)-3-[4-(spiro[4.5]dec-2-ylmethoxy)-phenyl]-hex-4-ynoic acid (20 mg) as the desired compound.

$^1$H-NMR (CDCl$_3$) δ: 1.11 (1H, dd, J=12.4, 9.6 Hz), 1.48-1.29 (13H, m) 1.85-1.79 (5H, m), 2.44-2.42 (1H, m), 2.84-2.69 (2H, m), 2.84-2.69 (2H, m), 3.82 (2H, d, J=6.5 Hz), 4.06-4.04 (1H, brm), 6.85 (2H, d, J=8.1 Hz), 7.28 (2H, d, J=8.1 Hz).

Example 27

Preparation of (3S)-3-[4-(spiro[4.5]dec-2-yl-methoxy)-phenyl]-hex-4-ynoic acid sodium salt In the same manner as in Example 2 or 4, the desired compound was obtained from the compound obtained in the same manner as in Example 26.

Example 28

Preparation of (3S)-3-[4-(spiro[5.5]undec-2-yl-methoxy)-phenyl]-hex-4-ynoic acid Step 1

In the same manner as in Step 1 of Example 26, spiro[5.5] undec-2-yl-methanol was obtained from spiro[5.5]undec-2-en-2-yl-methanol obtained in the same manner as in Step 7 of Example 1.

$^1$H-NMR (CDCl$_3$) δ: 0.65 (1H, t, J=13.2 Hz), 0.75-0.97 (2H, m), 1.81-1.18 (16H, m), 3.41 (2H, d, J=4.1 Hz).

Step 2

In the same manner as in Steps 2 to 3 of Example 26, the desired compound was obtained from the compound obtained in the above Step 1.

Example 29

Preparation of (3S)-3-[4-(spiro[5.5]undec-2-yl-methoxy)-phenyl]-hex-4-ynoic acid sodium salt In the same manner as in Example 27, the desired compound was obtained from the compound obtained in the same manner as in Example 28.

Example 30

Preparation of (3S)-3-[4-(spiro[4.4]non-2-yl-methoxy)-phenyl]-hex-4-ynoic acid

Step 1

In the same manner as in Step 1 of Example 26, spiro[4.4] non-2-yl-methanol was obtained from spiro[4.4]non-1-en-2-yl-methanol obtained in the same manner as in Step 1 of Example 17.

$^1$H-NMR (CDCl$_3$) δ: 1.18 (1H, td, J=9.0, 3.3 Hz), 1.38-1.31 (1H, m), 1.53-1.42 (6H, m), 1.64-1.57 (4H, m), 1.69 (1H, dd, J=12.6, 8.0 Hz), 1.85-1.75 (1H, m), 2.22 (1H, tt, J=16.0, 5.3 Hz), 3.54 (2H, d, J=7.0 Hz).

Step 2

In the same manner as in Steps 2 to 3 of Example 26, the desired compound was obtained from the compound obtained in the above Step 1.

Example 31

Preparation of (3S)-3-[4-(spiro[4.4]non-2-yl-methoxy)-phenyl]-hex-4-ynoic acid sodium salt In the same manner as in Example 27, the desired compound was obtained from the compound obtained in Example 30.

Example 32

Preparation of (3S)-3-[4-(spiro[5.5]undec-2-yl-methoxy)-phenyl]-hex-4-ynoic acid (chiral: A)

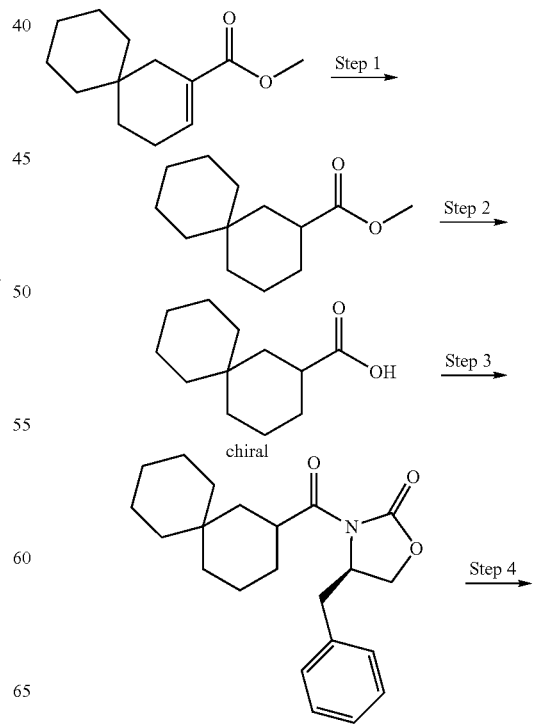

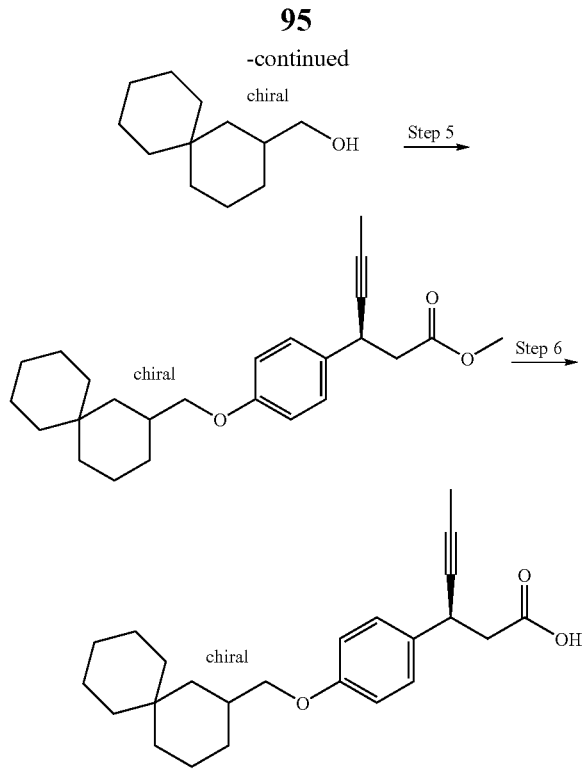

Step 1

To a solution of spiro[5.5]undec-2-ene-2-carboxylic acid methyl ester (300 mg) obtained in the same manner as in Step 6 of Example 1 in tetrahydrofuran (15 mL) was added 5% palladium carbon (50 mg), followed by stirring the reaction mixture under increased pressure of 0.3 MPa in an atmosphere of hydrogen at room temperature for 4 hours. Then, the reaction mixture was filtered through Celite. The filtrate was concentrated in vacuo to give spiro[5.5]undecane-2-carboxylic acid methyl ester (300 mg).

$^1$H-NMR (CDCl$_3$) δ: 0.98 (1H, td, J=13.2, 4.1 Hz), 1.16 (1H, t, J=13.2 Hz), 1.22-1.50 (13H, m), 1.65 (1H, d, J=12.3 Hz), 1.82-1.94 (2H, m), 2.47 (1H, tt, J=12.3, 3.6 Hz), 3.67 (3H, s).

Step 2

To a solution of spiro[5.5]undecane-2-carboxylic acid methyl ester (500 mg) obtained in the same manner as in Step 1 in a mixed solvent of tetrahydrofuran (5 mL)-methanol (5 mL) was added 2N aqueous sodium hydroxide solution (3.57 mL), followed by stirring the reaction mixture at 50° C. for 3 hours. After cooling down to room temperature, 2N aqueous hydrochloric acid solution (3.57 mL) was added to the reaction mixture. Methanol in the reaction mixture was evaporated off in vacuo, followed by extraction with ethyl acetate. The organic layer was dried and then concentrated to give spiro[5.5]undecane-2-carboxylic acid (440 mg).

Step 3

To a solution of spiro[5.5]undecane-2-carboxylic acid (570 mg) obtained in the same manner as in Step 2 in chloroform (6 mL) were added thionyl chloride (0.425 mL) and N,N-dimethylformamide (0.06 mL), followed by stirring the reaction mixture at room temperature for 2.5 hours. Then, the reaction mixture was concentrated and the resulting residue was dissolved in tetrahydrofuran (6 mL). To the solution were added successively triethylamine (1.21 mL), (R)-4-benzyl-2-oxazolidinone (670 mg) and 4-dimethylaminopyridine (35 mg) under ice-cooling, followed by stirring the reaction mixture at room temperature for 12 hours. Then, after addition of ice-cold water, the reaction mixture was extracted with ethyl acetate. The organic layer was washed with aqueous potassium hydrogen sulfate solution, dried and concentrated. The residue was purified by column chromatography on silica gel (hexane:ethyl acetate (volume ratio)=20:1) to give (4R)-4-benzyl-3-(spiro[5.5]undecane-2-carbonyl)-oxazolidin-2-one (less-polar isomer (chiral: A); 430 mg, more-polar isomer (chiral: B); 390 mg).

Less-Polar Isomer (Chiral: A):

$^1$H-NMR (CDCl$_3$) δ: 0.98-1.06 (1H, m), 1.12-1.29 (3H, m), 1.38-1.63 (11H, m), 1.70 (1H, d, J=13.2 Hz), 1.78-1.85 (1H, m), 1.92 (1H, dd, J=12.6, 2.2 Hz), 2.79 (1H, dd, J=13.4, 9.5 Hz), 3.26 (1H, dd, J=13.4, 3.2 Hz), 3.67-3.75 (1H, m), 4.14-4.23 (2H, m), 4.65-4.71 (1H, m), 7.22-7.37 (5H, m).

More-Polar Isomer (Chiral: B):

$^1$H-NMR (CDCl$_3$) δ: 1.02 (1H, td, J=13.0, 4.6 Hz), 1.18-1.28 (3H, m), 1.37-1.66 (11H, m), 1.67-1.82 (2H, m), 1.91-1.98 (1H, m), 2.77 (1H, dd, J=13.2, 9.5 Hz), 3.26 (1H, dd, J=13.2, 3.3 Hz), 3.72 (1H, tt, J=12.1, 3.3H z), 4.14-4.24 (2H, m), 4.63-4.69 (1H, m), 7.17-7.40 (5H, m).

As used herein, when a carbon atom at the spiro junction is a chiral carbon as represented by, for example, the following formula:

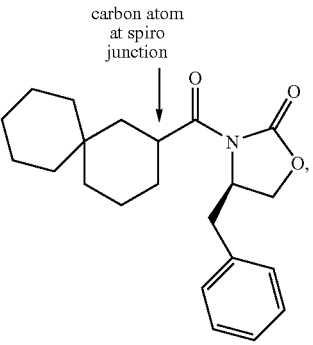

chiral: A refers to a chirality of a carbon atom at the spiro junction in a less-polar isomer. Also, the following compounds obtained from the compounds having the above chirality will be represented by the names with (chiral: A) at the end thereof. Similarly, chiral: B refers to a chirality of a carbon atom at the spiro junction in a more-polar isomer. Also, the following compounds obtained from the compounds having the above chirality will be represented by the names with (chiral: B) at the end thereof.

Step 4

To a suspension of lithium aluminum hydride (55 mg) in tetrahydrofuran (5 mL) was added dropwise a solution of (4R)-4-benzyl-3-(spiro[5.5]undecane-2-carbonyl)-oxazolidin-2-one (chiral: A) (425 mg) obtained in Step 3 in tetrahydrofuran (5 mL) under ice-cooling and nitrogen atmosphere, followed by stirring the reaction mixture in the range of ice-cooling to room temperature for 1.5 hours. Then, to the reaction mixture were added successively water (0.06 mL), 4N aqueous sodium hydroxide solution (0.06 mL) and water (0.18 mL), followed by stirring the reaction mixture at room temperature for 30 minutes. The precipitated insolubles in the reaction mixture were filtered off and the filtrate was concentrated in vacuo. The residue was purified by column chromatography on silica gel (ethyl acetate:hexane (volume ratio)=1:20 to 1:10) to give spiro[5.5]undec-2-yl-methanol (chiral: A)(185 mg).

¹H-NMR (CDCl₃) δ: 0.65 (1H, t, J=13.2 Hz), 0.75-0.97 (2H, m), 1.81-1.18 (16H, m), 3.41 (2H, d, J=4.1 Hz).

Step 5

Spiro[5.5]undec-2-yl-methanol (chiral: A) (100 mg) obtained in Step 4 and (S)-3-(4-hydroxy-phenyl)-hex-4-ynoic acid methyl ester obtained in the same manner as in Substep 5 of Example 1 were subjected to the reaction in the same condition as in Step 8 of Example 1 to give (3S)-3-[4-(spiro[5.5]undec-2-ylmethoxy)-phenyl]-hex-4-ynoic acid methyl ester (chiral: A)(200 mg).

¹H-NMR (CDCl₃) δ: 0.76 (1H, t, J=12.6 Hz), 0.86-0.99 (2H, m), 1.30-1.20 (3H, m), 1.49-1.37 (9H, m), 1.65-1.79 (2H, m), 1.82 (3H, d, J=2.4 Hz), 1.87-1.99 (2H, m), 2.65 (1H, dd, J=15.2, 8.4 Hz), 2.75 (1H, dd, J=15.2, 8.4 Hz), 3.65-3.72 (5H, m), 4.03-4.07 (1H, m), 6.83 (2H, d, J=8.4 Hz), 7.26 (2H, d, J=8.4 Hz).

Step 6

(3S)-3-[4-(spiro[5.5]undec-2-ylmethoxy)-phenyl]-hex-4-ynoic acid methyl ester (chiral: A) (200 mg) obtained in Step 5 was subjected to the reaction in the same condition as in Step 9 of Example 1 to give (3S)-3-[4-(spiro[5.5]undec-2-ylmethoxy)-phenyl]-hex-4-ynoic acid (chiral: A)(190 mg) as the desired compound.

Example 33

Preparation of (3S)-3-[4-(spiro[5.5]undec-2-yl-methoxy)-phenyl]-hex-4-ynoic acid sodium salt (chiral: A)

In the same manner as in Example 2 or 4, the desired compound was obtained from the compound obtained in Example 32.

Example 34

Preparation of (3S)-3-[4-(spiro[5.5]undec-2-yl-methoxy)-phenyl]-hex-4-ynoic acid (chiral: B)

Step 1

In the same manner as in Step 4 of Example 32, spiro[5.5]undec-2-yl-methanol (chiral: B) was obtained from the more-polar isomer (chiral: B) obtained in Step 3 of Example 32.

¹H-NMR (CDCl₃) δ: 0.65 (1H, t, J=13.2 Hz), 0.75-0.97 (2H, m), 1.81-1.18 (16H, m), 3.41 (2H, d, J=4.1 Hz).

Step 2

In the same manner as in Steps 5 to 6 of Example 32, the desired compound was obtained from the compound obtained in the above Step 1.

Example 35

Preparation of (3S)-3-[4-(spiro[5.5]undec-2-yl-methoxy)-phenyl]-hex-4-ynoic acid sodium salt (chiral: B)

In the same manner as in Example 33, the desired compound was obtained from the compound obtained in the same manner as in Example 34.

Example 36

Preparation of (3S)-3-[4-(spiro[4.5]dec-7-yl-methoxy)-phenyl]-hex-4-ynoic acid (chiral: A)

Step 1

In the same manner as in Steps 1 to 3 of Example 32, less-polar isomer (chiral: A) and more-polar isomer (chiral: B) of (4R)-4-benzyl-3-(spiro[4.5]decane-7-carbonyl)-oxazolidin-2-one were obtained from spiro[4.5]dec-7-ene-7-carboxylic acid methyl ester obtained from cyclopentanecarbaldehyde in the same manner as in Steps 1 to 6 and 6' of Example 1.

Less-Polar Isomer (Chiral: A):

¹H-NMR (CDCl₃) δ: 1.22-1.75 (15H, m), 1.90-1.96 (1H, m), 2.77 (1H, dd, J=13.2, 9.5 Hz), 3.27 (1H, dd, J=13.2, 3.4 Hz), 3.59-3.67 (1H, m), 4.15-4.23 (2H, m), 4.63-4.69 (1H, m), 7.20-7.23 (2H, m), 7.26-7.36 (3H, m)

More-Polar Isomer (Chiral: B):

¹H-NMR (CDCl₃) δ: 1.23-1.83 (16H, m), 2.76 (1H, dd, J=13.2, 9.6 Hz), 3.27 (1H, dd, J=13.2, 3.2 Hz), 3.57-3.65 (1H, m), 4.15-4.22 (2H, m), 4.65-4.71 (1H, m), 7.20-7.24 (2H, m), 7.25-7.36 (3H, m).

Step 2

In the same manner as in Step 4 of Example 32, spiro[4.5]dec-7-yl-methanol (chiral: A) was obtained from the less-polar isomer (chiral: A) obtained in Step 1.

¹H-NMR (CDCl₃) δ: 0.84 (1H, dddd, J=12.7, 12.7, 12.7, 3.9 Hz), 0.92 (1H, dd, J=12.7, 12.7 Hz), 1.15 (1H, ddd, J=12.7, 12.7, 3.9 Hz), 1.25-1.67 (14H, m), 1.71-1.78 (1H, m), 3.43 (2H, t, J=5.1 Hz).

Step 3

In the same manner as in Steps 5 to 6 of Example 32, the desired compound was obtained from the compound obtained in Step 2.

Example 37

Preparation of (3S)-3-[4-(spiro[4.5]dec-7-yl-methoxy)-phenyl]-hex-4-ynoic acid sodium salt (chiral: A)

In the same manner as in Example 33, the desired compound was obtained from the compound obtained in Example 36.

Example 38

Preparation of (3S)-3-[4-(spiro[4.5]dec-7-yl-methoxy)-phenyl]-hex-4-ynoic acid (chiral: B)

Step 1

In the same manner as in Step 4 of Example 32, spiro[4.5]dec-7-yl-methanol (chiral: B) was obtained from the more-polar isomer (chiral: B) obtained in Step 1 of Example 36.

¹H-NMR (CDCl₃) δ: 0.84 (1H, dddd, J=12.7, 12.7, 12.7, 3.9 Hz), 0.92 (1H, dd, J=12.7, 12.7 Hz), 1.15 (1H, ddd, J=12.7, 12.7, 3.9 Hz), 1.24-1.67 (14H, m), 1.71-1.78 (1H, m), 3.43 (2H, brs).

Step 2

In the same manner as in Steps 5 to 6 of Example 32, the desired compound was obtained from the compound obtained in the above Step 1.

Example 39

Preparation of (3S)-3-[4-(spiro[4.5]dec-7-yl-methoxy)-phenyl]-hex-4-ynoic acid sodium salt (chiral: B)

In the same manner as in Example 33, the desired compound was obtained from the compound obtained in Example 38.

Example 40

Preparation of 3-(1-methyl-1H-tetrazol-5-yl)-3-[4-(spiro[5.5]undec-2-ylmethoxy)-phenyl]-propionic acid

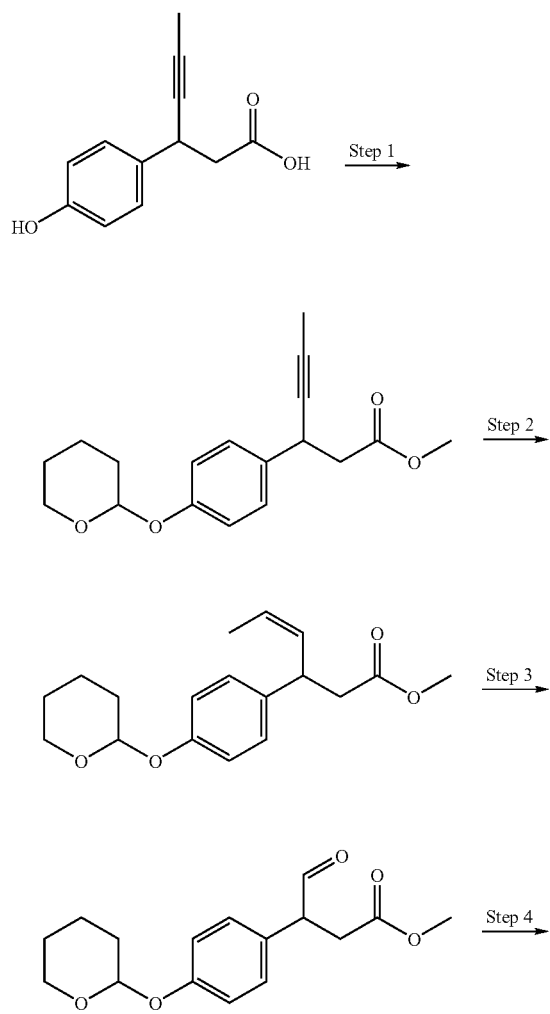

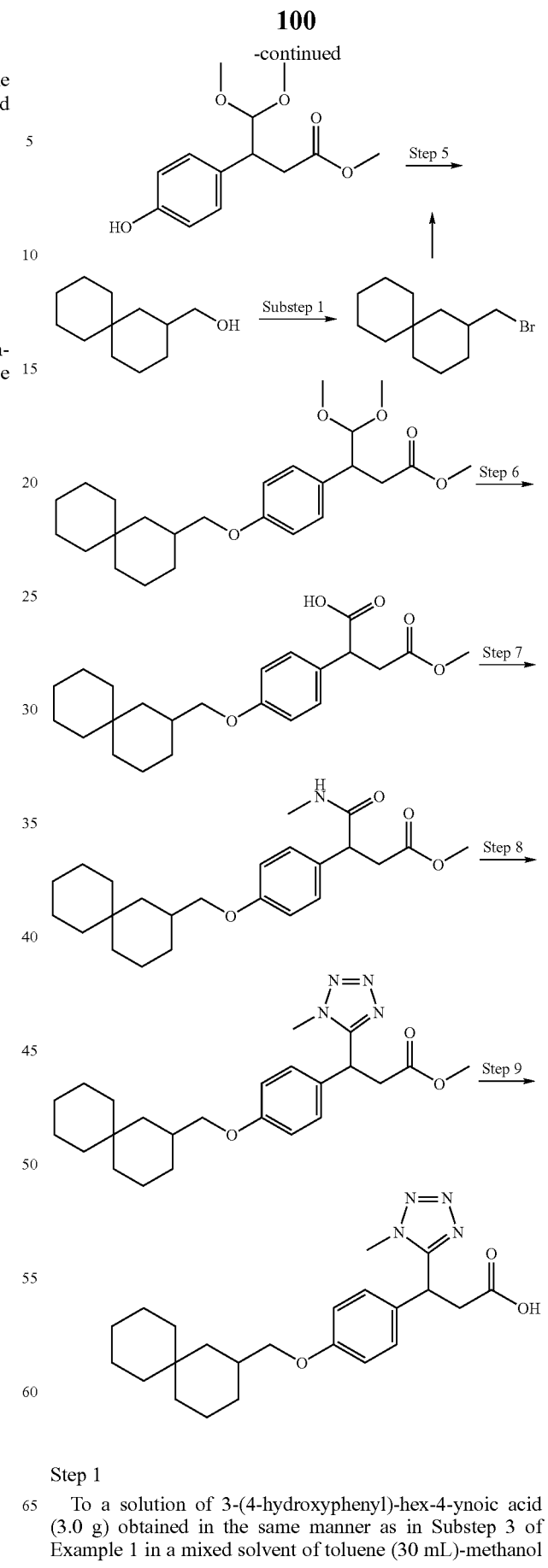

Step 1

To a solution of 3-(4-hydroxyphenyl)-hex-4-ynoic acid (3.0 g) obtained in the same manner as in Substep 3 of Example 1 in a mixed solvent of toluene (30 mL)-methanol (10 mL) was added dropwise a hexane solution of trimethylsilyldiazomethane (2M, 8.8 mL) under ice-cooling over 8 minutes, followed by stirring the reaction mixture at room temperature for 2 hours. Then, the reaction mixture was concentrated and the residue was dissolved in chloroform (60 mL). To the solution were added successively 3,4-dihydro-2H-pyrane (1.6 mL) and camphorsulfonic acid (0.17 g) under ice-cooling, followed by stirring the reaction mixture under ice-cooling for 2 hours. Then, after addition of saturated aqueous sodium bicarbonate solution to the reaction mixture, methanol was evaporated off in vacuo, followed by extraction with ethyl acetate. The organic layer was washed with saturated brine, dried and concentrated. The residue was purified by column chromatography on silica gel (ethyl acetate:hexane (volume ratio)=1:4 to 1:3) to give 3-[4-(tetrahydropyran-2-yloxy)-phenyl]-hex-4-ynoic acid methyl ester (4.07 g).

$^1$H-NMR (CDCl$_3$) δ: 1.57-1.73 (3H, m), 1.82-1.89 (5H, m), 1.96-2.06 (1H, m), 2.66 (1H, dd, J=15.3, 7.0 Hz), 2.76 (1H, dd, J=15.3, 8.6 Hz), 3.59-3.61 (1H, m), 3.68 (3H, s), 3.87-3.94 (1H, m), 4.05-4.09 (1H, m), 5.40 (1H, t, J=3.3 Hz), 7.00 (2H, d, J=8.6 Hz), 7.28 (2H, d, J=8.6 Hz).

Step 2

To a solution of 3-[4-(tetrahydropyran-2-yloxy)-phenyl]-hex-4-ynoic acid methyl ester (4.07 g) obtained in Step 1 in ethyl acetate (70 mL) were added successively quinoline (1.52 mL) and 5% palladium-barium sulfate (0.4 g), followed by stirring the reaction mixture under hydrogen at normal pressure in an atmosphere of hydrogen at room temperature for 15.5 hours. Then, after the reaction mixture was filtered through Celite, water and 1N aqueous hydrochloric acid solution were added to the filtrate, followed by extraction with ethyl acetate. The organic layer was washed successively with 1N aqueous hydrochloric acid solution and saturated brine, dried and concentrated to give (Z)-3-[4-(tetrahydropyran-2-yloxy)-phenyl]-hex-4-enoic acid methyl ester (3.83 g).

Step 3

To a solution of (Z)-3-[4-(tetrahydropyran-2-yloxy)-phenyl]-hex-4-enoic acid methyl ester (3.83 g) obtained in Step 2 in a mixed solvent of dioxane (60 mL)-water (15 mL) was added 2,6-lutidine (2.8 mL). Then, to this was added dropwise a tert-butanol solution of osmium tetroxide (5 mg/mL, 12 mL) over 5 minutes, followed by stirring the reaction mixture at room temperature for 3 minutes. Then, to the reaction mixture was added dropwise aqueous sodium periodate solution (10.3 g/25 mL) over 7 minutes, followed by stirring the reaction mixture at room temperature for 2 hours. After addition of ethyl acetate to the reaction mixture, the organic layer was separated. The organic layer was washed successively with 1N aqueous hydrochloric acid solution, water, saturated aqueous sodium bicarbonate solution, saturated aqueous sodium thiosulfate solution and saturated brine, dried and concentrated. The residue was purified by column chromatography on silica gel (ethyl acetate:hexane (volume ratio)=1:4 to 1:3) to give 4-oxo-3-[4-(tetrahydropyran-2-yloxy)-phenyl]-butyric acid methyl ester (2.59 g).

$^1$H-NMR (CDCl$_3$) δ: 1.57-1.72 (3H, m), 1.84-1.88 (2H, m), 1.95-2.03 (1H, m), 2.58 (1H, dd, J=16.9, 6.2 Hz), 3.13 (1H, dd, J=16.9, 8.3 Hz), 3.58-3.64 (1H, m), 3.66 (3H, s), 3.85-3.93 (1H, m), 4.15-4.07 (1H, m), 5.41 (1H, q, J=3.1 Hz), 7.04-7.12 (4H, m), 9.67 (1H, s).

Step 4

To a solution of 4-oxo-3-[4-(tetrahydropyran-2-yloxy)-phenyl]-butyric acid methyl ester (1.29 g) obtained in Step 3 in methanol (13 mL) was added camphorsulfonic acid (98 mg), followed by stirring the reaction mixture at room temperature for 6 hours. Then, after addition of 1N aqueous sodium hydroxide solution (0.42 mL), the reaction mixture was concentrated. To the residue was added water, followed by extraction with ethyl acetate. The organic layer was washed with saturated brine, dried and concentrated. The residue was purified by column chromatography on silica gel (ethyl acetate:hexane (volume ratio)=1:2 to 2:3) to give 3-(4-hydroxyphenyl)-4,4-dimethoxy butyric acid methyl ester (0.99 g).

$^1$H-NMR (CDCl$_3$) δ: 2.60 (1H, dd, J=15.7, 9.0 Hz), 2.85 (1H, dd, J=15.7, 5.7 Hz), 3.29 (3H, s), 3.39-3.43 (1H, m), 3.58 (3H, s), 4.38 (1H, d, J=6.0 Hz), 4.95 (1H, s), 6.74 (2H, d, J=9.2 Hz), 7.12 (2H, d, J=9.2 Hz).

Step 5

To a solution of 3-(4-hydroxyphenyl)-4,4-dimethoxy butyric acid methyl ester (0.257 g) obtained in Step 4 and 2-bromomethyl-spiro[5.5]undecane (0.225 g) obtained in the following Substep 1 in N,N-dimethylformamide (3 mL) was added cesium carbonate (0.597 g), followed by stirring the reaction mixture at 80° C. for 2.5 hours. Then, after addition of water, the reaction mixture was extracted with ethyl acetate. The organic layer was washed successively with water and saturated brine, dried and concentrated. The residue was purified by column chromatography on silica gel (ethyl acetate:hexane (volume ratio)=1:20 to 1:6) to give 4,4-dimethoxy-3-[4-(spiro[5.5]undec-2-ylmethoxy)-phenyl]-butyric acid methyl ester (0.297 g).

Step 6

To a solution of 4,4-dimethoxy-3-[4-(spiro[5.5]undec-2-ylmethoxy)-phenyl]-butyric acid methyl ester (820 mg) obtained in the same manner as in Step 5 in acetone (8 mL), trifluoroacetic acid (6 mL) was added in three portions hourly, followed by stirring the reaction mixture at room temperature for 3 hours. Then, after addition of saturated aqueous sodium bicarbonate solution under ice-cooling, the reaction mixture was extracted with ethyl acetate. The organic layer was washed successively with saturated aqueous sodium bicarbonate solution and saturated brine, dried and concentrated to give a crude aldehyde. To a solution of the crude aldehyde in a mixed solvent of tert-butanol (6 mL)-water (1.5 mL) were added successively sodium dihydrogen phosphate (88 mg), 2-methyl-2-butene (0.3 mL) and sodium chlorite (218 mg), followed by stirring the reaction mixture at room temperature for 1 hour. Then, after addition of 1N aqueous hydrochloric acid solution, the reaction mixture was extracted with ethyl acetate. The organic layer was washed with saturated brine, dried and concentrated to give 2-[4-(spiro[5.5]undec-2-ylmethoxy)-phenyl]-succinic acid 4-methyl ester (310 mg).

Step 7

To a solution of 2-[4-(spiro[5.5]undec-2-ylmethoxy)-phenyl]-succinic acid 4-methyl ester (310 mg) obtained in Step 6 in N,N-dimethylformamide (4 mL) were added successively 1-ethyl-3-(3-dimethylaminopropyl)carbodiimide hydrochloride (163 mg), 1-hydroxybenzotriazole hydrate (115 mg) and a tetrahydrofuran solution of methylamine (2M, 0.53 mL), followed by stirring the reaction mixture at room temperature for 13 hours. Then, after addition of water, the reaction mixture was extracted with ethyl acetate. The organic layer was washed successively with 1N aqueous hydrochloric acid solution, water, saturated aqueous sodium bicarbonate solution and saturated brine, dried and concentrated. The residue was purified by column chromatography on silica gel (ethyl acetate:hexane (volume ratio)=1:1) to give N-methyl-3-[4-(spiro[5.5]undec-2-ylmethoxy)-phenyl]-succinamic acid methyl ester (278 mg).

$^1$H-NMR (CDCl$_3$) δ: 0.77 (1H, t, J=15.1 Hz), 0.88-1.02 (2H, m), 1.21-1.29 (2H, m), 1.38-1.54 (10H, m), 1.66-2.02 (4H, m), 2.61 (1H, dd, J=16.6, 6.3 Hz), 2.75 (3H, d, J=4.4 Hz), 3.28 (1H, dd, J=16.6, 8.5 Hz), 3.66 (3H, s), 3.70 (2H, dd, J=5.6, 2.8 Hz), 3.87 (1H, dd, J=8.6, 6.3 Hz), 5.36-5.43 (1H, m), 6.86 (2H, d, J=8.1 Hz), 7.19 (2H, d, J=8.1 Hz).

Step 8

To a solution of N-methyl-3-[4-(spiro[5.5]undec-2-ylmethoxy)-phenyl]-succinamic acid methyl ester (178 mg)

obtained in Step 7 in acetonitrile (5 mL) were added successively sodium azide (85 mg) and trifluoromethanesulfonic anhydride (0.29 mL), followed by stirring the reaction mixture at room temperature for 24 hours. Then, after addition of saturated aqueous sodium bicarbonate solution, the reaction mixture was extracted with ethyl acetate. The organic layer was washed with brine, dried and concentrated. The residue was purified by thin-layer column chromatography on silica gel (ethyl acetate:hexane (volume ratio)=1:1) to give 3-(1-methyl-1H-tetrazol-5-yl)-3-[4-(spiro[5.5]undec-2-yl-methoxy)-phenyl]-propionic acid methyl ester (41 mg).

$^1$H-NMR (CDCl$_3$) δ: 0.75 (1H, t, J=12.1 Hz), 0.86-0.99 (2H, m), 1.19-1.28 (2H, m), 1.36-1.99 (14H, m), 3.00 (1H, dd, J=17.4, 5.5 Hz), 3.53 (1H, dd, J=17.4, 8.8 Hz), 3.63-3.70 (5H, m), 3.82 (3H, s), 4.57 (1H, dd, J=5.5, 8.8 Hz), 6.83 (2H, d, J=8.4 Hz), 7.11 (2H, d, J=8.4 Hz).

Step 9

To a solution of 3-(1-methyl-1H-tetrazol-5-yl)-3-[4-(spiro[5.5]undec-2-ylmethoxy)-phenyl]-propionic acid methyl ester (41 mg) obtained in Step 8 in a mixed solvent of tetrahydrofuran (1 mL)-methanol (0.5 mL)-water (0.5 mL) was added 2N aqueous sodium hydroxide solution (0.144 mL), followed by stirring the reaction mixture at room temperature for 18 hours. Then, after addition of 1N aqueous hydrochloric acid solution (0.3 mL), the reaction mixture was extracted with ethyl acetate. The organic layer was washed with saturated brine, dried and concentrated. The residue was purified by thin-layer column chromatography on silica gel (acetic acid:ethyl acetate:chloroform (volume ratio)=0.1:1:10) to give 3-(1-methyl-1H-tetrazol-5-yl)-3-[4-(spiro[5.5]undec-2-ylmethoxy)-phenyl]-propionic acid (39 mg) as the desired compound.

Substep 1

To a solution of spiro[5.5]undec-2-ylmethanol (0.65 g) obtained in the same manner as in Step 1 of Example 26 from spiro[5.5]undec-2-en-2-yl-methanol obtained in the same manner as in Step 7 of Example 1, in chloroform (10 mL) were added successively triphenylphosphine (1.12 g) and N-bromosuccinimide (0.76 g), followed by stirring the reaction mixture at room temperature for 19 hours. Then, after addition of hexane, the precipitate was filtered off and the filtrate was concentrated. The residue was purified by column chromatography on silica gel (ethyl acetate:hexane (volume ratio)=1:4) to give 2-bromomethyl-spiro[5.5]undecane (0.83 g).

$^1$H-NMR (CDCl$_3$) δ: 0.69 (1H, t, J=13.2 Hz), 0.81-0.96 (2H, m), 1.19-1.24 (2H, m), 1.91-1.36 (14H, m), 3.25 (2H, d, J=5.7 Hz).

Example 41

Preparation of 3-ethoxy-3-[4-(spiro[5.5]undec-1-en-2-ylmethoxy)-phenyl]-propionic acid

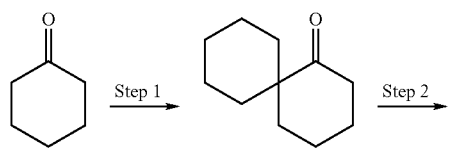

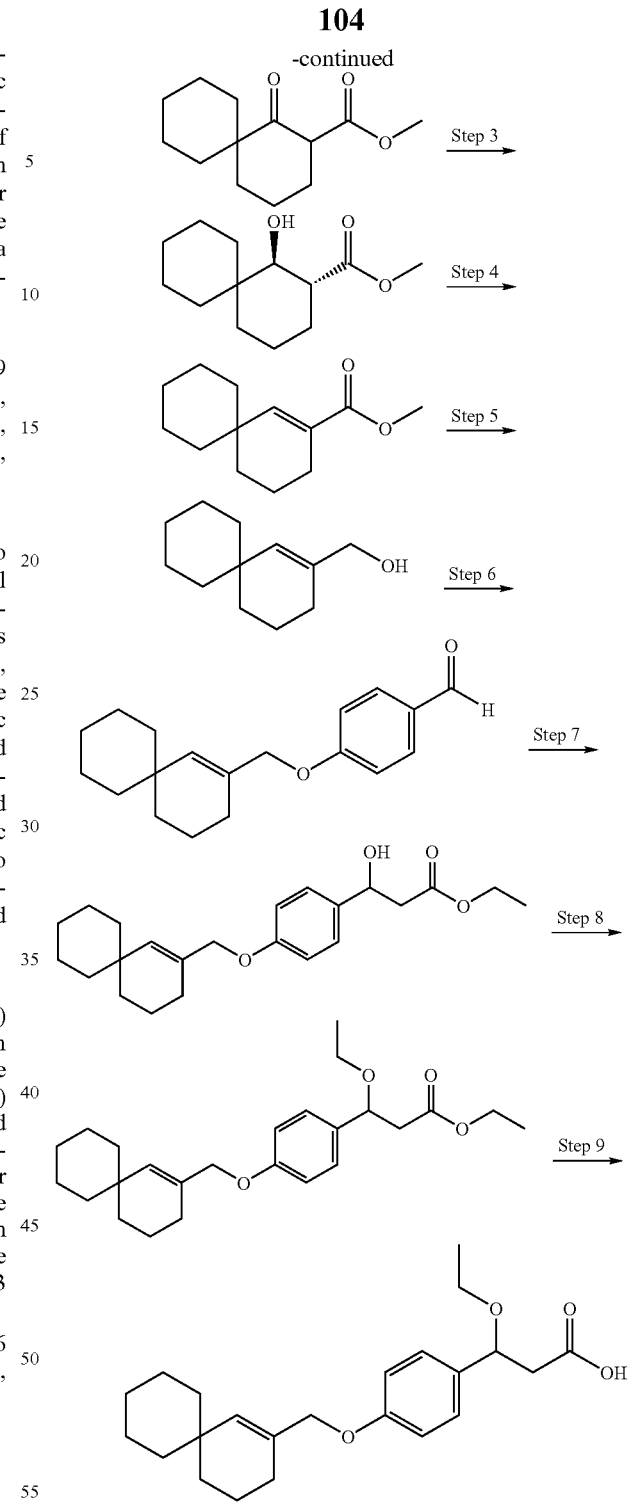

Step 1

To a suspension of potassium tert-butoxide (24.4 g) in toluene (100 mL) was added a solution of cyclohexanone (10.67 g) and 1,5-dibromopentane (25 g) in toluene (50 mL) while stirring. The mixture was stirred at 100° C. for 4 hours. After cooling down to room temperature, the resulting solid was filtered and washed with toluene. The filtrate was concentrated and the residue was purified by column chromatography on silica gel (ethyl acetate:hexane (volume ratio)=1:15) to give spiro[5.5]undecan-1-one (11.85 g).

¹H-NMR (CDCl₃) δ: 1.30-1.51 (8H, m), 1.66-1.74 (4H, m), 1.79-1.91 (4H, m), 2.38 (2H, t, J=6.8 Hz).

Step 2

To a suspension of 60% sodium hydride (5.7 g) and potassium tert-butoxide (1.6 g) in tetrahydrofuran (200 mL) was added dimethyl carbonate (9.6 mL) at room temperature while stirring. The reaction mixture was heated under reflux. To the reaction mixture was added dropwise a solution of spiro[5.5]undecan-1-one (11.85 g) obtained in Step 1 in tetrahydrofuran (40 mL) over 1 hour, followed by heating the reaction mixture under reflux for 2 hours. After ice-cooling, acetic acid (14.6 mL) was added dropwise to the reaction mixture. Then, the reaction mixture was poured into saturated brine, followed by extraction with ethyl acetate. The organic layer was washed with saturated brine, dried and concentrated. The residue was purified by column chromatography on silica gel (ethyl acetate:hexane (volume ratio)=1:15) to give 1-oxo-spiro[5.5]undecane-2-carboxylic acid methyl ester (13.02 g).

¹H-NMR (CDCl₃) δ: 1.29-1.74 (8H, m), 1.78-1.98 (6H, m), 2.16-2.22 (2H, m), 3.74 (3H, s), 12.64 (1H, m).

Step 3

To a solution of 1-oxo-spiro[5.5]undecane-2-carboxylic acid methyl ester (13.02 g) obtained in Step 2 in methanol (300 mL), sodium borohydride (2.2 g) was added in small portions under ice-cooling, followed by stirring the reaction mixture under ice-cooling for 30 minutes. Then, after addition of saturated brine, 2N aqueous hydrochloric acid solution was further added dropwise to the reaction mixture until the evolution of gases ceased, followed by extraction with ethyl acetate twice. The organic layer was washed with saturated brine, dried and concentrated. The residue was purified by column chromatography on silica gel (ethyl acetate:hexane (volume ratio)=1:8 to 1:5) to give trans-1-hydroxy-spiro[5.5]undecane-2-carboxylic acid methyl ester (2.74 g).

¹H-NMR (CDCl₃) δ: 0.82 (1H, tt, J=13.6, 5.0 Hz), 1.07-1.22 (2H, m), 1.31-1.67 (10H, m), 1.84-2.01 (2H, m), 2.17 (1H, dt, J=12.0, 4.2 Hz), 2.39 (1H, d, J=4.4 Hz), 2.52-2.59 (1H, m), 3.42 (1H, dd, J=10.7, 4.2 Hz), 3.71 (3H, s).

Step 4

To a solution of trans-1-hydroxy-spiro[5.5]undecane-2-carboxylic acid methyl ester (2.74 g) obtained in Step 3 in chloroform (20 mL) was added triethylamine (2.02 mL). To the reaction mixture was added dropwise a solution of methanesulfonyl chloride (1.03 mL) in chloroform (5 mL) under ice-cooling, followed by stirring the reaction mixture at room temperature overnight. Then, after addition of water, the reaction mixture was washed therewith. The separated organic layer was dried and concentrated. To the residue were added tetrahydrofuran (30 mL) and 1,8-diazabicyclo[5.4.0]undec-7-ene (3.62 mL), followed by heating the reaction mixture at 60° C. for 3 hours. After cooling down to room temperature, the reaction mixture was poured into water, followed by extraction with ethyl acetate. The organic layer was washed successively with 1N aqueous hydrochloric acid solution and saturated brine, dried and concentrated. The residue was purified by column chromatography on silica gel (ethyl acetate:hexane (volume ratio)=1:8) to give spiro[5.5]undec-1-ene-2-carboxylic acid methyl ester (2.075 g).

¹H-NMR (CDCl₃) δ: 1.32-1.65 (14H, m), 2.20-2.27 (2H, m) 3.73 (3H, s), 6.84 (1H, s).

Step 5

To a solution of spiro[5.5]undec-1-ene-2-carboxylic acid methyl ester (2.07 g) obtained in Step 4 in tetrahydrofuran (30 mL) was added dropwise a 1M toluene solution of diisobutylaluminum hydride (30 mL) at −70° C. under argon atmosphere over 15 minutes, followed by stirring the reaction mixture at −70° C. for 1 hour. Then after careful addition of methanol (2 mL) and 6N aqueous hydrochloric acid solution (5 mL) to the reaction mixture, the temperature was raised to room temperature. The reaction mixture was poured into saturated brine, followed by extraction with ethyl acetate. The organic layer was washed with saturated brine, dried and concentrated. The residue was purified by column chromatography on silica gel (ethyl acetate:hexane (volume ratio)=1:5) to give spiro[5.5]undec-1-ene-2-methanol (1.685 g).

¹H-NMR (CDCl₃) δ: 1.24-1.53 (12H, m), 1.55-1.57 (1H, m), 1.62 (2H, tt, J=9.2, 3.1 Hz), 1.97 (2H, t, J=6.2 Hz), 3.99 (2H, d, J=6.0 Hz), 5.55 (1H, s).

Step 6

To a solution of spiro[5.5]undec-1-ene-2-methanol (3.189 g) obtained in the same manner as in Step 5, 4-hydroxybenzaldehyde (2.589 g) and triphenylphosphine (5.56 g) in tetrahydrofuran (100 mL) was added dropwise a solution of 94% 1,1'-diisopropyl azodicarboxylate (4.446 mL) in tetrahydrofuran (3 mL) under ice-cooling, followed by stirring the reaction mixture at room temperature overnight. Then, the reaction mixture was concentrated and the residue was purified by column chromatography on silica gel (ethyl acetate:hexane (volume ratio)=1:9) to give 4-(spiro[5.5]undec-1-en-2-ylmethoxy)-benzaldehyde (4.27 g).

¹H-NMR (CDCl₃) δ: 1.24-1.51 (12H, m), 1.60-1.68 (2H, m), 2.03 (2H, dt, J=6.2, 2.7 Hz), 4.46 (2H, s), 5.70 (1H, s), 7.01 (2H, dt, J=9.3, 2.3 Hz), 7.82 (2H, dt, J=9.3, 2.3 Hz), 9.89 (1H, s).

Step 7

To a solution of ethyl acetate (2.2 mL) in tetrahydrofuran (100 mL) was added dropwise a 2M heptane/tetrahydrofuran/ethylbenzene solution of lithium diisopropylamide (11.25 mL) at −78° C. under argon atmosphere over 15 minutes, followed by stirring the reaction mixture at −78° C. for 30 minutes. Then, to the reaction mixture was added dropwise a solution of 4-(spiro[5.5]undec-1-en-2-ylmethoxy)-benzaldehyde (4.27 g) obtained in Step 6 in tetrahydrofuran (15 mL) over 10 minutes, followed by stirring the reaction mixture at −78° C. for 40 minutes. After the temperature was raised to room temperature, saturated aqueous ammonium chloride solution (100 mL) was added carefully to the reaction mixture, followed by extraction with ethyl acetate. The organic layer was washed with saturated brine, dried and concentrated. The residue was purified by column chromatography on silica gel (ethyl acetate:hexane (volume ratio)=1:4 to 1:3) to give 3-hydroxy-3-[4-(spiro[5.5]undec-1-en-2-ylmethoxy)-phenyl]-propionic acid ethyl ester (4.98 g).

¹H-NMR (CDCl₃) δ: 1.26 (3H, dq, J=10.4, 2.7 Hz), 1.30-1.49 (8H, m), 1.54 (2H, s), 1.64 (2H, tt, J=9.2, 3.1 Hz), 2.01-2.04 (4H, m), 2.67 (1H, dd, J=16.2, 3.9 Hz), 2.75 (1H, dd, J=16.4, 9.3 Hz), 3.11 (1H, d, J=3.4 Hz), 4.15-4.22 (2H, m), 4.36 (2H, s), 5.08 (1H, dt, J=9.1, 3.4 Hz), 5.67 (1H, s), 6.90 (2H, dt, J=9.3, 2.5 Hz), 7.25-7.29 (2H, m).

Step 8

To a solution of 3-hydroxy-3-[4-(spiro[5.5]undec-1-en-2-ylmethoxy)-phenyl]-propionic acid ethyl ester (4.98 g) obtained in Step 7 and N,N-diisopropylethylamine (6.97 mL) in chloroform (100 mL) was added dropwise a 1M dichloromethane solution of triethyloxonium tetrafluoroborate (20 mL) under ice-cooling over 5 minutes, followed by stirring the reaction mixture under ice-cooling for 10 minutes and then at room temperature for 2.5 hours. Then, the reaction mixture was concentrated and the residue was extracted with ethyl acetate. The organic layer was washed successively with water and saturated brine, dried and concentrated. The residue was purified by column chromatography on silica gel (ethyl acetate:hexane (volume ratio) 1:5) to give 3-ethoxy-3-[4-(spiro[5.5]undec-1-en-2-ylmethoxy)-phenyl]-pr opionic acid ethyl ester (2.175 g).

$^1$H-NMR (CDCl$_3$) δ: 1.13 (3H, t, J=7.0 Hz), 1.22 (3H, td, J=7.6, 3.1 Hz) 1.31-1.50 (10H, m), 1.53 (2H, d, J=4.8 Hz), 1.64 (2H, tt, J=9.2, 3.1 Hz), 2.06 (2H, dt, J=12.8, 7.1 Hz), 2.5 (1H, dd, J=15.0, 5.1 Hz), 2.79 (1H, dd, J=15.0, 8.9 Hz), 3.28-3.41 (2H, m), 4.12 (2H, ddd, J=14.3, 7.1, 2.1 Hz), 4.35 (2H, s), 4.68 (1H, dd, J=8.9, 5.1 Hz), 5.67 (1H, s), 6.89 (2H, dt, J=9.2, 2.4 Hz), 7.23 (2H, dt, J=9.2, 2.4 Hz).

Step 9

To a solution of 3-ethoxy-3-[4-(spiro[5.5]undec-1-en-2-ylmethoxy)-phenyl]-propionic acid ethyl ester (3.169 g) obtained in the same manner as in Step 8 in a mixed solvent of ethanol (10 mL)-tetrahydrofuran (10 mL) was added 4N aqueous sodium hydroxide solution (4 mL) under ice-cooling, followed by stirring the reaction mixture at room temperature for 10 minutes. Then, after addition of ethanol (5 mL) and tetrahydrofuran (5 mL), the reaction mixture was stirred at room temperature overnight. Then, the reaction mixture was diluted with saturated brine and 2N aqueous hydrochloric acid solution (8 mL) was added thereto, followed by extraction with ethyl acetate. The organic layer was washed with saturated brine, dried and concentrated to give 3-ethoxy-3-[4-(spiro[5.5]undec-1-en-2-ylmethoxy)-phenyl]-propionic acid (2.95 g).

Example 42

Preparation of (−)-3-ethoxy-3-[4-(spiro[5.5]undec-1-en-2-ylmethoxy)-phenyl]-propionic acid

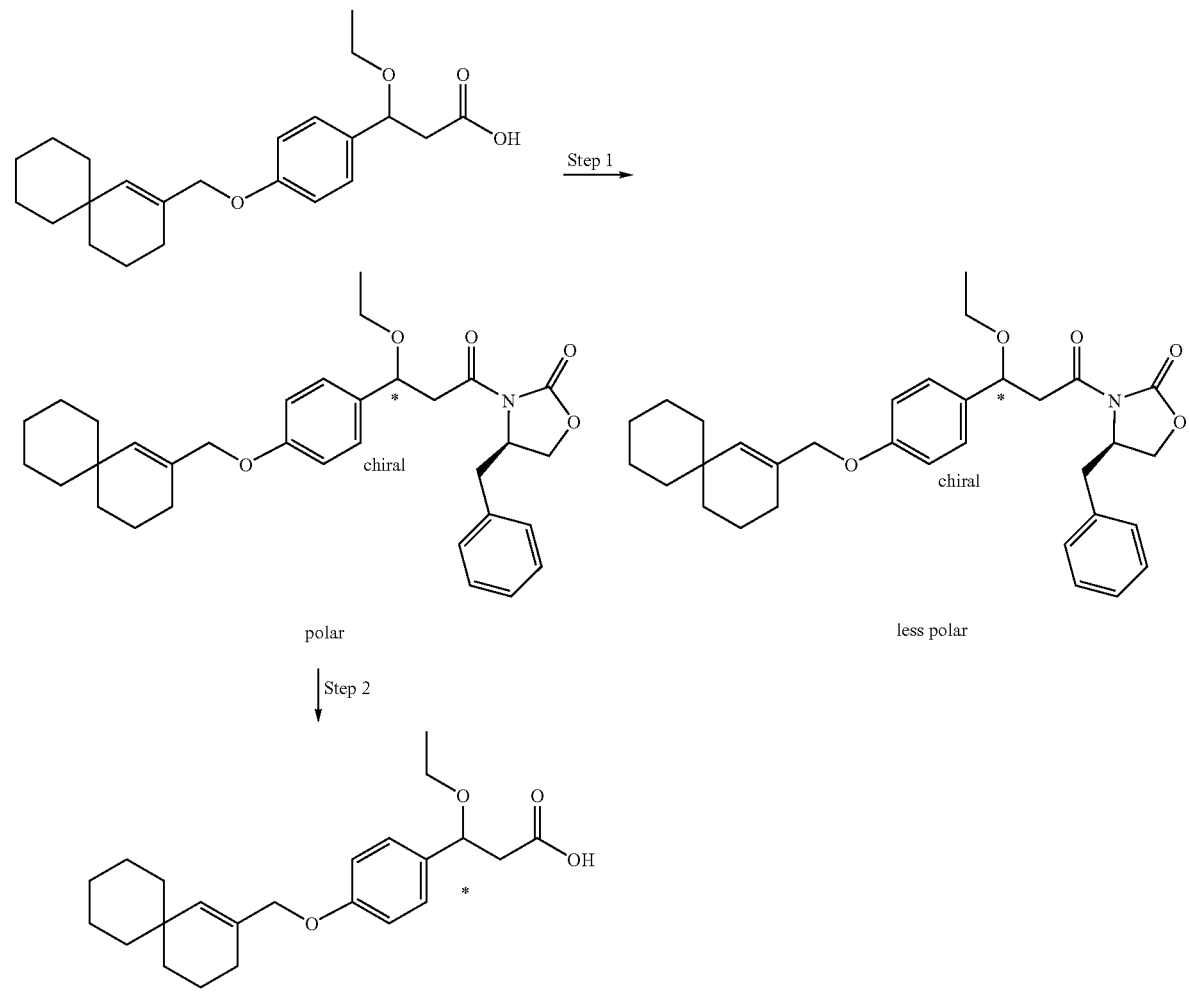

Step 1

To a solution of 3-ethoxy-3-[4-(spiro[5.5]undec-1-en-2-ylmethoxy)-phenyl]-pr opionic acid (2.95 g) obtained in Example 41 and triethylamine (3.3 mL) in tetrahydrofuran (60 mL) was added dropwise a solution of pivaloyl chloride (1.265 mL) in tetrahydrofuran (5 mL) at −35° C., followed by stirring the reaction mixture at −35 to −30° C. for 30 minutes. Then, to the reaction mixture was added dropwise a solution of (R)-4-benzyl-2-oxazolidinone (1.82 g) and lithium bromide (892 mg) in tetrahydrofuran (10 mL), followed by raising the temperature up to 0° C. over 2 hours while stirring the reaction mixture. The reaction mixture was poured into ice-cold water, followed by extraction with ethyl acetate. The organic layer was washed with saturated brine, dried and concentrated. The residue was purified by mid-pressure preparative chromatography on silica gel (ethyl acetate:hexane (volume ratio)=1:5) to give (R)-4-benzyl-3-(3-ethoxy-3-[4-(spiro[5.5]undec-1-en-2-ylmethoxy)-phenyl]-propionyl)oxazolidin-2-one.

Less-Polar Diastereomer (1.24 g)

$^1$H-NMR (CDCl$_3$) δ: 1.14 (3H, t, J=7.0 Hz), 1.34-1.54 (15H, m), 1.64 (2H, tt, J=9.2, 3.1 Hz), 2.02-2.10 (1H, m), 2.78 (1H, dd, J=13.5, 9.4 Hz), 3.10 (1H, dd, J=16.1, 5.0 Hz), 3.29 (1H, dd, J=13.5, 3.1 Hz), 3.37 (2H, ddt, J=16.5, 7.0, 2.7 Hz), 3.67 (1H, dd, J=16.2, 8.7 Hz), 4.36 (2H, s), 4.62-4.68 (1H, m), 4.82 (1H, dd, J=8.7, 5.1 Hz), 5.67 (1H, s), 6.88-6.92 (2H, m), 7.21-7.36 (7H, m).

More-Polar Diastereomer (1.18 g)

$^1$H-NMR (CDCl$_3$) δ: 1.14 (3H, t, J=7.12 Hz), 1.34-1.49 (9H, m), 1.55 (2H, s), 1.64 (2H, tt, J=9.2, 3.1 Hz), 2.04 (2H, q, J=3.5 Hz), 2.70 (1H, dd, J=13.4, 9.5 Hz), 3.18 (1H, dd, J=16.2, 4.1 Hz), 3.25 (1H, dd, J=13.4, 3.3 Hz), 3.34-3.41 (2H, m), 3.50 (1H, dd, J=16.2, 9.4 Hz), 4.18 (2H, dt, J=12.6, 5.0 Hz), 4.36 (2H, s), 4.67-4.72 (1H, m), 4.84 (1H, dd, J=9.4, 4.1 Hz), 5.67 (1H, s), 6.90 (2H, dt, J=9.3, 2.4 Hz), 7.15-7.18 (2H, m), 7.27-7.34 (5H, m).

Step 2

To a solution of (R)-4-benzyl-3-{3-ethoxy-3-[4-(spiro[5.5]undec-1-en-2-ylmethoxy)-phenyl]-propionyl}oxazolidin-2-one (more-polar diastereomer 1.178 g) obtained in Step 1 in tetrahydrofuran (20 mL) and water (5 mL) was added a mixture of 4N aqueous lithium hydroxide solution (1.1 mL) and 30% hydrogen peroxide solution (0.88 mL) under ice-cooling, followed by stirring the reaction mixture at room temperature. After 1.5 and 5.5 hours, to the reaction mixture was further added a mixture of 4N aqueous lithium hydroxide solution (0.55 mL) and 30% hydrogen peroxide solution (0.44 mL), followed by stirring the reaction mixture at room temperature. After 7 hours, to the reaction mixture were added successively sodium sulfite (2.785 g) and an aqueous potassium hydrogen sulfate (1.2 g) solution (30 mL) under ice-cooling, followed by extraction with ethyl acetate. The organic layer was washed with saturated brine, dried and concentrated. The residue was purified by column chromatography on silica gel (ethyl acetate:hexane (volume ratio)=1:3) to give (−)-3-ethoxy-3-[4-(spiro[5.5]undec-1-en-2-ylmethoxy)-phenyl]-propionic acid (443 mg) as the desired compound.

The specific optical rotation of this compound was as follows. [α]$_D^{25}$=−33.3° (c1.020, EtOH)

Example 43

Preparation of (−)-3-ethoxy-3-[4-(spiro[5.5]undec-1-en-2-ylmethoxy)-phenyl]-propionic acid sodium salt In the same manner as in Example 2 or 4, the desired compound was obtained from the compound obtained in Example 42.

Example 44

Preparation of (+)-3-ethoxy-3-[4-(spiro[5.5]undec-1-en-2-ylmethoxy)-phenyl]-propionic acid In the same manner as in Step 2 of Example 42, the desired compound was obtained from the less-polar diastereomer obtained in Step 1 of Example 42.

Examples 45 to 89

The compounds shown in Tables 1 to 13 were prepared by the same preparation method as in any of Examples 1 to 44.

Example 90

Preparation of (S)-3-[4-(spiro[5.5]undec-2-en-2-ylmethoxy)-phenyl]-hex-4-ynoic acid 0.5 calcium salt

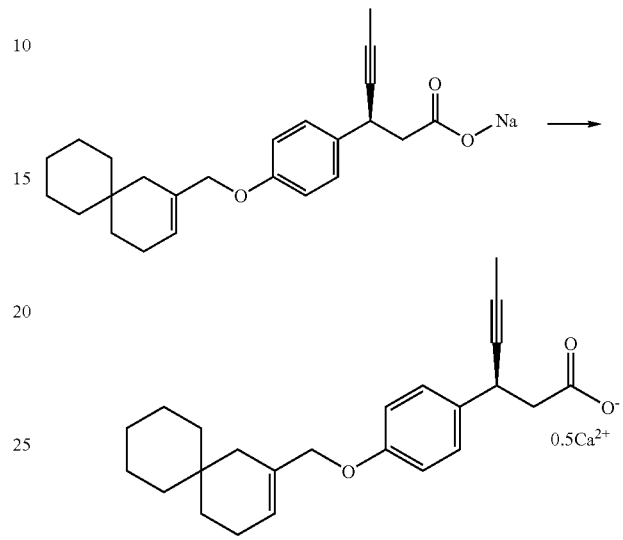

To a solution of (S)-3-[4-(spiro[5.5]undec-2-en-2-ylmethoxy)-phenyl]-hex-4-ynoic acid sodium salt (2.33 g) obtained in the same manner as in Example 2 in water (60 mL) was added 0.1M aqueous calcium chloride solution (30 mL), followed by stirring the mixture at room temperature for 1 hour. The precipitate was filtered and dried to give (S)-3-[4-(spiro[5.5]undec-2-en-2-ylmethoxy)-phenyl]-hex-4-ynoic acid 0.5 calcium salt (1.82 g).

Example 91

Preparation of (S)-3-[4-(spiro[4.5]dec-6-en-7-ylmethoxy)-phenyl]-hex-4-ynoic acid 0.5 calcium salt

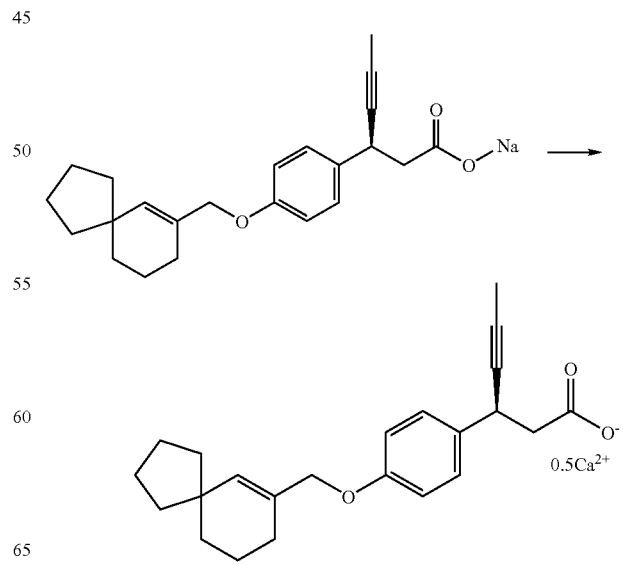

To a solution of (S)-3-[4-(spiro[4.5]dec-6-en-7-yl-methoxy)-phenyl]-hex-4-ynoic acid sodium salt (2.50 g) obtained in the same manner as in Example 8 in water (35 mL) were added successively 0.1M aqueous calcium chloride solution (33.4 mL) and water (20 mL), followed by stirring the mixture at room temperature for 0.5 hour. The precipitate was filtered and dried to give (S)-3-[4-(spiro[4.5]dec-6-en-7-ylmethoxy)-phenyl]-hex-4-ynoic acid 0.5 calcium salt (2.47 g).

Example 92

Preparation of (S)-3-[4-(spiro[4.5]dec-6-en-7-yl-methoxy)-phenyl]-hex-4-ynoic acid L-lysine salt

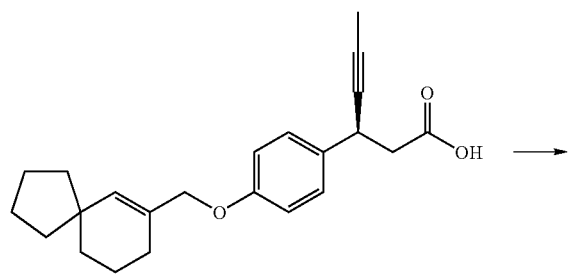

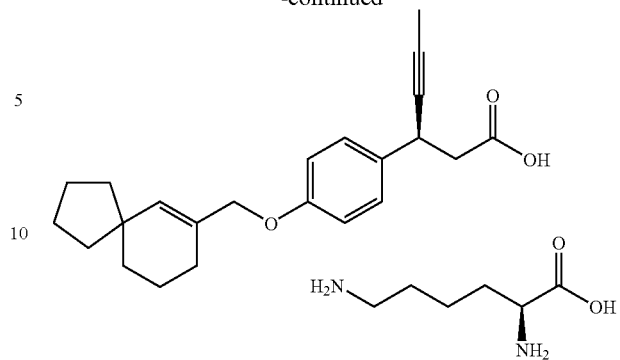

To a solution of (S)-3-[4-(spiro[4.5]dec-6-en-7-yl-methoxy)-phenyl]-hex-4-ynoic acid (82.5 mg) obtained in the same manner as in Example 7 in 2-propanol (1.75 mL) was added a solution of L-lysine (32.5 mg) in water (0.14 mL) at 60° C. The mixture was stirred at 50° C. for 12 hours and then stirred at room temperature for 8 hours. The precipitate was filtered, washed with 2-propanol and dried to give (S)-3-[4-(spiro[4.5]dec-6-en-7-ylmethoxy)-phenyl]-hex-4-ynoic acid L-lysine salt (87.8 mg).

Example 93

Preparation of (R)-3-[4-(spiro[4.5]dec-6-en-7-yl-methoxy)-phenyl]-hex-4-ynoic acid

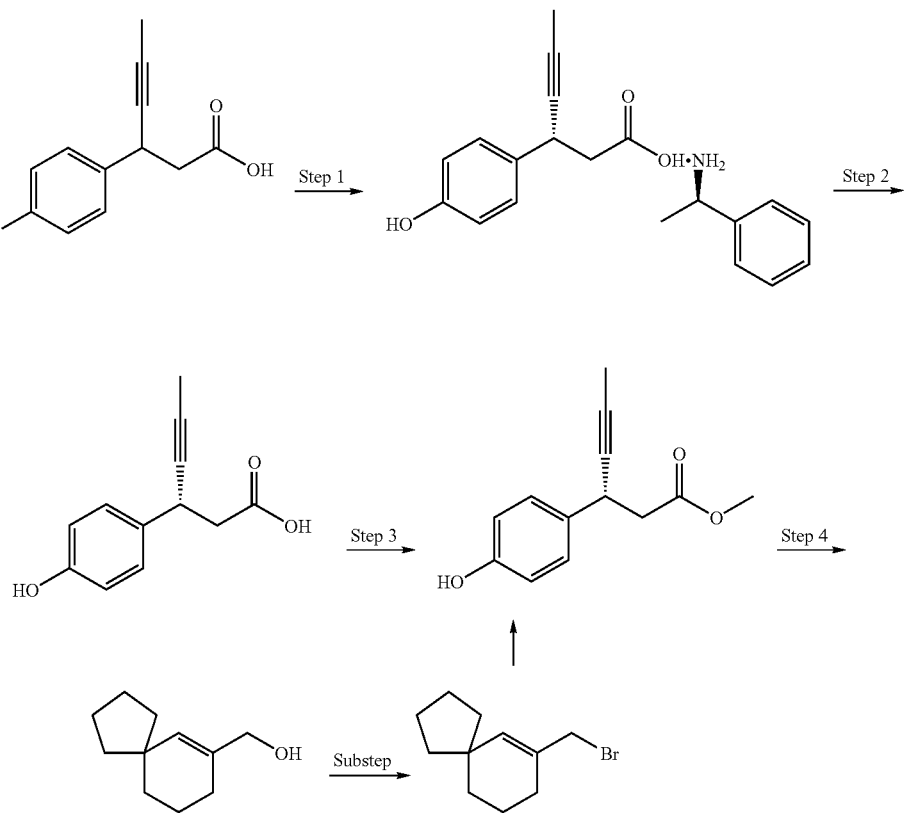

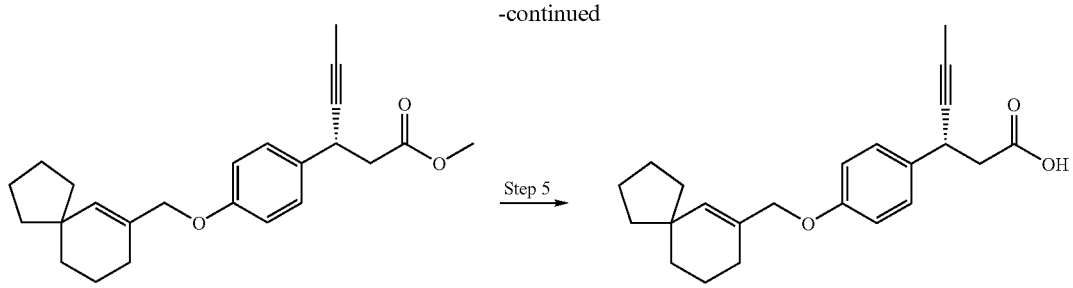

Step 1

To a solution of 3-(4-hydroxyphenyl)-hex-4-ynoic acid (100 mg) obtained in the same manner as in Substep 3 of Example 1 in 2-propanol (2 mL) was added (R)-α-methylbenzylamine (58 mg) at 85° C. The mixture was stirred successively at 85° C. for 0.5 hour, at 40° C. for 2 hours and at room temperature overnight. The resulting crystal was filtered and then dried to give (R)-3-(4-hydroxyphenyl)-hex-4-ynoic acid (R)-α-methylbenzylamine salt (68 mg, 66% ee). Meanwhile, to a solution of (R)-3-(4-hydroxyphenyl)-hex-4-ynoic acid (300 g, 58% ee), which has been obtained by concentration of the filtrate byproduced in the same manner as upon recrystallization in Substep 4 of Example 1 and extraction of the concentrate under acidic condition in the same manner as upon crystallization in Substep 4 of Example 1, in 2-propanol (6 L), (R)-α-methylbenzylamine (151 g) was added at 75° C. This solution was heated at 80° C. and (R)-3-(4-hydroxyphenyl)-hex-4-ynoic acid (R)-α-methylbenzylamine salt (30 mg) obtained earlier was added thereto. The mixture was stirred at 80° C. for 2 hours, and further stirred for 20 hours while gradually cooling down to room temperature. The resulting crystal was filtered and then dissolved in 2-propanol (5.5 L) while heating. The mixture was stirred at 65° C. for 4 hours, and further stirred overnight while gradually cooling down to room temperature. The resulting crystal was filtered and dried to give (R)-3-(4-hydroxyphenyl)-hex-4-ynoic acid (R)-α-methylbenzylamine salt (181 g, 98% ee). The optical purity was determined by chiral HPLC analysis (column: DaicelChiralpakAD-RH, mobile phase: 15 v/v % aqueous acetonitrile solution containing 0.01% trifluoroacetic acid).

$^1$H-NMR (DMSO-d$_6$) δ: 1.28 (3H, d, J=6.5 Hz), 1.75 (3H, d, J=3.0 Hz), 2.32-2.55 (2H, m), 3.88 (1H, ddd, J=8.0, 3.0, 8.5 Hz), 4.04 (1H, q, J=6.5% z), 6.67 (2H, d, J=9.0 Hz), 7.12 (2H, d, J=8.5 Hz), 7.17-7.25 (1H, m), 7.27-7.35 (2H, m), 7.35-7.42 (2H, m).

Step 2

(R)-3-(4-hydroxyphenyl)-hex-4-ynoic acid (R)-α-methylbenzylamine salt (40 g) obtained in Step 1 was suspended in ethyl acetate (300 mL)-saturated aqueous potassium hydrogen sulfate solution (30 mL). The suspension was vigorously stirred until it became a solution, followed by extraction of the reaction mixture with ethyl acetate twice. The organic layer was washed successively with water and saturated brine, dried and concentrated to give (R)-3-(4-hydroxyphenyl)-hex-4-ynoic acid (25 g).

$^1$H-NMR (DMSO-d$_6$) δ: 1.76 (3H, brs), 2.55 (2H, d, J=7.7 Hz), 3.87 (1H, t, J=7.7 Hz), 6.68 (2H, dd, J=8.6, 1.4 Hz), 7.13 (2H, dd, J=8-0.6, 1.2 Hz), 9.28 (1H, s), 12.20 (1H, s).

Step 3

To a solution of (R)-3-(4-hydroxyphenyl)-hex-4-ynoic acid (25 g) obtained in Step 2 in methanol (125 mL) was added concentrated sulfuric acid (1.25 mL), followed by stirring the mixture at 80° C. for 2.5 hours. After cooling down to room temperature, water (100 mL) and sodium bicarbonate (4.14 g) were added to the reaction mixture, followed by concentration of the mixture. To the reaction mixture were added water and saturated aqueous sodium bicarbonate solution, followed by extraction with ethylacetate. The organic layer was washed with saturated brine, dried and concentrated. The residue was distilled azeotropically with toluene to give (R)-3-(4-hydroxyphenyl)-hex-4-ynoic acid methyl ester (28.5 g).

$^1$H-NMR (CDCl$_3$) δ: 1.84 (3H, d, J=2.6 Hz), 2.66 (1H, dd, J=15.2, 7.1 Hz), 2.77 (1H, dd, J=15.3, 8.3 Hz), 3.67 (3H, s), 4.03-4.09 (1H, m), 4.80 (1H, s), 6.78 (2H, d, J=8.6 Hz), 7.25 (2H, d, J=8.6 Hz).

Step 4

To a solution of (R)-3-(4-hydroxyphenyl)-hex-4-ynoic acid methyl ester (15 g) obtained in Step 3 and 7-bromomethyl-spiro[4.5]dec-6-ene (17.3 g) obtained in the following Substep in N,N-dimethylformamide (150 mL) was added potassium carbonate (12.4 g), followed by stirring the reaction mixture at room temperature for 19 hours. To the reaction mixture was added water, followed by extraction with n-hexane twice. The organic layers were combined, washed successively with water and saturated brine, dried and concentrated. The residue was purified by column chromatography on silica gel (ethyl acetate:hexane (volume ratio)=1:100 to 1:30) to give (R)-3-[4-(spiro[4.5]dec-6-en-7-ylmethoxy)-phenyl]-hex-4-ynoic acid methyl ester (23.5 g).

$^1$H-NMR (CDCl$_3$) δ: 1.45-1.48 (6H, m), 1.62-1.69 (6H, m), 1.82 (3H, d, J=2.4 Hz), 2.03 (2H, brdd, J=6.3, 6.3 Hz), 2.65 (1H, dd, J=15.2, 7.0 Hz), 2.75 (1H, dd, J=15.2, 8.2 Hz), 3.66 (3H, s), 4.02-4.08 (1H, m), 4.33 (2H, s), 5.58 (1H, s), 6.84-6.88 (2H, m), 7.24-7.27 (2H, m).

Step 5

To a solution of (R)-3-[4-(spiro[4.5]dec-6-en-7-ylmethoxy)-phenyl]-hex-4-ynoic acid methyl ester (23.5 g) obtained in Step 4 in a mixed solvent of tetrahydrofuran (94 mL)-methanol (94 mL) was added 2N aqueous sodium hydroxide solution (48 mL), followed by stirring the mixture at room temperature overnight. To the reaction mixture was added 2N aqueous hydrochloric acid solution (48 mL), followed by extraction with n-hexane twice. The organic layers were combined, washed with saturated brine, dried and concentrated to give (R)-3-[4-(spiro[4.5]dec-6-en-7-ylmethoxy)-phenyl]-hex-4-ynoic acid (26 g).

Substep

To a solution of spiro[4.5]dec-6-ene-7-methanol (21.1 g) obtained in the same manner as in Step 6 of Example 7 in tetrahydrofuran (320 mL) was added triethylamine (1.25 mL) under ice-cooling, and then to this was added dropwise methanesulfonyl chloride (10.8 mL), followed by stirring the mixture under ice-cooling for 1.5 hours. To the reaction mixture was added lithium bromide (33 g), followed by stirring the mixture under ice-cooling for 2 hours. To the reaction mixture was added water, followed by extraction with n-hexane. The organic layer was washed with saturated brine, dried and concentrated to give 7-bromomethyl-spiro[4.5]dec-6-ene (29.2 g).

$^1$H-NMR (DMSO-d$_6$) δ: 1.31-1.46 (6H, m), 1.53-1.68 (6H, m), 1.98-2.06 (2H, m), 4.07 (2H, s), 5.72 (1H, s).

Example 94

Preparation of (R)-3-[4-(spiro[4.5]dec-6-en-7-yl-methoxy)-phenyl]-hex-4-ynoic acid L-lysine salt

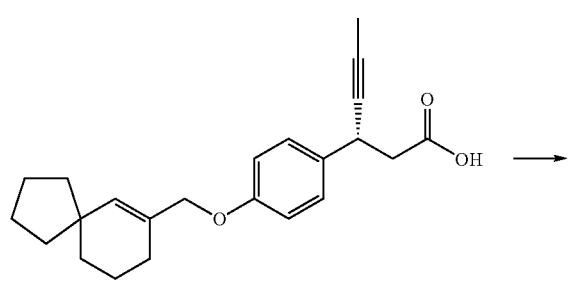

To a solution of (R)-3-[4-(spiro[4.5]dec-6-en-7-yl-methoxy)-phenyl]-hex-4-ynoic acid (5.0 g) obtained in Example 93 in 2-propanol (75 mL) was added a solution of L-lysine (2.07 g) in water (5.75 mL) at 70° C., followed by stirring overnight while gradually cooling the mixture down to room temperature. The precipitate was filtered and then dried to give (R)-3-[4-(spiro[4.5]dec-6-en-7-ylmethoxy)-phenyl]-hex-4-ynoic acid L-lysine salt (5.64 g).

Example 95

Preparation of (−)-3-ethoxy-3-[4-(spiro[5.5]undec-1-en-2-ylmethoxy)-phenyl]-propionic acid 0.5 calcium salt

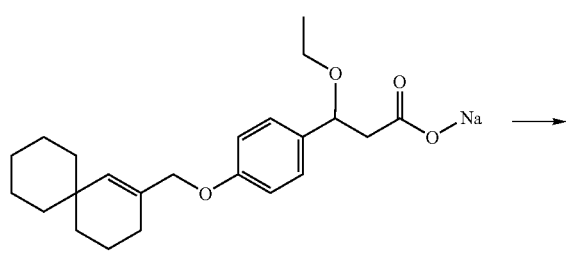

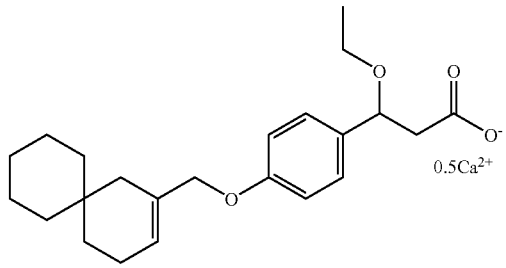

To a solution of (−)-3-ethoxy-3-[4-(spiro[5.5]undec-1-en-2-ylmethoxy)-phenyl]-propionic acid sodium salt (3.71 g) obtained in the same manner as in Example 43 in water (70 mL) was added 0.1M aqueous calcium chloride solution (47.1 mL), followed by stirring the mixture at room temperature for 0.5 hour. The precipitate was filtered and then dried to give (−)-3-ethoxy-3-[4-(spiro[5.5]undec-1-en-2-ylmethoxy)-phenyl]-propionic acid 0.5 calcium salt (3.60 g).

Example 96

Preparation of (3S)-3-[4-((5S)-2-oxo-spiro[4.5]dec-6-en-7-ylmethoxy)-phenyl]-hex-4-ynoic acid

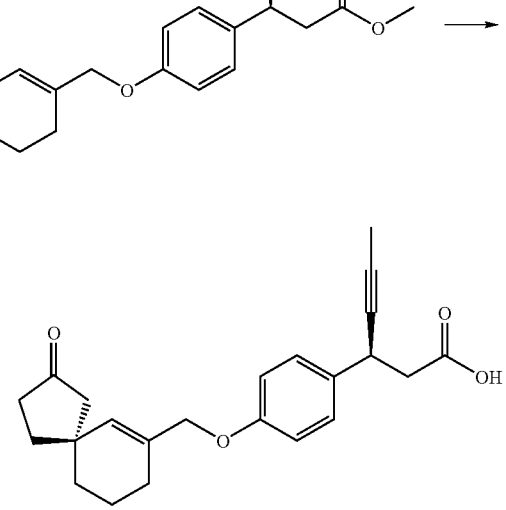

In the same manner as in Example 102, (3S)-3-[4-((5S)-2-oxo-spiro[4.5]dec-6-en-7-ylmethoxy)-phenyl]-hex-4-ynoic acid (40 mg) was obtained from (3S)-3-[4-((2S,5S)-2-hydroxy-spiro[4.5]dec-6-en-7-ylmethoxy)-phenyl]-hex-4-ynoic acid methyl ester (120 mg) obtained in Step 3 of Example 98.

Example 97

Preparation of (3S)-3-[4-((5S)-2-oxo-spiro[4.5]dec-6-en-7-ylmethoxy)-phenyl]-hex-4-ynoic acid sodium salt

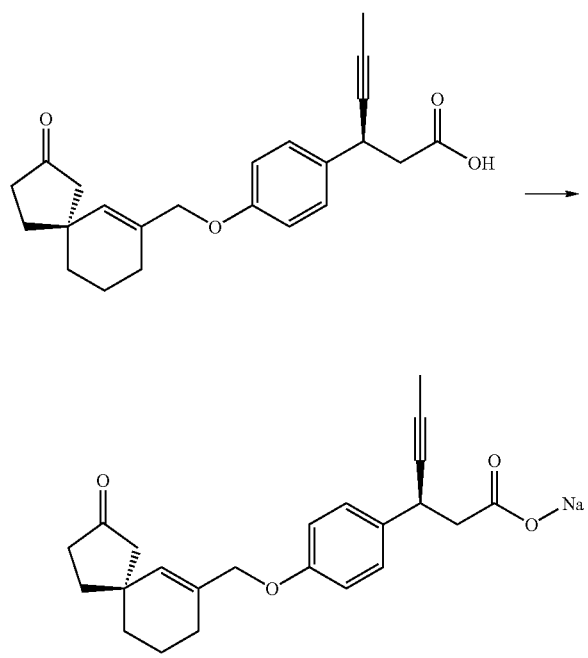

To a solution of (3S)-3-[4-((5S)-2-oxo-spiro[4.5]dec-6-en-7-ylmethoxy)-phenyl]-hex-4-ynoic acid (82 mg) obtained in the same manner as in Example 96 in a mixed solvent of ethanol (5 mL)-water (1 mL) was added dropwise 0.1N aqueous sodium hydroxide solution (2.13 mL) at −10° C., followed by stirring the reaction mixture at −10° C. for 15 minutes. The reaction mixture was concentrated and the residue was distilled azeotropically with ethanol. The residue was dried in vacuo to give (3S)-3-[4-((5S)-2-oxo-spiro[4.5]dec-6-en-7-ylmethoxy)-phenyl]-hex-4-ynoic acid sodium salt (87 mg).

Example 98

Preparation of (3S)-3-[4-((2S,5S)-2-hydroxy-spiro[4.5]dec-6-en-7-ylmethoxy)-phenyl]-hex-4-ynoic acid

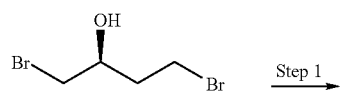

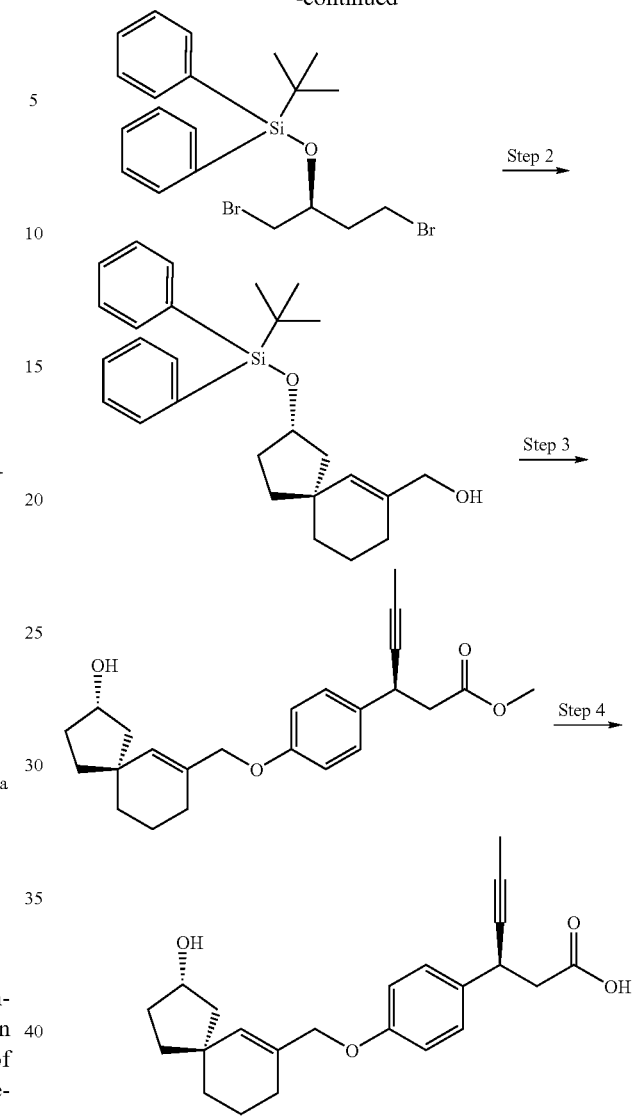

Step 1

To a solution of (S)-1,4-dibromo-2-butanol (5.0 g) in N,N-dimethylformamide (30 mL) were added imidazole (1.91 g) and tert-butylchlorodiphenylsilane (7.1 mL) under ice-cooling, followed by stirring the mixture at room temperature for 13 hours. To the reaction mixture were further added imidazole (0.59 g) and tert-butylchlorodiphenylsilane (1.77 mL), followed by stirring the mixture at room temperature for 7 hours To the reaction mixture was added water, followed by extraction with ethyl acetate. The organic layer was washed successively with 1N aqueous hydrochloric acid solution, saturated aqueous sodium bicarbonate solution and saturated brine, dried and concentrated. The residue was purified by column chromatography on silica gel (ethyl acetate:hexane (volume ratio)=1:50) to give ((S)-3-bromo-1-bromomethyl-propoxy)-tert-butyldiphenylsilane (8.56 g).

$^1$H-NMR (CDCl$_3$) δ: 1.09 (9H, s), 2.16-2.26 (2H, m), 3.27 (2H, d, J=5.0 Hz), 3.42 (2H, t, J=7.0 Hz), 4.01-4.06 (1H, m), 7.38-7.50 (6H, m), 7.73-7.70 (4H, m).

Step 2

In the same manner as in Steps 4 to 7 of Example 104, [(2S,5S)-2-(tert-butyldiphenylsilanyloxy)-spiro[4.5]dec-6-e n-7-yl]-methanol (0.90 g) was obtained from ((S)-3-bromo-1-bromomethyl-propoxy)-tert-butyldiphenylsilane (9.7 g) obtained in the same manner as in Step 1.

$^1$H-NMR (CDCl$_3$) δ: 1.06 (9H, s), 1.18-1.23 (1H, m), 1.35-1.43 (1H, m), 1.62-1.85 (8H, m), 1.93-1.98 (2H, m), 3.94 (2H, d, J=4.4 Hz), 4.34 (1H, tt, J=5.1, 5.1 Hz), 5.32 (1H, s), 7.35-7.45 (6H, m), 7.65-7.68 (4H, m).

Step 3

In the same manner as in Steps 8 to 9 of Example 104, (3S)-3-[4-((2S,5S)-2-hydroxy-spiro[4.5]dec-6-en-7-yl-methoxy)-phenyl]-hex-4-ynoic acid methyl ester (335 mg) was obtained from [(2S,5S)-2-(tert-butyldiphenylsilanyloxy)-spiro[4.5]dec-6-e n-7-yl]-methanol (452 mg) obtained in Step 2.

$^1$H-NMR (CDCl$_3$) δ: 1.38-1.78 (9H, m), 1.83 (3H, d, J=2.3 Hz), 1.89 (1H, d d, J=13.8, 5.4 Hz), 1.98-2.07 (3H, m), 2.66 (1H, dd, J=15.1, 7.0 Hz), 2.76 (1H, dd, J=15.1, 8.3 Hz), 3.67 (3H, s), 4.03-4.09 (1H, m), 4.32 (2H, s), 4.38-4.44 (1H, m), 5.56 (1H, s), 6.86 (2H, d, J=8.6 Hz), 7.27 (2H, d, J=8.6 Hz).

Step 4

In the same manner as in Step 9 of Example 1, (3S)-3-[4-((2S,5S)-2-hydroxy-spiro[4.5]dec-6-en-7-ylmethoxy)-phenyl]-hex-4-ynoic acid (37 mg) was obtained from (3S)-3-[4-((2S,5S)-2-hydroxy-spiro[4.5]dec-6-en-7-ylmethoxy)-phenyl]-hex-4-ynoic acid methyl ester (77 mg) obtained in Step 3. Configuration of the structure was determined by NMR spectrum (NOESY, HSQC).

Example 99

Preparation of (3S)-3-[4-((2S,5S)-2-hydroxy-spiro [4.5]dec-6-en-7-ylmethoxy)-phenyl]-hex-4-ynoic acid sodium salt

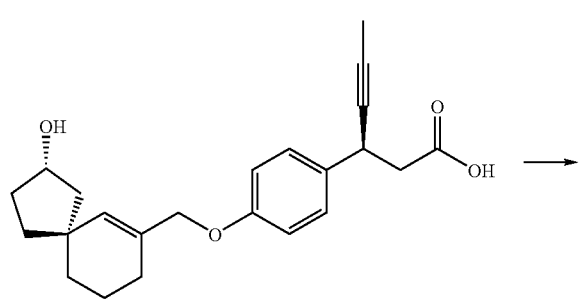

In the same manner as in Example 97, the desired compound was obtained from the compound obtained in Example 98.

Example 100

Preparation of (3S)-3-[4-((2R,5S)-2-hydroxy-spiro [4.5]dec-6-en-7-ylmethoxy)-phenyl]-hex-4-ynoic acid

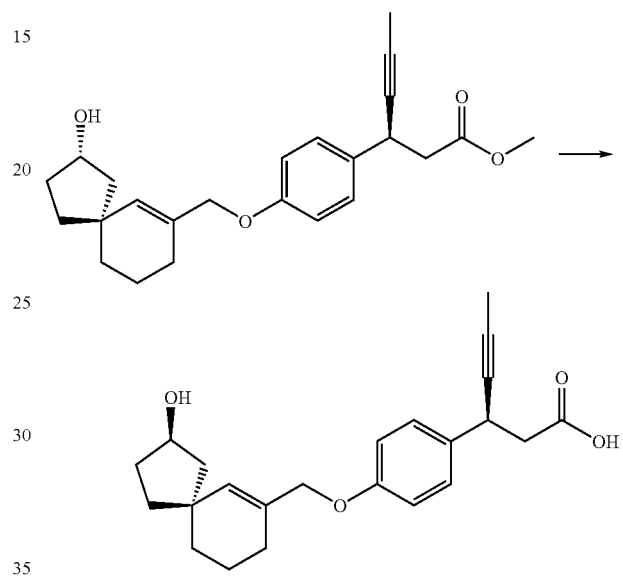

In the same manner as in Example 106, (3S)-3-[4-((2R, 5S)-2-hydroxy-spiro[4.5]dec-6-en-7-ylmethoxy)-phenyl]-hex-4-ynoic acid (33 mg) was obtained from (3S)-3-[4-((2S, 5S)-2-hydroxy-spiro[4.5]dec-6-en-7-ylmethoxy)-phenyl]-hex-4-ynoic acid methyl ester (65 mg) obtained in the same manner as in step 3 of Example 98. Configuration of the structure was determined by NMR spectrum (NOESY, HSQC).

Example 101

Preparation of (3S)-3-[4-((2R,5S)-2-hydroxy-spiro [4.5]dec-6-en-7-ylmethoxy)-phenyl]-hex-4-ynoic acid sodium salt

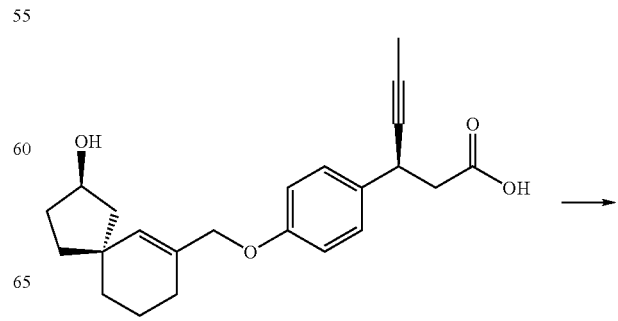

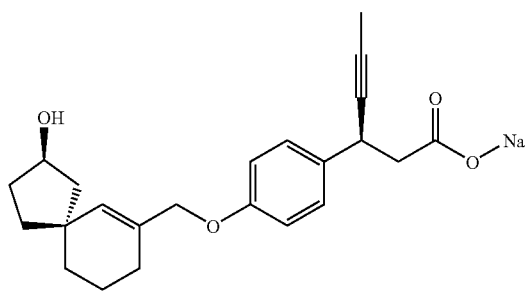

In the same manner as in Example 97, the desired compound was obtained from the compound obtained in Example 100.

Example 102

Preparation of (3S)-3-[4-((5R)-2-oxo-spiro[4.5]dec-6-en-7-ylmethoxy)-phenyl]-hex-4-ynoic acid

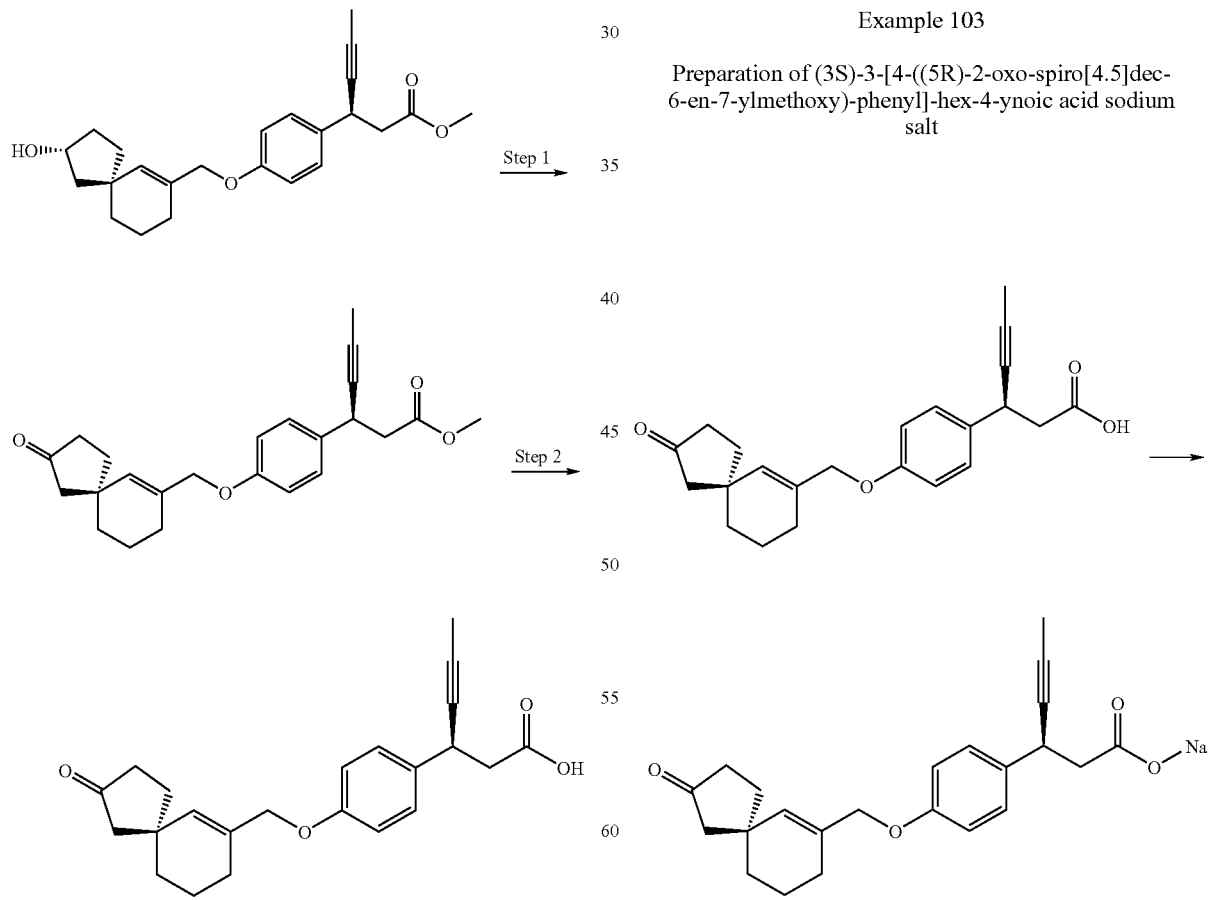

To a solution of (3S)-3-[4-((2R,5R)-2-hydroxy-spiro[4.5]dec-6-en-7-ylmethoxy)-phenyl]-hex-4-ynoic acid methyl ester (195 mg) obtained in Step 9 of Example 104 in chloroform (2 mL) was added 1,1,1-tris(acetyloxy)-1,1-dihydro-1,2-benziodoxol-3-(1H)-one (Dess-Martin periodinane; 259 mg) under ice-cooling, followed by stirring the mixture under ice-cooling for 3 hours and then at room temperature for 1 hour. To the reaction mixture was added aqueous sodium sulfite solution, followed by extraction with ethyl acetate. The organic layer was washed successively with saturated aqueous sodium bicarbonate solution and saturated brine, dried and concentrated. The residue was purified by column chromatography on silica gel (ethyl acetate:hexane (volume ratio)=1:6 to 1:4) to give (3S)-3-[4-((5R)-2-oxo-spiro[4.5]dec-6-en-7-ylmethoxy)-phenyl]-hex-4-ynoic acid methyl ester (190 mg).

$^1$H-NMR (DMSO-$d_6$) δ: 1.43-1.71 (4H, m), 1.77 (3H, d, J=2.3 Hz), 1.79-1.84 (2H, m), 1.98-2.07 (3H, m), 2.15-2.26 (3H, m), 2.68 (2H, d, J=7.9 Hz), 3.56 (3H, s), 3.94-3.99 (1H, m), 4.36 (2H, s), 5.69 (1H, s), 6.87 (2H, d, J=8.6 Hz), 7.25 (2H, d, J=8.6 Hz).

Step 2

In the same manner as in Step 9 of Example 1, (3S)-3-[4-((5R)-2-oxo-spiro[4.5]dec-6-en-7-ylmethoxy)-phenyl]-hex-4-ynoic acid (129 mg) was obtained from (3S)-3-[4-((5R)-2-oxo-spiro[4.5]dec-6-en-7-ylmethoxy)-phenyl]-hex-4-ynoic acid methyl ester (190 mg) obtained in Step 1.

Example 103

Preparation of (3S)-3-[4-((5R)-2-oxo-spiro[4.5]dec-6-en-7-ylmethoxy)-phenyl]-hex-4-ynoic acid sodium salt In the same manner as in Example 97, the desired compound was obtained from the compound obtained in Example 102.

Example 104
Preparation of (3S)-3-[4-((2R,5R)-2-hydroxy-spiro[4.5]dec-6-en-7-ylmethoxy)-phenyl]-hex-4-ynoic acid
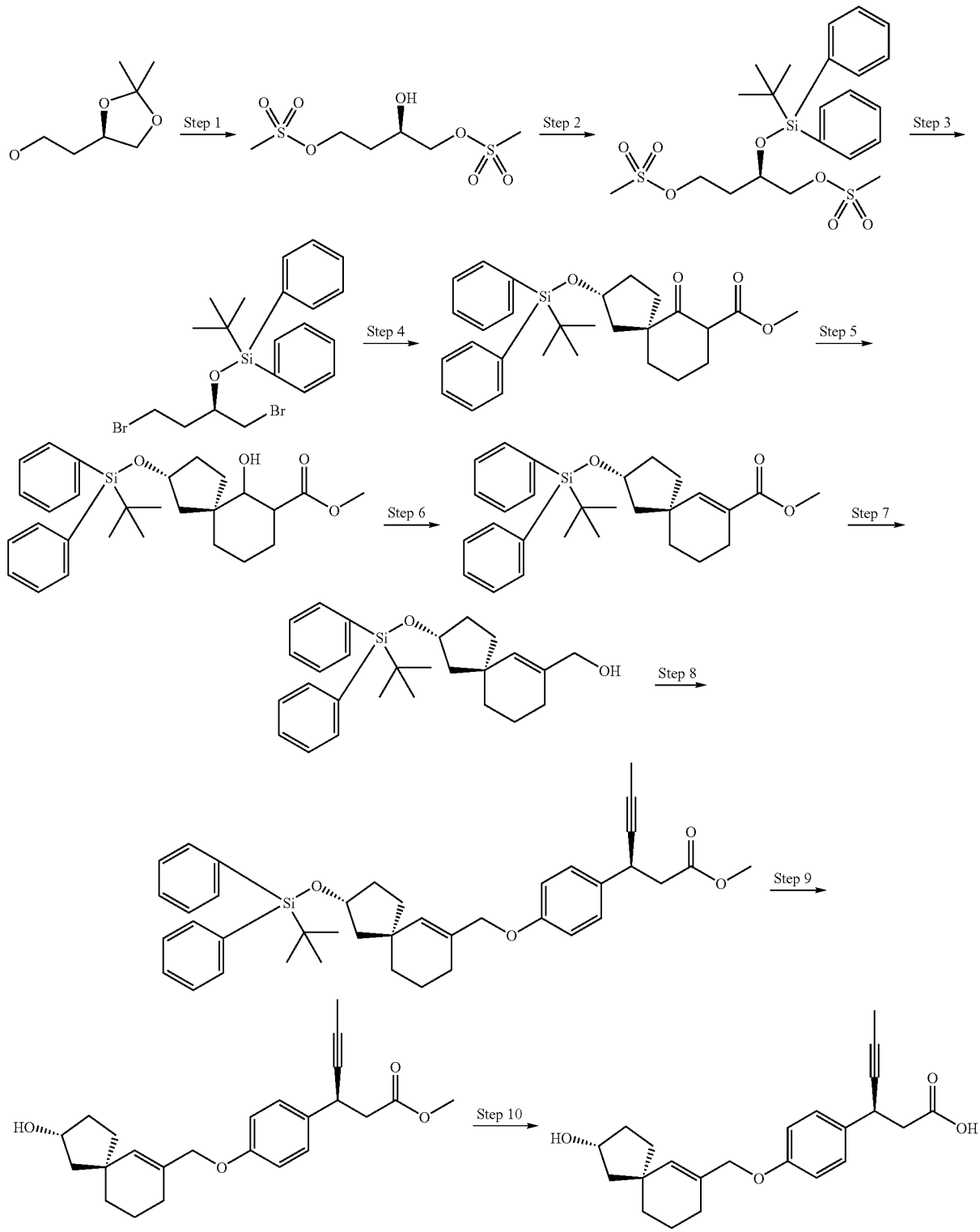

Step 1

To (4R)-4-(2-hydroxyethyl)-2,2-dimethyl-1,3-dioxolane (10.27 g) was added 2N aqueous hydrochloric acid solution (20 mL), followed by stirring the mixture at room temperature for 5 minutes. The reaction mixture was concentrated and distilled azeotropically with toluene. The residue was dissolved in pyridine (40 mL), and to this was added dropwise methanesulfonyl chloride (10.87 mL) under ice-cooling, followed by stirring the reaction mixture at room temperature for 1 hour. After addition of 2N aqueous hydrochloric acid solution under ice-cooling, the reaction mixture was extracted successively with ethyl acetate twice and with ethyl acetate:tetrahydrofuran (volume ratio)=1:1 once. The organic layers were combined, dried and then concentrated. The residue was recrystallized from ethyl acetate to give methanesulfonic acid (R)-3-hydroxy-4-methanesulfonyloxy-butyl ester (7.88 g).

$^1$H-NMR (DMSO-$d_6$) δ: 1.66-1.75 (1H, m), 1.83-1.91 (1H, m), 3.17 (3H, s), 3.18 (3H, s), 3.79-3.87 (1H, m), 4.03-4.08 (1H, m), 4.11-4.16 (1H, m), 4.27-4.32 (2H, m), 5.35 (1H, brs).

Step 2

To a solution of methanesulfonic acid (R)-3-hydroxy-4-methanesulfonyloxy-butyl ester (7.5 g) obtained in Step 1 in N,N-dimethylformamide (30 mL) were added imidazole (2.9 g) and tert-butylchlorodiphenylsilane (10.3 mL) under ice-cooling, followed by stirring the reaction mixture at room temperature for 12 hours. To the reaction mixture was added water under ice-cooling, followed by extraction with ethyl acetate. The organic layer was washed with saturated brine, dried and concentrated. The residue was purified by column chromatography on silica gel (ethyl acetate:hexane (volume ratio)=1:2 to 1:1) to give methanesulfonic acid (R)-3-(tert-butyldiphenylsilanyloxy)-4-methanesulfonyloxy-butyl ester (11.4 g).

$^1$H-NMR (DMSO-$d_6$) δ: 1.01 (9H, s), 1.91 (2H, dt, J=6.1, 6.1 Hz), 3.00 (3H, s), 3.06 (3H, s), 3.99-4.12 (3H, m), 4.15-4.29 (2H, m), 7.41-7.51 (6H, m), 7.61-7.66 (4H, m).

Step 3

To a solution of methanesulfonic acid (R)-3-((tert-butyl-diphenylsilanyl)-oxy)-4-methanesulfonyloxy-butyl ester (10.9 g) obtained in Step 2 in N,N-dimethylformamide (80 mL) was added lithium bromide (5.7 g), followed by stirring the mixture at 105° C. for 2 hours. To the reaction mixture was added water under ice-cooling, followed by extraction with ethyl acetate. The organic layer was washed with saturated brine, dried and concentrated. The residue was distilled azeotropically with toluene to give ((R)-3-bromo-1-bromomethyl-propoxy)-tert-butyldiphenylsilane (10.8 g) as a crude product.

$^1$H-NMR (CDCl$_3$) δ: 1.09 (9H, s), 2.16-2.26 (2H, m), 3.27 (2H, d, J=4.9 Hz), 3.42 (2H, t, J=7.0 Hz), 4.01-4.06 (1H, m), 7.38-7.49 (6H, m), 7.67-7.73 (4H, m).

Step 4

In the same manner as in Steps 1 to 2 of Example 7, (2R,5R)-2-(tert-butyldiphenylsilanyloxy)-6-oxo-spiro[4.5]de cane-7-carboxylic acid methyl ester (1.65 g) as a crude product was obtained from the crude ((R)-3-bromo-1-bromomethyl-propoxy)-tert-butyldiphenylsilane (10.3 g) obtained in Step 3.

$^1$H-NMR (CDCl$_3$) δ: 1.06 (9H, s), 1.47-2.22 (12H, m) 3.67-3.71 (0.5H, m), 3.73 (3H, s), 4.44-4.49 (1H, m), 7.35-7.45 (6H, m), 7.62-7.71 (4H, m), 12.27 (0.5H, s).

Step 5

To a solution of the crude (2R,5R)-2-(tert-butyldiphenyl-silanyloxy)-6-oxo-spiro[4.5]de cane-7-carboxylic acid methyl ester (1.65 g) obtained in Step 4 in toluene (1.6 mL) were added trifluoroacetic acid (5 mL) and triethylsilane (0.52 mL) under ice-cooling, followed by stirring the mixture under ice-cooling for 3 hours. Then, to the reaction mixture was added dropwise a solution of potassium carbonate (4.95 g) in water (20 mL), and the mixture was stirred under ice-cooling for 10 minutes, followed by extraction with ethyl acetate. The organic layer was washed with saturated brine, dried and concentrated to give (2R,5R)-2-(tert-butyldiphenylsilanyloxy)-6-hydroxy-spiro[4.5]decane-7-carboxylic acid methyl ester (1.76 g) as a crude product.

$^1$H-NMR (CDCl$_3$) δ: 1.06 (9H, s), 1.21-2.04 (13H, m), 3.50-3.73 (2H, m), 3.69 (3H, s), 4.27-4.39 (1H, m), 7.35-7.44 (6H, m), 7.64-7.69 (4H, m).

Step 6

To a solution of the crude (2R,5R)-2-(tert-butyldiphenyl-silanyloxy)-6-hydroxy-spiro[4.5]decane-7-carboxylic acid methyl ester (1.76 g) obtained in Step 5 in pyridine (5 mL) was added methanesulfonyl chloride (0.25 mL) under ice-cooling, followed by stirring the mixture at room temperature for 15 hours. Then, to the reaction mixture was added water, followed by extraction with ethyl acetate. The organic layer was washed with saturated brine, dried and concentrated. The residue was dissolved in tetrahydrofuran (10 mL). To this solution was added 1,8-diazabicyclo[5.4.0]undec-7-ene (0.88 mL), followed by stirring the mixture at 70° C. for 3.5 hours. After cooling down to room temperature and adding water, the reaction mixture was extracted with ethyl acetate. The organic layer was washed successively with 1N aqueous hydrochloric acid solution and saturated brine, dried and concentrated. The residue was purified by column chromatography on silica gel (ethyl acetate:hexane (volume ratio)=1:30 to 1:25) to give (2R,5R)-2-(tert-butyldiphenylsilanyloxy)-spiro[4.5]dec-6-en e-7-carboxylic acid methyl ester (0.615 g).

$^1$H-NMR (CDCl$_3$) δ: 1.06 (9H, s), 1.46-1.54 (1H, m), 1.61-1.85 (8H, m), 2.19-2.23 (2H, m), 2.37 (1H, s), 3.70 (3H, s), 4.38 (1H, tt, J=5.8, 3.9 Hz), 6.60 (1H, t, J=1.7 Hz), 7.35-7.46 (6H, m), 7.64-7.68 (4H, m).

Step 7

To a solution of (2R,5R)-2-(tert-butyldiphenylsilanyloxy)-spiro[4.5]dec-6-en e-7-carboxylic acid methyl ester (615 mg) obtained in Step 6 in toluene (7 mL) was added dropwise sodium bis(2-methoxyethoxy)aluminum hydride (65% toluene solution; 486 mg) under ice-cooling, followed by stirring the mixture under ice-cooling for 0.5 hour. To the reaction mixture was added dropwise 1M aqueous Rochelle salt solution (10 mL), followed by stirring at room temperature for 2 hours, and the reaction mixture was extracted with toluene. The organic layer was washed with saturated brine, dried and concentrated. The residue was purified by column chromatography on silica gel (ethyl acetate:hexane (volume ratio)=1:6 to 1:5) to give [(2R,5R)-2-(tert-butyldiphenylsilanyloxy)-spiro[4.5]dec-6-en-7-yl]-methanol (539 mg).

$^1$H-NMR (CDCl$_3$) δ: 1.06 (9H, s), 1.18-1.23 (1H, m), 1.35-1.43 (1H, m), 1.62-1.86 (8H, m), 1.93-1.98 (2H, m), 3.94 (2H, d, J=4.2 Hz), 4.34 (1H, tt, J=5.1, 5.1 Hz), 5.32 (1H, s), 7.35-7.45 (6H, m), 7.65-7.69 (4H, m).

Step 8

In the same manner as in Step 7 of Example 7, (3S)-3-{4-[(2R,5R)-2-(tert-butyldiphenylsilanyloxy)-spiro[4.5]dec-6-en-7-ylmethoxy]-phenyl}-hex-4-ynoic acid methyl ester (738 mg) was obtained from [(2R,5R)-2-(tert-butyldiphenyl-silanyloxy)-spiro[4.5]dec-6-e n-7-yl]-methanol (529 mg) obtained in Step 7.

$^1$H-NMR (CDCl$_3$) δ: 1.06 (9H, s), 1.37-1.44 (1H, m), 1.64-1.81 (9H, m), 1.83 (3H, d, J=2.6 Hz), 2.00-2.05 (2H, m), 2.65 (1H, dd, J=15.2, 6.8 Hz), 2.75 (1H, dd, J=15.2, 8.3 Hz), 3.67 (3H, s), 4.02-4.08 (1H, m), 4.28 (2H, s), 4.32-4.37 (1H, m), 5.44 (1H, s), 6.83 (2H, d, J=8.8 Hz), 7.25 (2H, d, J=8.8 Hz), 7.35-7.45 (6H, m), 7.65-7.69 (4H, m).

Step 9

To a solution of (3S)-3-{4-[(2R,5R)-2-(tert-butyldiphenyl-silanyloxy)-spiro[4.5]dec-6-en-7-ylmethoxy]-phenyl}-hex-4-ynoic acid methyl ester (738 mg) obtained in step 8 in tetrahydrofuran (3.7 mL) was added tetra-n-butylammonium fluoride (1M tetrahydrofuran solution; 2.97 mL), followed by stirring the mixture at room temperature for 17 hours. To the reaction mixture was added water, followed by extraction with ethyl acetate. The organic layer was washed with saturated brine, dried and concentrated. The residue was purified by column chromatography on silica gel (ethyl acetate:hexane (volume ratio)=1:3) to give (3S)-3-[4-((2R,5R)-2-hydroxy-spiro[4.5]dec-6-en-7-ylmethoxy)-phenyl]-hex-4-ynoic acid methyl ester (395 mg).

$^1$H-NMR (DMSO-$d_6$) δ: 1.34-1.42 (2H, m), 1.47-1.63 (6H, m), 1.65-1.71 (1H, m), 1.77 (3H, d, J=2.6 Hz), 1.80-1.89 (1H, m), 1.92-1.97 (2H, m), 2.68 (2H, d, J=7.9 Hz), 3.56 (3H, s), 3.92-4.00 (1H, m), 4.12-4.20 (1H, m), 4.31 (2H, s), 4.49 (1H, d, J=3.7 Hz), 5.57 (1H, s), 6.86 (2H, d, J=8.6 Hz), 7.24 (2H, d, J=8.6 Hz).

Step 10

In the same manner as in Step 9 of Example 1, (3S)-3-[4-((2R,5R)-2-hydroxy-spiro[4.5]dec-6-en-7-ylmethoxy)-phenyl]-hex-4-ynoic acid (71 mg) was obtained from (3S)-3-[4-((2R,5R)-2-hydroxy-spiro[4.5]dec-6-en-7-ylmethoxy)-phenyl]-hex-4-ynoic acid methyl ester (75 mg) obtained in Step 9. Configuration of the structure was determined by NMR spectrum (NOESY, HSQC).

Example 105

Preparation of (3S)-3-[4-((2R,5R)-2-hydroxy-spiro[4.5]dec-6-en-7-ylmethoxy)-phenyl]-hex-4-ynoic acid sodium salt

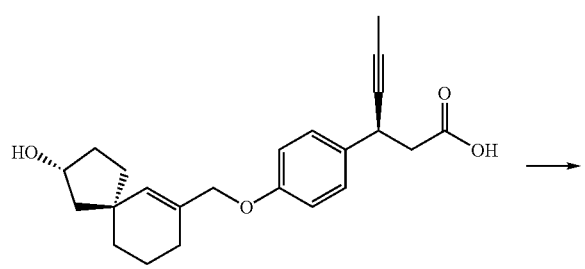

In the same manner as in Example 97, the desired compound was obtained from the compound obtained in Example 104.

Example 106

Preparation of (3S)-3-[4-((2S,5R)-2-hydroxy-spiro[4.5]dec-6-en-7-ylmethoxy)-phenyl]-hex-4-ynoic acid

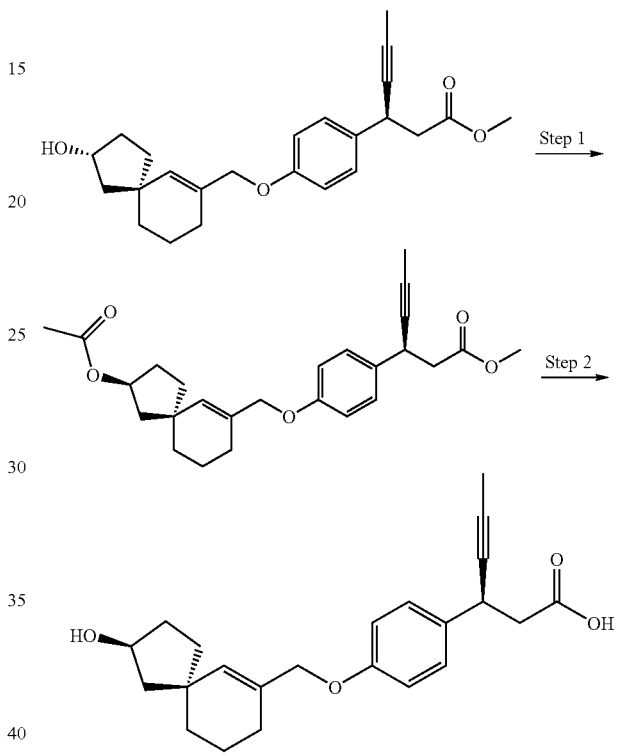

Step 1

To a solution of (3S)-3-[4-((2R,5R)-2-hydroxy-spiro[4.5]dec-6-en-7-ylmethoxy)-phenyl]-hex-4-ynoic acid methyl ester (133 mg) obtained in the same manner as in Step 9 of Example 104 in tetrahydrofuran (1.5 mL) were added successively triphenylphosphine (119 mg), acetic acid (0.03 mL) and dimethyl azodicarboxylate (0.168 mL) under ice-cooling, followed by stirring the mixture at room temperature for 16 hours. The reaction mixture was concentrated and the residue was purified by thin-layer column chromatography on silica gel (ethyl acetate:hexane (volume ratio)=1:5) to give (3S)-3-[4-((2S,5R)-2-acetoxy-spiro[4.5]dec-6-en-7-ylmethoxy)-phenyl]-hex-4-ynoic acid methyl ester (107 mg).

$^1$H-NMR (DMSO-$d_6$) δ: 1.41-1.70 (8H, m), 1.77 (3H, d, J=2.6 Hz), 1.84-1.91 (1H, m), 1.94-1.98 (5H, m), 1.99-2.07 (1H, m), 2.68 (2H, d, J=7.9 Hz), 3.56 (3H, s), 3.93-4.00 (1H, m), 4.34 (2H, s), 5.04-5.10 (1H, m), 5.66 (1H, s), 6.87 (2H, d, J=8.6 Hz), 7.24 (2H, d, J=8.6 Hz).

Step 2

To a solution of (3S)-3-[4-((2S,5R)-2-acetoxy-spiro[4.5]dec-6-en-7-ylmethoxy)-phenyl]-hex-4-ynoic acid methyl ester (107 mg) obtained in Step 1 in a mixed solvent of methanol (0.65 mL)-tetrahydrofuran (0.65 mL) was added 2N aqueous sodium hydroxide solution (0.28 mL) under ice-cooling, followed by stirring the mixture at room temperature overnight. To the reaction mixture was added 2N aqueous hydrochloric acid solution (0.28 mL), followed by extraction with ethyl acetate. The organic layer was washed with saturated brine, dried and concentrated. The residue was purified by thin-layer column chromatography on silica gel (acetic acid: methanol:chloroform (volume ratio)=0.1:1:20) to give (3S)-3-[4-((2S,5R)-2-hydroxy-spiro[4.5]dec-6-en-7-ylmethoxy)-phenyl]-hex-4-ynoic acid (79 mg). Configuration of the structure was determined by NMR spectrum (NOESY, HSQC).

Example 107

Preparation of (3S)-3-[4-((2S,5R)-2-hydroxy-spiro[4.5]dec-6-en-7-ylmethoxy)-phenyl]-hex-4-ynoic acid sodium salt

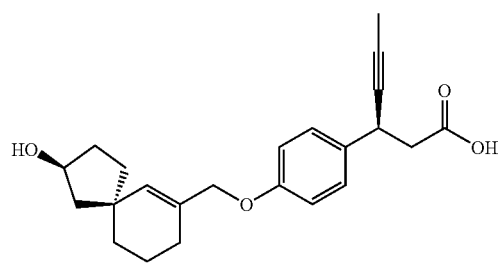

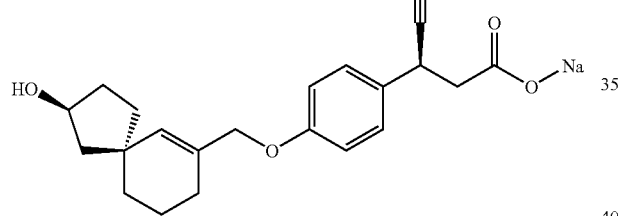

In the same manner as in Example 97, the desired compound was obtained from the compound obtained in Example 106.

Example 108

Preparation of 3-[2-chloro-4-(spiro[4.5]dec-6-en-7-ylmethoxy)-phenyl]-prop ionic acid

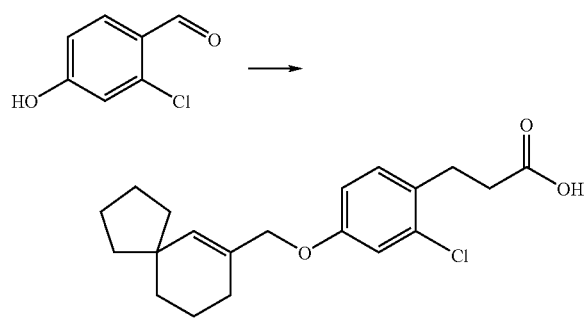

In the same manner as in Steps 2 and 4 to 6 of Example 110, 3-[2-chloro-4-(spiro[4.5]dec-6-en-1-ylmethoxy)-phenyl]-prop ionic acid (75 mg) was obtained from 2-chloro-4-hydroxybenzaldehyde (250 mg).

Example 109

Preparation of 3-[2-methyl-4-(spiro[4.5]dec-6-en-7-ylmethoxy)-phenyl]-prop ionic acid

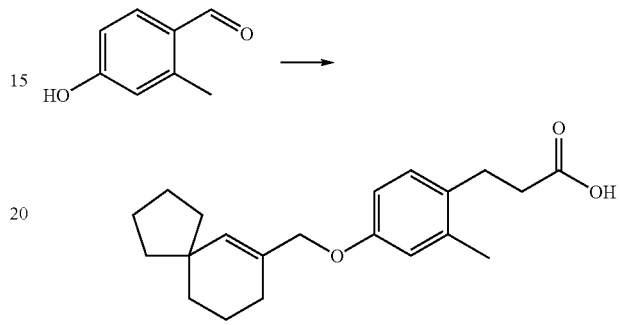

In the same manner as in Steps 2 and 4 to 6 of Example 110, 3-[2-methyl-4-(spiro[4.5]dec-6-en-7-ylmethoxy)-phenyl]-prop ionic acid (107 mg) was obtained from 4-hydroxy-2-methylbenzaldehyde (507 mg).

Example 110

Preparation of 3-[3-hydroxy-4-(spiro[4.5]dec-6-en-7-ylmethoxy)-phenyl]-propionic acid

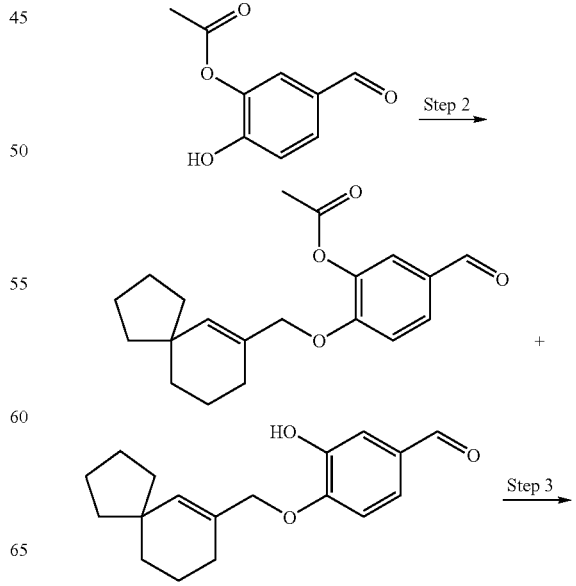

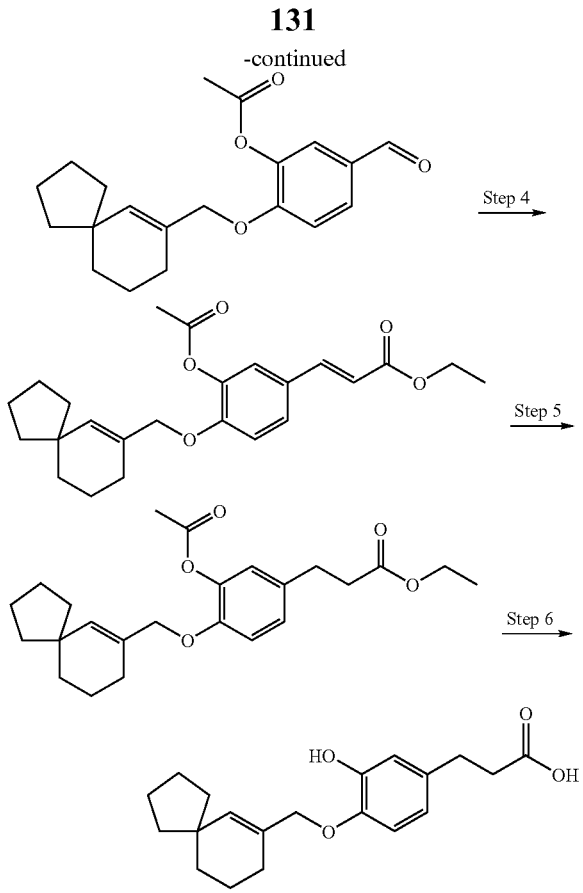

Step 1

To a solution of 3,4-dihydroxybenzaldehyde (5.0 g) in N,N-dimethylformamide (36 mL) was added 60% sodium hydride (1.45 g) under ice-cooling, followed by stirring the reaction mixture at room temperature for 10 minutes. Then, after addition of acetic anhydride (3.6 mL), the reaction mixture was stirred at room temperature for 1 hour. To the reaction mixture was added 2N aqueous hydrochloric acid solution under ice-cooling, followed by extraction with ethyl acetate. The organic layer was washed with saturated aqueous sodium bicarbonate solution and saturated brine, dried and concentrated. The residue was purified by column chromatography on silica gel (ethyl acetate:hexane (volume ratio)=1:2 to 1:1) to give acetic acid 5-formyl-2-hydroxyphenyl ester (4.9 g).

$^1$H-NMR (acetone-$d_6$) δ: 2.29 (3H, s), 7.13 (1H, d, J=8.4 Hz), 7.61 (1H, d, J=2.1 Hz), 7.70 (1H, dd, J=8.4, 2.1 Hz), 9.35 (1H, brs), 9.85 (1H, s).

Step 2

To a solution of acetic acid 5-formyl-2-hydroxyphenyl ester (2.1 g) obtained in Step 1 in tetrahydrofuran (20 mL) were added successively triphenylphosphine (4.3 g), spiro[4.5]dec-6-ene-7-methanol (3.55 g) obtained in the same manner as in Step 6 of Example 7 and 1,1'-azobis(N,N-dimethylformamide) (2.8 g) under ice-cooling, followed by stirring the reaction mixture at room temperature for 1.5 hours. After addition of diethyl ether to the reaction mixture, the insolubles were filtered off and the filtrate was concentrated. The residue was purified by column chromatography on silica gel (ethyl acetate:hexane (volume ratio)=1:9 to 1:6) to give a mixture (1.8 g) of acetic acid 5-formyl-2-(spiro[4.5]dec-6-en-7-ylmethoxy)-phenyl ester and 3-hydroxy-4-(spiro[4.5]dec-6-en-7-ylmethoxy)-benzaldehyde.

$^1$H-NMR (3-hydroxy-4-(spiro[4.5]dec-6-en-7-ylmethoxy)-benzaldehyde, CDCl$_3$) δ: 1.45-1.50 (6H, m), 1.63-1.70 (6H, m), 2.04 (2H, t, J=5.7 Hz), 4.54 (2H, s), 5.64 (1H, s), 5.79 (1H, s), 6.98 (1H, d, J=8.4 Hz), 7.41 (1H, dd, J=8.4, 2.0 Hz), 7.45 (1H, d, J=2.0 Hz), 9.85 (1H, s).

Step 3

To a solution of a mixture (1.7 g) of acetic acid 5-formyl-2-(spiro[4.5]dec-6-en-7-ylmethoxy)-phenyl ester and 3-hydroxy-4-(spiro[4.5]dec-6-en-7-ylmethoxy)-benzaldehyde obtained in Step 2 in chloroform (9 mL) were added triethylamine (1.7 mL) and acetyl chloride (0.4 mL) under ice-cooling, followed by stirring the reaction mixture under ice-cooing for 1 hour. After addition of saturated aqueous sodium bicarbonate solution, the reaction mixture was extracted with ethyl acetate. The organic layer was washed with saturated brine, dried and concentrated. The residue was purified by column chromatography on silica gel (ethyl acetate:hexane (volume ratio)=1:19 to 1:9) to give acetic acid 5-formyl-2-(spiro[4.5]dec-6-en-7-ylmethoxy)-phenyl ester (1.59 g).

$^1$H-NMR (CDCl$_3$) δ: 1.46-1.49 (6H, m), 1.63-1.71 (6H, m), 1.99 (2H, t, J=5.7 Hz), 2.33 (3H, s), 4.48 (2H, s), 5.61 (1H, s), 7.08 (1H, d, J=8.6 Hz), 7.59 (1H, d, J=2.1 Hz), 7.73 (1H, dd, J=8.5, 2.1 Hz), 9.87 (1H, s).

Step 4

To a solution of 60% sodium hydride (0.118 g) in tetrahydrofuran (11.5 mL) was added triethyl phosphonoacetate (0.64 mL) under argon atmosphere and ice-cooling, followed by stirring under ice-cooling for 10 minutes. To this mixture was added a solution of acetic acid 5-formyl-2-(spiro[4.5]dec-6-en-7-ylmethoxy)-phenyl ester (0.75 g) obtained in Step 3 in tetrahydrofuran (3.8 mL), followed by stirring at room temperature for 10 minutes. After addition of ice-cold water, the reaction mixture was extracted with ethyl acetate. The organic layer was washed with saturated brine, dried and concentrated. The residue was purified by column chromatography on silica gel (hexane→ethyl acetate:hexane (volume ratio)=1:19 to 1:9) to give (E)-3-[3-acetoxy-4-(spiro[4.5]dec-6-en-7-ylmethoxy)-phenyl]-acrylic acid ethyl ester (0.9 g).

$^1$H-NMR (CDCl$_3$) δ: 1.28-1.38 (3H, m), 1.43-1.53 (6H, m), 1.60-1.69 (6H, m), 1.99 (2H, t, J=6.0 Hz), 2.32 (3H, s), 4.26 (2H, q, J=7.2 Hz), 4.42 (2H, s), 5.58 (1H, s), 6.29 (1H, d, J=16.0 Hz), 6.96 (1H, d, J=8.6 Hz), 7.24 (1H, d, J=2.1 Hz), 7.34 (1H, dd, J=8.6, 2.1 Hz), 7.60 (1H, d, J=16.0 Hz).

Step 5

To a solution of (E)-3-[3-acetoxy-4-(spiro[4.5]dec-6-en-7-ylmethoxy)-phenyl]-acrylic acid ethyl ester (0.43 g) obtained in Step 4 in ethyl acetate (8 mL) were added 10% palladium carbon (86 mg) and a 0.1M ethyl acetate solution of diphenyl sulfide (1.08 mL), followed by stirring under increased pressure (0.4 MPa) in an atmosphere of hydrogen at room temperature for 6 hours. The reaction mixture was filtered through Celite and the filtrate was concentrated. The residue was purified by column chromatography on silica gel (hexane→ethyl acetate:hexane (volume ratio)=1:19 to 1:9) to give 3-[3-acetoxy-4-(spiro[4.5]dec-6-en-7-ylmethoxy)-phenyl]-propionic acid ethyl ester (0.332 g).

$^1$H-NMR (CDCl$_3$) δ: 1.24 (3H, t, J=7.2 Hz), 1.44-1.51 (6H, m), 1.62-1.68 (6H, m), 1.99 (2H, t, J=5.8 Hz), 2.30 (3H, s), 2.59 (2H, t, J=7.8 Hz), 2.89 (2H, t, J=7.8 Hz), 4.13 (2H, q, J=7.1 Hz), 4.35 (2H, s), 5.56 (1H, s), 6.89 (2H, t, J=4.1 Hz), 7.00 (1H, dd, J=8.4, 2.1 Hz).

Step 6

In the same manner as in Step 9 of Example 1, 3-[3-hydroxy-4-(spiro[4.5]dec-6-en-7-ylmethoxy)-phenyl]-propionic acid (51 mg) was obtained from 3-[3-acetoxy-4-(spiro

[4.5]dec-6-en-7-ylmethoxy)-phenyl]-propionic acid ethyl ester (100 mg) obtained in Step 5.

Example 111

Preparation of 3-[3-methoxy-4-(spiro[4.5]dec-6-en-7-ylmethoxy)-phenyl]-propionic acid

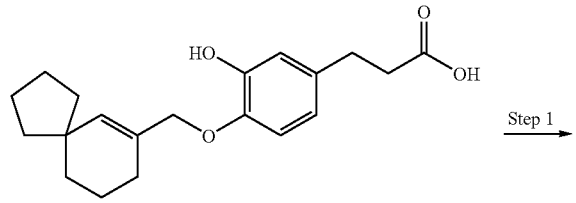

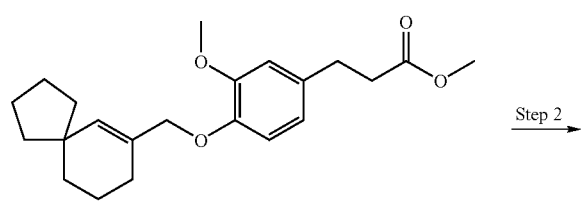

Step 1

To a solution of 3-[3-hydroxy-4-(spiro[4.5]dec-6-en-7-ylmethoxy)-phenyl]-propionic acid (188 mg) obtained in the same manner as in Example 110 in N,N-dimethylformamide (2 mL) were added methyl iodide (0.082 mL) and potassium carbonate (0.30 mg), followed by stirring the mixture at room temperature for 16 hours. To the reaction mixture was added 1N aqueous hydrochloric acid solution, followed by extraction with ethyl acetate. The organic layer was washed with water and saturated brine, dried and concentrated. The residue was purified by column chromatography on silica gel (ethyl acetate:hexane (volume ratio)=1:40 to 1:10) to give 3-[3-methoxy-4-(spiro[4.5]dec-6-en-7-ylmethoxy)-phenyl]-propionic acid methyl ester (176 mg).

$^1$H-NMR (CDCl$_3$) δ: 1.43-1.47 (6H, m) 1.61-1.68 (6H, m), 2.04-2.09 (2H, m), 2.60-2.64 (2H, m), 2.90 (2H, t, J=7.9 Hz), 3.68 (3H, s), 3.85 (3H, s), 4.42 (2H, s), 5.56 (1H, s), 6.69 (1H, dd, J=8.1, 2.1 Hz), 6.72 (1H, d, J=2.1 Hz), 6.82 (1H, d, J=8.1 Hz).

Step 2

3-[3-Methoxy-4-(spiro[4.5]dec-6-en-7-ylmethoxy)-phenyl]-propionic acid methyl ester (176 mg) obtained in Step 1 was subjected to the reaction in the same condition as in Step 9 of Example 1 to give 3-[3-methoxy-4-(spiro[4.5]dec-6-en-7-ylmethoxy)-phenyl]-propionic acid (159 mg).

Example 112

Preparation of 3-[3-fluoro-4-(spiro[4.5]dec-6-en-7-ylmethoxy)-phenyl]-propionic acid

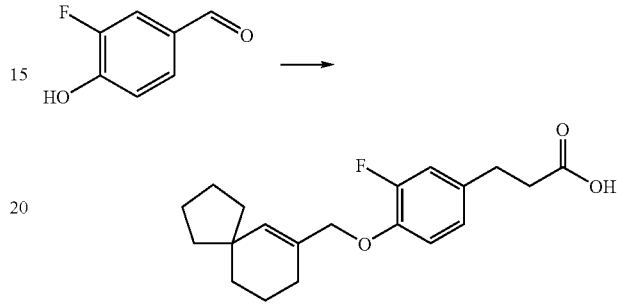

In the same manner as in Steps 2 and 4 to 6 of Example 110, 3-[3-fluoro-4-(spiro[4.5]dec-6-en-7-ylmethoxy)-phenyl]-propionic acid (80 mg) was obtained from 3-fluoro-4-hydroxybenzaldehyde (500 mg).

Example 113

Preparation of 3-[6-(spiro[4.5]dec-7-ylmethoxy)-pyridin-3-yl]-propionic acid hydrochloride

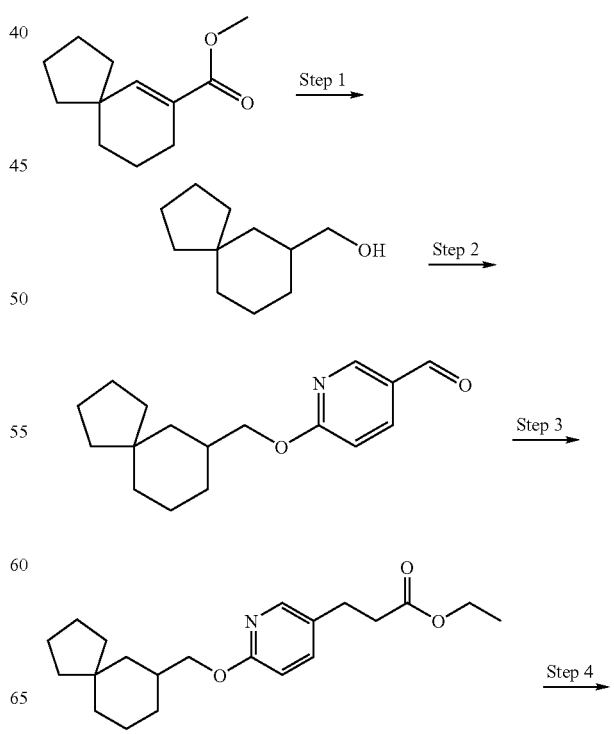

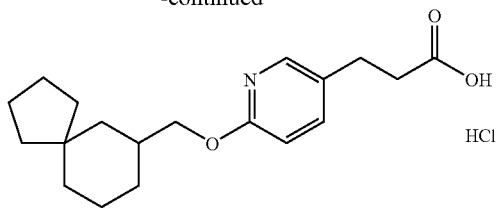

Step 1

To a solution of spiro[4.5]dec-6-ene-7-carboxylic acid methyl ester (4.5 g) obtained in the same manner as in Step 5 of Example 7 in tetrahydrofuran (45 mL) was added 5% palladium carbon (0.5 g), followed by stirring under increased pressure (0.4 MPa) in an atmosphere of hydrogen at room temperature for 17 hours. The reaction mixture was filtered through Celite and the filtrate was washed with tetrahydrofuran (50 mL). To this solution was added dropwise a 1M toluene solution of diisobutylaluminum hydride (70 mL) under argon atmosphere at −70° C., followed by raising the temperature to −20° C. over 1.5 hours while stirring the reaction mixture. 2N aqueous hydrochloric acid solution was added to the reaction mixture and the temperature was raised to room temperature, followed by extraction with ethyl acetate. The organic layer was washed with saturated brine, dried and concentrated. The residue was purified by column chromatography on silica gel (hexane→ethyl acetate:hexane (volume ratio)=1:9) to give spiro[4.5]dec-7-yl-methanol (3.6 g).

$^1$H-NMR (CDCl$_3$) δ: 0.84 (1H, qd, J=12.6, 4.2 Hz), 0.92 (1H, t, J=12.6 Hz), 1.15 (1H, td, J=12.6, 4.2 Hz), 1.27 (1H, t, J=4.2 Hz), 1.31-1.67 (13H, m), 1.71-1.78 (1H, m), 3.42 (2H, t, J=6.0 Hz).

Step 2

To a mixture of palladium(II) acetate (135 mg), 2-(di-tert-butylphosphino)-1,1'-binaphthyl (478 mg) and cesium carbonate (3.9 g) was added toluene (15 mL), followed by stirring under argon atmosphere at room temperature for 10 minutes. To this reaction mixture were added spiro[4.5]dec-7-yl-methanol (1.0 g) obtained in Step 1 and 6-bromopyridine-3-carboxaldehyde (1.1 g), followed by stirring the mixture at 90° C. for 1.5 hours. The reaction mixture was filtered through Celite and the filtrate was concentrated. The residue was purified by column chromatography on silica gel (ethyl acetate:hexane (volume ratio)=1:49 to 1:9) to give 6-(spiro[4.5]dec-7-ylmethoxy)-pyridine-3-carboxaldehyde (0.313 g).

$^1$H-NMR (CDCl$_3$) δ: 0.95-1.23 (4H, m), 1.32-1.52 (4H, m), 1.55-1.68 (9H, m), 1.82-1.97 (2H, m), 4.19 (2H, d, J=6.4 Hz), 6.83 (1H, d, J=8.6 Hz), 8.05 (1H, dd, J=8.6, 2.4 Hz), 8.60 (1H, dd, J=2.3, 0.6 Hz), 9.94 (1H, d, J=0.6 Hz).

Step 3

6-(Spiro[4.5]dec-7-ylmethoxy)-pyridine-3-carboxaldehyde (0.313 g) obtained in Step 2 was subjected to the reaction in the same condition as in Steps 4 and 5 of Example 110 to give 3-[6-(spiro[4.5]dec-7-ylmethoxy)-pyridin-3-yl]-propionic acid ethyl ester (36 mg).

$^1$H-NMR (CDCl$_3$) δ: 0.90-1.08 (4H, m), 1.15-1.31 (3H, m), 1.38-1.50 (7H, m), 1.56-1.67 (9H, m), 1.83-1.93 (2H, m), 2.58 (2H, t, J=7.7 Hz), 2.87 (2H, t, J=7.7 Hz), 4.03 (2H, d, J=6.3 Hz), 4.13 (2H, q, J=7.2 Hz), 6.67 (1H, d, J=8.6 Hz), 7.42 (1H, dd, J=8.6, 2.5 Hz), 7.98 (1H, d, J=2.4 Hz).

Step 4

To a solution of 3-[6-(spiro[4.5]dec-7-ylmethoxy)-pyridin-3-yl]-propionic acid ethyl ester (36 mg) obtained in Step 3 in a mixed solvent of tetrahydrofuran (0.36 mL)-ethanol (0.36 mL) was added 1N aqueous sodium hydroxide solution (0.21 mL), followed by stirring the reaction mixture at room temperature for 1.5 hours. Then, to the reaction mixture was added 1N aqueous hydrochloric acid solution, followed by extraction with ethyl acetate. The organic layer was washed with saturated brine, dried and concentrated. The residue was dissolved in a 1,4-dioxane solution of hydrogen chloride (4M, 0.5 mL), and to this was added hexane (0.5 mL) while stirring. The resulting solid was filtered and then dried to give 3-[6-(spiro[4.5]dec-7-ylmethoxy)-pyridin-3-yl]-propionic acid hydrochloride (33 mg).

Example 114

Preparation of 3-[4-(9-methoxy-spiro[5.5]undec-3-ylmethoxy)-phenyl]-propionic acid

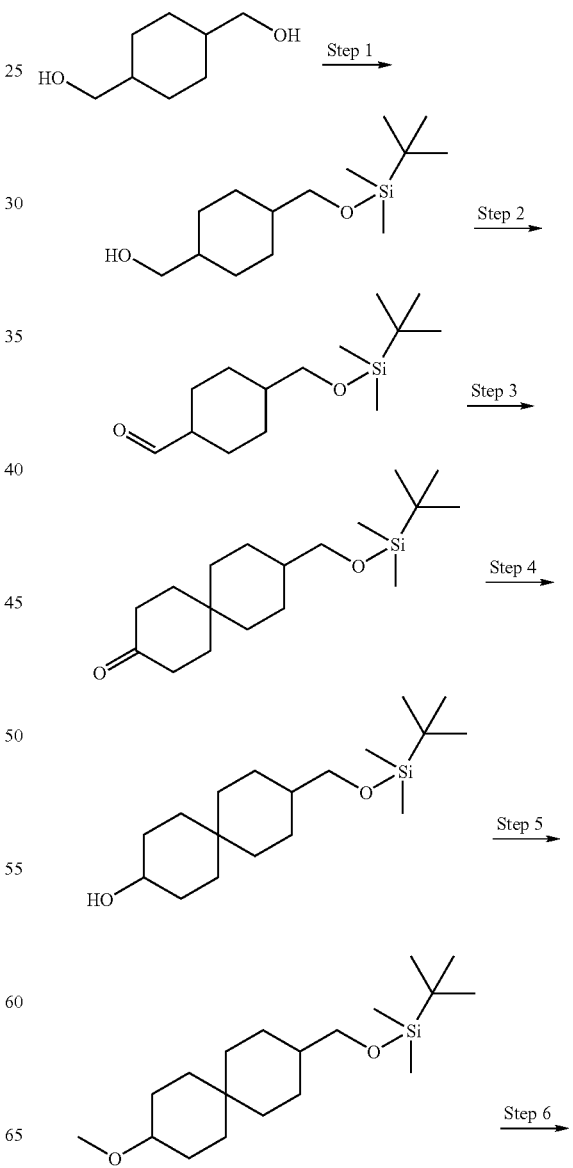

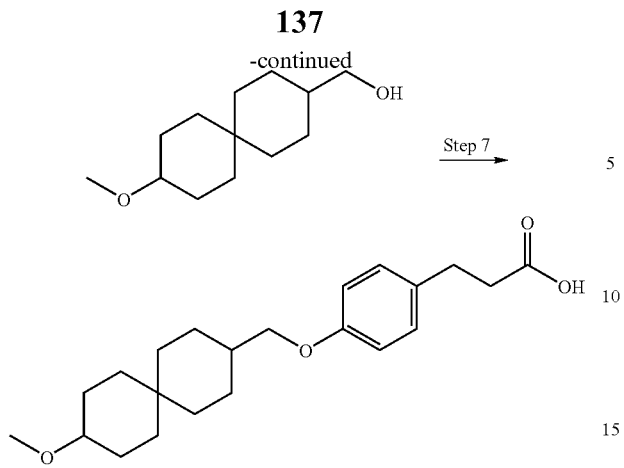

Step 1

To a solution of cyclohexane-1,4-dimethanol (10.0 g) in N,N-dimethylformamide (100 mL) were added successively tert-butyldimethylchlorosilane (8.9 g) and imidazole (9.5 g), followed by stirring the reaction mixture at room temperature for 16 hours. To the reaction mixture were added ice and saturated aqueous lithium bromide solution, followed by extraction with diethyl ether. The organic layer was washed with saturated aqueous lithium bromide solution and saturated brine, dried and concentrated. The residue was purified by column chromatography on silica gel (ethyl acetate:hexane (volume ratio)=1:9 to 2:3) to give [4-(tert-butyldimethylsilanyloxymethyl)-cyclohexyl]-methano 1 (8.7 g).

$^1$H-NMR (CDCl$_3$) δ: 0.04 (6H, s), 0.85-1.05 (3H, m), 0.89 (9H, s), 1.21-1.31 (2H, m), 1.33-1.56 (3.4H, m), 1.61-1.72 (0.6H, m), 1.82 (2H, d, J=10.4 Hz), 3.41 (1.4H, d, J=6.7 Hz), 3.47 (2H, q, J=6.3 Hz), 3.55 (0.6H, dd, J=6.7, 5.8 Hz).

Step 2

To a solution of [4-(tert-butyldimethylsilanyloxymethyl)-cyclohexyl]-methanol (8.5 g) obtained in Step 1 in chloroform (85 mL) was added 1,1,1-tris(acetyloxy)-1,1-dihydro-1,2-benziodoxol-3-(1H)-one (Dess-Martin periodinane; 15.3 g) under ice-cooling, followed by stirring the mixture under ice-cooling for 2.5 hours. After addition of aqueous sodium sulfite solution and aqueous sodium bicarbonate solution, the reaction mixture was filtered through Celite, followed by extraction with ethyl acetate. The organic layer was washed with saturated brine, dried and concentrated. The residue was purified by column chromatography on silica gel (ethyl acetate:hexane (volume ratio)=1:19 to 1:9) to give 4-(tert-butyldimethylsilanyloxymethyl)-cyclohexanecarbaldehyde (6.9 g).

$^1$H-NMR (CDCl$_3$) δ: 0.06 (6H, s), 0.85-0.93 (9H, m), 0.93-1.09 (2H, m), 1.23-1.33 (1H, m), 1.40-1.69 (3H, m), 1.88-1.92 (2H, m), 2.00-2.04 (1H, m), 2.09-2.22 (1H, m), 3.38-3.44 (2H, m), 9.63 (0.5H, d, J=1.6 Hz), 9.71 (0.5H, s).

Step 3

In the same manner as in Steps 1 to 2 of Example 1, 9-(tert-butyldimethylsilanyloxymethyl)-spiro[5.5]undecan-3-one (1.5 g) was obtained from 4-(tert-butyldimethylsilanyloxymethyl)-cyclohexanecarbaldehyde (1.16 g) obtained in Step 2.

$^1$H-NMR (CDCl$_3$) δ: 0.04 (6H, s), 0.90 (9H, s), 1.12 (2H, qd, J=12.8, 3.4H z), 1.25 (2H, td, J=12.8, 3.4 Hz), 1.43-1.54 (1H, m), 1.61-1.67 (4H, m), 1.73-1.79 (4H, m), 2.28 (2H, t, J=7.0 Hz), 2.35 (2H, t, J=7.0 Hz), 3.45 (2H, d, J=6.3 Hz).

Step 4

To a solution of 9-(tert-butyldimethylsilanyloxymethyl)-spiro[5.5]undecan-3-one (1.5 g) obtained in Step 3 in methanol (24 mL) was added sodium borohydride (0.17 g) under ice-cooling, followed by stirring the reaction mixture under ice-cooling for 0.5 hour. After addition of saturated aqueous citric acid solution, the reaction mixture was concentrated in vacuo, followed by extraction with ethyl acetate. The organic layer was washed with saturated brine, dried and concentrated. The residue was purified by column chromatography on silica gel (ethyl acetate:hexane (volume ratio)=1:19 to 1:4) to give 9-(tert-butyldimethylsilanyloxymethyl)-spiro[5.5]undecan-3-ol (0.47 g).

$^1$H-NMR (CDCl$_3$) δ: 0.01 (6H, s), 0.84 (9H, s), 0.87-1.21 (7H, m), 1.29-1.55 (5H, m), 1.65-1.73 (3H, m), 1.80-1.90 (2H, m), 3.38 (2H, d, J=6.2 Hz), 3.57-3.61 (1H, m).

Step 5

To a solution of 9-(tert-butyldimethylsilanyloxymethyl)-spiro[5.5]undecan-3-ol (309 mg) obtained in Step 4 in N,N-dimethylformamide (5 mL) was added 60% sodium hydride (60 mg) under ice-cooling, followed by stirring the reaction mixture at room temperature for 5 minutes. To the reaction mixture was added iodomethane (0.19 mL), followed by stirring at room temperature for 15 minutes. To the reaction mixture were further added 60% sodium hydride (120 mg) and iodomethane (0.38 mL), followed by stirring at room temperature for 15 minutes. To the reaction mixture was added 1N aqueous hydrochloric acid solution under ice-cooling, followed by extraction with diethyl ether three times. The organic layer was dried and then concentrated to give tert-butyl-(9-methoxyspiro[5.5]undec-3-ylmethoxy)-dimethylsilane (393 mg) as a crude product.

$^1$H-NMR (CDCl$_3$) δ: 0.04 (6H, s), 0.90 (9H, s), 0.95-1.20 (8H, m), 1.27-1.58 (4H, m), 1.72-1.87 (5H, m), 3.12-3.18 (1H, m), 3.34 (3H, s), 3.42 (2H, d, J=6.5 Hz).

Step 6

To a solution of the crude tert-butyl-(9-methoxyspiro[5.5]undec-3-ylmethoxy)-dimethylsilane (393 mg) obtained in Step 5 in tetrahydrofuran (5 mL) was added a 1M tetrahydrofuran solution of tetra-n-butylammonium fluoride (3 mL) under ice-cooling, followed by stirring the reaction mixture at room temperature for 1.5 hours. To the reaction mixture was added water, followed by extraction with ethyl acetate. The organic layer was washed with saturated brine, dried and concentrated. The residue was purified by column chromatography on silica gel (ethyl acetate:hexane (volume ratio)=1:19 to 1:4) to give (9-methoxyspiro[5.5]undec-3-yl)methanol (217 mg).

$^1$H-NMR (CDCl$_3$) δ: 0.94-1.51 (4H, m), 1.56 (4H, m), 1.70-1.89 (7H, m), 3.12-3.18 (1H, m), 3.33 (3H, s), 3.47 (2H, d, J=6.0 Hz).

Step 7

In the same manner as in Steps 8 to 9 of Example 21, 3-[4-(9-methoxy-spiro[5.5]undec-3-ylmethoxy)-phenyl]- propionic acid (109 mg) was obtained from (9-methoxyspiro[5.5]undec-3-yl)methanol (208 mg) obtained in Step 6.

Example 115

Preparation of 3-[4-(9,9-dimethyl-spiro[4.5]dec-7-ylmethoxy)-phenyl]-propionic acid

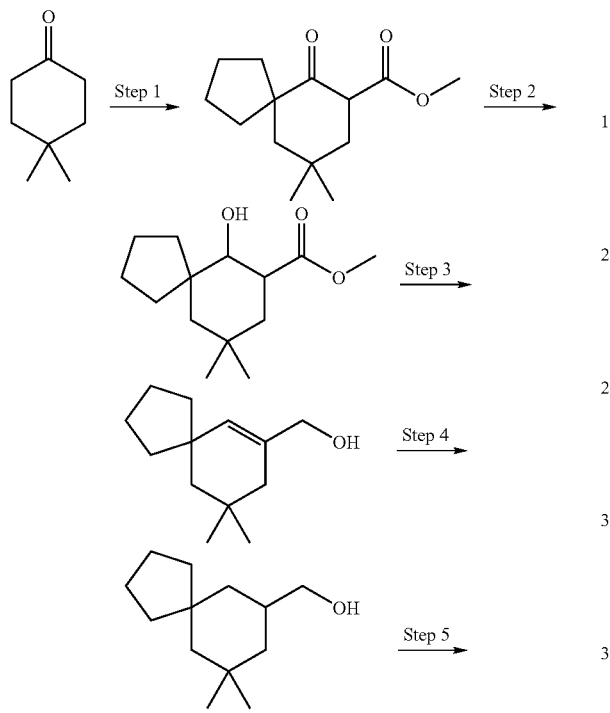

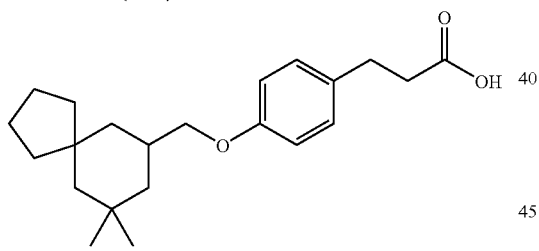

Step 1

In the same manner as in Steps 1 to 2 of Example 7, 9,9-dimethyl-6-oxo-spiro[4.5]decane-7-carboxylic acid methyl ester (461 mg) was obtained from 4,4-dimethylcyclohexanone (800 mg).

$^1$H-NMR (CDCl$_3$) δ: 0.96 (4.2H, s), 1.02 (0.9H, s), 1.21 (0.9H, s), 1.49-1.89 (8H, m), 2.01-2.07 (4H, m), 3.74 (3H, s), 3.78 (0.3H, dd, J=13.9, 5.3 Hz), 12.46 (0.7H, s).

Step 2

To a solution of 9,9-dimethyl-6-oxo-spiro[4.5]decane-7-carboxylic acid methyl ester (450 mg) obtained in Step 1 in methanol (4.5 mL) was added calcium chloride dihydrate (417 mg), followed by stirring under ice-cooling for 15 minutes. Then, to the reaction mixture was added sodium borohydride (90 mg) in three portions, followed by stirring the reaction mixture under ice-cooling for 1.5 hours. To the reaction mixture were added successively 2N aqueous hydrochloric acid solution, toluene and saturated brine, and the mixture was stirred for 5 minutes, followed by separation of the aqueous layer. The organic layer was washed successively with water and saturated brine, dried and concentrated. The residue was purified by column chromatography on silica gel (ethyl acetate:hexane (volume ratio)=1:19 to 1:6) to give 6-hydroxy-9,9-dimethyl-spiro[4.5]decane-7-carboxylic acid methyl ester (341 mg).

$^1$H-NMR (CDCl$_3$) δ: 0.91-1.02 (6H, m), 1.18-1.72 (8H, m), 1.73-2.01 (4H, m), 2.44 (0.6H, d, J=4.4 Hz), 2.63 (0.6H, ddd, J=13.6, 10.1, 3.0 Hz), 2.76 (0.4H, dq, J=13.5, 1.8 Hz), 2.89 (0.4H, d, J=2.6 Hz), 3.62 (0.6H, dd, J=10.6, 4.1 Hz), 3.69 (0.4H, s), 3.72 (3H, s).

Step 3

In the same manner as in Step 6 of Example 104, (9,9-dimethyl-spiro[4.5]dec-6-en-7-yl)-methanol (243 mg) was obtained from 6-hydroxy-9,9-dimethyl-spiro[4.5]decane-7-carboxylic acid methyl ester (330 mg) obtained in Step 2.

$^1$H-NMR (CDCl$_3$) δ: 0.96 (6H, s), 1.49-1.54 (4H, m), 1.56 (2H, s), 1.62-1.70 (4H, m), 1.78 (2H, s), 3.99 (2H, d, J=4.9 Hz), 5.50 (1H, s).

Step 4

In the same manner as in Step 5 of Example 22, (9,9-dimethyl-spiro[4.5]dec-7-yl)-methanol (169 mg) was obtained from (9,9-dimethyl-spiro[4.5]dec-6-en-7-yl)-methanol (199 mg) obtained in Step 3.

$^1$H-NMR (CDCl$_3$) δ: 0.90 (3H, s), 0.96 (3H, s), 1.23-1.57 (10H, m), 1.57-1.69 (4H, m), 1.69-1.81 (1H, m), 3.45 (2H, d, J=4.4 Hz).

Step 5

In the same manner as in Steps of 8 to 9 of Example 21, 3-[4-(9,9-dimethyl-spiro[4.5]dec-7-ylmethoxy)-phenyl]-propionic acid (129 mg) was obtained from (9,9-dimethyl-spiro[4.5]dec-7-yl)-methanol (100 mg) obtained in Step 4.

Example 116

Preparation of (3S)-3-[4-(spiro[2.6]non-5-yl-methoxy)-phenyl]-hex-4-ynoic acid

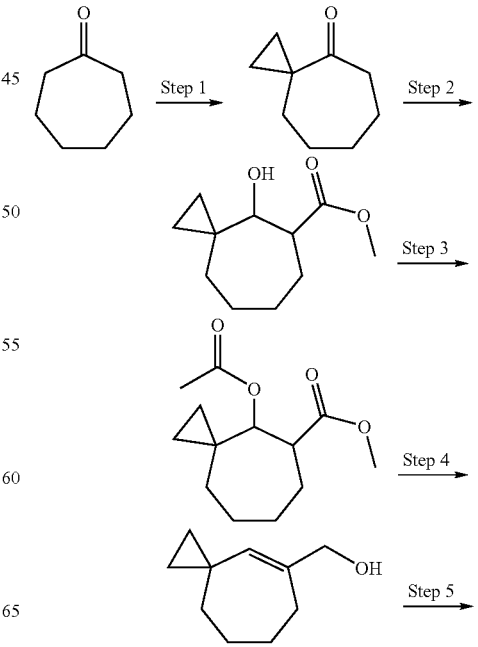

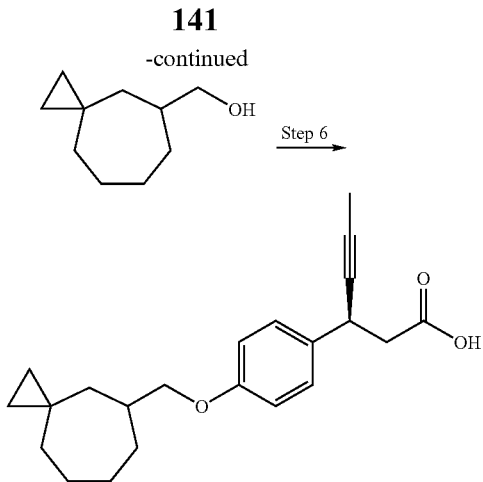

Step 1

To a suspension of potassium tert-butoxide (3.48 g) in tert-butanol (32 mL) was added cycloheptanone (1.9 mL) while stirring under nitrogen atmosphere, followed by stirring the mixture at room temperature for 0.5 hour. Then, to the reaction mixture was added (2-chloroethyl)-dimethylsulfonium iodide (3.7 g) in eight portions over 1.6 hours, followed by stirring the mixture at room temperature for 16.5 hours. To the reaction mixture was added water, followed by extraction with diethyl ether. The organic layer was washed with saturated brine, dried and concentrated. The residue was purified by column chromatography on silica gel (diethyl ether:hexane (volume ratio)=1:15) to give spiro[2.6]nonan-4-one (1.40 g).

$^1$H-NMR (CDCl$_3$) δ: 0.67 (2H, ddd, J=3.4, 3.4, 3.4 Hz), 1.24 (2H, ddd, J=3.4, 3.4, 3.4 Hz), 1.66-1.73 (6H, m), 1.73-1.78 (2H, m), 2.63-2.66 (2H, m).

Step 2

In the same manner as in Step 2 of Example 7 and Step 2 of Example 115, 4-hydroxy-spiro[2.6]nonane-5-carboxylic acid methyl ester (1.47 g) was obtained from spiro[2.6]nonan-4-one (1.40 g) obtained in Step 1.

$^1$H-NMR (CDCl$_3$) δ: 0.31-0.44 (3H, m) 0.57-0.63 (1H, m), 0.74-0.80 (1H, m), 1.55-1.71 (3H, m), 1.77-1.84 (2H, m), 2.08-2.25 (2H, m), 2.66 (1H, dt, J=11.1, 2.2 Hz), 2.71 (1H, d, J=2.2 Hz), 3.22 (1H, s), 3.69 (3H, s).

Step 3

To a solution of 4-hydroxy-spiro[2.6]nonane-5-carboxylic acid methyl ester (0.899 g) obtained in Step 2 in chloroform (18 mL) were added successively triethylamine (6.33 mL), 4-dimethylaminopyridine (0.11 g) and acetic anhydride (2.15 mL) under argon atmosphere and ice-cooling, followed by stirring the mixture at room temperature for 3.5 hours. After ice-cooling the reaction mixture and adding saturated aqueous sodium bicarbonate solution thereto, the reaction mixture was extracted with ethyl acetate. The organic layer was washed successively with saturated aqueous sodium bicarbonate solution and saturated brine, dried and concentrated. The residue was purified by column chromatography on silica gel (diethyl ether:hexane (volume ratio)=1:9) to give 4-acetoxy-spiro[2.6]nonane-5-carboxylic acid methyl ester (1.06 g).

$^1$H-NMR (CDCl$_3$) δ: 0.35-0.40 (1H, m) 0.43-0.48 (1H, m), 0.50-0.55 (1H, m), 0.72-0.77 (1H, m), 0.82-0.89 (1H, m), 1.55-1.74 (3H, m), 1.77-1.85 (1H, m), 1.87-1.95 (1H, m), 1.97-2.15 (2H, m), 2.07 (3H, s), 2.78 (1H, dq, J=11.2, 1.8 Hz), 3.63 (3H, s), 4.64 (1H, t, J=0.9 Hz).

Step 4

To a solution of 4-acetoxy-spiro[2.6]nonane-5-carboxylic acid methyl ester (1.06 g) obtained in Step 3 in toluene (11 mL) was added 1,8-diazabicyclo[5.4.0]undec-7-ene (3.3 mL), followed by stirring the reaction mixture at 120° C. for 5.5 hours. After ice-cooling the reaction mixture, water (25 mL) and 1N aqueous hydrochloric acid solution (25 mL) were added thereto, followed by extraction with ethyl acetate. The organic layer was washed successively with saturated aqueous sodium bicarbonate solution and saturated brine, dried and concentrated. The residue was purified by column chromatography on silica gel (diethyl ether:hexane (volume ratio)=1:20) to give spiro[2.6]non-4-en-5-yl-methanol (0.32 g).

$^1$H-NMR (CDCl$_3$) δ: 0.49-0.57 (4H, m), 1.27 (1H, brs), 1.46 (2H, t, J=5.7 Hz), 1.65-1.75 (4H, m), 2.22 (2H, dd, J=6.8, 4.1 Hz), 3.95 (2H, s), 5.24 (1H, s).

Step 5

To a solution of spiro[2.6]non-4-en-5-yl-methanol (170 mg) obtained in Step 4 in ethanol (3.4 mL) was added platinum oxide (35 mg), followed by stirring the reaction mixture at room temperature under normal pressure in an atmosphere of hydrogen for 2 hours. Then, the reaction mixture was filtered through Celite. The filtrate was concentrated and the residue was purified by column chromatography on silica gel (ethyl acetate:hexane (volume ratio)=1:7) to give spiro[2.6]non-5-yl-methanol (164 mg).

$^1$H-NMR (CDCl$_3$) δ: 0.23-0.36 (3.6H, m), 0.86-0.93 (0.4H, m), 1.12-1.37 (4H, m), 1.44-1.83 (7H, m), 3.35-3.44 (2H, m).

Step 6

In the same manner as in Steps 8 to 9 of Example 1, (3S)-3-[4-(spiro[2.6]non-5-ylmethoxy)-phenyl]-hex-4-ynoic acid (157 mg) was obtained from spiro[2.6]non-5-yl-methanol (100 mg) obtained in Step 5.

Example 117

Preparation of 3-[4-(spiro[3.4]oct-5-en-6-yl-methoxy)-phenyl]-propionic acid

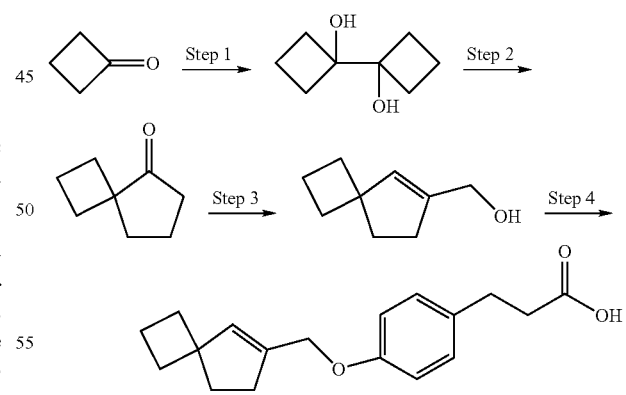

Step 1

To a solution of lithium chloride (2.12 g) in tetrahydrofuran (60 mL) was added samarium(II) iodide (5.0 g) under argon atmosphere, followed by stirring the mixture at room temperature for 15 minutes. To this reaction mixture was added dropwise a solution of cyclobutanone (825 mg) in tetrahydrofuran (5 mL), followed by stirring the mixture at room temperature for 1 hour. To the reaction mixture was added saturated aqueous sodium thiosulfate solution under ice-cooling, followed by extraction with diethyl ether three times. The organic layers were combined, washed with saturated brine, dried and concentrated. The residue was purified by column chromatography on silica gel (ethyl acetate:hexane (volume ratio)=1:19 to 3:2) to give bicyclobutyl-1,1'-diol (399 mg).

$^1$H-NMR (CDCl$_3$) δ: 1.58-1.71 (2H, m), 1.93-2.07 (6H, m), 2.15 (2H, s), 2.27-2.37 (4H, m).

Step 2

To bicyclobutyl-1,1'-diol (1.95 g) obtained in the same manner as in Step 1 was added 10% aqueous sulfuric acid solution (20 mL), followed by stirring the mixture at 90° C. for 3 hours. The reaction mixture was ice-cooled and extracted with diethyl ether. The organic layer was washed successively with water and saturated brine, dried and concentrated. The residue was purified by column chromatography on silica gel (hexane→diethyl ether:hexane (volume ratio)=1:6) to give spiro[3.4]octan-5-one (583 mg).

$^1$H-NMR (CDCl$_3$) δ: 1.77-1.86 (4H, m), 1.90-2.03 (4H, m), 2.17 (2H, t, J=7.6 Hz), 2.23-2.30 (2H, m).

Step 3

In the same manner as in Steps 2 to 4 of Example 116, spiro[3.4]oct-5-en-6-yl-methanol (116 mg) was obtained from spiro[3.4]octan-5-one (545 mg) obtained in Step 2.

$^1$H-NMR (CDCl$_3$) δ: 1.77-1.90 (2H, m), 1.92-2.10 (6H, m), 2.30 (2H, t, J=7.0 Hz), 4.17 (2H, s), 5.73 (1H, s).

Step 4

In the same manner as in Steps 8 to 9 of Example 21, 3-[4-(spiro[3.4]oct-5-en-6-ylmethoxy)-phenyl]-propionic acid (108 mg) was obtained from spiro[3.4]oct-5-en-6-yl-methanol (58 mg) obtained in Step 3.

Example 118

Preparation of (3S)-3-[4-(spiro[3.4]oct-6-yl-methoxy)-phenyl]-hex-4-ynoic acid

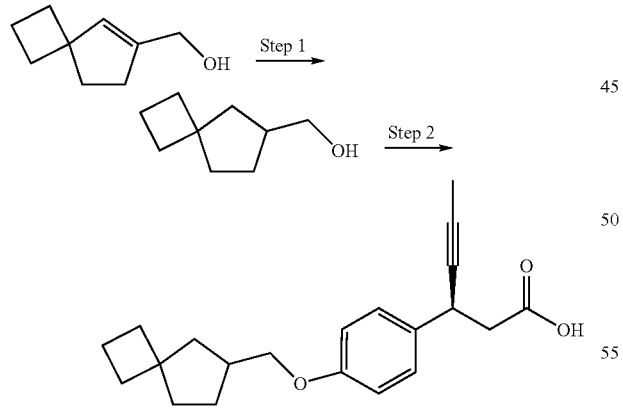

Step 1

In the same manner as in Step 5 of Example 116, spiro[3.4] oct-6-yl-methanol (53 mg) was obtained from spiro[3.4]oct-5-en-6-yl-methanol (50 mg) obtained in Step 3 of Example 117.

$^1$H-NMR (CDCl$_3$) δ: 1.24-1.32 (3H, m), 1.63 (2H, t, J=7.2 Hz) 1.70-1.79 (1H, m), 1.79-1.91 (7H, m), 2.08-2.20 (1H, m), 3.49 (2H, d, J=7.2 Hz).

Step 2

In the same manner as in Steps 8 to 9 of Example 1, (3S)-3-[4-(spiro[3.4]oct-6-ylmethoxy)-phenyl]-hex-4-ynoic acid (88 mg) was obtained from spiro[3.4]oct-6-yl-methanol (50 mg) obtained in Step 1.

Example 119

Preparation of (S)-3-[4-(spiro[5.5]undec-2-en-2-ylmethoxy)-phenyl]-hex-4-ynoic acid L-lysine salt

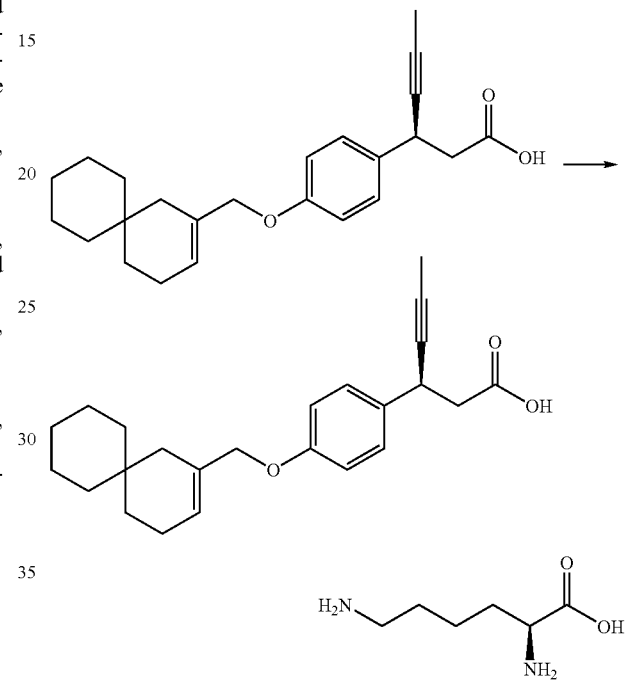

To a solution of (S)-3-[4-(spiro[5.5]undec-2-en-2-yl-methoxy)-phenyl]-hex-4-ynoic acid (50 mg) obtained in the same manner as in Example 1 in a mixed solvent of N,N-dimethylformamide (0.75 mL)-water (0.059 mL) was added 50% aqueous L-lysine solution (0.032 mL) at 50° C., followed by stirring overnight while gradually cooling the mixture down to room temperature. The precipitate was filtered and then dried to give (S)-3-[4-(spiro[5.5]undec-2-en-2-yl-methoxy)-phenyl]-hex-4-ynoic acid L-lysine salt (45 mg).

Example 120

Preparation of (−)-3-ethoxy-3-[4-(spiro[5.5]undec-1-en-2-ylmethoxy)-phenyl]-propionic acid L-lysine salt

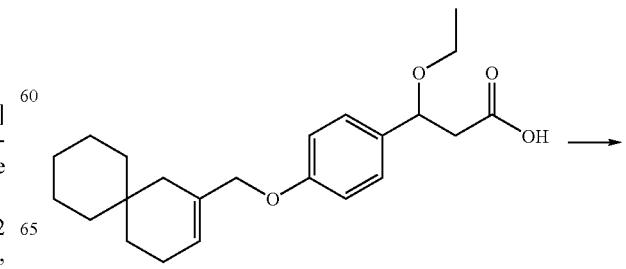

-continued

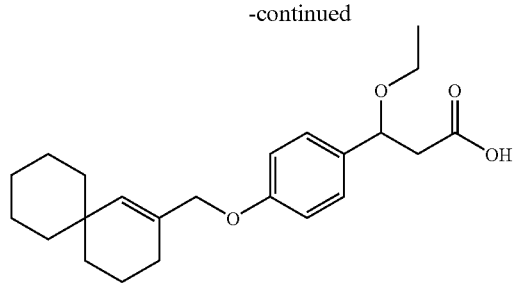

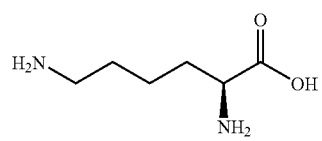

To a solution of (−)-3-ethoxy-3-[4-(spiro[5.5]undec-1-en-2-ylmethoxy)-phenyl]-propionic acid (50 mg) obtained in the same manner as in Example 42 in a mixed solvent of N,N-dimethylformamide (0.75 mL)-water (0.044 mL) was added 50% aqueous L-lysine solution (0.032 mL) at 50° C., followed by stirring overnight while gradually cooling the mixture down to room temperature. The precipitate was filtered and then dried to give (−)-3-ethoxy-3-[4-(spiro[5.5]undec-1-en-2-ylmethoxy)-phenyl]-propionic acid L-lysine salt (52 mg).

The structural formulae of the compounds obtained in Examples 1 to 120 are shown in Tables 1 to 17. In Tables 1 to 17, the chirality of the carbon atom in a methine group substituted by a phenyl group or a pyridyl group is represented as "the chirality at the benzylic carbon".

With regard to the compounds obtained in Examples 1 to 120, the compound names and NMR data are shown in Tables 18 to 26 and in Tables 27 to 38, respectively.

TABLE 1

| Ex. No. | Structural formula | Chirality at benzylic carbon | Chirality of carbon at spiro junction | Other chiral carbon |
|---|---|---|---|---|
| 1 | | S-isomer | — | — |
| 2 | | S-isomer | — | — |
| 3 | | S-isomer | — | — |

TABLE 1-continued
| Ex. No. | Structural formula | Chirality at benzylic carbon | Chirality of carbon at spiro junction | Other chiral carbon |
|---|---|---|---|---|
| 4 | 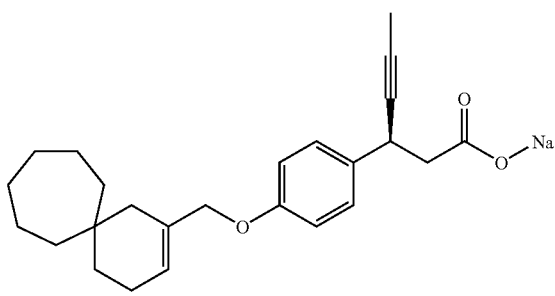 | S-isomer | — | — |
| 5 | 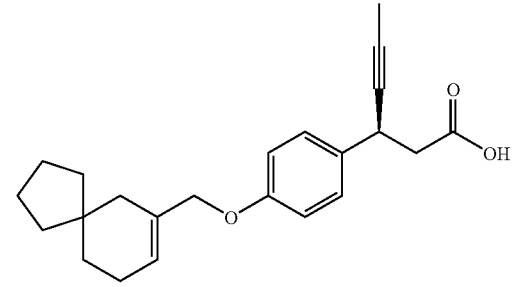 | S-isomer | — | — |
| 6 | 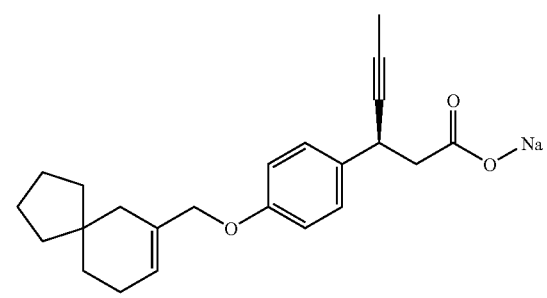 | S-isomer | — | — |
| 7 | 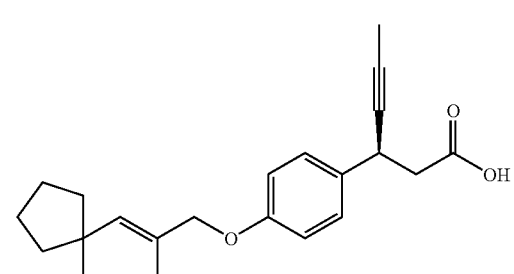 | S-isomer | — | — |

TABLE 2

| Ex. No. | Structural formula | Chirality at benzylic carbon | Chirality of carbon at spiro junction | Other chiral carbon |
| --- | --- | --- | --- | --- |
| 8 | | S-isomer | — | — |
| 9 | | S-isomer | — | — |
| 10 | | S-isomer | — | — |
| 11 | | S-isomer | — | — |
| 12 | | S-isomer | — | — |

TABLE 2-continued

| Ex. No. | Structural formula | Chirality at benzylic carbon | Chirality of carbon at spiro junction | Other chiral carbon |
|---|---|---|---|---|
| 13 | (structure) | S-isomer | — | — |
| 14 | (structure) | S-isomer | — | — |

TABLE 3

| Ex. No. | Structural formula | Chirality at benzylic carbon | Chirality of carbon at spiro junction | Other chiral carbon |
|---|---|---|---|---|
| 15 | (structure) | S-isomer | — | — |
| 16 | (structure) | S-isomer | — | — |

TABLE 3-continued

| Ex. No. | Structural formula | Chirality at benzylic carbon | Chirality of carbon at spiro junction | Other chiral carbon |
|---|---|---|---|---|
| 17 | | S-isomer | — | — |
| 18 | | S-isomer | — | — |
| 19 | | S-isomer | racemate | spiro-C6: racemate |
| 20 | | S-isomer | racemate | spiro-C6: racemate |
| 21 | | — | racemate | — |

TABLE 4

| Ex. No. | Structural formula | Chirality at benzylic carbon | Chirality of carbon at spiro junction | Other chiral carbon |
| --- | --- | --- | --- | --- |
| 22 | | S-isomer | — | — |
| 23 | | S-isomer | — | — |
| 24 | | S-isomer | — | — |
| 25 | | S-isomer | — | — |

TABLE 4-continued
| Ex. No. | Structural formula | Chirality at benzylic carbon | Chirality of carbon at spiro junction | Other chiral carbon |
|---|---|---|---|---|
| 26 | 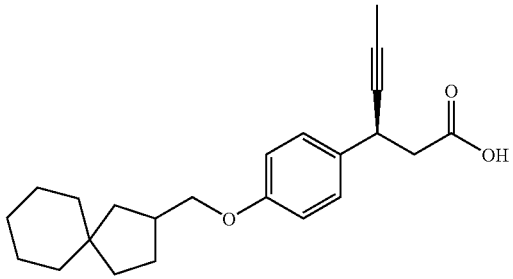 | S-isomer | racemate | — |
| 27 | 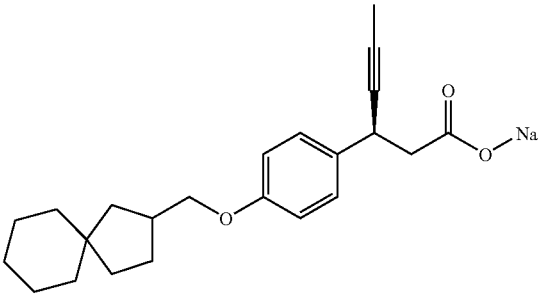 | S-isomer | racemate | — |
| 28 | 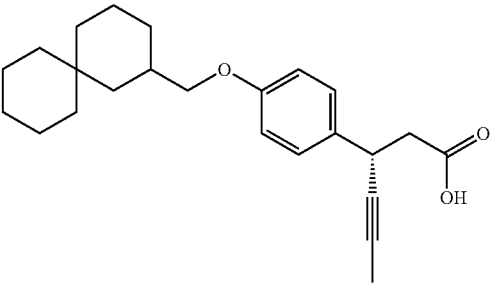 | S-isomer | racemate | — |
TABLE 5
| Ex. No. | Structural formula | Chirality at benzylic carbon | Chirality of carbon at spiro junction | Other chiral carbon |
|---|---|---|---|---|
| 29 | 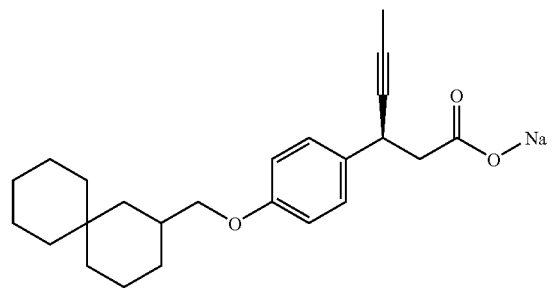 | S-isomer | racemate | — |

TABLE 5-continued

| Ex. No. | Structural formula | Chirality at benzylic carbon | Chirality of carbon at spiro junction | Other chiral carbon |
|---|---|---|---|---|
| 30 | | S-isomer | racemate | — |
| 31 | | S-isomer | racemate | — |
| 32 | | S-isomer | chiral: A | — |
| 33 | | S-isomer | chiral: A | — |
| 34 | | S-isomer | chiral: B | — |

TABLE 5-continued
| Ex. No. | Structural formula | Chirality at benzylic carbon | Chirality of carbon at spiro junction | Other chiral carbon |
|---|---|---|---|---|
| 35 | 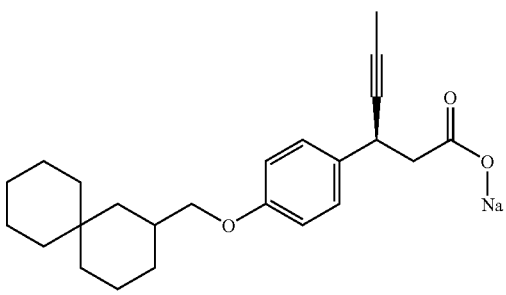 | S-isomer | chiral: B | — |
TABLE 6
| Ex. No. | Structural formula | Chirality at benzylic carbon | Chirality of carbon at spiro junction | Other chiral carbon |
|---|---|---|---|---|
| 36 | 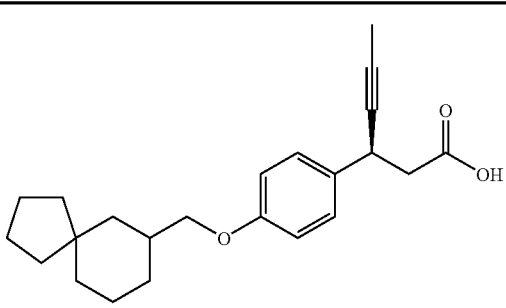 | S-isomer | chiral: A | — |
| 37 | 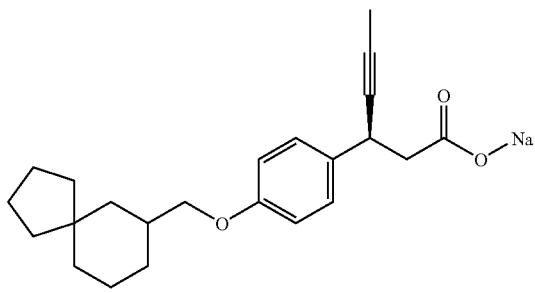 | S-isomer | chiral: A | — |
| 38 | 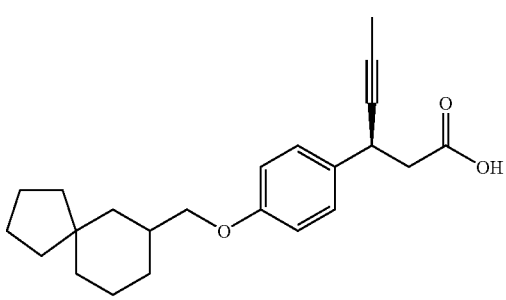 | S-isomer | chiral: B | — |

TABLE 6-continued

| Ex. No. | Structural formula | Chirality at benzylic carbon | Chirality of carbon at spiro junction | Other chiral carbon |
| --- | --- | --- | --- | --- |
| 39 | | S-isomer | chiral: B | — |
| 40 | | racemate | racemate | — |
| 41 | | racemate | — | — |
| 42 | | (−)-isomer | — | — |

TABLE 7

| Ex. No. | Structural formula | Chirality at benzylic carbon | Chirality of carbon at spiro junction | Other chiral carbon |
| --- | --- | --- | --- | --- |
| 43 | | (−)-isomer | — | — |
| 44 | | (+)-isomer | — | — |
| 45 | | racemate | — | — |
| 46 | | — | racemate | — |
| 47 | | racemate | racemate | — |
| 48 | | — | racemate | spiro-C6: racemate |

TABLE 7-continued

| Ex. No. | Structural formula | Chirality at benzylic carbon | Chirality of carbon at spiro junction | Other chiral carbon |
|---|---|---|---|---|
| 49 | | — | racemate | — |

TABLE 8

| Ex. No. | Structural formula | Chirality at benzylic carbon | Chirality of carbon at spiro junction | Other chiral carbon |
|---|---|---|---|---|
| 50 | | — | racemate | spiro-C6, C11: racemate |
| 51 | | — | racemate | spiro-C7, C11: racemate |
| 52 | | — | racemate | — |
| 53 | | — | racemate | spiro-C6: racemate |
| 54 | | — | racemate | — |

TABLE 8-continued

| Ex. No. | Structural formula | Chirality at benzylic carbon | Chirality of carbon at spiro junction | Other chiral carbon |
|---|---|---|---|---|
| 55 | | — | racemate | spiro-C6: racemate |
| 56 | | — | racemate | spiro-C6: racemate |

TABLE 9

| Ex. No. | Structural formula | Chirality at benzylic carbon | Chirality of carbon at spiro junction | Other chiral carbon |
|---|---|---|---|---|
| 57 | | — | — | — |
| 58 | | R-isomer | racemate | — |
| 59 | | racemate | racemate | — |

TABLE 9-continued

| Ex. No. | Structural formula | Chirality at benzylic carbon | Chirality of carbon at spiro junction | Other chiral carbon |
|---|---|---|---|---|
| 60 | | racemate | racemate | — |
| 61 | | — | racemate | — |
| 62 | | — | racemate | — |
| 63 | | S-isomer | — | — |

TABLE 10

| Ex. No. | Structural formula | Chirality at benzylic carbon | Chirality of carbon at spiro junction | Other chiral carbon |
|---|---|---|---|---|
| 64 | | S-isomer | racemate | — |

TABLE 10-continued

| Ex. No. | Structural formula | Chirality at benzylic carbon | Chirality of carbon at spiro junction | Other chiral carbon |
|---|---|---|---|---|
| 65 | | racemate | racemate | — |
| 66 | | racemate | racemate | — |
| 67 | | — | racemate | thiazolidine-dione-C5: racemate |
| 68 | | S-isomer | racemate | thiazolidine-dione-C5: racemate |
| 69 | | racemate | racemate | — |

TABLE 10-continued

| Ex. No. | Structural formula | Chirality at benzylic carbon | Chirality of carbon at spiro junction | Other chiral carbon |
|---|---|---|---|---|
| 70 | | S-isomer | racemate | spiro-C1-C2: cis-isomer |

TABLE 11

| Ex. No. | Structural formula | Chirality at benzylic carbon | Chirality of carbon at spiro junction | Other chiral carbon |
|---|---|---|---|---|
| 71 | | racemate | racemate | — |
| 72 | | S-isomer | racemate | — |
| 73 | | S-isomer | — | — |

TABLE 11-continued

| Ex. No. | Structural formula | Chirality at benzylic carbon | Chirality of carbon at spiro junction | Other chiral carbon |
|---|---|---|---|---|
| 74 | | S-isomer | racemate | — |
| 75 | | racemate | racemate | — |
| 76 | | S-isomer | racemate | — |
| 77 | | R-isomer | racemate | — |

TABLE 12

| Ex. No. | Structural formula | Chirality at benzylic carbon | Chirality of carbon at spiro junction | Other chiral carbon |
|---|---|---|---|---|
| 78 | | S-isomer | racemate | — |

TABLE 12-continued

| Ex. No. | Structural formula | Chirality at benzylic carbon | Chirality of carbon at spiro junction | Other chiral carbon |
|---|---|---|---|---|
| 79 | | racemate | racemate | — |
| 80 | | racemate | racemate | — |
| 81 | | racemate | racemate | — |
| 82 | | racemate | racemate | — |
| 83 | | racemate | racemate | — |

TABLE 12-continued

| Ex. No. | Structural formula | Chirality at benzylic carbon | Chirality of carbon at spiro junction | Other chiral carbon |
|---|---|---|---|---|
| 84 | | racemate | racemate | — |

TABLE 13

| Ex. No. | Structural formula | Chirality at benzylic carbon | Chirality of carbon at spiro junction | Other chiral carbon |
|---|---|---|---|---|
| 85 | | racemate | racemate | — |
| 86 | | racemate | racemate | — |
| 87 | | racemate | racemate | — |
| 88 | | — | chiral: A | — |

TABLE 13-continued

| Ex. No. | Structural formula | Chirality at benzylic carbon | Chirality of carbon at spiro junction | Other chiral carbon |
|---|---|---|---|---|
| 89 | (spiro[5.5]undecane-CH₂-O-C₆H₄-CH₂CH₂-COOH) | — | chiral: B | — |
| 90 | (spiro[5.5]undec-2-ene-CH₂-O-C₆H₄-CH(C≡CH)-CH₂-COO⁻ · 0.5Ca²⁺) | S-isomer | — | — |
| 91 | (spiro[4.5]dec-7-ene-CH₂-O-C₆H₄-CH(C≡CH)-CH₂-COO⁻ · 0.5Ca²⁺) | S-isomer | — | — |

TABLE 14

| Ex. No. | Structural formula | Chirality at benzylic carbon | Chirality of carbon at spiro junction | Other chiral carbon |
|---|---|---|---|---|
| 92 | (spiro[4.5]dec-7-ene-CH₂-O-C₆H₄-CH(C≡CH)-CH₂-COOH with L-lysine) | S-isomer | — | — |

TABLE 14-continued

| Ex. No. | Structural formula | Chirality at benzylic carbon | Chirality of carbon at spiro junction | Other chiral carbon |
| --- | --- | --- | --- | --- |
| 93 | | R-isomer | — | — |
| 94 | | R-isomer | — | — |
| 95 | | (−)-isomer | — | — |
| 96 | | S-isomer | — | spiro-C5: S-isomer |
| 97 | | S-isomer | — | spiro-C5: S-isomer |

TABLE 14-continued

| Ex. No. | Structural formula | Chirality at benzylic carbon | Chirality of carbon at spiro junction | Other chiral carbon |
|---|---|---|---|---|
| 98 | | S-isomer | — | spiro-C2: S-isomer spiro-C5: S-isomer |

TABLE 15

| Ex. No. | Structural formula | Chirality at benzylic carbon | Chirality of carbon at spiro junction | Other chiral carbon |
|---|---|---|---|---|
| 99 | | S-isomer | — | spiro-C2: S-isomer spiro-C5: S-isomer |
| 100 | | S-isomer | — | spiro-C2: R-isomer spiro-C5: S-isomer |
| 101 | | S-isomer | — | spiro-C2: R-isomer spiro-C5: S-isomer |

TABLE 15-continued

| Ex. No. | Structural formula | Chirality at benzylic carbon | Chirality of carbon at spiro junction | Other chiral carbon |
|---|---|---|---|---|
| 102 | | S-isomer | — | spiro-C5: R-isomer |
| 103 | | S-isomer | — | spiro-C5: R-isomer |
| 104 | | S-isomer | — | spiro-C2: R-isomer spiro-C5: R-isomer |
| 105 | | S-isomer | — | spiro-C2: R-isomer spiro-C5: R-isomer |

TABLE 16

| Ex. No. | Structural formula | Chirality at benzylic carbon | Chirality of carbon at spiro junction | Other chiral carbon |
| --- | --- | --- | --- | --- |
| 106 | | S-isomer | — | spiro-C2: S-isomer spiro-C5: R-isomer |
| 107 | | S-isomer | — | spiro-C2: S-isomer spiro-C5: R-isomer |
| 108 | | — | — | — |
| 109 | | — | — | — |
| 110 | | — | — | — |
| 111 | | — | — | — |

TABLE 16-continued
| Ex. No. | Structural formula | Chirality at benzylic carbon | Chirality of carbon at spiro junction | Other chiral carbon |
|---|---|---|---|---|
| 112 | 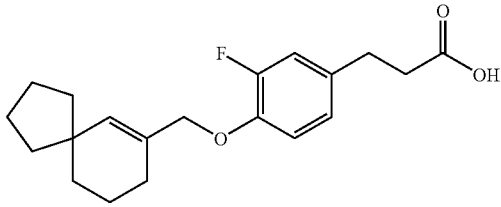 | — | — | — |
TABLE 17
| Ex. No. | Structural formula | Chirality at benzylic carbon | Chirality of carbon at spiro junction | Other chiral carbon |
|---|---|---|---|---|
| 113 | 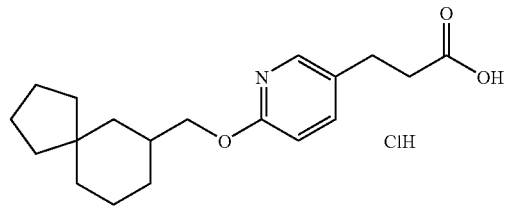 | — | racemate | — |
| 114 | 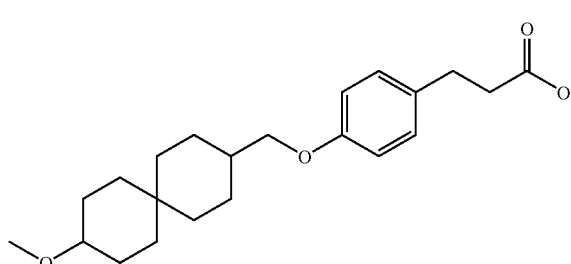 | — | — | spiro structure (axial chirality): racemate |
| 115 | 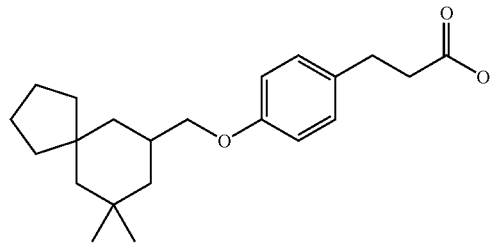 | — | racemate | — |
| 116 | 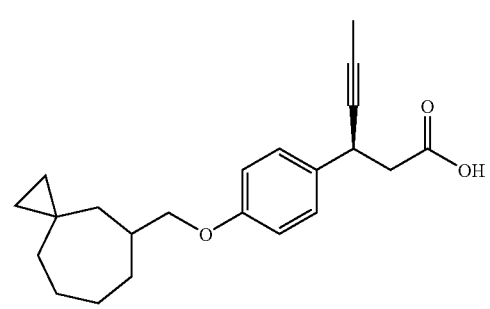 | S-isomer | racemate | — |

TABLE 17-continued

| Ex. No. | Structural formula | Chirality at benzylic carbon | Chirality of carbon at spiro junction | Other chiral carbon |
|---|---|---|---|---|
| 117 | | — | — | — |
| 118 | | S-isomer | racemate | — |
| 119 | | S-isomer | — | — |
| 120 | | (−)-isomer | — | — |

TABLE 18

| Ex. No. | Compound name |
|---|---|
| 1 | (S)-3-[4-(spiro[5.5]undec-2-en-2-ylmethoxy)-phenyl]-hex-4-ynoic acid |
| 2 | (S)-3-[4-(spiro[5.5]undec-2-en-2-ylmethoxy)-phenyl]-hex-4-ynoic acid sodium salt |
| 3 | (S)-3-[4-(spiro[5.6]dodec-2-en-2-ylmethoxy)-phenyl]-hex-4-ynoic acid |
| 4 | (S)-3-[4-(spiro[5.6]dodec-2-en-2-ylmethoxy)-phenyl]-hex-4-ynoic acid sodium salt |
| 5 | (S)-3-[4-(spiro[4.5]dec-7-en-7-ylmethoxy)-phenyl]-hex-4-ynoic acid |
| 6 | (S)-3-[4-(spiro[4.5]dec-7-en-7-ylmethoxy)-phenyl]-hex-4-ynoic acid sodium salt |
| 7 | (S)-3-[4-(spiro[4.5]dec-6-en-7-ylmethoxy)-phenyl]-hex-4-ynoic acid |
| 8 | (S)-3-[4-(spiro[4.5]dec-6-en-7-ylmethoxy)-phenyl]-hex-4-ynoic acid sodium salt |

TABLE 18-continued

| Ex. No. | Compound name |
|---|---|
| 9 | (S)-3-[4-(spiro[5.5]undec-1-en-2-ylmethoxy)-phenyl]-hex-4-ynoic acid |
| 10 | (S)-3-[4-(spiro[5.5]undec-1-en-2-ylmethoxy)-phenyl]-hex-4-ynoic acid sodium salt |
| 11 | (S)-3-[4-(spiro[4.4]non-2-en-2-ylmethoxy)-phenyl]-hex-4-ynoic acid |
| 12 | (S)-3-[4-(spiro[4.4]non-2-en-2-ylmethoxy)-phenyl]-hex-4-ynoic acid sodium salt |
| 13 | (S)-3-[4-(spiro[4.5]dec-2-en-2-ylmethoxy)-phenyl]-hex-4-ynoic acid |
| 14 | (S)-3-[4-(spiro[4.5]dec-2-en-2-ylmethoxy)-phenyl]-hex-4-ynoic acid sodium salt |

TABLE 19

| Ex. No. | Compound name |
|---|---|
| 15 | (S)-3-[4-(spiro[4.5]dec-1-en-2-ylmethoxy)-phenyl]-hex-4-ynoic acid |
| 16 | (S)-3-[4-(spiro[4.5]dec-1-en-2-ylmethoxy)-phenyl]-hex-4-ynoic acid sodium salt |
| 17 | (S)-3-[4-(spiro[4.4]non-1-en-2-ylmethoxy)-phenyl]-hex-4-ynoic acid |
| 18 | (S)-3-[4-(spiro[4.4]non-1-en-2-ylmethoxy)-phenyl]-hex-4-ynoic acid sodium salt |
| 19 | (3S)-3-[4-(11,11-dimethyl-spiro[5.5]undec-7-en-2-ylmethoxy)-phenyl]-hex-4-ynoic acid |
| 20 | (3S)-3-[4-(11,11-dimethyl-spiro[5.5]undec-7-en-2-ylmethoxy)-phenyl]-hex-4-ynoic acid sodium salt |
| 21 | 3-[4-(spiro[4.6]undec-2-ylmethoxy)-phenyl]-propionic acid |
| 22 | (S)-3-[4-(spiro[4.5]dec-8-ylmethoxy)-phenyl]-hex-4-ynoic acid |
| 23 | (S)-3-[4-(spiro[4.5]dec-8-ylmethoxy)-phenyl]-hex-4-ynoic acid sodium salt |
| 24 | (S)-3-[4-(spiro[5.5]undec-3-ylmethoxy)-phenyl]-hex-4-ynoic acid |
| 25 | (S)-3-[4-(spiro[4.5]dec-7-en-8-ylmethoxy)-phenyl]-hex-4-ynoic acid |
| 26 | (3S)-3-[4-(spiro[4.5]dec-2-ylmethoxy)-phenyl]-hex-4-ynoic acid |
| 27 | (3S)-3-[4-(spiro[4.5]dec-2-ylmethoxy)-phenyl]-hex-4-ynoic acid sodium salt |
| 28 | (3S)-3-[4-(spiro[5.5]undec-2-ylmethoxy)-phenyl]-hex-4-ynoic acid |

TABLE 20

| Ex. No. | Compound name |
|---|---|
| 29 | (3S)-3-[4-(spiro[5.5]undec-2-ylmethoxy)-phenyl]-hex-4-ynoic acid sodium salt |
| 30 | (3S)-3-[4-(spiro[4.4]non-2-ylmethoxy)-phenyl]-hex-4-ynoic acid |
| 31 | (3S)-3-[4-(spiro[4.4]non-2-ylmethoxy)-phenyl]-hex-4-ynoic acid sodium salt |
| 32 | (3S)-3-[4-(spiro[5.5]undec-2-ylmethoxy)-phenyl]-hex-4-ynoic acid (chiral: A) |
| 33 | (3S)-3-[4-(spiro[5.5]undec-2-ylmethoxy)-phenyl]-hex-4-ynoic acid sodium salt (chiral: A) |
| 34 | (3S)-3-[4-(spiro[5.5]undec-2-ylmethoxy)-phenyl]-hex-4-ynoic acid (chiral: B) |
| 35 | (3S)-3-[4-(spiro[5.5]undec-2-ylmethoxy)-phenyl]-hex-4-ynoic acid sodium salt (chiral: B) |
| 36 | (3S)-3-[4-(spiro[4.5]dec-7-ylmethoxy)-phenyl]-hex-4-ynoic acid (chiral: A) |
| 37 | (3S)-3-[4-(spiro[4.5]dec-7-ylmethoxy)-phenyl]-hex-4-ynoic acid sodium salt (chiral: A) |
| 38 | (3S)-3-[4-(spiro[4.5]dec-7-ylmethoxy)-phenyl]-hex-4-ynoic acid (chiral: B) |
| 39 | (3S)-3-[4-(spiro[4.5]dec-7-ylmethoxy)-phenyl]-hex-4-ynoic acid sodium salt (chiral: B) |

TABLE 20-continued

| Ex. No. | Compound name |
|---|---|
| 40 | 3-(1-methyl-1H-tetrazol-5-yl)-3-[4-(spiro[5.5]undec-2-ylmethoxy)-phenyl]-propionic acid |
| 41 | 3-ethoxy-3-[4-(spiro[5.5]undec-1-en-2-ylmethoxy)-phenyl]-propionic acid |
| 42 | (−)-3-ethoxy-3-[4-(spiro[5.5]undec-1-en-2-ylmethoxy)-phenyl]-propionic acid |

TABLE 21

| Ex. No. | Compound name |
|---|---|
| 43 | (−)-3-ethoxy-3-[4-(spiro[5.5]undec-1-en-2-ylmethoxy)-phenyl]-propionic acid sodium salt |
| 44 | (+)-3-ethoxy-3-[4-(spiro[5.5]undec-1-en-2-ylmethoxy)-phenyl]-propionic acid |
| 45 | 3-ethoxy-3-[4-(spiro[5.5]undec-1-en-2-ylmethoxy)-phenyl]-propionic acid sodium salt |
| 46 | 3-[4-(spiro[5.5]undec-2-ylmethoxy)-phenyl]-propionic acid |
| 47 | 3-[4-(spiro[5.5]undec-2-ylmethoxy)-phenyl]-hex-4-ynoic acid |
| 48 | 3-[4-(8,8-dimethyl-spiro[5.5]undec-2-ylmethoxy)-phenyl]-propionic acid |
| 49 | 3-[4-(spiro[5.6]dodec-2-ylmethoxy)-phenyl]-propionic acid |
| 50 | 3-[4-(7,11-dimethyl-spiro[5.5]undec-7-en-2-ylmethoxy)-phenyl]-propionic acid |
| 51 | 3-[4-(7,11-dimethyl-spiro[5.5]undec-2-ylmethoxy)-phenyl]-propionic acid |
| 52 | 3-[4-(spiro[4.5]dec-2-ylmethoxy)-phenyl]-propionic acid |
| 53 | 3-[4-(9,9-dimethyl-spiro[5.5]undec-7-en-2-ylmethoxy)-phenyl]-propionic acid |
| 54 | 3-[4-(9,9-dimethyl-spiro[5.5]undec-2-ylmethoxy)-phenyl]-propionic acid |
| 55 | 3-[4-(11,11-dimethyl-spiro[5.5]undec-7-en-2-ylmethoxy)-phenyl]-propionic acid |
| 56 | 3-[4-(7,7-dimethyl-spiro[5.5]undec-2-ylmethoxy)-phenyl]-propionic acid |

TABLE 22

| Ex. No. | Compound name |
|---|---|
| 57 | 3-[4-(spiro[5.5]undec-3-ylmethoxy)-phenyl]-propionic acid |
| 58 | (3R)-3-[4-(spiro[5.5]undec-2-ylmethoxy)-phenyl]-hex-4-ynoic acid |
| 59 | N,N-dimethyl-3-[4-(spiro[5.5]undec-2-ylmethoxy)-phenyl]-succinamic acid |
| 60 | 3-phenyl-3-[4-(spiro[5.5]undec-2-ylmethoxy)-phenyl]-propionic acid |
| 61 | 3-[4-(spiro[5.5]undec-2-yloxy)-phenyl]-propionic acid |
| 62 | 3-[4-(2-spiro[5.5]undec-2-yl-ethoxy)-phenyl]-propionic acid |
| 63 | (3S)-3-[4-(spiro[5.5]undec-3-yloxy)-phenyl]-hex-4-ynoic acid |
| 64 | (3S)-3-[4-(spiro[5.5]undec-2-yloxy)-phenyl]-hex-4-ynoic acid |
| 65 | N-methyl-3-[4-(spiro[5.5]undec-2-ylmethoxy)-phenyl]-succinamic acid |
| 66 | 3-oxazol-2-yl-3-[4-(spiro[5.5]undec-2-ylmethoxy)-phenyl]-propionic acid |
| 67 | 5-[4-(spiro[5.5]undec-2-ylmethoxy)-benzyl]-thiazolidine-2,4-dione |
| 68 | 5-{(1S)-1-[4-(spiro[5.5]undec-2-ylmethoxy)-phenyl]-but-2-ynyl}-thiazolidine-2,4-dione |
| 69 | 4-hydroxy-3-[4-(spiro[5.5]undec-2-ylmethoxy)-phenyl]-butyric acid |
| 70 | (3S)-3-[4-(1-hydroxy-spiro[5.5]undec-2-ylmethoxy)-phenyl]-hex-4-ynoic acid |

TABLE 23

| Ex. No. | Compound name |
|---|---|
| 71 | 4-methoxy-3-[4-(spiro[5.5]undec-2-ylmethoxy)-phenyl]-butyric acid |
| 72 | (3S)-3-[4-(spiro[5.5]undec-1-ylmethoxy)-phenyl]-hex-4-ynoic acid |
| 73 | (3S)-3-[4-(spiro[5.5]undec-2-en-3-ylmethoxy)-phenyl]-hex-4-ynoic acid |
| 74 | (3S)-3-[4-(spiro[5.5]undec-2-yloxy)-phenyl]-hex-4-ynoic acid sodium salt |
| 75 | 3-ethoxy-3-[4-(spiro[5.5]undec-2-ylmethoxy)-phenyl]-propionic acid |
| 76 | (3S)-3-[4-(spiro[5.5]undec-1-ylmethoxy)-phenyl]-hex-4-ynoic acid sodium salt |
| 77 | (Z)-(3R)-3-[4-(spiro[5.5]undec-2-ylmethoxy)-phenyl]-hex-4-enoic acid |
| 78 | (3S)-3-[4-(spiro[5.5]undec-2-ylmethoxy)-phenyl]-hexanoic acid |
| 79 | 3-ethoxy-3-[4-(spiro[5.5]undec-2-ylmethoxy)-phenyl]-propionic acid sodium salt |
| 80 | 3-methoxy-3-[4-(spiro[5.5]undec-2-ylmethoxy)-phenyl]-propionic acid |
| 81 | 3-isopropoxy-3-[4-(spiro[5.5]undec-2-ylmethoxy)-phenyl]-propionic acid |
| 82 | 3-[4-(spiro[5.5]undec-2-yloxymethyl)-phenyl]-hex-4-ynoic acid |
| 83 | 3-propoxy-3-[4-(spiro[5.5]undec-2-ylmethoxy)-phenyl]-propionic acid |
| 84 | 3-[4-(spiro[5.5]undec-2-ylmethoxy)-phenyl]-hept-4-ynoic acid |

TABLE 24

| Ex. No. | Compound name |
|---|---|
| 85 | 3-[4-(spiro[5.5]undec-2-ylmethoxy)-phenyl]-pent-4-ynoic acid |
| 86 | 3-[4-(spiro[5.5]undec-2-ylmethoxy)-phenyl]-pent-4-enoic acid |
| 87 | 3-[4-(spiro[5.5]undec-2-ylmethoxy)-phenyl]-pentanoic acid |
| 88 | 3-[4-(spiro[5.5]undec-2-ylmethoxy)-phenyl]-propionic acid (chiral: A) |
| 89 | 3-[4-(spiro[5.5]undec-2-ylmethoxy)-phenyl]-propionic acid (chiral: B) |
| 90 | (S)-3-[4-(spiro[5.5]undec-2-en-2-ylmethoxy)-phenyl]-hex-4-ynoic acid 0.5 calcium salt |
| 91 | (S)-3-[4-(spiro[4.5]dec-6-en-7-ylmethoxy)-phenyl]-hex-4-ynoic acid 0.5 calcium salt |
| 92 | (S)-3-[4-(spiro[4.5]dec-6-en-7-ylmethoxy)-phenyl]-hex-4-ynoic acid L-lysine salt |
| 93 | (R)-3-[4-(spiro[4.5]dec-6-en-7-ylmethoxy)-phenyl]-hex-4-ynoic acid |
| 94 | (R)-3-[4-(spiro[4.5]dec-6-en-7-ylmethoxy)-phenyl]-hex-4-ynoic acid L-lysine salt |
| 95 | (−)-3-ethoxy-3-[4-(spiro[5.5]undec-1-en-2-ylmethoxy)-phenyl]-propionic acid 0.5 calcium salt |
| 96 | (3S)-3-[4-((5S)-2-oxo-spiro[4.5]dec-6-en-7-ylmethoxy)-phenyl]-hex-4-ynoic acid |
| 97 | (3S)-3-[4-((5S)-2-oxo-spiro[4.5]dec-6-en-7-ylmethoxy)-phenyl]-hex-4-ynoic acid sodium salt |
| 98 | (3S)-3-[4-((2S,5S)-2-hydroxy-spiro[4.5]dec-6-en-7-ylmethoxy)-phenyl]-hex-4-ynoic acid |

TABLE 25

| Ex. No. | Compound name |
|---|---|
| 99 | (3S)-3-[4-((2S,5S)-2-hydroxy-spiro[4.5]dec-6-en-7-ylmethoxy)-phenyl]-hex-4-ynoic acid sodium salt |
| 100 | (3S)-3-[4-((2R,5S)-2-hydroxy-spiro[4.5]dec-6-en-7-ylmethoxy)-phenyl]-hex-4-ynoic acid |
| 101 | (3S)-3-[4-((2R,5S)-2-hydroxy-spiro[4.5]dec-6-en-7-ylmethoxy)-phenyl]-hex-4-ynoic acid sodium salt |
| 102 | (3S)-3-[4-((5R)-2-oxo-spiro[4.5]dec-6-en-7-ylmethoxy)-phenyl]-hex-4-ynoic acid |
| 103 | (3S)-3-[4-((5R)-2-oxo-spiro[4.5]dec-6-en-7-ylmethoxy)-phenyl]-hex-4-ynoic acid sodium salt |
| 104 | (3S)-3-[4-((2R,5R)-2-hydroxy-spiro[4.5]dec-6-en-7-ylmethoxy)-phenyl]-hex-4-ynoic acid |
| 105 | (3S)-3-[4-((2R,5R)-2-hydroxy-spiro[4.5]dec-6-en-7-ylmethoxy)-phenyl]-hex-4-ynoic acid sodium salt |
| 106 | (3S)-3-[4-((2S,5R)-2-hydroxy-spiro[4.5]dec-6-en-7-ylmethoxy)-phenyl]-hex-4-ynoic acid |
| 107 | (3S)-3-[4-((2S,5R)-2-hydroxy-spiro[4.5]dec-6-en-7-ylmethoxy)-phenyl]-hex-4-ynoic acid sodium salt |
| 108 | 3-[2-chloro-4-(spiro[4.5]dec-6-en-7-ylmethoxy)-phenyl]-propionic acid |
| 109 | 3-[2-methyl-4-(spiro[4.5]dec-6-en-7-ylmethoxy)-phenyl]-propionic acid |
| 110 | 3-[3-hydroxy-4-(spiro[4.5]dec-6-en-7-ylmethoxy)-phenyl]-propionic acid |
| 111 | 3-[3-methoxy-4-(spiro[4.5]dec-6-en-7-ylmethoxy)-phenyl]-propionic acid |
| 112 | 3-[3-fluoro-4-(spiro[4.5]dec-6-en-7-ylmethoxy)-phenyl]-propionic acid |

TABLE 26

| Ex. No. | Compound name |
|---|---|
| 113 | 3-[6-(spiro[4.5]dec-7-ylmethoxy)-pyridin-3-yl]-propionic acid hydrochloride |
| 114 | 3-[4-(9-methoxy-spiro[5.5]undec-3-ylmethoxy)-phenyl]-propionic acid |
| 115 | 3-[4-(9,9-dimethyl-spiro[4.5]dec-7-ylmethoxy)-phenyl]-propionic acid |
| 116 | (3S)-3-[4-(spiro[2.6]non-5-ylmethoxy)-phenyl]-hex-4-ynoic acid |
| 117 | 3-[4-(spiro[3.4]oct-5-en-6-ylmethoxy)-phenyl]-propionic acid |
| 118 | (3S)-3-[4-(spiro[3.4]oct-6-ylmethoxy)-phenyl]-hex-4-ynoic acid |
| 119 | (S)-3-[4-(spiro[5.5]undec-2-en-2-ylmethoxy)-phenyl]-hex-4-ynoic acid L-lysine salt |
| 120 | (−)-3-ethoxy-3-[4-(spiro[5.5]undec-1-en-2-ylmethoxy)-phenyl]-propionic acid L-lysine salt |

TABLE 27

| Ex. No. | NMR data of compound |
|---|---|
| 1 | $^1$H-NMR (CDCl$_3$) δ: 1.42-1.28 (12H, m), 1.84 (3H, d, J = 2.6 Hz), 1.90 (2H, s), 2.05 (2H, s), 2.70 (1H, dd, J = 15.8, 6.8 Hz), 2.80 (1H, dd, J = 15.8, 8.5 Hz), 4.06-4.04 (1H, m), 5.73 (1H, s), 4.34 (2H, s), 6.86 (2H, d, J = 8.7 Hz), 7.27 (2H, d, J = 8.7 Hz). |
| 2 | $^1$H-NMR (DMSO-d$_6$) δ: 1.29-1.18 (4H, m), 1.32-1.43 (8H, m), 1.74 (3H, d, J = 2.6 Hz), 1.84 (2H, s), 1.95-2.02 (2H, m), 2.09 (1H, dd, J = 14.6, 7.42 Hz), 2.2 (1H, dd, J = 14.6, 6.7 Hz), 3.92-4.00 (1H, m), 4.32 (2H, s), 5.68-5.73 (1H, m), 6.79 (2H, d, J = 8.6 Hz), 7.20 (2H, d, J = 8.6 Hz). |
| 3 | $^1$H-NMR (CDCl$_3$) δ: 1.36-1.30 (2H, m), 1.40-1.55 (12H, m), 1.81-1.86 (5H, m), 2.00-2.09 (2H, m), 2.71 (1H, dd, J = 15.8, 6.7 Hz), 2.80 (1H, dd, J = 15.8, 8.6 Hz), 4.02-4.09 (1H, m), 4.35 (2H, s), 5.76-5.80 (1H, m), 6.87 (2H, d, J = 8.6 Hz), 7.28 (2H, d, J = 8.6 Hz). |
| 4 | $^1$H-NMR (DMSO-d$_6$) δ: 1.50-1.23 (14H, m), 1.47 (H, s), 1.74 (3H, d, J = 2.6 Hz), 1.95-2.02 (2H, m), 2.11 (1H, dd, J = 14.6, 7.2 Hz), 2.26 (1H, dd, J = 14.6, 6.5 Hz), 3.93-4.00 (1H, m), 4.32 (2H, s), 5.71-5.76 (1H, m), 6.79 (2H, d, J = 8.6 Hz), 7.20 (2H, d, J = 8.6 Hz). |

TABLE 27-continued

| Ex. No. | NMR data of compound |
|---|---|
| 5 | $^1$H-NMR (DMSO-$d_6$) δ: 1.31-1.36 (4H, m), 1.41 (2H, dd, J = 6.4, 6.4 Hz), 1.56-1.61 (4H, m), 1.78 (3H, d, J = 2.3 Hz), 1.89 (2H, br s), 2.03-2.07 (2H, m), 2.55-2.61 (2H, m), 3.90-3.96 (1H, m), 4.35 (2H, s), 5.74 (1H, s), 6.84-6.88 (2H, m), 7.22-7.26 (2H, m), 12.23 (1H, s). |
| 6 | $^1$H-NMR (DMSO-$d_6$) δ: 1.37-1.31 (4H, m), 1.41 (2H, t, J = 6.3 Hz), 1.55-1.62 (4H, m), 1.76 (3H, d, J = 2.4 Hz), 1.87-1.90 (2H, m), 2.01-2.08 (2H, m), 2.11 (1H, dd, J = 14.5, 7.2 Hz), 2.27 (1H, dd, J = 14.5, 7.2 Hz), 3.94-4.01 (1H, m), 4.33 (2H, s), 5.71-5.75 (1H, m), 6.79 (2H, d, J = 8.5 Hz), 7.21 (2H, d, J = 8.5 Hz). |
| 7 | $^1$H-NMR (DMSO-$d_6$) δ: 1.39-1.44 (6H, m), 1.57-1.66 (6H, m), 1.78 (3H, d, J = 2.3 Hz), 1.98 (2H, dd, J = 5.7, 5.7 Hz), 2.57-2.60 (2H, m), 3.91-3.96 (1H, m), 4.33 (2H, s), 5.59 (1H, s), 6.87 (2H, d, J = 8.4 Hz), 7.24 (2H, d, J = 8.4 Hz), 12.23 (1H, br s). |
| 8 | $^1$H-NMR (DMSO-$d_6$) δ: 1.40-1.45 (6H, m), 1.57-1.65 (6H, m), 1.75 (3H, d, J = 2.6 Hz), 1.98 (2H, dd, J = 5.6, 5.6 Hz), 2.13 (1H, dd, J = 14.7, 7.3 Hz), 2.28 (1H, dd, J = 14.7, 7.3 Hz), 3.94-4.00 (1H, m), 4.31 (2H, s), 5.59 (1H, s), 6.81 (2H, d, J = 8.8 Hz), 7.21 (2H, d, J = 8.8 Hz). |
| 9 | $^1$H-NMR (CDCl$_3$) δ: 1.66-1.34 (14H, m), 1.84 (3H, d, J = 2.3 Hz), 2.03 (2H, t, J = 5.1 Hz), 2.70 (1H, dd, J = 15.5, 6.8 Hz), 2.80 (1H, dd, J = 15.5, 8.5 Hz), 4.06-4.03 (1H, m), 4.34 (2H, s), 5.66 (1H, s), 6.87 (2H, d, J = 8.7 Hz), 7.27 (2H, d, J = 8.7 Hz). |
| 10 | $^1$H-NMR (DMSO-$d_6$) δ: 1.27-1.48 (12H, m), 1.54-1.60 (2H, m), 1.74 (3H, d, J = 2.3 Hz), 2.00-1.95 (2H, m), 2.10 (1H, dd, J = 14.6, 6.7 Hz), 2.25 (1H, dd, J = 14.6, 6.7 Hz), 3.93-4.00 (1H, m), 4.31 (2H, s), 5.66 (1H, s), 6.80 (2H, d, J = 8.1 Hz), 7.20 (2H, d, J = 8.1 Hz). |

TABLE 28

| Ex. No. | NMR data of compound |
|---|---|
| 11 | $^1$H-NMR (DMSO-$d_6$) δ: 1.45-1.55 (4H, m), 1.63-1.57 (4H, m), 1.77 (3H, d, J = 2.6 Hz), 2.23-2.26 (4H, m), 2.55-2.61 (2H, m), 3.90-3.96 (1H, m), 4.52 (2H, s), 5.61-5.65 (1H, m), 6.87 (2H, d, J = 9.0 Hz), 7.24 (2H, d, J = 9.0 Hz), 12.23 (1H, br s). |
| 12 | $^1$H-NMR (DMSO-$d_6$) δ: 1.63-1.48 (8H, m), 1.75 (3H, d, J = 2.0 Hz), 2.12 (1H, dd, J = 14.6, 7.4 Hz), 2.23-2.30 (5H, m), 3.94-4.01 (1H, m), 4.50 (2H, s), 5.61-5.65 (1H, m), 6.81 (2H, d, J = 8.7 Hz), 7.21 (2H, d, J = 8.7 Hz). |
| 13 | $^1$H-NMR (CDCl$_3$) δ: 1.49-1.35 (10H, m), 1.83 (3H, d, J = 2.4 Hz), 2.18-2.23 (4H, m), 2.70 (1H, dd, J = 15.7, 8.5 Hz), 2.79 (1H, dd, J = 15.7, 8.5 Hz), 4.01-4.08 (1H, m), 4.5 (2H, s), 5.58-5.62 (1H, m), 6.86 (2H, d, J = 8.2 Hz), 7.27 (2H, d, J = 8.2 Hz). |
| 14 | $^1$H-NMR (DMSO-$d_6$) δ: 1.45-1.32 (10H, m), 1.75 (3H, d, J = 2.4 Hz), 2.08-2.17 (5H, m), 2.26 (1H, dd, J = 14.5, 6.8 Hz), 3.95-3.99 (1H, m), 4.49 (2H, s), 5.56-5.60 (1H, m), 6.80 (2H, d, J = 8.5 Hz), 7.21 (2H, d, J = 8.5 Hz). |
| 15 | $^1$H-NMR (CDCl$_3$) δ: 1.54-1.27 (10H, m), 1.76 (2H, t, J = 9.6 Hz), 1.85 (3H, d, J = 3.0 Hz), 2.39 (2H, t, J = 6.8 Hz), 2.71 (1H, dd, J = 15.7, 6.6 Hz), 2.80 (1H, dd, J = 15.7, 8.5 Hz), 4.52 (2H, s), 4.08-4.03 (1H, m), 5.68 (1H, s), 6.88 (2H, d, J = 9.4 Hz), 7.28 (2H, d, J = 9.4 Hz). |
| 16 | $^1$H-NMR (DMSO-$d_6$) δ: 1.47-1.30 (10H, m), 1.68 (2H, t, J = 7.2 Hz), 1.74 (3H, d, J = 2.3 Hz), |

TABLE 28-continued

| Ex. No. | NMR data of compound |
|---|---|
|  | 2.10 (1H, dd, J = 14.6, 7.4 Hz), 2.26 (1H, dd, J = 14.6, 6.8 Hz), 2.33 (2H, t, J = 6.8 Hz), 3.99-3.94 (1H, m), 4.49 (2H, s), 5.66 (1H, s), 6.81 (2H, d, J = 8.6 Hz), 7.21 (2H, d, J = 8.6 Hz). |
| 17 | $^1$H-NMR (CDCl$_3$) δ: 1.68-1.48 (7H, m), 1.86-1.82 (6H, m), 2.40 (2H, t, J = 7.2 Hz), 2.71 (1H, dd, J = 15.7, 6.6 Hz), 4.08-4.04 (1H, m), 4.53 (2H, s), 5.60 (1H, br s), 6.88 (2H, d, J = 8.6 Hz), 7.29 (2H, d, J = 8.6 Hz). |
| 18 | $^1$H-NMR (DMSO-$d_6$) δ: 1.58-1.50 (8H, m), 1.76-1.73 (5H, m), 2.12 (1H, dd, J = 14.7, 7.5 Hz), 2.28 (1H, dd, J = 14.7, 6.7 Hz), 2.34 (2H, t, J = 7.7 Hz), 4.00-3.94 (1H, m), 4.50 (2H, s), 5.59 (1H, s), 6.82 (2H, d, J = 8.7 Hz), 7.22 (2H, d, J = 8.7 Hz). |
| 19 | $^1$H-NMR (CDCl$_3$) δ: 0.98-0.84 (7H, m), 1.14 (1H, t, J = 12.5 Hz), 1.26-1.72 (7H, m), 1.83 (3H, d, J = 2.4 Hz), 1.88-2.13 (4H, m), 2.70 (1H, dd, J = 15.7, 6.8 Hz), 2.80 (1H, dd, J = 15.7, 8.4 Hz), 3.67-3.74 (2H, m), 4.01-4.08 (1H, m), 5.61 (1H, dt, J = 10.6, 3.5 Hz), 5.88 (1H, dt, J = 10.6, 2.0 Hz), 6.84 (2H, d, J = 8.4 Hz), 7.27 (2H, d, J = 8.4 Hz). |
| 20 | $^1$H-NMR (DMSO-$d_6$) δ: 0.95-0.81 (7H, m), 1.13 (1H, t, J = 12.4 Hz), 1.29-1.47 (4H, m), 1.51-1.62 (3H, m), 1.74 (3H, d, J = 2.4 Hz), 1.79-1.87 (1H, m), 1.92-2.01 (3H, m), 2.08 (1H, dd, J = 14.7, 7.5 Hz), 2.24 (1H, dd, J = 14.7, 6.7 Hz), 3.70 (2H, d, J = 6.2 Hz), 3.92-3.99 (1H, m), 5.59 (1H, dt, J = 10.4, 3.5 Hz), 5.88 (1H, dt, J = 10.4, 2.0 Hz), 6.77 (2H, d, J = 8.6 Hz), 7.20 (2H, d, J = 8.6 Hz). |

TABLE 29

| Ex. No. | NMR data of compound |
|---|---|
| 21 | $^1$H-NMR (CDCl$_3$) δ: 1.10 (1H, dd, J = 12.8, 9.3 Hz), 1.48 (15H, m), 1.91-1.77 (2H, m), 2.47-2.39 (1H, m), 2.66 (2H, t, J = 7.8 Hz), 2.91 (2H, t, J = 7.8 Hz), 3.82 (2H, d, J = 7.0 Hz), 6.83 (2H, d, J = 8.6 Hz), 7.12 (2H, d, J = 8.6 Hz). |
| 22 | $^1$H-NMR (CDCl$_3$) δ: 1.44-1.11 (8H, m), 1.65-1.50 (7H, m), 1.77-1.73 (2H, m), 1.84 (3H, d, J = 2.6 Hz), 2.71 (1H, dd, J = 15.5, 6.7 Hz), 2.81 (1H, dd, J = 15.5, 8.5 Hz), 3.76 (2H, d, J = 6.3 Hz), 4.07-4.04 (1H, m), 6.85 (2H, d, J = 8.0 Hz), 7.28 (2H, d, J = 8.6 Hz). |
| 23 | $^1$H-NMR (DMSO-$d_6$) δ: 1.78-1.04 (17H, m), 1.74 (3H, d, J = 2.3 Hz), 2.12 (1H, dd, J = 14.5, 7.42 Hz), 2.3 (1H, dd, J = 14.5, 6.8 Hz), 3.73 (2H, d, J = 6.0 Hz), 3.93-3.99 (1H, m), 6.78 (2H, d, J = 8.6 Hz), 7.20 (2H, d, J = 8.6 Hz). |
| 24 | $^1$H-NMR (CDCl$_3$) δ: 1.28-1.02 (7H, m), 1.40-1.37 (8H, m), 1.68-1.65 (2H, m), 1.80 (3H, d, J = 2.2 Hz), 2.77-2.67 (2H, m), 3.73 (2H, d, J = 6.4 Hz), 4.04-4.01 (1H, m), 6.82 (2H, d, J = 8.7 Hz), 7.26 (2H, d, J = 8.7 Hz). |
| 25 | $^1$H-NMR (CDCl$_3$) δ: 1.41-1.38 (4H, m), 1.65-1.51 (6H, m), 1.83 (3H, d, J = 2.3 Hz), 1.94 (2H, s), 2.11 (2H, s), 2.70 (1H, dd, J = 6.8, 14.6 Hz), 2.80 (1H, dd, J = 14.6, 7.7 Hz), 4.07-4.01 (1H, m), 4.36 (2H, s), 5.73 (1H, s), 6.86 (2H, d, J = 8.7 Hz), 7.27 (2H, d, J = 8.7 Hz). |
| 26 | $^1$H-NMR (CDCl$_3$) δ: 1.11 (1H, dd, J = 12.4, 9.6 Hz), 1.48-1.29 (13H, m), 1.85-1.79 (5H, m), 2.44-2.42 (1H, m), 2.84-2.69 (2H, m), 2.84-2.69 (2H, m), 3.82 (2H, d, J = 6.5 Hz), 4.06-4.04 (1H, br m), 6.85 (2H, d, J = 8.1 Hz), 7.28 (2H, d, J = 8.1 Hz). |
| 27 | $^1$H-NMR (DMSO-$d_6$) δ: 1.07 (1H, dd, J = 12.9, 10.4 Hz), 1.47-1.30 (14H, m), 1.78-1.73 (5H, m), 2.11 (1H, dd, J = 14.6, 7.4 Hz), 2.26 (1H, dd, J = 14.6, 6.7 Hz), 2.26 (1H, dd, J = 14.6, 6.7 Hz), 2.26 (1H, dd, J = 14.6, 6.7 Hz), |

TABLE 29-continued

| Ex. No. | NMR data of compound |
|---|---|
|  | 2.36 (1H, td, J = 15.5, 7.9 Hz), 3.79 (2H, d, J = 7.3 Hz), 4.00-3.94 (1H, m), 6.78 (2H, d, J = 8.8 Hz), 7.2 (2H, d, J = 8.8 Hz). |
| 28 | $^1$H-NMR (CDCl$_3$) δ: 0.76 (1H, t, J = 12.6 Hz), 0.97-0.89 (2H, m), 1.26-1.21 (3H, m), 1.53-1.41 (8H, m), 1.72 (3H, t, J = 16.9 Hz), 1.83 (3H, d, J = 2.3 Hz), 1.92-1.88 (2H, m), 2.70 (1H, dd, J = 15.8, 6.8 Hz), 2.80 (1H, dd, J = 15.6, 8.5 Hz), 3.71-3.67 (2H, m), 4.06-4.03 (1H, m), 6.84 (2H, d, J = 8.7 Hz), 7.27 (2H, d, J = 8.7 Hz). |
| 29 | $^1$H-NMR (DMSO-d$_6$) δ: 0.75 (1H, t, J = 12.9 Hz), 0.96-0.83 (2H, m), 1.53-1.16 (12H, m), 1.61-1.75 (5H, m), 1.76-1.91 (2H, m), 2.07 (1H, dd, J = 14.6, 7.4 Hz), 2.23 (1H, dd, J = 14.6, 6.7 Hz), 3.64-3.72 (2H, m), 3.92-3.98 (1H, m), 6.77 (2H, d, J = 8.6 Hz), 7.19 (2H, d, J = 8.6 Hz). |
| 30 | $^1$H-NMR (CDCl$_3$) δ: 1.28 (1H, dd, J = 12.8, 8.7 Hz), 1.63-1.40 (9H, br m), 1.86-1.79 (5H, m), 2.47-2.44 (1H, m), 2.47-2.44 (1H, m), 2.47-2.44 (1H, m), 2.47-2.44 (1H, m), 2.70 (1H, dd, J = 15.6, 6.8 Hz), 2.80 (1H, dd, J = 15.6, 8.5 Hz), 3.82 (2H, d, J = 6.4 Hz), 4.06-4.03 (1H, br m), 6.84 (2H, d, J = 8.7 Hz), 7.27 (2H, d, J = 8.7 Hz). |

TABLE 30

| Ex. No. | NMR data of compound |
|---|---|
| 31 | $^1$H-NMR (DMSO-d$_6$) δ: 1.25 (1H, dd, J = 12.6, 8.5 Hz), 1.62-1.37 (11H, m), 1.71-1.69 (1H, m), 1.74 (3H, d, J = 2.4 Hz), 1.86-1.77 (1H, m), 2.12 (1H, dd, J = 14.5, 7.5 Hz), 2.28 (1H, dd, J = 14.5, 6.9 Hz), 2.44-2.33 (1H, m), 3.80 (2H, dd, J = 7.0, 2.0 Hz), 3.98-3.96 (1H, m), 6.79 (2H, d, J = 8.6 Hz), 7.21 (2H, d, J = 8.6 Hz). |
| 32 | $^1$H-NMR (DMSO-d$_6$) δ: 0.75 (1H, t, J = 12.6 Hz), 0.96-0.84 (2H, m), 1.17-1.21 (2H, m), 1.33-1.54 (10H, m), 1.61-1.75 (2H, m), 1.77 (3H, d, J = 2.3 Hz), 1.79-1.92 (2H, m), 2.58 (2H, dd, J = 7.5, 1.7 Hz), 3.66-3.73 (2H, m), 3.90-3.94 (1H, m), 6.84 (2H, d, J = 8.1 Hz), 7.23 (2H, d, J = 8.1 Hz), 12.23 (1H, br s). |
| 33 | $^1$H-NMR (DMSO-d$_6$) δ: 0.75 (1H, t, J = 12.68 Hz), 0.97-0.84 (2H, m), 1.16-1.22 (2H, m), 1.32-1.46 (9H, m), 1.47-1.54 (1H, m), 1.61-1.72 (2H, m), 1.75 (3H, d, J = 2.4 Hz), 1.80-1.90 (2H, m), 2.10 (1H, dd, J = 14.7, 6.8 Hz), 2.25 (1H, dd, J = 14.7, 6.8 Hz), 3.65-3.72 (2H, m), 3.93-4.00 (1H, m), 6.78 (2H, d, J = 8.7 Hz), 7.20 (2H, d, J = 8.7 Hz). |
| 34 | $^1$H-NMR (DMSO-d$_6$) δ: 0.75 (1H, t, J = 12.5 Hz), 0.96-0.84 (2H, m), 1.15-1.24 (2H, m), 1.33-1.45 (9H, m), 1.47-1.54 (1H, m), 1.62-1.91 (7H, m), 2.56-2.59 (2H, m), 3.66-3.73 (2H, m), 3.89-3.95 (1H, m), 6.84 (2H, d, J = 8.6 Hz), 7.23 (2H, d, J = 8.6 Hz), 12.23 (1H, br s). |
| 35 | $^1$H-NMR (DMSO-d$_6$) δ: 0.75 (1H, t, J = 12.7 Hz), 0.84-0.96 (2H, m), 1.17-1.24 (2H, m), 1.34-1.52 (10H, m), 1.63-1.71 (2H, m), 1.74 (3H, d, J = 2.7 Hz), 1.79-1.91 (2H, m), 2.08 (1H, dd, J = 14.5, 7.5 Hz), 2.24 (1H, dd, J = 14.5, 6.8 Hz), 3.65-3.72 (2H, m), 3.93-3.99 (1H, m), 6.77 (2H, d, J = 8.7 Hz), 7.20 (2H, d, J = 8.7 Hz). |
| 36 | $^1$H-NMR (DMSO-d$_6$) δ: 0.93 (1H, dddd, J = 12.8, 12.8, 12.8, 3.7 Hz), 1.02 (1H, dd, J = 12.8, 12.8 Hz), 1.15 (1H, ddd, J = 12.8, 12.8, 3.7 Hz), 1.30-1.48 (6H, m), 1.51-1.63 (6H, m), 1.76-1.82 (2H, m), 1.77 (3H, d, J = 2.4 Hz), 2.57-2.60 (2H, m), 3.68-3.75 (2H, m), 3.90-3.96 (1H, m), 6.84 (2H, d, J = 8.4 Hz), 7.24 (2H, d, J = 8.4 Hz), 12.21 (1H, br s). |
| 37 | $^1$H-NMR (DMSO-d$_6$) δ: 0.92 (1H, dddd, J = 12.7, 12.7, 12.7, 3.7 Hz), 1.01 (1H, dd, J = 12.7, 6.3 Hz), 1.15 (1H, ddd, J = 12.7, 12.7, 3.7 Hz), 1.29-1.47 (6H, m), 1.50-1.62 (6H, m), 1.75 (3H, d, J = 2.3 Hz), 1.75-1.82 (2H, m), 2.13 (1H, dd, J = 14.6, 6.9 Hz), 2.28 (1H, dd, J = 14.6, 6.9 Hz), 3.66-3.73 (2H, m), 3.94-4.00 (1H, m), 6.78 (2H, d, J = 8.5 Hz), 7.21 (2H, d, J = 8.5 Hz). |

TABLE 30-continued

| Ex. No. | NMR data of compound |
|---|---|
| 38 | $^1$H-NMR (DMSO-d$_6$) δ: 0.93 (1H, dddd, J = 12.8, 12.8, 12.8, 3.8 Hz), 1.02 (1H, dd, J = 12.8, 12.8 Hz), 1.15 (1H, ddd, J = 12.8, 12.8, 3.8 Hz), 1.29-1.47 (6H, m), 1.51-1.63 (6H, m), 1.76-1.82 (2H, m), 1.78 (3H, d, J = 2.4 Hz), 2.53-2.63 (2H, m), 3.68-3.75 (2H, m), 3.90-3.96 (1H, m), 6.84 (2H, d, J = 8.6 Hz), 7.24 (2H, d, J = 8.6 Hz), 12.21 (1H, br s). |
| 39 | $^1$H-NMR (DMSO-d$_6$) δ: 0.92 (1H, dddd, J = 12.7, 12.7, 12.7, 3.7 Hz), 1.01 (1H, dd, J = 12.7, 12.7 Hz), 1.15 (1H, ddd, J = 12.7, 12.7, 3.7 Hz), 1.29-1.47 (6H, m), 1.50-1.62 (6H, m), 1.75 (3H, d, J = 2.6 Hz), 1.76-1.83 (2H, m), 2.24 (1H, dd, J = 14.8, 7.3 Hz), 2.37 (1H, dd, J = 14.8, 7.3 Hz), 3.66-3.73 (2H, m), 3.93-3.98 (1H, m), 6.79 (2H, d, J = 8.5 Hz), 7.21 (2H, d, J = 8.5 Hz). |

TABLE 31

| Ex. No. | NMR data of compound |
|---|---|
| 40 | $^1$H-NMR (CDCl$_3$) δ: 0.76 (1H, t, J = 12.52 Hz), 0.86-0.99 (2H, m), 1.19-1.25 (2H, m), 1.35-1.60 (9H, m), 1.66-1.77 (2H, m), 1.83-2.00 (2H, m), 2.06-2.09 (1H, m), 2.88-3.04 (1H, m), 3.41-3.54 (1H, m), 3.64-3.69 (2H, m), 3.78 (3H, s), 4.50-4.63 (1H, m), 6.82 (2H, d, J = 8.4 Hz), 7.10 (2H, d, J = 8.4 Hz). |
| 41 | $^1$H-NMR (DMSO-d$_6$) δ: 0.99-1.04 (3H, m), 1.23-1.49 (12H, m), 1.54-1.60 (2H, m), 1.95-2.00 (2H, m), 2.45 (1H, dd, J = 5.2, 14.8 Hz), 2.60 (1H, dd, J = 8.7, 14.8 Hz), 3.17-3.26 (1H, m), 4.35 (2H, s), 4.57 (1H, dd, J = 8.7, 5.2 Hz), 5.66 (1H, s), 6.89 (2H, d, J = 9.0 Hz), 7.19 (2H, d, J = 9.0 Hz), 12.11 (1H, br s). |
| 42 | $^1$H-NMR (CDCl$_3$) δ: 1.18 (3H, t, J = 7.0 Hz), 1.30-1.51 (12H, m), 1.64 (2H, tt, J = 9.2, 3.1 Hz), 2.01-2.16 (2H, m), 2.62 (1H, dd, J = 15.7, 4.1 Hz), 2.83 (1H, dd, J = 15.7, 9.7 Hz), 3.34-3.47 (2H, m), 4.36 (2H, s), 4.66 (1H, dd, J = 9.5, 4.0 Hz), 5.67 (1H, s), 6.91 (1H, dt, J = 9.3, 2.4 Hz), 7.22 (2H, dt, J = 9.2, 2.4 Hz). |
| 43 | $^1$H-NMR (DMSO-d$_6$) δ: 1.02 (3H, dt, J = 22.9, 7.9 Hz), 1.30-1.60 (13H, m), 1.97-2.07 (3H, m), 2.32 (1H, dd, J = 14.5, 7.0 Hz), 3.13-3.29 (4H, m), 4.34 (2H, s), 4.59 (1H, t, J = 6.5 Hz), 5.67 (1H, s), 6.84 (2H, d, J = 8.5 Hz), 7.16 (2H, d, J = 8.7 Hz). |
| 44 | $^1$H-NMR (CDCl$_3$) δ: 1.18 (3H, t, J = 7.0 Hz), 1.30-1.51 (12H, m), 1.64 (2H, tt, J = 9.2, 3.1 Hz), 2.01-2.16 (2H, m), 2.62 (1H, dd, J = 15.7, 4.1 Hz), 2.83 (1H, dd, J = 15.7, 9.7 Hz), 3.34-3.47 (2H, m), 4.36 (2H, s), 4.66 (1H, dd, J = 9.5, 4.0 Hz), 5.67 (1H, s), 6.91 (1H, dt, J = 9.3, 2.4 Hz), 7.22 (2H, dt, J = 9.2, 2.4 Hz). |
| 45 | $^1$H-NMR (DMSO-d$_6$) δ: 1.01 (3H, t, J = 7.0 Hz), 1.48-1.24 (12H, m), 1.55-1.61 (2H, m), 1.96-2.04 (3H, m), 2.30 (1H, dd, J = 14.4, 7.0 Hz), 3.12-3.25 (2H, m), 4.33 (2H, s), 4.58 (1H, t, J = 6.6 Hz), 5.67 (1H, s), 6.83 (2H, d, J = 9.3 Hz), 7.15 (2H, d, J = 9.3 Hz). |
| 46 | $^1$H-NMR (CDCl$_3$) δ: 0.76 (1H, t, J = 12.6 Hz), 0.97-0.90 (2H, m), 1.30-1.23 (3H, m), 1.57-1.42 (9H, m), 1.76-1.69 (2H, m), 1.96-1.92 (2H, m), 2.65 (2H, t, J = 7.8 Hz), 2.90 (2H, t, J = 7.8 Hz), 3.71-3.67 (2H, m), 6.82 (2H, d, J = 8.6 Hz), 7.11 (2H, d, J = 8.6 Hz). |
| 47 | $^1$H-NMR (CDCl$_3$) δ: 0.75 (1H, t, J = 12.6 Hz), 0.99-0.83 (2H, m), 1.49-1.24 (11H, br m), 1.87-1.74 (8H, m), 2.67 (1H, dd, J = 6.6, 15.6 Hz), 2.77 (1H, dd, J = 8.6, 15.6 Hz), |

TABLE 31-continued

| Ex. No. | NMR data of compound |
|---|---|
|  | 3.70-3.65 (2H, m), 4.06-4.00 (1H, m), 6.82 (2H, d, J = 8.7 Hz), 7.26 (2H, d, J = 8.7 Hz). |
| 48 | $^1$H-NMR (DMSO-d$_6$) δ: 0.72-1.03 (10H, m), 1.15-1.48 (10H, m), 1.64-1.99 (3H, m), 2.45 (2H, t, J = 6.5 Hz), 2.72 (2H, t, J = 6.5 Hz), 3.68 (2H, t, J = 13.6 Hz), 6.79 (2H, d, J = 8.6 Hz), 7.10 (2H, d, J = 8.6 Hz), 12.10 (1H, s). |
| 49 | $^1$H-NMR (DMSO-d$_6$) δ: 0.74 (1H, t, J = 12.6 Hz), 0.94-0.87 (2H, m), 1.67 (1H, d, J = 12.4 Hz), 1.50-1.36 (15H, m), 2.47 (2H, t, J = 7.5 Hz), 1.81-1.77 (2H, m), 2.74 (2H, t, J = 7.5 Hz), 3.32 (2H, s), 3.68 (2H, d, J = 7.0 Hz), 6.80 (2H, d, J = 8.7 Hz), 7.10 (2H, d, J = 8.7 Hz). |

TABLE 32

| Ex. No. | NMR data of compound |
|---|---|
| 50 | $^1$H-NMR (DMSO-d$_6$) δ: 0.81 (3H, d, J = 6.8 Hz), 1.01-0.89 (1H, m), 1.18 (1H, t, J = 12.9 Hz), 1.28-2.08 (14H, m), 2.12-2.20 (1H, m), 2.47 (2H, t, J = 7.6 Hz), 2.73 (2H, t, J = 7.6 Hz), 3.70 (2H, dd, J = 1.9, 6.2 Hz), 5.28-5.33 (1H, m), 6.80 (2H, d, J = 8.4 Hz), 7.10 (2H, d, J = 8.4 Hz), 12.06 (1H, s). |
| 51 | $^1$H-NMR (DMSO-d$_6$) ca.2:1 diastereomeric mixture δ: 0.76 (2H Me, d, J = 6.8 Hz), 0.87 (3H, d, J = 6.6 Hz), 0.98 (1H Me, d, J = 7.3 Hz), 1.15-2.10 (17H, m), 2.47 (1H, t, J = 7.5 Hz), 2.74 (2H, t, J = 7.5 Hz), 3.66-3.76 (2H, m), 6.81 (2H, d, J = 8.6 Hz), 7.10 (2H, d, J = 8.6 Hz), 12.06 (1H, s). |
| 52 | $^1$H-NMR (CDCl$_3$) δ: 1.10 (1H, dd, J = 13.0, 9.2 Hz), 1.42 (13H, tt, J = 17.7, 5.8 Hz), 1.86-1.77 (2H, m), 2.47-2.37 (1H, m), 2.64 (2H, t, J = 7.7 Hz), 2.90 (2H, t, J = 7.7 Hz), 3.81 (2H, t, J = 7.2 Hz), 6.82 (2H, d, J = 8.3 Hz), 7.11 (2H, d, J = 8.3 Hz). |
| 53 | $^1$H-NMR (DMSO-d$_6$) δ: 0.94-1.12 (9H, m), 1.33-1.65 (8H, m), 1.78-2.01 (2H, m), 2.46 (2H, d, J = 7.6 Hz), 2.73 (2H, t, J = 7.6 Hz), 3.66-3.73 (2H, m), 5.11 (0.5H, d, J = 9.9 Hz), 5.29 (0.5H, d, J = 9.9 Hz), 5.34 (0.5H, d, J = 10.4 Hz), 5.82 (0.5H, d, J = 10.4 Hz), 6.81 (2H, t, J = 4.3 Hz), 7.10 (2H, d, J = 8.6 Hz), 12.07 (1H, s). |
| 54 | $^1$H-NMR (DMSO-d$_6$) δ: 0.71-0.94 (9H, m), 1.16-1.26 (6H, m), 1.34-1.54 (4H, m), 1.64-1.92 (4H, m), 2.46 (2H, t, J = 7.6 Hz), 2.74 (2H, t, J = 7.6 Hz), 3.65-3.73 (2H, m), 6.79-6.82 (2H, m), 7.10 (2H, d, J = 8.6 Hz), 12.07 (1H, s). |
| 55 | $^1$H-NMR (DMSO-d$_6$) δ: 0.83 (6H, s), 0.86-0.95 (1H, m), 1.13 (1H, t, J = 12.5 Hz), 1.46-1.29 (4H, m), 1.51-1.62 (3H, m), 1.78-1.86 (1H, m), 1.92-2.03 (3H, m), 2.47 (2H, t, J = 7.5 Hz), 2.74 (2H, t, J = 7.5 Hz), 3.70 (2H, d, J = 7.4 Hz), 5.59 (1H, dt, J = 9.9, 3.1 Hz), 5.9 (1H, dt, J = 10.0, 2.0 Hz), 6.81 (2H, d, J = 8.6 Hz), 7.10 (2H, d, J = 8.6 Hz), 12.05 (1H, s). |
| 56 | $^1$H-NMR (DMSO-d$_6$) δ: 0.77-0.87 (7H, m), 1.02 (1H, t, J = 12.6 Hz), 1.20-1.53 (12H, m), 1.61-1.68 (1H, m), 1.74-1.92 (2H, m), 2.47 (2H, t, J = 7.5 Hz), 2.74 (2H, t, J = 7.5 Hz), 3.65-3.74 (2H, m), 6.81 (2H, d, J = 8.4 Hz), 7.10 (2H, d, 8.4 Hz), 12.06 (1H, s). |
| 57 | $^1$H-NMR (CDCl$_3$) δ: 1.10-1.06 (2H, m), 1.27-1.21 (4H, m), 1.45-1.40 (8H, m), 1.79-1.63 (5H, m), 2.65 (2H, t, J = 7.8 Hz), 2.91 (2H, t, J = 7.8 Hz), 3.76 (2H, d, J = 6.5 Hz), 6.83 (2H, d, J = 8.6 Hz), 7.12 (2H, d, J = 8.6 Hz). |
| 58 | $^1$H-NMR (CDCl$_3$) δ: 0.73 (1H, t, J = 12.8 Hz), 0.96-0.88 (2H, m), 1.51-1.21 (11H, m), 1.69-1.65 (6H, m), 1.88-1.84 (2H, m), 2.51 (1H, dd, J = 15.6, 6.8 Hz), 2.62 (1H, dd, J = 15.6, 8.6 Hz), 3.62-3.57 (2H, m), 3.98-3.95 (1H, m), 6.73 (2H, d, J = 8.6 Hz), 7.18 (2H, d, J = 8.6 Hz). |
| 59 | $^1$H-NMR (DMSO-d$_6$) δ: 0.75 (1H, t, J = 12.7 Hz), 0.86-0.96 (2H, m), 1.16-1.22 (2H, m), |

TABLE 32-continued

| Ex. No. | NMR data of compound |
|---|---|
|  | 1.33-1.54 (10H, m), 1.61-1.92 (4H, m), 2.36 (1H, dd, J = 16.8, 4.6 Hz), 2.79 (3H, s), 2.85-2.93 (4H, m), 3.67-3.72 (2H, m), 4.21 (1H, dd, J = 10.1, 4.6 Hz), 6.85 (2H, d, J = 8.6 Hz), 7.16 (2H, d, J = 8.6 Hz), 12.06 (1H, br s). |

TABLE 33

| Ex. No. | NMR data of compound |
|---|---|
| 60 | $^1$H-NMR (DMSO-d$_6$) δ: 0.74 (1H, dd, J = 12.6, 12.6 Hz), 0.83-0.95 (2H, m), 1.16-1.24 (2H, m), 1.32-1.52 (10H, m), 1.61-1.73 (2H, m), 1.76-1.90 (2H, m), 2.96 (2H, d, J = 8.0 Hz), 3.65 (1H, dd, J = 8.7, 6.3 Hz), 3.68 (1H, dd, J = 8.7, 6.3 Hz), 4.34 (1H, t, J = 8.0 Hz), 6.80 (2H, d, J = 8.8 Hz), 7.12-7.20 (3H, m), 7.23-7.29 (4H, m), 12.06 (1H, br s). |
| 61 | $^1$H-NMR (CDCl$_3$) δ: 0.87-0.90 (1H, m), 1.02-1.17 (2H, m), 1.24-1.69 (13H, m), 2.03-2.10 (2H, m), 2.65 (2H, dt, J = 7.4, 3.6 Hz), 2.90 (2H, t, J = 7.7 Hz), 4.32 (1H, tt, J = 10.6, 4.2 Hz), 6.81 (2H, dt, J = 9.2, 2.5 Hz), 7.08-7.11 (2H, m). |
| 62 | $^1$H-NMR (CDCl$_3$) δ: 0.65-0.94 (3H, m), 1.17-1.52 (12H, m), 1.59-1.78 (6H, m), 2.65 (2H, dt, J = 7.2, 3.6 Hz), 2.90 (2H, t, J = 7.7 Hz), 3.96 (2H, t, J = 6.6 Hz), 6.83 (2H, dt, J = 9.3, 2.5 Hz), 7.11 (2H, dt, J = 9.3, 2.5 Hz). |
| 63 | $^1$H-NMR (DMSO-d$_6$) δ: 1.18-1.60 (14H, m), 1.74-1.78 (5H, m), 2.50 (2H, t, J = 7.7 Hz), 2.57 (2H, t, J = 7.7 Hz), 3.92 (1H, td, J = 7.6, 2.4 Hz), 4.28 (1H, td, J = 8.3, 4.0 Hz), 6.85 (2H, t, J = 4.3 Hz), 7.23 (2H, d, J = 8.6 Hz), 12.22 (1H, s). |
| 64 | $^1$H-NMR (CDCl$_3$) δ: 1.79-0.92 (16H, m), 1.82-1.85 (3H, m), 2.02-2.12 (2H, m), 2.68-2.83 (2H, m), 4.01-4.08 (1H, m), 4.29-4.38 (1H, m), 6.81-6.86 (2H, m), 7.25-7.29 (2H, m). |
| 65 | $^1$H-NMR (CDCl$_3$) δ: 0.72-0.81 (1H, m), 0.87-0.99 (2H, m), 1.18-1.27 (2H, m), 1.37-1.50 (8H, m), 1.51-1.60 (1H, m), 1.65-1.79 (2H, m), 1.83-2.01 (2H, m), 2.67 (1H, dd, J = 16.3, 4.63 Hz), 2.75 (3H, d, J = 4.6 Hz), 3.26 (1H, dd, J = 16.3, 9.0 Hz), 3.65-3.77 (2H, m), 3.85 (1H, dd, J = 9.0, 4.6 Hz), 5.49-5.69 (1H, m), 6.81-6.89 (2H, m), 7.12-7.21 (2H, m). |
| 66 | $^1$H-NMR (DMSO-d$_6$) δ: 0.74 (1H, dd, J = 12.6, 12.6 Hz), 0.84-0.95 (2H, m), 1.17-1.24 (2H, m), 1.34-1.52 (10H, m), 1.62-1.73 (2H, m), 1.77-1.92 (2H, m), 2.78 (1H, dd, J = 16.5, 6.3 Hz), 3.13 (1H, dd, J = 16.5, 9.2 Hz), 3.65-3.73 (2H, m), 4.48 (1H, dd, J = 9.2, 6.3 Hz), 6.84 (2H, d, J = 8.6 Hz), 7.11 (1H, s), 7.13 (2H, d, J = 8.6 Hz), 7.95 (1H, s), 12.39 (1H, br s). |
| 67 | $^1$H-NMR (CDCl$_3$) δ: 0.77 (1H, t, J = 12.6 Hz), 1.00-0.87 (1H, m), 1.28-1.20 (3H, m), 1.45 (9H, m), 1.73 (2H, t, J = 15.8 Hz), 1.98-1.86 (2H, m), 3.10 (1H, dd, J = 14.1, 9.4 Hz), 3.45 (1H, dd, J = 14.1, 4.0 Hz), 3.69 (1H, dd, J = 7.0, 2.0 Hz), 4.50 (1H, dd, J = 9.6, 4.0 Hz), 6.84 (2H, d, J = 8.7 Hz), 7.13 (2H, d, J = 8.7 Hz), 7.87 (1H, s). |
| 68 | $^1$H-NMR (CDCl$_3$) δ: 0.79-0.75 (1H, m), 0.96-0.90 (2H, m), 1.28-1.20 (3H, m), 1.48-1.41 (10H, m), 1.72 (2H, t, J = 15.3 Hz), 1.89 (3H, d, J = 2.8 Hz), 1.96-1.95 (1H, m), 3.70-3.67 (2H, m), 4.49 (1H, d, J = 3.4 Hz), 4.65-4.64 (1H, m), 6.86 (2H, d, J = 8.7 Hz), 7.31 (2H, d, J = 8.7 Hz). |
| 69 | $^1$H-NMR (DMSO-d$_6$) δ: 0.76 (1H, dd, J = 12.6, 12.6 Hz), 0.85-0.96 (2H, m), 1.17-1.22 (2H, m), 1.33-1.53 (10H, m), 1.63-1.75 (2H, m), 1.78-1.92 (2H, m), 2.37 (1H, dd, J = 15.9, 9.6 Hz), 2.72 (1H, dd, J = 15.5, 5.4 Hz), 3.00-3.07 (1H, m), 3.39 (1H, dd, J = 10.0, 7.5 Hz), 3.46 (1H, dd, J = 10.0, 6.0 Hz), 3.67 (1H, dd, J = 9.6, 6.0 Hz), 3.70 (1H, dd, J = 9.6, 6.0 Hz), 4.69 (1H, br s), |

TABLE 33-continued

| Ex. No. | NMR data of compound |
|---|---|
| | 6.80 (2H, d, J = 8.5 Hz), 7.10 (2H, d, J = 8.5 Hz), 11.88 (1H, br s). |

TABLE 34

| Ex. No. | NMR data of compound |
|---|---|
| 70 | $^1$H-NMR (CDCl$_3$) δ: 1.52-1.24 (16H, m), 1.83 (3H, d, J = 2.64 Hz), 2.14 (1H, s), 2.69 (1H, dd, J = 15.64, 6.59 Hz), 2.79 (1H, dd, J = 15.60, 7.80 Hz), 3.70 (1H, s), 3.87 (1H, dd, J = 9.23, 5.46 Hz), 4.04-4.01 (2H, m), 6.86 (2H, d, J = 8.67 Hz), 7.28 (2H, d, J = 8.70 Hz). |
| 71 | $^1$H-NMR (DMSO-d$_6$) δ: 0.76 (1H, dd, J = 12.6, 12.6 Hz), 0.85-0.96 (1H, m), 1.17-1.24 (2H, m), 1.35-1.53 (10H, m), 1.63-1.75 (2H, m), 1.79-1.91 (2H, m), 2.37 (1H, dd, J = 15.7, 8.7 Hz), 2.58 (1H, dd, J = 15.7, 6.1 Hz), 3.19 (3H, s), 3.21-3.24 (1H, m), 3.36-3.40 (2H, m), 3.67 (1H, dd, J = 9.5, 6.0 Hz), 3.70 (1H, dd, J = 9.5, 6.0 Hz), 6.80 (2H, d, J = 8.6 Hz), 7.12 (2H, d, J = 8.6 Hz). |
| 72 | $^1$H-NMR (CDCl$_3$) δ: 1.05-0.99 (1H, m), 1.17-1.10 (1H, m), 1.80-1.21 (16H, m), 1.83 (3H, d, J = 2.4 Hz), 1.91-1.87 (1H, m), 2.71 (1H, dd, J = 15.6, 6.7 Hz), 2.80 (1H, dd, J = 15.6, 8.4 Hz), 3.74 (1H, t, J = 8.8 Hz), 4.07-4.02 (2H, m), 4.15 (1H, dd, J = 9.3, 4.0 Hz), 6.85 (1H, d, J = 8.8 Hz), 7.28 (6H, d, J = 8.8 Hz). |
| 73 | $^1$H-NMR (CDCl$_3$) δ: 1.30-1.24 (4H, m), 1.50-1.40 (8H, m), 1.83 (3H, d, J = 2.2 Hz), 1.90 (2H, s), 2.05 (2H, s), 2.70 (1H, dd, J = 15.7, 6.6 Hz), 2.79 (1H, dd, J = 15.7, 8.6 Hz), 4.06-4.02 (1H, m), 4.34 (2H, s), 5.70 (1H, s), 6.86 (2H, d, J = 8.6 Hz), 7.27 (2H, d, J = 8.6 Hz). |
| 74 | $^1$H-NMR (DMSO-d$_6$) δ: 1.00-1.58 (16H, m), 1.74 (3H, d, J = 2.4 Hz), 2.03-1.90 (2H, m), 2.08 (1H, dd, J = 14.3, 6.6 Hz), 2.23 (1H, dd, J = 14.3, 6.6 Hz), 3.92-3.99 (1H, m), 4.32-4.40 (1H, m), 6.76 (2H, d, J = 8.4 Hz), 7.20 (2H, d, J = 8.4 Hz). |
| 75 | $^1$H-NMR (CDCl$_3$) δ: 0.88-0.99 (2H, m), 1.17-1.28 (6H, m), 1.42-2.01 (14H, m), 2.62 (1H, dd, J = 15.66, 3.97 Hz), 2.83 (1H, dd, J = 15.8, 9.6 Hz), 3.34-3.47 (2H, m), 3.71 (2H, ddd, J = 13.5, 7.3, 4.7 Hz), 4.66 (1H, dd, J = 9.7, 4.0 Hz), 6.88 (2H, dt, J = 10.9, 3.5 Hz), 7.22 (2H, dt, J = 9.2, 2.4 Hz). |
| 76 | $^1$H-NMR (DMSO-d$_6$) δ: 1.02-0.99 (1H, m), 1.75-1.13 (17H, m), 1.90-1.85 (1H, m), 2.12 (1H, dd, J = 14.7, 7.4 Hz), 2.28 (1H, dd, J = 14.7, 6.8 Hz), 3.72 (1H, t, J = 8.6 Hz) 3.98-3.93 (1H, m), 4.11 (1H, dd, J = 9.6, 4.0 Hz), 6.81 (2H, d, J = 8.6 Hz), 7.21 (2H, d, J = 8.6 Hz). |
| 77 | $^1$H-NMR (CDCl$_3$) δ: 0.75 (1H, t, J = 12.6 Hz), 0.97-0.90 (2H, m), 1.22-1.20 (3H, m), 1.77-1.41 (13H, m), 1.90-1.85 (3H, m), 2.63 (1H, dd, J = 15.1, 8.7 Hz), 2.74 (1H, dd, J = 15.1, 6.8 Hz), 3.68 (2H, dd, J = 6.0, 3.0 Hz), 4.16-4.10 (1H, m), 5.55-5.51 (2H, m), 6.82 (2H, d, J = 8.6 Hz), 7.14 (2H, d, J = 8.6 Hz). |
| 78 | $^1$H-NMR (CDCl$_3$) δ: 1.00-0.72 (6H, m), 1.22-1.14 (4H, m), 1.75-1.51 (13H, m), 1.97-1.86 (2H, m), 2.66-2.51 (2H, m), 3.08-2.98 (1H, m), 3.62 (2H, m), 3.70-3.66 (2H, m), 6.81 (2H, d, J = 8.2 Hz), 7.07 (2H, d, J = 8.2 Hz). |
| 79 | $^1$H-NMR (DMSO-d$_6$) δ: 0.73-0.96 (3H, m), 1.01 (3H, t, J = 7.0 Hz), 1.18-1.88 (16H, m), 2.05 (1H, dd, J = 14.5, 6.5 Hz), 2.33 (1H, dd, J = 14.5, 7.0 Hz), 3.13-3.26 (2H, m), 3.66-3.74 (2H, m), 4.59 (1H, t, J = 6.6 Hz), 6.81 (2H, d, J = 8.6 Hz), 7.16 (2H, d, J = 8.6 Hz). |

TABLE 35

| Ex. No. | NMR data of compound |
|---|---|
| 80 | $^1$H-NMR (CDCl$_3$) δ: 0.75-1.00 (3H, m), 1.21-1.26 (2H, m), 1.43-2.01 (14H, m), 2.63 (1H, dd, J = 15.7, 4.1 Hz), 2.85 (1H, dd, J = 15.7, 9.5 Hz), 3.24 (3H, s), 3.69-3.77 (2H, m), 4.57 (1H, dd, J = 9.5, 4.2 Hz), 6.90 (2H, ddd, J = 9.0, 4.4, 2.1 Hz), 7.24 (2H, dt, J = 9.3, 2.4 Hz). |
| 81 | $^1$H-NMR (CDCl$_3$) δ: 0.75-1.00 (3H, m), 1.10 (3H, d, J = 6.3 Hz), 1.19 (3H, d, J = 6.0 Hz), 1.21-1.26 (2H, m), 1.43-1.79 (12H, m), 1.88-2.04 (2H, m), 2.61 (1H, dd, J = 15.7, 3.8 Hz), 2.80 (1H, dd, J = 15.7, 9.6 Hz), 3.53-3.62 (1H, m), 3.73 (2H, dq, J = 15.6, 5.0 Hz), 4.79 (1H, dd, J = 9.6, 3.8 Hz), 6.87-6.90 (2H, m), 7.22-7.27 (2H, m). |
| 82 | $^1$H-NMR (DMSO-d$_6$) δ: 0.77-1.57 (16H, m), 1.78 (3H, d, J = 2.3 Hz), 1.87-1.99 (2H, m), 2.62 (2H, d, J = 7.7 Hz), 3.34-3.53 (1H, m), 3.96-4.01 (1H, m), 4.45 (2H, s), 7.25 (2H, d, J = 8.1 Hz), 7.32 (2H, d, J = 8.1 Hz), 12.26 (1H, br s). |
| 83 | $^1$H-NMR (CDCl$_3$) δ: 0.78 (1H, t, J = 12.6 Hz), 0.90 (3H, dd, J = 12.6, 5.2 Hz), 0.94-1.00 (1H, m), 1.22 (2H, dt, J = 17.9, 5.2 Hz), 1.43-1.79 (15H, m), 1.88-2.03 (2H, m), 2.63 (1H, dt, J = 11.8, 3.9 Hz), 2.84 (1H, dd, J = 15.7, 9.9 Hz), 3.26-3.37 (2H, m), 3.73 (2H, tt, J = 10.2, 4.1 Hz), 4.66 (1H, dd, J = 9.7, 3.7 Hz), 6.88-6.91 (2H, m), 7.23 (2H, ddd, J = 9.7, 5.3, 2.9 Hz). |
| 84 | $^1$H-NMR (CDCl$_3$) δ: 0.76 (1H, t, J = 12.7 Hz), 0.86-0.99 (2H, m), 1.13 (3H, t, J = 7.5 Hz), 1.20-1.27 (3H, m), 1.37-2.03 (13H, m), 2.21 (2H, ddd, J = 15.0, 7.5, 2.2 Hz), 2.75 (2H, ddd, J = 33.4, 15.5, 7.6 Hz), 3.65-3.73 (2H, m), 4.06 (1H, td, J = 6.5, 2.1 Hz), 6.82-6.85 (2H, m), 7.27-7.30 (2H, m). |
| 85 | $^1$H-NMR (CDCl$_3$) δ: 0.76 (1H, t, J = 12.6 Hz), 0.86-0.99 (2H, m), 1.20-1.24 (2H, m), 1.38-1.49 (8H, m), 1.51-1.59 (1H, m), 1.65-1.79 (2H, m), 1.85-2.00 (2H, m), 2.29 (1H, d, J = 2.4 Hz), 2.76 (1H, dd, J = 15.9, 6.4 Hz), 2.87 (1H, dd, J = 15.9, 8.4 Hz), 3.65-3.73 (2H, m), 4.08-4.13 (1H, m), 6.85 (2H, d, J = 8.4 Hz), 7.29 (2H, d, J = 8.4 Hz). |
| 86 | $^1$H-NMR (DMSO-d$_6$) δ: 0.75 (1H, dd, J = 12.6, 12.6 Hz), 0.85-0.96 (2H, m), 1.18-1.24 (2H, m), 1.34-1.53 (10H, m), 1.62-1.75 (2H, m), 1.79-1.92 (2H, m), 2.54 (1H, dd, J = 15.4, 7.5 Hz), 2.63 (1H, dd, J = 15.4, 7.5 Hz), 3.65-3.73 (3H, m), 4.98 (2H, br d, J = 14.0 Hz), 5.89-5.98 (1H, m), 6.83 (2H, d, J = 8.6 Hz), 7.11 (2H, d, J = 8.6 Hz), 12.06 (1H, br s). |
| 87 | $^1$H-NMR (DMSO-d$_6$) δ: 0.69 (3H, dd, J = 7.4, 7.4 Hz), 0.76 (1H, dd, J = 12.6, 12.6 Hz), 0.85-0.97 (2H, m), 1.18-1.24 (2H, m), 1.35-1.53 (11H, m), 1.56-1.75 (3H, m), 1.79-1.92 (2H, m), 2.39 (1H, dd, J = 15.3, 8.0 Hz), 2.53 (1H, dd, J = 15.3, 6.5 Hz), 2.77-2.84 (1H, m), 3.65-3.73 (2H, m), 6.81 (2H, d, J = 8.6 Hz), 7.08 (2H, d, J = 8.6 Hz), 11.93 (1H, br s). |
| 88 | $^1$H-NMR (CDCl$_3$) δ: 0.77 (1H, t, J = 12.6 Hz), 1.00-0.87 (2H, m), 1.21-1.27 (2H, m), 1.39-1.59 (10H, m), 1.67-1.81 (2H, m), 1.88-2.01 (2H, m), 2.66 (2H, t, J = 7.8 Hz), 2.91 (2H, t, J = 7.8 Hz), 3.66-3.74 (2H, m), 6.83 (2H, d, J = 8.6 Hz), 7.12 (2H, d, J = 8.6 Hz). |
| 89 | $^1$H-NMR (CDCl$_3$) δ: 0.77 (1H, t, J = 12.6 Hz), 1.01-0.87 (2H, m), 1.20-1.27 (2H, m), 1.39-1.59 (10H, m), 1.66-1.80 (2H, m), 1.86-2.01 (2H, m), 2.66 (2H, t, J = 7.7 Hz), 2.91 (2H, t, J = 7.7 Hz), 3.66-3.74 (2H, m), 6.83 (2H, d, J = 8.6 Hz), 7.12 (2H, d, J = 8.6 Hz). |

TABLE 36

| Ex. No. | NMR data of compound |
|---|---|
| 90 | $^1$H-NMR (DMSO-d$_6$) δ: 1.19-1.43 (12H, m), 1.74 (3H, s), 1.82-1.84 (2H, m), 1.95-2.02 (2H, m), 2.19-2.28 (1H, m), 2.34-2.44 (1H, m), |

TABLE 36-continued

| Ex. No. | NMR data of compound |
|---|---|
|  | 3.97-4.06 (1H, m), 4.31 (2H, s), 5.69 (1H, s), 6.79 (2H, d, J = 7.2 Hz), 7.23 (2H, d, J = 7.2 Hz). |
| 91 | $^1$H-NMR (DMSO-$d_6$) δ: 1.38-1.45 (6H, m), 1.55-1.65 (6H, m), 1.74 (3H, d, J = 2.3 Hz), 1.96 (2H, t, J = 5.7 Hz), 2.19-2.28 (1H, m), 2.34-2.44 (1H, m), 4.05-3.97 (1H, m), 4.29 (2H, s), 5.57 (1H, s), 6.81 (2H, d, J = 8.6 Hz), 7.23 (2H, d, J = 8.6 Hz). |
| 92 | $^1$H-NMR (DMSO-$d_6$) δ: 1.27-1.39 (8H, m), 1.47-1.74 (13H, m), 1.91 (2H, t, J = 5.7 Hz), 2.23 (1H, dd, J = 14.7, 7.0 Hz), 2.31 (1H, dd, J = 14.7, 8.0 Hz), 2.73 (2H, t, J = 7.5 Hz), 3.28 (1H, t, J = 6.0 Hz), 3.84-3.91 (1H, m), 4.27 (2H, s), 5.53 (1H, s), 6.79 (2H, d, J = 8.6 Hz), 7.18 (2H, d, J = 8.6 Hz). |
| 93 | $^1$H-NMR (DMSO-$d_6$) δ: 1.38-1.44 (6H, m), 1.56-1.65 (6H, m), 1.77 (3H, d, J = 2.6 Hz), 1.97 (2H, t, J = 6.3 Hz), 2.58 (2H, dd, J = 8.1, 1.9 Hz), 3.89-3.96 (1H, m), 4.32 (2H, s), 5.59 (1H, s), 6.86 (2H, d, J = 8.8 Hz), 7.24 (2H, d, J = 8.8 Hz), 12.22 (1H, s). |
| 94 | $^1$H-NMR (DMSO-$d_6$) δ: 1.27-1.42 (8H, m), 1.44-1.52 (2H, m), 1.53-1.70 (8H, m), 1.73 (3H, d, J = 2.3 Hz), 1.94 (2H, t, J = 5.9 Hz), 2.28 (2H, dq, J = 40.2, 7.4 Hz), 2.68 (2H, t, J = 7.3 Hz), 3.19 (1H, t, J = 6.6 Hz), 3.88-3.95 (1H, m), 4.29 (2H, s), 5.56 (1H, s), 6.80 (2H, d, J = 8.8 Hz), 7.19 (2H, d, J = 8.8 Hz). |
| 95 | $^1$H-NMR (DMSO-$d_6$) δ: 1.02 (3H, t, J = 7.1 Hz), 1.27-1.48 (12H, m), 1.54-1.62 (2H, m), 1.95-2.01 (2H, m), 2.08-2.17 (1H, m), 2.31-2.44 (1H, m), 3.15-3.28 (2H, m), 4.34 (2H, s), 4.61 (1H, t, J = 6.7 Hz), 5.67 (1H, s), 6.85 (2H, d, J = 8.6 Hz), 7.18 (2H, d, J = 8.6 Hz). |
| 96 | $^1$H-NMR (DMSO-$d_6$) δ: 1.42-1.71 (4H, m), 1.77 (3H, d, J = 2.6 Hz), 1.79-1.85 (2H, m), 1.98-2.07 (3H, m), 2.16-2.27 (3H, m), 2.56-2.60 (2H, m), 3.90-3.96 (1H, m), 4.36 (2H, s), 5.69 (1H, s), 6.87 (2H, d, J = 8.8 Hz), 7.25 (2H, d, J = 8.8 Hz), 12.13 (1H, br s). |
| 97 | $^1$H-NMR (DMSO-$d_6$) δ: 1.42-1.71 (4H, m), 1.74 (3H, d, J = 2.3 Hz), 1.79-1.85 (2H, m), 1.98-2.11 (4H, m), 2.17-2.27 (4H, m), 3.92-3.99 (1H, m), 4.33 (2H, s), 5.69 (1H, s), 6.81 (2H, d, J = 8.6 Hz), 7.20 (2H, d, J = 8.6 Hz). |
| 98 | $^1$H-NMR (DMSO-$d_6$) δ: 1.35-1.42 (2H, m), 1.47-1.63 (6H, m), 1.65-1.71 (1H, m), 1.77 (3H, d, J = 2.3 Hz), 1.80-1.90 (1H, m), 1.92-1.97 (2H, m), 2.55-2.59 (2H, m), 3.89-3.95 (1H, m), 4.13-4.19 (1H, m), 4.30 (2H, s), 4.48 (1H, br s), 5.57 (1H, s), 6.86 (2H, d, J = 8.8 Hz), 7.23 (3H, d, J = 8.8 Hz), 12.28 (1H, br s). |
| 99 | $^1$H-NMR (DMSO-$d_6$) δ: 1.34-1.42 (2H, m), 1.47-1.62 (6H, m), 1.64-1.71 (1H, m), 1.74 (3H, d, J = 2.6 Hz), 1.80-1.89 (1H, m), 1.92-1.97 (2H, m), 2.09 (1H, dd, J = 14.6, 7.0 Hz), 2.25 (1H, dd, J = 14.6, 7.0 Hz), 3.96 (1H, td, J = 7.0, 2.6 Hz), 4.12-4.18 (1H, m), 4.29 (2H, s), 4.55 (1H, br s), 5.56 (1H, s), 6.79 (2H, d, J = 8.6 Hz), 7.20 (2H, d, J = 8.6 Hz). |

TABLE 37

| Ex. No. | NMR data of compound |
|---|---|
| 100 | $^1$H-NMR (DMSO-$d_6$) δ: 1.35-1.42 (4H, m), 1.47-1.71 (5H, m), 1.77 (3H, d, J = 2.3 Hz), 1.78-1.85 (1H, m), 1.92-1.97 (2H, m), 2.56 (2H, dd, J = 7.7, 2.3 Hz), 3.93 (1H, td, J = 7.7, 2.3 Hz), 4.13-4.18 (1H, m), 4.32 (2H, s), 5.69 (1H, s), 6.86 (2H, d, J = 8.6 Hz), 7.24 (2H, d, J = 8.6 Hz). |
| 101 | $^1$H-NMR (DMSO-$d_6$) δ: 1.35-1.42 (4H, m), 1.47-1.71 (5H, m), 1.74 (3H, d, J = 2.3 Hz), 1.77-1.85 (1H, m), 1.91-1.96 (2H, m), 2.09 (1H, dd, J = 14.6, 7.4 Hz), 2.25 (1H, dd, J = 14.6, 7.4 Hz), |

TABLE 37-continued

| Ex. No. | NMR data of compound |
|---|---|
|  | 3.96 (1H, td, J = 7.4, 2.3 Hz), 4.12-4.18 (1H, m), 4.30 (2H, s), 4.52 (1H, br s), 5.67 (1H, s), 6.80 (2H, d, J = 8.6 Hz), 7.20 (2H, d, J = 8.6 Hz). |
| 102 | $^1$H-NMR (DMSO-$d_6$) δ: 1.44-1.70 (4H, m), 1.77 (3H, d, J = 2.4 Hz), 1.80-1.85 (2H, m), 1.99-2.08 (3H, m), 2.16-2.27 (3H, m), 2.57 (2H, dd, J = 8.2, 2.4 Hz), 3.94 (1H, td, J = 8.2, 2.4 Hz), 4.36 (2H, s), 5.70 (1H, s), 6.88 (2H, d, J = 8.6 Hz), 7.25 (3H, d, J = 8.6 Hz). |
| 103 | $^1$H-NMR (DMSO-$d_6$) δ: 1.42-1.70 (4H, m), 1.74 (3H, d, J = 2.3 Hz), 1.78-1.85 (2H, m), 1.98-2.30 (8H, m), 3.96 (1H, td, J = 7.0, 2.3 Hz), 4.33 (2H, s), 5.69 (1H, s), 6.81 (2H, d, J = 8.6 Hz), 7.21 (2H, d, J = 8.6 Hz). |
| 104 | $^1$H-NMR (DMSO-$d_6$) δ: 1.36-1.44 (2H, m), 1.48-1.64 (6H, m), 1.66-1.73 (1H, m), 1.77 (3H, d, J = 2.4 Hz), 1.81-1.90 (1H, m), 1.93-1.98 (2H, m), 2.57 (2H, dd, J = 7.6, 2.4 Hz), 3.93 (1H, td, J = 7.6, 2.4 Hz), 4.14-4.20 (1H, m), 4.31 (2H, s), 5.58 (1H, s), 6.86 (2H, d, J = 8.6 Hz), 7.24 (2H, d, J = 8.6 Hz). |
| 105 | $^1$H-NMR (DMSO-$d_6$) δ: 1.35-1.43 (2H, m), 1.48-1.63 (6H, m), 1.68 (1H, dd, J = 13.3, 6.7 Hz), 1.74 (3H, d, J = 2.4 Hz), 1.80-1.89 (1H, m), 1.93-1.98 (2H, m), 2.09 (1H, dd, J = 14.6, 7.5 Hz), 2.24 (1H, dd, J = 14.6, 7.5 Hz), 3.93-4.00 (1H, m), 4.13-4.19 (1H, m), 4.29 (2H, s), 4.53 (1H, br s), 5.56 (1H, s), 6.79 (2H, d, J = 8.6 Hz), 7.20 (2H, d, J = 8.6 Hz). |
| 106 | $^1$H-NMR (DMSO-$d_6$) δ: 1.35-1.43 (4H, m), 1.47-1.71 (5H, m), 1.77 (3H, d, J = 2.3 Hz), 1.78-1.85 (1H, m), 1.92-1.97 (2H, m), 2.52-2.57 (2H, m), 3.93 (1H, td, J = 7.5, 2.3 Hz), 4.13-4.19 (1H, m), 4.32 (2H, s), 5.69 (1H, s), 6.86 (2H, d, J = 8.8 Hz), 7.16 (2H, d, J = 8.8 Hz). |
| 107 | $^1$H-NMR (DMSO-$d_6$) δ: 1.35-1.42 (4H, m), 1.47-1.71 (5H, m), 1.74 (3H, d, J = 2.6 Hz), 1.77-1.85 (1H, m), 1.92-1.97 (2H, m), 2.09 (1H, dd, J = 14.5, 7.5 Hz), 2.24 (1H, dd, J = 14.6, 7.5 Hz), 3.96 (1H, td, J = 7.5, 2.6 Hz), 4.12-4.19 (1H, m), 4.30 (2H, s), 4.51 (1H, br s), 5.67 (1H, s), 6.80 (2H, d, J = 8.8 Hz), 7.20 (2H, d, J = 8.8 Hz). |
| 108 | $^1$H-NMR (DMSO-$d_6$) δ: 1.38-1.43 (6H, m), 1.55-1.65 (6H, m), 1.94-1.96 (2H, m), 2.45-2.52 (2H, m), 2.83 (2H, t, J = 7.7 Hz), 4.34 (2H, d, J = 15.3 Hz), 5.60 (1H, s), 6.85 (1H, dd, J = 8.5, 2.7 Hz), 7.00 (1H, d, J = 2.6 Hz), 7.22 (1H, d, J = 8.7 Hz), 12.17 (1H, s). |
| 109 | $^1$H-NMR (DMSO-$d_6$) δ: 1.46-1.49 (6H, m), 1.62-1.70 (6H, m), 1.96 (2H, t, J = 5.7 Hz), 2.21 (3H, s), 2.42 (2H, t, J = 7.8 Hz), 2.71 (2H, t, J = 7.8 Hz), 4.29 (2H, s), 5.58 (1H, s), 6.66 (1H, dd, J = 8.4, 2.8 Hz), 6.72 (1H, d, J = 2.88 Hz), 7.01 (1H, d, J = 8.4 Hz), 12.08 (1H, s). |

TABLE 38

| Ex. No. | NMR data of compound |
|---|---|
| 110 | $^1$H-NMR (CDCl$_3$) δ: 1.46-1.49 (6H, m), 1.62-1.70 (6H, m), 2.02-2.05 (2H, m), 2.65 (2H, dt, J = 7.3, 3.5 Hz), 2.88 (2H, t, J = 7.8 Hz), 4.40 (2H, s), 5.59 (1H, s), 5.64 (1H, d, J = 12.5 Hz), 6.66 (1H, dd, J = 8.2, 2.2 Hz), 6.79 (2H, t, J = 4.1 Hz). |
| 111 | $^1$H-NMR (CDCl$_3$) δ: 1.41-1.51 (6H, m), 1.59-1.70 (6H, m), 2.06 (2H, t, J = 7.0 Hz), 2.67 (2H, t, J = 8.0 Hz), 2.91 (2H, t, J = 8.0 Hz), 3.85 (3H, s), 4.42 (2H, s), 5.57 (1H, s), 6.67-6.78 (2H, m), 6.80-6.87 (1H, m). |
| 112 | $^1$H-NMR (DMSO-$d_6$) δ: 1.38-1.42 (6H, m), 1.55-1.63 (6H, m), 1.98 (2H, t, J = 5.68 Hz), 2.47-2.50 (2H, m), 2.74 (2H, t, J = 7.54 Hz), 4.40 (2H, d, J = 9.3 Hz), 5.58 (1H, s), 6.93 (1H, dd, J = 8.45, |

TABLE 38-continued

| Ex. No. | NMR data of compound |
|---|---|
| | 1.2 Hz), 7.02 (1H, d, J = 8.8 Hz), 7.05-7.08 (1H, m), 12.11 (1H, s). |
| 113 | $^1$H-NMR (CDCl$_3$) δ: 0.97-1.22 (3H, m), 1.35-1.50 (6H, m), 1.54-1.69 (6H, m), 1.88 (1H, d, J = 12.8 Hz), 1.95-2.03 (1H, m), 2.75 (2H, t, J = 6.8 Hz), 2.99 (2H, t, J = 6.8 Hz), 4.31 (1H, dd, J = 9.5, 6.2 Hz), 4.35 (1H, dd, J = 9.5, 6.2 Hz), 7.08 (1H, d, J = 8.8 Hz), 8.05 (1H, dd, J = 8.8, 2.2 Hz), 8.33 (1H, d, J = 2.2 Hz). |
| 114 | $^1$H-NMR (CDCl$_3$) δ: 0.99-1.30 (6H, m), 1.34-1.52 (4H, m), 1.67-1.91 (7H, m), 2.64 (2H, t, J = 7.8 Hz), 2.89 (2H, t, J = 7.8 Hz), 3.14-3.20 (1H, m), 3.35 (3H, s), 3.75 (2H, d, J = 6.3 Hz), 6.82 (2H, dt, J = 9.3, 2.5 Hz), 7.11 (2H, d, J = 8.6 Hz). |
| 115 | $^1$H-NMR (DMSO-d$_6$) δ: 0.89 (3H, s), 0.95 (3H, s), 1.22-1.62 (10H, m), 1.60-1.66 (4H, m), 1.97 (1H, brs), 2.45-2.51 (2H, m), 2.74 (2H, t, J = 7.6 Hz), 3.68-3.75 (2H, m), 6.81 (2H, d, J = 8.6 Hz), 7.10 (2H, d, J = 8.6 Hz), 12.06 (1H, s). |
| 116 | $^1$H-NMR (DMSO-d$_6$) δ: 0.26-0.31 (4H, m), 1.17-1.26 (2H, m), 1.36-1.38 (1H, m), 1.56-1.65 (6H, m), 1.76-1.83 (4H, m), 1.93-2.03 (1H, m), 2.55-2.59 (2H, m), 3.64-3.72 (2H, m), 3.90-3.94 (1H, m), 6.83 (2H, dt, J = 9.4, 2.5 Hz), 7.23 (2H, dt, J = 9.4, 2.5 Hz), 12.23 (1H, s). |
| 117 | $^1$H-NMR (CDCl$_3$) δ: 1.78-1.90 (2H, m), 1.93-2.11 (6H, m), 2.36 (2H, t, J = 7.0 Hz), 2.66 (2H, t, J = 8.0 Hz), 2.92 (2H, t, J = 8.0 Hz), 4.52 (2H, s), 5.85 (1H, s), 6.86 (2H, d, J = 9.0 Hz), 7.12 (2H, d, J = 9.0 Hz). |
| 118 | $^1$H-NMR (DMSO-d$_6$) δ: 1.30-1.40 (2H, m), 1.61-1.66 (2H, m), 1.71-1.91 (8H, m), 1.77 (3H, d, J = 2.4 Hz), 2.26-2.38 (1H, m), 2.56 (1H, dd, J = 15.1, 7.2 Hz), 2.60 (1H, dd, J = 15.1, 8.0 Hz), 3.78 (2H, d, J = 6.8 Hz), 3.93 (1H, ddq, J = 8.0, 7.2, 2.4 Hz), 6.83-6.86 (2H, m), 7.22-7.26 (2H, m), 12.26 (1H, br s). |
| 119 | $^1$H-NMR (DMSO-d$_6$) δ: 1.15-1.40 (14H, m), 1.45-1.52 (2H, m), 1.60-1.68 (1H, m), 1.71 (3H, d, J = 2.6 Hz), 1.79 (2H, brs), 1.95 (2H, brs), 2.21 (1H, dd, J = 14.7, 7.4 Hz), 2.31 (1H, dd, J = 14.7, 7.4 Hz) 2.71 (2H, t, J = 7.4 Hz), 3.24 (1H, t, J = 6.2 Hz), 3.85-3.93 (2H, m), 4.30 (2H, s), 5.67 (1H, s), 6.78 (2H, d, J = 8.8 Hz), 7.18 (2H, d, J = 8.8 Hz). |
| 120 | $^1$H-NMR (DMSO-d$_6$) δ: 0.98 (3H, t, J = 7.1 Hz), 1.24-1.68 (21H, m), 1.93 (2H, t, J = 5.8 Hz), 2.14 (1H, dd, J = 14.6, 5.8 Hz), 2.38 (1H, dd, J = 14.6, 7.9 Hz), 2.71 (2H, t, J = 7.4 Hz), 3.18 (3H, m), 4.30 (2H, s), 4.56 (1H, dd, J = 7.9, 5.8 Hz), 5.62 (1H, s), 6.83 (2H, d, J = 8.8 Hz), 7.16 (2H, d, J = 8.6 Hz). |

Preparation examples of the present invention are as follows, but the present invention is not limited thereto.

Preparation Example 1

Capsule Preparation

| 1) Compound of Example 1 | 30 mg |
|---|---|
| 2) Microcrystalline cellulose | 10 mg |
| 3) Lactose | 19 mg |
| 4) Magnesium stearate | 1 mg |

The ingredients 1) to 4) are mixed and filled into a gelatin capsule.

Preparation Example 2

Tablet Preparation

| 1) Compound of Example 1 | 10 g |
|---|---|
| 2) Lactose | 50 g |
| 3) Cornstarch | 15 g |
| 4) Carmellose calcium | 44 g |
| 5) Magnesium stearate | 1 g |

The whole amounts of 1), 2) and 3), and 30 g of 4) are kneaded with water, dried in vacuo and sieved to give a granular powder. 14 g of 4) and 1 g of 5) are mixed with the granular powder and the mixture is compressed by a tableting machine. In this way, 1,000 tablets containing 10 mg of the compound of Example 1 per tablet are prepared.

Test Example 1

Evaluation of effect of test compounds on $Ca^{2+}$ mobilization by using a stable GPR40-expressing cell
Test Method
(1) Cell
A stable human GPR40-expressing HEK293 cell was used.
(2) Cell Medium Preparation and Cell Culture
A cell suspension was prepared such that the above-mentioned cells were present at $6\times10^5$ cells/mL in a cell culture medium (D-MEM (Nikken Bio Medical Laboratory) supplemented with 10% (v/v) fetal bovine serum (Biowest) and 1% (v/v) penicillin-streptomycin solution (Invitrogen)). The cell suspension was plated in a 384-well plate (poly-D-lysine coated plate; Falcon) in a volume of 25 μl/well, and the plate was incubated at 37° C. in an atmosphere of 5% $CO_2$ overnight. Each test compound was added to the cell at each concentration as below, and then the change in intracellular calcium level was measured by FLIPR$^{TETRA}$ (Molecular Devices). Before the FLIPR assay, the following preparative solutions were prepared.
(3) Preparation of Preparative Solutions for FLIPR Assay
First, an assay buffer was prepared for use in the preparation of a fluorescent dye solution and a diluent buffer solution. The assay buffer was prepared by adding 1M HEPES solution (Invitrogen) to Hanks' Balanced Salt Solution (Invitrogen), followed by adjusting the pH to 7.4 with 1M NaOH (Nacalai Tesque). Next, the fluorescent dye solution and the diluent buffer solution were prepared. The fluorescent dye solution was prepared in accordance with the instruction manual attached to Fluo-4NW calcium assay kit (Invitrogen), followed by addition of bovine serum albumin (Sigma) to a final concentration of 0.1% (w/v). The diluent buffer solution was prepared by adding bovine serum albumin (Sigma) to the assay buffer to give a final concentration of 0.1% (w/v).
(4) Pretreatment for FLIPR Assay
After removing a medium supernatant from the cell culture plate incubated overnight, the fluorescent dye solution was added to the plate in a volume of 25 μl/well. The plate was incubated at 37° C. in an atmosphere of 5% $CO_2$ for 90 minutes to promote the fluorescent dye uptake in the cell. Meanwhile, the test compounds (i.e., the compounds prepared in Examples) dissolved in dimethyl sulfoxide (DMSO; Nacalai Tesque) were diluted with the diluent buffer solution, to prepare each compound solution at each concentration. In addition, a palmitic acid solution was prepared as a positive control solution (hereinafter abbreviated as PosiC). A 40 μl aliquot of each sample solution prepared as above was added to each well of a 384-well polypropylene plate to prepare a compound plate. Finally, after the sufficient uptake of the fluorescent dye in the cell, the cell plate and the compound plate were set to FLIPR$^{TETRA}$.

(5) FLIPR Assay

After the above pretreatment, the change in intracellular calcium level was measured by FLIPR$^{TETRA}$ upon addition of 25 μl of each test compound solution at each concentration.

The GPR40 agonist activity of each test compound at each concentration was determined as a relative activity level (% PosiC) with the intracellular calcium level induced by 80 μM palmitic acid (a GPR40 agonist) set to 100%. Next, each compound concentration corresponding to 50% PosiC was calculated based on the % PosiC value, to compare between agonist activities of the test compounds.

(6) Result

The results are shown in tables 39 to 42. In the tables, "++++" indicates 0.01 μM or more but less than 0.1 μM, "+++" indicates 0.1 μM or more but less than 1 μM, "++" indicates 1 μM or more but less than 10 μM, and "+" indicates 10 μM or more for 50% posiC value.

In the tables, "N.T." indicates "not tested".

TABLE 39

| Ex. No. | 50% PosiC value |
|---|---|
| 1 | ++++ |
| 2 | ++++ |
| 3 | N.T. |
| 4 | ++++ |
| 5 | N.T. |
| 6 | +++ |
| 7 | N.T. |
| 8 | +++ |
| 9 | +++ |
| 10 | N.T. |
| 11 | +++ |
| 12 | N.T. |
| 13 | N.T. |
| 14 | +++ |
| 15 | N.T. |
| 16 | +++ |
| 17 | +++ |
| 18 | N.T. |
| 19 | ++++ |
| 20 | N.T. |
| 21 | + |
| 22 | +++ |
| 23 | N.T. |
| 24 | +++ |
| 25 | +++ |
| 26 | N.T. |
| 27 | +++ |
| 28 | ++++ |
| 29 | +++ |
| 30 | +++ |

TABLE 40

| Ex. No. | 50% PosiC value |
|---|---|
| 31 | N.T. |
| 32 | +++ |
| 33 | N.T. |
| 34 | +++ |
| 35 | N.T. |
| 36 | N.T. |
| 37 | +++ |
| 38 | N.T. |
| 39 | +++ |
| 40 | ++++ |
| 41 | ++++ |
| 42 | ++++ |
| 43 | N.T. |
| 44 | ++ |
| 45 | N.T. |
| 46 | ++ |
| 47 | +++ |
| 48 | ++ |
| 49 | ++ |
| 50 | +++ |
| 51 | ++ |
| 52 | ++ |
| 53 | ++ |
| 54 | ++ |
| 55 | +++ |
| 56 | ++ |
| 57 | ++ |
| 58 | ++ |
| 59 | +++ |
| 60 | ++ |

TABLE 41

| Ex. No. | 50% PosiC value |
|---|---|
| 61 | + |
| 62 | + |
| 63 | +++ |
| 64 | +++ |
| 65 | ++ |
| 66 | +++ |
| 67 | + |
| 68 | ++ |
| 69 | ++ |
| 70 | +++ |
| 71 | ++ |
| 72 | ++ |
| 73 | +++ |
| 74 | N.T. |
| 75 | +++ |
| 76 | N.T. |
| 77 | +++ |
| 78 | ++ |
| 79 | N.T. |
| 80 | ++ |
| 81 | +++ |
| 82 | ++ |
| 83 | +++ |
| 84 | ++ |
| 85 | ++ |
| 86 | ++ |
| 87 | ++ |
| 88 | ++ |
| 89 | ++ |
| 90 | N.T. |

TABLE 42

| Ex. No. | 50% PosiC value |
|---|---|
| 91 | +++ |
| 92 | +++ |
| 93 | N.T. |
| 94 | ++ |
| 95 | N.T. |
| 96 | N.T. |
| 97 | +++ |
| 98 | N.T. |
| 99 | ++ |
| 100 | N.T. |
| 101 | +++ |

TABLE 42-continued

| Ex. No. | 50% PosiC value |
|---|---|
| 102 | N.T. |
| 103 | +++ |
| 104 | N.T. |
| 105 | ++ |
| 106 | N.T. |
| 107 | +++ |
| 108 | ++ |
| 109 | ++ |
| 110 | +++ |
| 111 | + |
| 112 | + |
| 113 | ++ |
| 114 | + |
| 115 | ++ |
| 116 | ++ |
| 117 | ++ |
| 118 | +++ |
| 119 | +++ |
| 120 | +++ |

Test Example 2

Evaluation of test compounds on insulin secretion using rat isolated islets of Langerhans
Test Method
(1) Rat Islets of Langerhans are Isolated from Male Wister Rats (Charles River Laboratories).
(2) Preparation of Each Solution for Use in the Isolation of Islets of Langerhans Each solution for use in the isolation of islets of Langerhans is prepared. A collagenase solution is prepared by dissolving collagenase at a concentration of 1 mg/mL in Hanks' Balanced Salt Solution (Invitrogen) containing 1% (v/v) kanamycin sulfate (Invitrogen) (hereinafter referred to as HBSS/1% (v/v) kanamycin solution). Ficoll-Conray solution A is prepared by dissolving Ficoll (Nacalai Tesque) in Milli Q water, followed by adding Conray400 (Conray is the trademark registered by Daiichi Pharmaceutical Co.) thereto. Ficoll-Conray solution D is prepared by mixing equal volumes of the above solution A and Otsuka Distilled Water (Otsuka Pharmaceutical Factory). Ficoll-Conray solution C is prepared by mixing equal volumes of the Ficoll-Conray solutions A and D, and Ficoll-Conray solution B is prepared by mixing equal volumes of the Ficoll-Conray solutions A and C. A culture medium for islets of Langerhans is prepared by supplementing D-MEM (low glucose) (Nikken Bio Medical Laboratory) with 10% (v/v) fetal bovine serum (Biowest) and 1% (v/v) kanamycin sulfate (Invitrogen) (hereinafter referred to as D-MEM (LG)/10% FBS/1% kanamycin).
(3) Method for Isolating Islets of Langerhans from Wister Rats Rats are anesthetized with pentobarbital and subjected to laparotomy for exposing the abdominal organs. After the common bile duct is clamped at the duodenal side and then cannulated from the liver side, a collagenase solution (1 mg/ml) is injected slowly to fill the pancreas with. The pancreas is isolated and then incubated at 37° C. in an atmosphere of 5% $CO_2$ for about 20 minutes. The digested pancreas is suspended in HBSS/1% (v/v) kanamycin solution and the suspension is transferred to a glass tube. After centrifuging the suspension and then removing the supernatant, the resulting precipitate is suspended in 3.8 mL of Ficoll-Conray solution A. On this, 1.8 mL of Ficoll-Conray solution B, 1.8 mL of Ficoll-Conray solution C and 2.0 mL of Ficoll-Conray solution D are superposed successively. After centrifugation, islets of Langerhans present in the boundary between the solutions C and D are collected into 6 mL of D-MEM (LG)/10% FBS/1% kanamycin, followed by further centrifugation. After removing the supernatant, the precipitate is resuspended in 6 mL of D-MEM (LG)/10% FBS/1% kanamycin. After removing contaminants, the suspension is maintained at 37° C. in an atmosphere of 5% $CO_2$ until it is used for the evaluation of the compounds.
(4) Method for Evaluating the Test Compounds on Insulin Secretion D-MEM (LG)/10% FBS/1% kanamycin is added to a 6-well plate (Falcon) in a volume of 1.5 mL/well. After islets of Langerhans of almost the same size are selected with a stereomicroscope, 5 islets are placed into each well. The islets of Langerhans are transferred into another 6-well plate (Falcon) filled with 3.3 mM glucose-contained Krebs Ringer Bicarbonate/0.2% (w/v) bovine serum albumin without free fatty acids (Sigma) (hereinafter referred to as KRB/0.2% BSA solution), and incubated at 37° C. in an atmosphere of 5% $CO_2$. After 60 minutes, the above KRB/0.2% BSA solution is replaced with 3.3 mM or 11.2 mM glucose-contained KRB/0.2% BSA solution containing the respective test compounds, followed by incubation at 37° C. in an atmosphere of 5% $CO_2$ for 60 minutes. The respective test compounds are dissolved in dimethyl sulfoxide (DMSO; Nacalai Tesque) and the final concentration of DMSO is 1% (v/v) upon addition of the test compound to the cell. 60 minutes after addition of the respective test compounds, the supernatants are collected. The insulin level in the supernatant is determined by using ultrasensitive rat insulin kit (Morinaga Institute of Biological Science). The result of the evaluation is shown as a relative activity level (% Control), which is represented as the insulin secretion level of the group treated by the respective test compounds relative to that of the control group.

Test Example 3

Glucose Tolerance Test in Wister Rats

Male Wister rats (Charles River Laboratories) are fasted for about 16 hours since the day before the experiment day. 30 minutes after oral administration of the respective test compounds at a dose of 0.1 to 30 mg/kg body weight, rats are administered orally with a glucose solution at a dose of 2 g/kg body weight. 0, 30, 60 and 120 minutes after the administration, blood samples (about 200 µl) are collected via the tail vein of each rat to determine plasma glucose levels and plasma insulin levels. The plasma glucose levels are determined by Hexokinase method using a biochemistry automatic analyzer. The plasma insulin levels are determined by ELISA using ultrasensitive rat insulin kit (Morinaga Institute of Biological Science). The respective test compounds are suspended in 0.5% (w/v) methyl cellulose for use in the oral administration. The control group is administered with 0.5% (w/v) methyl cellulose solution. For evaluation, a paired or multiple comparison test is performed with the control group to determine an efficacy.

INDUSTRIAL APPLICABILITY

The compound, a pharmaceutically acceptable salt thereof or a solvate thereof of the present invention is useful as a GPR40 agonist medicament for treating or preventing diabetes mellitus, hyperglycemia, impaired glucose tolerance, impaired fasting glucose and the like.

The invention claimed is:

1. A spiro compound of the following general formula [Ia]:

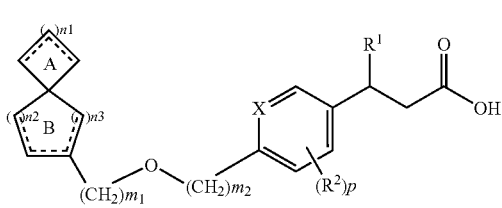

or a pharmaceutically acceptable salt thereof, wherein:

$R^1$ is
(1) a hydrogen atom,
(2) a $C_1$-$C_6$ alkyl group,
(3) a $C_2$-$C_6$ alkenyl group,
(4) a $C_2$-$C_6$ alkynyl group,
(5) a $C_1$-$C_6$ alkoxy group,
(6) a hydroxy $C_1$-$C_6$ alkyl group,
(7) a $C_1$-$C_6$ alkoxy($C_1$-$C_6$)alkyl group,
(8) —$CONR^{11}R^{12}$ in which $R^{11}$ and $R^{12}$ are the same or different and each represents a hydrogen atom or a $C_1$-$C_6$ alkyl group,
(9) a phenyl group or
(10) a five-membered heteroaryl group which has at least one heteroatom selected from the group consisting of a nitrogen atom, an oxygen atom and a sulfur atom, and which is optionally substituted by a $C_1$-$C_6$ alkyl group;

$R^2$ is
(1) a halogen atom,
(2) a $C_1$-$C_6$ alkyl group,
(3) a hydroxy group or
(4) a $C_1$-$C_6$ alkoxy group;

p is 0, 1, 2 or 3;
X is a carbon atom or a nitrogen atom;
m1 is 0, 1 or 2;
m2 is 0 or 1;
spiro-ring AB is optionally substituted by 1 to 5 same or different substituent(s) selected from the group consisting of
(1) a hydroxy group,
(2) a $C_1$-$C_6$ alkyl group,
(3) a $C_1$-$C_6$ alkoxy group and
(4) an oxo group;
n1 is 0, 1, 2, 3 or 4;
n2 is 1, 2, 3 or 4;
n3 is 0, 1 or 2 with the proviso that n2+n3 is 2, 3 or 4; and
a bond represented by the symbol: 
means a single bond or a double bond with the proviso that three contiguous carbon atoms do not constitute an allene bond represented by the formula:

C=C=C.

2. The spiro compound as claimed in claim 1, or a pharmaceutically acceptable salt thereof, wherein the spiro-ring AB is represented by the formula:

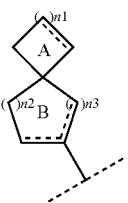

3. The spiro compound as claimed in claim 1, or a pharmaceutically acceptable salt thereof, wherein the number of double bonds in ring A of the spiro-ring AB is 0 or 1.

4. The spiro compound as claimed in claim 1, or a pharmaceutically acceptable salt thereof, wherein the number of double bonds in ring B of the spiro-ring AB is 0 or 1.

5. The spiro compound as claimed in claim 1, or a pharmaceutically acceptable salt thereof, wherein n3 is 1 or 2.

6. The spiro compound as claimed in claim 1, or a pharmaceutically acceptable salt thereof, wherein the spiro-ring AB is optionally substituted by 1 to 3 same or different substituent(s).

7. The spiro compound as claimed in claim 1, or a pharmaceutically acceptable salt thereof, wherein:

$R^1$ is
(1) a hydrogen atom,
(2) a $C_1$-$C_6$ alkyl group,
(3) a $C_2$-$C_6$ alkenyl group,
(4) a $C_2$-$C_6$ alkynyl group,
(5) a $C_1$-$C_6$ alkoxy group,
(6) a $C_1$-$C_6$ alkoxy($C_1$-$C_6$)alkyl group,
(7) —$CONR^{11}R^{12}$ in which $R^{11}$ and $R^{12}$ are the same or different and each represents a hydrogen atom or a $C_1$-$C_6$ alkyl group, or
(8) a five-membered heteroaryl group which has at least one heteroatom selected from the group consisting of a nitrogen atom, an oxygen atom and a sulfur atom, and which is optionally substituted by a $C_1$-$C_6$ alkyl group.

8. The spiro compound as claimed in claim 1, or a pharmaceutically acceptable salt thereof, wherein:

$R^1$ is
(1) a hydrogen atom,
(2) a $C_2$-$C_6$ alkenyl group,
(3) a $C_2$-$C_6$ alkynyl group,
(4) a $C_1$-$C_6$ alkoxy group or
(5) a five-membered heteroaryl group which has at least one heteroatom selected from the group consisting of a nitrogen atom, an oxygen atom and a sulfur atom, and which is optionally substituted by a $C_1$-$C_6$ alkyl group.

9. The spiro compound as claimed in claim 1, or a pharmaceutically acceptable salt thereof, wherein p is 0 or 1.

10. The spiro compound as claimed in claim 1, or a pharmaceutically acceptable salt thereof, wherein:

$R^2$ is
(1) a $C_1$-$C_6$ alkyl group,
(2) a hydroxy group or
(3) a $C_1$-$C_6$ alkoxy group.

11. The spiro compound as claimed in claim 1, or a pharmaceutically acceptable salt thereof, wherein m1 is 0 or 1.

12. The spiro compound as claimed in claim 1, or a pharmaceutically acceptable salt thereof, wherein the spiro-ring AB is represented by one of the following formulas:

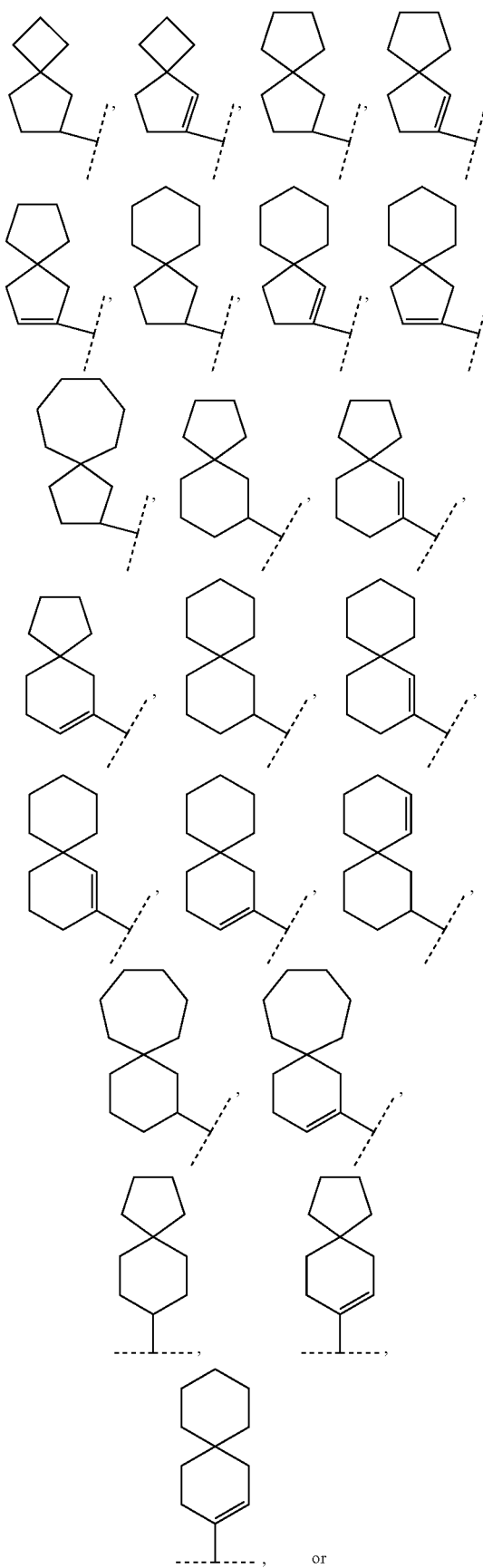

or

-continued

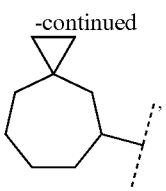

wherein the spiro-ring AB is optionally substituted by 1 to 5 same or different substituent(s) selected from the group consisting of
(1) a hydroxy group,
(2) a $C_1$-$C_6$ alkyl group,
(3) a $C_1$-$C_6$ alkoxy group and
(4) an oxo group.

13. A spiro compound of the following general formula [I]:

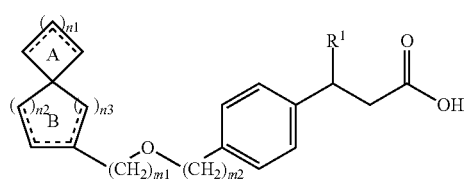

or a pharmaceutically acceptable salt thereof, wherein:
$R^1$ is
(1) a hydrogen atom,
(2) a $C_1$-$C_4$ alkyl group,
(3) a $C_2$-$C_4$ alkenyl group,
(4) a $C_2$-$C_4$ alkynyl group,
(5) a $C_1$-$C_4$ alkoxy group,
(6) a hydroxy $C_1$-$C_4$ alkyl group,
(7) a $C_1$-$C_4$ alkoxy($C_1$-$C_4$)alkyl group,
(8) —$CONR^{11}R^{12}$ in which $R^{11}$ and $R^{12}$ are the same or different and each represents a hydrogen atom or a $C_1$-$C_4$ alkyl group,
(9) a phenyl group or
(10) a five-membered heteroaryl group which has at least one heteroatom selected from a nitrogen atom, an oxygen atom and a sulfur atom, and which is optionally substituted by a $C_1$-$C_4$ alkyl group;
m1 is 0, 1 or 2;
m2 is 0 or 1;
spiro-ring AB is optionally substituted by 1 to 5 same or different substituent(s) selected from
(1) a hydroxy group and
(2) a $C_1$-$C_4$ alkyl group;
n1 is 2, 3 or 4;
n2 is 1, 2 or 3;
n3 is 0, 1 or 2 with the proviso that n2+n3 is 2 or 3; and
a bond represented by the symbol: 
means a single bond or a double bond with the proviso that three contiguous carbon atoms do not constitute an allene bond represented by the formula:

C=C=C.

14. The spiro compound as claimed in claim 1 which is represented by the following formula:

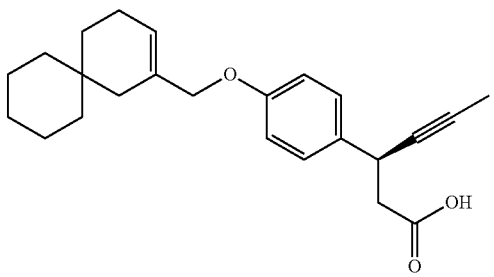

or a pharmaceutically acceptable salt thereof.

15. A pharmaceutically acceptable salt of the spiro compound as claimed in claim 14, which is represented by the following formula:

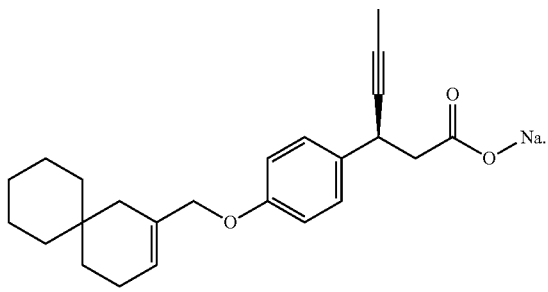

16. A pharmaceutically acceptable salt of the spiro compound as claimed in claim 14, which is represented by the following formula:

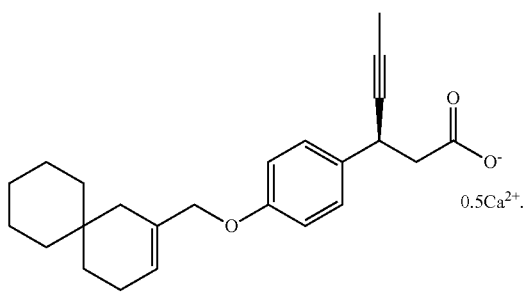

17. A pharmaceutically acceptable salt of the spiro compound as claimed in claim 14, which is represented by the following formula:

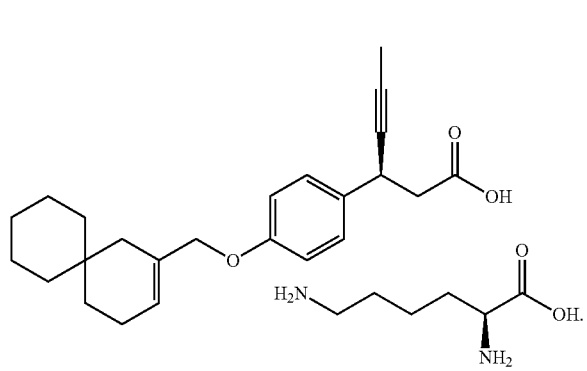

18. The spiro compound as claimed in claim 1, which is represented by the following formula:

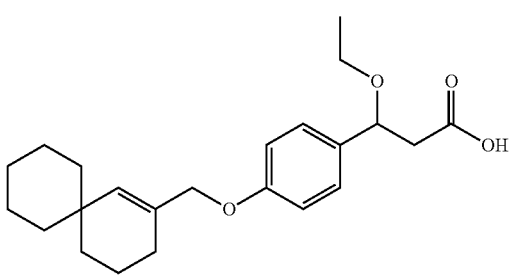

or a pharmaceutically acceptable salt thereof.

19. A pharmaceutically acceptable salt of the spiro compound as claimed in claim 18, which is represented by the following formula:

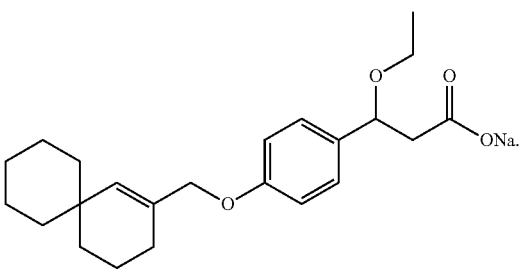

20. A pharmaceutically acceptable salt of the spiro compound as claimed in claim 18, which is represented by the following formula:

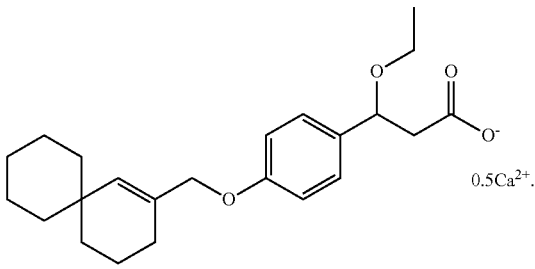

21. A pharmaceutically acceptable salt of the spiro compound as claimed in claim 18, which is represented by the following formula:

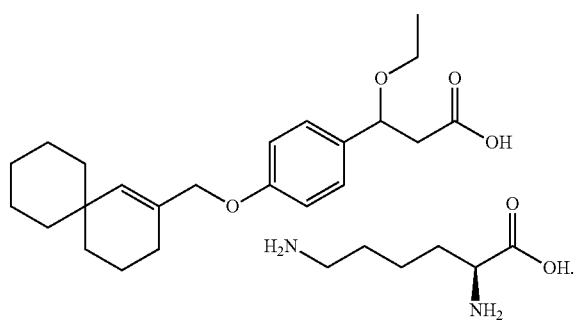

22. The spiro compound as claimed in claim 1, which is represented by the following formula:

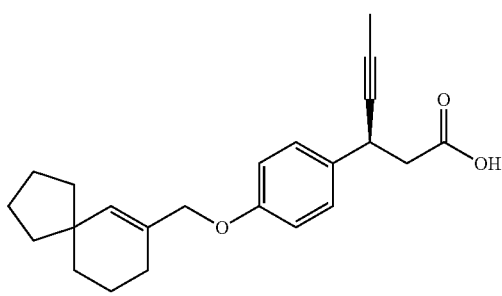

or a pharmaceutically acceptable salt thereof.

23. A pharmaceutically acceptable salt of the spiro compound as claimed in claim 22, which is represented by the following formula:

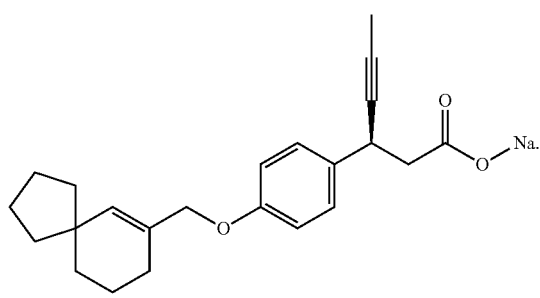

24. A pharmaceutically acceptable salt of the spiro compound as claimed in claim 22, which is represented by the following formula:

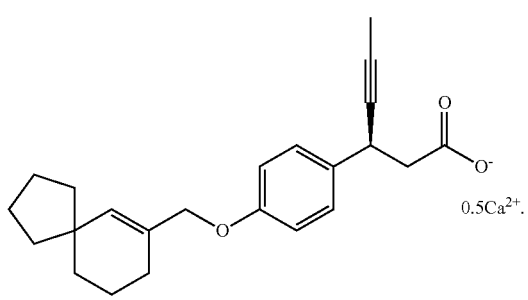

25. A pharmaceutically acceptable salt of the spiro compound as claimed in claim 22, which is represented by the following formula:

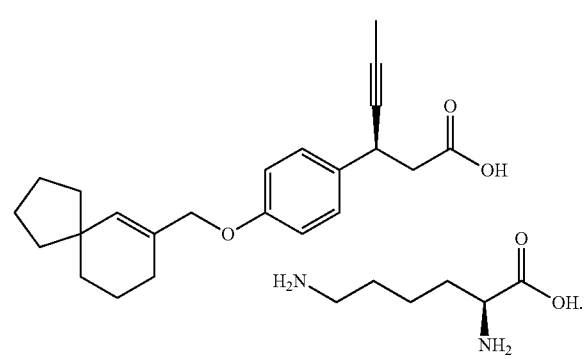

26. The spiro compound as claimed in claim 1, which is represented by the following formula:

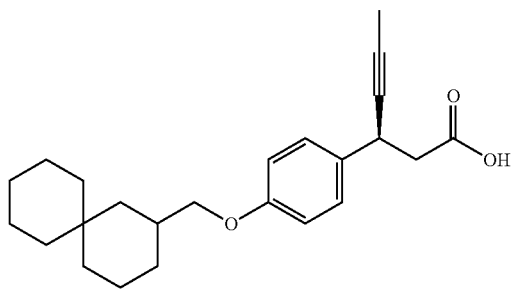

or a pharmaceutically acceptable salt thereof.

27. A pharmaceutically acceptable salt of the spiro compound as claimed in claim 26, which is represented by the following formula:

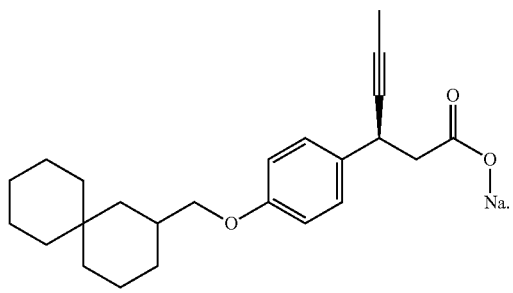

28. The spiro compound as claimed in claim 1, which represented by the following formula:

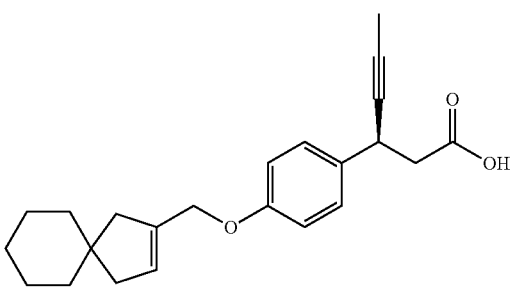

or a pharmaceutically acceptable salt thereof.

29. The spiro compound as claimed in claim 1, which represented by the following formula:

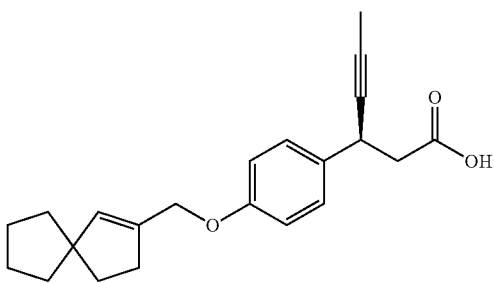

or a pharmaceutically acceptable salt thereof.

30. A pharmaceutical composition, which comprises the spiro compound as claimed in claim 1, or a pharmaceutically acceptable salt thereof, and a pharmaceutically acceptable carrier.

31. A pharmaceutical composition, which comprises the spiro compound as claimed in any one of claims 14, 18, 22, 26, 28, and 29, or a pharmaceutically acceptable salt thereof, and a pharmaceutically acceptable carrier.

32. A pharmaceutical composition, which comprises the salt as claimed in any one of claims 15, 16, 17, 19, 20, 21, 23, 24, 25, and 27, and a pharmaceutically acceptable carrier.

33. A method for treating or preventing type 2 diabetes mellitus, comprising administering a pharmaceutically effective amount of the spiro compound as claimed in claim 1, or a pharmaceutically acceptable salt thereof, to a mammal in need thereof.

34. The method of claim 33, wherein the method comprises treating type 2 diabetes mellitus.

35. A method for treating or preventing type 2 diabetes mellitus, comprising administering a pharmaceutically effective amount of the spiro compound as claimed in any one of claims 14, 18, 22, 26, 28, and 29, or a pharmaceutically acceptable salt thereof, to a mammal in need thereof.

36. The method of claim 35, wherein the method comprises treating type 2 diabetes mellitus.

37. A method for treating or preventing type 2 diabetes mellitus, comprising administering a pharmaceutically effective amount of the salt as claimed in any one of claims 15, 16, 17, 19, 20, 21, 23, 24, 25, and 27, to a mammal in need thereof.

38. The method of claim 37, wherein the method comprises treating type 2 diabetes mellitus.

39. The method of claim 33 wherein said mammal is human.

40. The method of claim 34 wherein said mammal is human.

41. The method of claim 35 wherein said mammal is human.

42. The method of claim 36 wherein said mammal is human.

43. The method of claim 37 wherein said mammal is human.

44. The method of claim 38 wherein said mammal is human.

* * * * *

UNITED STATES PATENT AND TRADEMARK OFFICE
CERTIFICATE OF CORRECTION

PATENT NO. : 8,299,296 B2  
APPLICATION NO. : 12/258033  
DATED : October 30, 2012  
INVENTOR(S) : Takashi Shimada et al.

Page 1 of 1

It is certified that error appears in the above-identified patent and that said Letters Patent is hereby corrected as shown below:

In column 219, line 33-40 (Approx.), in claim 12, before

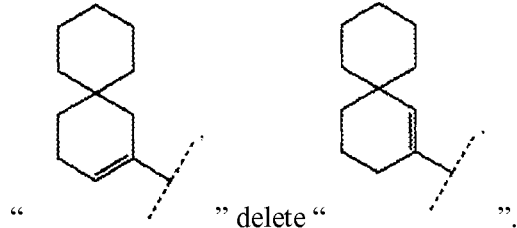

" delete " ".

In column 224, line 66, in claim 28, after "which" insert -- is --.

In column 225, line 15, in claim 29, after "which" insert -- is --.

Signed and Sealed this
Fifth Day of February, 2013

Teresa Stanek Rea
*Acting Director of the United States Patent and Trademark Office*